US012630521B2

(12) United States Patent
Liao et al.

(10) Patent No.: US 12,630,521 B2
(45) Date of Patent: May 19, 2026

(54) ARYLAMIDES AND METHODS OF USE THEREOF

(71) Applicant: Genzyme Corporation, Cambridge, MA (US)

(72) Inventors: Junkai Liao, Bridgewater, NJ (US); Mark Munson, Bridgewater, NJ (US); Zhongli Gao, Bridgewater, NJ (US); Gregory Hurlbut, Bridgewater, NJ (US); Hans Peter Nestler, Bridgewater, NJ (US); Ingrid Mechin, Bridgewater, NJ (US); Martin Smrcina, Bridgewater, NJ (US); Ronghua Li, Bridgewater, NJ (US); Ryan Hartung, Bridgewater, NJ (US); William Bock, Bridgewater, NJ (US); Bertrand Vivet, Bridgewater, NJ (US); Andrew Scholte, Bridgewater, NJ (US)

(73) Assignee: Genzyme Corporation, Cambridge, MA (US)

( * ) Notice: Subject to any disclaimer, the term of this patent is extended or adjusted under 35 U.S.C. 154(b) by 696 days.

(21) Appl. No.: 17/832,388

(22) Filed: Jun. 3, 2022

(65) Prior Publication Data

US 2023/0147360 A1 May 11, 2023

Related U.S. Application Data

(63) Continuation of application No. PCT/US2020/063590, filed on Dec. 7, 2020.

(60) Provisional application No. 62/944,188, filed on Dec. 5, 2019.

(51) Int. Cl.

| | |
|---|---|
| ***C07D 333/54*** | (2006.01) |
| ***A61K 45/06*** | (2006.01) |
| ***C07D 277/64*** | (2006.01) |
| ***C07D 333/64*** | (2006.01) |
| ***C07D 417/04*** | (2006.01) |
| ***C07D 417/12*** | (2006.01) |

(52) U.S. Cl.

CPC ............ *C07D 333/54* (2013.01); *A61K 45/06* (2013.01); *C07D 277/64* (2013.01); *C07D 333/64* (2013.01); *C07D 417/04* (2013.01); *C07D 417/12* (2013.01)

(58) Field of Classification Search

None

See application file for complete search history.

(56) References Cited

U.S. PATENT DOCUMENTS

| | | | |
|---|---|---|---|
| 4,172,896 | A | 10/1979 | Uno et al. |
| 5,358,970 | A | 10/1994 | Ruff et al. |
| 5,427,798 | A | 6/1995 | Ludwig et al. |
| 5,449,783 | A | 9/1995 | Saita et al. |
| 5,541,231 | A | 7/1996 | Ruff et al. |
| 5,731,000 | A | 3/1998 | Ruff et al. |
| 5,763,493 | A | 6/1998 | Ruff et al. |
| 5,856,347 | A | 1/1999 | Hashiguchi et al. |
| 6,110,973 | A | 8/2000 | Young |
| 8,999,976 | B2 | 4/2015 | Binch et al. |
| 9,790,219 | B2 | 10/2017 | Bastos et al. |
| 2007/0022507 | P1 | 1/2007 | Scully |
| 2009/0233975 | A1 | 9/2009 | Suetsugu et al. |
| 2010/0184739 | A1 | 7/2010 | Sheth et al. |
| 2011/0184177 | A1 | 7/2011 | Hachtel et al. |
| 2013/0186801 | A1 | 7/2013 | Verwijs |
| 2015/0005275 | A1 | 1/2015 | Plas et al. |
| 2015/0045327 | A1 | 2/2015 | Van Der Plas et al. |
| 2016/0095858 | A1 | 4/2016 | Miller et al. |
| 2016/0120841 | A1 | 5/2016 | Kym et al. |
| 2016/0122331 | A1 | 5/2016 | Kym et al. |
| 2016/0355480 | A1 | 12/2016 | Altenbach et al. |
| 2019/0248809 | A1 | 8/2019 | Clemens et al. |
| 2023/0137585 | A1 | 5/2023 | Gao et al. |
| 2023/0159438 | A1 | 5/2023 | Liao et al. |
| 2023/0159439 | A1 | 5/2023 | Liao et al. |
| 2024/0002374 | A1 | 1/2024 | Liao et al. |
| 2025/0197420 | A1 | 6/2025 | Liao et al. |
| 2025/0197422 | A1 | 6/2025 | Liao et al. |
| 2025/0248975 | A1 | 8/2025 | Liao et al. |
| 2025/0255859 | A1 | 8/2025 | Hurlbut |

FOREIGN PATENT DOCUMENTS

| | | | |
|---|---|---|---|
| EP | 0699438 | A2 | 3/1996 |
| EP | 0790057 | A1 | 8/1997 |
| EP | 3464282 | A1 | 4/2019 |
| JP | H07149745 | A | 6/1995 |
| JP | 2007504255 | A | 3/2007 |
| JP | 2017074057 | A | 4/2017 |
| WO | WO-9616650 | A1 | 6/1996 |

(Continued)

OTHER PUBLICATIONS

Damia "Contemporary pre-clinical development of anticancer agents—What are the optimal preclinical models?" European Journal of Cancer 2009, 45, 2768-2781.*
Sharma "Cell line-based platforms to evaluate the therapeutic efficacy of candidate anticancer agents" Nature Reviews Cancer Apr. 2010, vol. 10, 241-253.*
Ocana, A. "Preclinical development of molecular targeted agents for cancer" Nat. Rev. Clin. Oncol. 2011, 8, 200-209.*
Types of CFTR Mutations, Online: "https://www.cff.org/research-clinical-trials/types-cftr-mutations", accessed Jun. 2, 2025.*
Ledford "US cancer institute overhauls cell lines" Nature Feb. 25, 2016 vol. 530 p. 391.*
Johnson, et. al. "Relationships between drug activity in NCI preclinical in vitro and in vivo models and early clinical trials." British Journal of Cancer 2001, 84, 1424-1431.*
Felis "Current and Investigational Therapeutics for Fabry Disease" Kidney International Reports (2020) 5, 407-413.*

(Continued)

*Primary Examiner* — David K O'Dell
(74) *Attorney, Agent, or Firm* — Goodwin Procter LLP

(57) ABSTRACT

The present disclosure relates to heterocyclic compounds, pharmaceutically acceptable salts thereof, and pharmaceutical preparations thereof. Also described herein are compositions and the use of such compounds in methods of treating diseases and conditions mediated by deficient CFTR activity, in particular cystic fibrosis.

23 Claims, No Drawings

(56) References Cited

FOREIGN PATENT DOCUMENTS

| | | | |
|---|---|---|---|
| WO | WO-98024782 | A2 | 6/1998 |
| WO | WO-03039451 | A2 | 5/2003 |
| WO | WO-2005075435 | A1 | 8/2005 |
| WO | WO-2005120497 | A2 | 12/2005 |
| WO | WO-2006002421 | A2 | 1/2006 |
| WO | WO-2006069656 | A1 | 7/2006 |
| WO | WO-2006113704 | A2 | 10/2006 |
| WO | WO-2007056341 | A1 | 5/2007 |
| WO | WO-2007087066 | A2 | 8/2007 |
| WO | WO-2008000408 | A1 | 1/2008 |
| WO | WO-2008121877 | A2 | 10/2008 |
| WO | WO-2008147952 | A1 | 12/2008 |
| WO | WO-2009074575 | A2 | 6/2009 |
| WO | WO-2009076593 | A1 | 6/2009 |
| WO | WO-2010048526 | A2 | 4/2010 |
| WO | WO-2010048564 | A1 | 4/2010 |
| WO | WO-2010048573 | A1 | 4/2010 |
| WO | WO-2010151747 | A1 | 12/2010 |
| WO | WO-2011072241 | A1 | 6/2011 |
| WO | WO-20110113894 | A1 | 9/2011 |
| WO | WO-2012170889 | A1 | 12/2012 |
| WO | WO-2013003837 | A1 | 1/2013 |
| WO | WO-2013038373 | A1 | 3/2013 |
| WO | WO-2013038378 | A1 | 3/2013 |
| WO | WO-2013038381 | A1 | 3/2013 |
| WO | WO-2013038386 | A1 | 3/2013 |
| WO | WO-2013038390 | A1 | 3/2013 |
| WO | WO-2013043720 | A1 | 3/2013 |
| WO | WO-2014180562 | A1 | 11/2014 |
| WO | WO-2014186704 | A2 | 11/2014 |
| WO | WO-2015018823 | A1 | 2/2015 |
| WO | WO-2015138909 | A1 | 9/2015 |
| WO | WO-2015138934 | A1 | 9/2015 |
| WO | WO-2016130929 | A1 | 8/2016 |
| WO | WO-2016130943 | A1 | 8/2016 |
| WO | WO-2016183173 | A1 | 11/2016 |
| WO | WO-2017062581 | A1 | 4/2017 |
| WO | WO-2017173274 | A1 | 10/2017 |
| WO | WO-2017208115 | A1 | 12/2017 |
| WO | WO-2018042316 | A1 | 3/2018 |
| WO | WO-2018167690 | A1 | 9/2018 |
| WO | WO-2019161078 | | 8/2019 |
| WO | WO-2020206080 | A1 | 10/2020 |
| WO | WO-2021097054 | A1 | 5/2021 |
| WO | WO-2021097057 | A1 | 5/2021 |
| WO | WO-2021113806 | A1 | 6/2021 |
| WO | WO-2021113808 | A1 | 6/2021 |
| WO | WO-2022032068 | | 2/2022 |
| WO | WO-2022076622 | | 4/2022 |
| WO | WO-2022109573 | A1 | 5/2022 |
| WO | WO-2023034946 | A1 | 3/2023 |
| WO | WO-2023034992 | | 3/2023 |
| WO | WO-2024054840 | A1 | 3/2024 |
| WO | WO-2024054845 | A1 | 3/2024 |
| WO | WO-2024054851 | A1 | 3/2024 |
| WO | WO-2024097227 | A1 | 5/2024 |

OTHER PUBLICATIONS

Konstantinos Makrilakis "Pathophysiology of Type 2 diabetes" Chapter 3 in Diabetes in Clinical Practice: Questions and Answers from Case Studies, Nicholas Katsilambros et al. eds. John Wiley & Sons: 2006, pp. 43-58.*

Stavrou, "Genetic mechanisms of peripheral nerve disease." Neuroscience Letters, 2021, 742, 135357.*

University of Cambridge John van Geest Centre for Brain Repair School of Clinical Medicine "Alzheimer's disease and tauopathy" Online "http://www.brc.cam.ac.uk/research/alzheimers-disease-and-tauopathy/" accessed Sep. 10, 2015.*

Tomohiro Chiba "Emerging Therapeutic Strategies in Alzheimer's Disease" Intech 2013, 181-225.*

Azam S, Haque ME, Balakrishnan R, Kim I-S and Choi D-K (2021) The Ageing Brain: Molecular and Cellular Basis of Neurodegeneration. Front. Cell Dev. Biol. 9:683459.*

Ghelani, D.P., et al., Emerging Cystic Fibrosis Transmembrane Conductance Regulator Modulators as New Drugs for Cystic Fibrosis: A Portrait of in VitroA Pharmacology and Clinical Translation, ACS Pharmacol Transl Sci., 3(1):4-10 (2019).

Guan, X., et al., Dysregulated Chemokine Signaling in Cystic Fibrosis Lung Disease: A Potential Therapeutic Target, Curr Drug Targets, 17(13): 1535-1544 (2016).

Lopes-Pacheco, M., CFTR Modulators: The Changing Face of Cystic Fibrosis in the Era of Precision Medicine, Front Pharmacol., 10:1662 (2020).

PCT/US2020/063586 International Preliminary Report on Patentability mailed Jun. 16, 2022.

PCT/US2020/063586 International Search Report and Written Opinion mailed Feb. 15, 2021.

PCT/US2020/063589 International Preliminary Report on Patentability mailed Jun. 16, 2022.

PCT/US2020/063589 International Search Report and Written Opinion mailed Feb. 11, 2021.

PCT/US2020/063590 International Preliminary Report on Patentability mailed Jun. 16, 2022.

PCT/US2020/063590 International Search Report and Written Opinion mailed Feb. 15, 2021.

Van Goor, F., et al., Correction of the F508del-CFTR protein processing defect in vitro by the investigational drug VX-809, Proc Natl Acad Sci USA, 108(46):18843-8 (2011).

Derichs, Targeting a genetic defect: cystic fibrosis transmembrane conductance regulator modulators in cystic fibrosis, European Respiratory Review, 22:127, 58-65 (2013).

Gregory, R. J. et al., Expression and charaterization of the cystic fibrosis transmembrane conductance regulator, Nature, 347:382-386 (1990).

Hitchin, et al., Development and evaluation of selective, reversible LSD1 inhibitors derived from fragments, Medchemcomm, 4(11): 1513 (2013).

Jenkins et al., A 3D similarity method for scaffold hopping from the known drugs or natural ligands to new chemotypes, J. Medical Chemistry, 47(25): 6144-6159 (2004).

Ivacaftor Prescribing Information, 17 pages, Vertex Pharmaceuticals, Feb. 2017.

PCT/US2020/060176 International Preliminary Report on Patentability mailed May 27, 2022, 9 pages.

PCT/US2020/060176 International Search Report and Written Opinion mailed Jan. 29, 2021, 12 pages.

PCT/US2020/060180 International Preliminary Report on Patentability mailed Mar. 27, 2022, 9 pages.

PCT/US2020/060180 International Search Report and Written Opinion mailed Feb. 24, 2021, 13 pages.

PCT/US2024/060181 International Search Report and Written Opinion mailed Mar. 25, 2025.

Rich, D. P. et al., Expression of cystic fibrosis transmembrane conductance regulator corrects defective chloride channel regulation in cystic fibrosis airway epithelial cells, Nature, 347:358-362 (1990).

Riordan, J. R. et al., Identification of the Cystic Fibrosis Gene: Cloning and Characterization of Complementary DNA, Science, 245:1066-1073 (1989).

Saikachi et al., "Synthesis of the Furan Derivatives. XLVII. Synthesis of 5, 6-Bis (5-nitro-2-furyl)-2-aminopyrazine and Its Related Compound", Yakugaku Zasshi. 89(8):1071-1077 (1969).

Wang, et al., Synthesis and biological evaluation of diarylthiazole derivatives as antimitotic and antivascular agents with potent antitumor activity, Bioorganic & Medicinal Chemistry, 23: 3337-3350 (2015).

Weijlard et al., Some New Aminopyrazines and their Sulfanilamide Derivatives, J. Am. Chem. Soc., 67:802-806 (1945).

Yoshii et al., "Antiviral and Antibacterial Activities of 3-(Substituted benzenesulfonylamino)-5, 6-di(p-substituted phenyl)-1, 2, 4-triazines", Yakugaku Zasshi. 108(1):50-57 (1988).

Bartlett, P.A., Exploiting Chemical Diversity for Drug Discovery, Edited by Paul A Bartlett and Michael Entzeroth, The Royal Society of Chemistry: 113-118 (2006).

Find ETDs Home > Thesis Resources > Find ETDs, retrieved Jan. 31, 2023 from https://ndltd.org/thesis-resources/find-etds/.

(56) References Cited

OTHER PUBLICATIONS

He, et al., Restoration of NBD1 thermal stability is necessary and sufficient to correct F508 Cftr folding and assembly, J Mol Biol., 427(1): 106-120 (2015).
Irwin, J.J., et al., ZINC—A Free Database of Commercially Available Compounds for Virtual Screening, J. Chem. Inf. Model., 45: 177-182 (2005).
Kim, S. et al. PubChem in 2021: new data content and improved web interfaces, Nucleic Acids Research, 49 (2021).
Patani, G.A., et al., Bioisosterism: a rational approach in drug design, Chem Rev, 96(): 3147-3176 (1996).
STN Registry/Zregistry (CAS RegistrySM) Sep. 2016, 2 pages.

* cited by examiner

ARYLAMIDES AND METHODS OF USE THEREOF

CROSS-REFERENCE TO RELATED APPLICATIONS

This application is a Continuation of International Patent Application PCT/US2020/063590 filed on Dec. 7, 2020. International Patent Application PCT/US2020/063590 claims the benefit of and priority to U.S. Provisional Patent Application No. 62/944,188, filed Dec. 5, 2019, the entire disclosures of which are incorporated by reference herein.

BACKGROUND

Cystic fibrosis (CF), an autosomal recessive disorder, is caused by functional deficiency of the cAMP-activated plasma membrane chloride channel, cystic fibrosis transmembrane conductance regulator (CFTR), which can result in damage to the lung, pancreas, and other organs. The gene encoding CFTR has been identified and sequenced (See Gregory, R. J. et al. (1990) Nature 347:382-386; Rich, D. P. et al. (1990) Nature 347:358-362; Riordan, J. R. et al. (1989) Science 245:1066-1073). CFTR, a member of the ATP binding cassette (ABC) superfamily is composed of two six membrane-spanning domains (MSD1 and MSD2), two nucleotide binding domains (NBD1 and NBD2), a regulatory region (R) and four cytosolic loops (CL1-4). Normally, CFTR protein is located primarily in the apical membrane of epithelial cells where it functions to conduct anions, including chloride, bicarbonate and thiocyanate into and out of the cell. CFTR may have a regulatory role over other electrolyte channels, including the epithelial sodium channel ENaC.

In cystic fibrosis patients, the absence or dysfunction of CFTR leads to exocrine gland dysfunction and a multisystem disease, characterized by pancreatic insufficiency and malabsorption, as well as abnormal mucociliary clearance in the lung, mucostasis, chronic lung infection and inflammation, decreased lung function and ultimately respiratory failure.

While more than 1,900 mutations have been identified in the CFTR gene, a detailed understanding of how each CFTR mutation may impact channel function is known for only a subset. (Derichs, European Respiratory Review, 22:127, 58-65 (2013)). The most frequent CFTR mutation is the in-frame deletion of phenylalanine at residue 508 (AF508) in the first nucleotide binding domain (NBD1). Over 80% of cystic fibrosis patients have the deletion at residue 508 in at least one CFTR allele. The loss of this key phenylalanine renders the CFTR NBD1 domain conformationally unstable at physiological temperature and compromises the integrity of the interdomain interface between NBD1 and CFTR's second transmembrane domain (ICL4). The AF508 mutation causes production of misfolded CFTR protein which, rather than traffic to the plasma membrane, is instead retained in the endoplasmic reticulum and targeted for degradation by the ubiquitin-proteasome system.

The loss of a functional CFTR channel at the plasma membrane disrupts ionic homeostasis and airway surface hydration leading to reduced lung function. Reduced periciliary liquid volume and increased mucus viscosity impede mucociliary clearance resulting in chronic infection and inflammation. In the lung, the loss of CFTR-function leads to numerous physiological effects downstream of altered anion conductance that result in the dysfunction of additional organs such as the pancreas, intestine and gall bladder.

Guided, in part, by studies of the mechanistic aspects of CFTR misfolding and dysfunction, small molecule CFTR modulators have been identified that can increase CFTR channel function.

Despite the identification of compounds that modulate CFTR, there is no cure for this fatal disease and identification of new compounds and new methods of therapy are needed as well as new methods for treating or lessening the severity of cystic fibrosis and other CFTR mediated conditions and diseases in a patient.

SUMMARY

Disclosed herein are compounds of Formula (I):

I

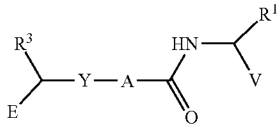

or a pharmaceutically acceptable salt thereof, wherein:

A is selected from

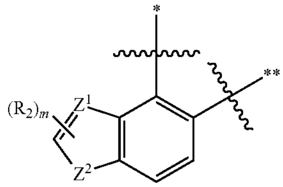

and

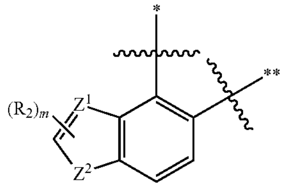

wherein * marks the point of attachment to Y and ** marks the point of attachment to —C(O)—;

$Z^1$ and $Z^2$ are each independently CH, S or N, wherein at least one of $Z^1$ and $Z^2$ is N or S;

Y is —O—;

E is $C_{3-9}$-cycloalkyl, $C_{6-10}$-aryl, 3-10 membered heteroaryl, or a 3-9 membered heterocycloalkyl, each of which is optionally substituted with one, two, three, four, or five occurrences of $R^5$;

V is —C(O)—O—$R^7$;

$R^1$ is

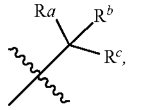

wherein $R^a$ is $C_{1-6}$ alkyl, $R^b$ is $C_{1-6}$ alkyl, $R^c$ is $C_{1-6}$ alkyl or $C_{6-10}$ aryl, or any two of $R^a$, $R^b$, and $R^c$, taken together with the atoms to which they are attached, form a $C_{3-9}$ cycloalkyl ring;

each $R^2$ is independently halo, $C_{1-6}$ alkyl, halo$C_{1-6}$ alkyl, —O—$C_{1-6}$ alkyl, —O-halo$C_{1-6}$ alkyl, $C_{3-9}$-cycloalkyl or 3-10 membered heteroaryl;

$R^3$ is H or alkyl;

each $R^5$ is independently halo, $C_{1-6}$ alkyl, $C_{1-6}$ haloalkyl, —O—$C_{1-6}$alkyl, —O—$C_{1-6}$haloalkyl, —S—$C_{1-6}$alkyl and —S—$C_{1-6}$haloalkyl;

$R^7$ is hydrogen, $C_{1-6}$-alkyl, $C_{6-10}$-aryl, or benzyl; and m is 0, 1, or 2.

Disclosed herein are methods of augmenting deficient CFTR activity, thereby treating a disease or condition mediated by deficient CFTR activity. Such diseases and conditions include, but are not limited to, cystic fibrosis, congenital bilateral absence of vas deferens (CBAVD), acute, recurrent, or chronic pancreatitis, disseminated bronchiectasis, asthma, allergic pulmonary aspergillosis, congenital pneumonia, intestinal malabsorption, celiac disease, nasal polyposis, non-tuberculous mycobacterial infection, pancreatic steatorrhea, intestinal atresia, chronic obstructive pulmonary disease (COPD), rhinosinusitis, dry eye disease, protein C deficiency, abetalipoproteinemia, lysosomal storage disease, type 1 chylomicronemia, mild pulmonary disease, lipid processing deficiencies, type 1 hereditary angioedema, coagulation-fibrinolyis, hereditary hemochromatosis, CFTR-related metabolic syndrome, chronic bronchitis, constipation, pancreatic insufficiency, hereditary emphysema, and Sjogren's syndrome. In some embodiments, the disease is cystic fibrosis.

In certain embodiments, the present invention provides a pharmaceutical composition suitable for use in a subject in the treatment or prevention of disease and conditions associate with deficient CFTR activity, comprising any of the compounds described herein (e.g., a compound of the invention, such as a compound of formula (I)), and one or more pharmaceutically acceptable carriers or excipients. In certain embodiments, the pharmaceutical preparations may be for use in treating or preventing a condition or disease as described herein.

Provided herein are combination therapies of compounds of formula (I) with CFTR-active agents that can enhance the therapeutic benefit beyond the ability of the primary therapy alone.

DETAILED DESCRIPTION

The present invention provides compounds of Formula (I):

I

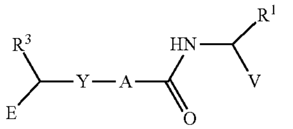

or a pharmaceutically acceptable salt thereof, wherein:

A is selected from

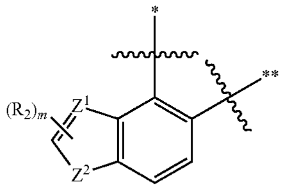

and

-continued

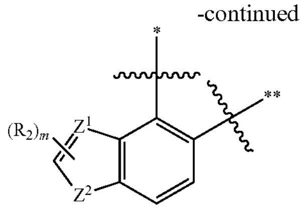

wherein * marks the point of attachment to Y and ** marks the point of attachment to —C(O)—;

$Z^1$ and $Z^2$ are each independently CH, S or N, wherein at least one of $Z^1$ and $Z^2$ is N or S;

Y is —O—;

E is $C_{3-9}$-cycloalkyl, $C_{6-10}$-aryl, 3-10 membered heteroaryl, or a 3-9 membered heterocycloalkyl, each of which is optionally substituted with one, two, three, four, or five occurrences of $R^5$;

V is —C(O)—O—$R^7$;

$R^1$ is

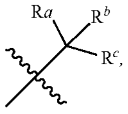

R wherein $R^a$ is $C_{1-6}$ alkyl, $R^b$ is $C_{1-6}$ alkyl, $R^c$ is $C_{1-6}$ alkyl or $C_{6-10}$ aryl, or any two of $R^a$, $R^b$, and $R^c$, taken together with the atoms to which they are attached, form a $C_{3-9}$ cycloalkyl ring;

each $R^2$ is independently halo, $C_{1-6}$ alkyl, halo$C_{1-6}$ alkyl, —O—$C_{1-6}$ alkyl, —O-halo$C_{1-6}$ alkyl, $C_{3-9}$-cycloalkyl or 3-10 membered heteroaryl;

$R^3$ is H or alkyl;

each $R^5$ is independently halo, $C_{1-6}$ alkyl, $C_{1-6}$ haloalkyl, —O—$C_{1-6}$alkyl, —O—$C_{1-6}$haloalkyl, —S—$C_{1-6}$alkyl and —S—$C_{1-6}$haloalkyl;

$R^7$ is hydrogen, $C_{1-6}$-alkyl, $C_{6-10}$-aryl, or benzyl; and m is 0, 1, or 2.

Variables A, $Z^1$, and $Z^2$ of Formula (I)

Below are exemplary embodiments of variables A, $Z^1$ and $Z^2$ of the disclosed compound of Formula (I). The values for the remaining variables are as described above.

In some embodiments, A is

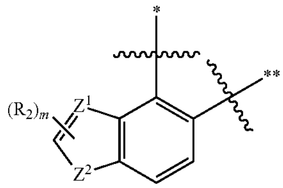

, $Z^1$ is CH and $Z^2$ is S.

In some embodiments, A is

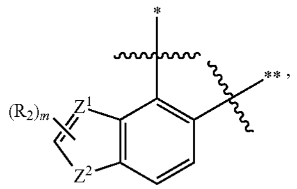

$Z^1$ is N and $Z^2$ is S.

In some embodiments, A is

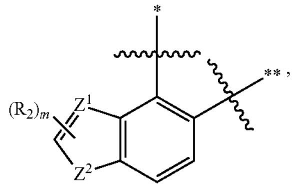

$Z^1$ is S and $Z^2$ is $CR^6$.

Variable E of Formula (I)

Below are exemplary embodiments of variable E of the disclosed compound of Formula (I). The values for the remaining variables are as described above.

In some embodiments, E is optionally substituted $C_{3-9}$-cycloalkyl, aryl, or 3-10 membered heteroaryl. In certain embodiments, E is optionally substituted cyclohexyl, phenyl, or 2-benzthiazolyl.

Variables $R^a$, $R^b$, and $R^c$ of Formula (I)

Below are exemplary embodiments of variables $R^a$, $R^b$, and $R^c$ of the disclosed compound of Formula (I). The values for the remaining variables are as described above.

In some embodiments, $R^a$ is methyl. In some embodiments, $R^b$ is methyl. In some embodiments, $R^c$ is methyl, ethyl, or phenyl. In some embodiments, any two of $R^a$, $R^b$, and $R^c$, taken together with the atoms to which they are attached, form a cyclopropyl, cyclobutyl or cyclohexyl ring.

Variable $R^2$ of Formula (I)

Below are exemplary embodiments of variable $R^2$ of the disclosed compound of Formula (I). The values for the remaining variables are as described above.

In some embodiments, $R^2$ is chloro, methyl, ethyl, isopropyl, isopentyl, $—CHF_2$, $—CF_3$, —OMe, cyclopropyl, cyclobutyl, cyclopentyl, or thiazolyl.

Variable $R^5$ of Formula (I)

Below are exemplary embodiments of variable $R^5$ of the disclosed compound of Formula (I). The values for the remaining variables are as described above.

In some embodiments, each $R^5$ is independently halo, $C_{1-4}$-alkyl, $C_{1-4}$-haloalkyl, $—O—C_{1-4}$-haloalkyl, or $—S—C_{1-4}$haloalkyl. In other embodiments, each $R^5$ is independently fluoro, chloro, $—CF_3$, $—OCHF_2$, $—OCF_3$, or $—SCF_3$.

Variable $R^1$ of Formula (I)

In some embodiments, $R^1$ is in the α-configuration, such that the structure of Formula (I) is that of Formula (IA):

(IA)

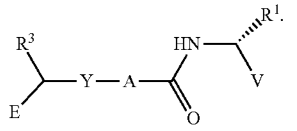

In some embodiments, $R^1$ is in the β-configuration, such that the structure of Formula (I) is that of Formula (IB):

(IB)

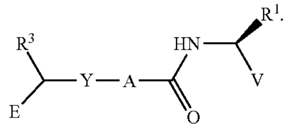

In some embodiments, the compound of formula (I) is selected from:

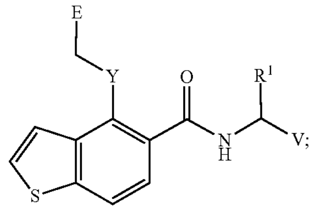

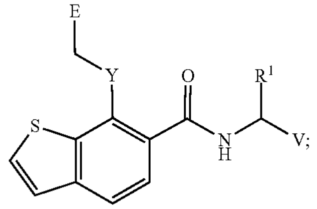

and

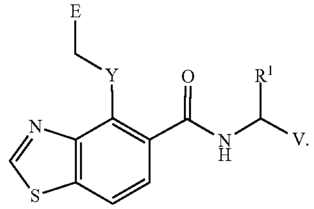

The values for variables $R^1$, E, Y, and V are as described above.

In some embodiments, the compound of formula (I) is selected from the following compounds represented in Table 1 below:

TABLE 1
| Compound | Structure |
| --- | --- |
| 1 | 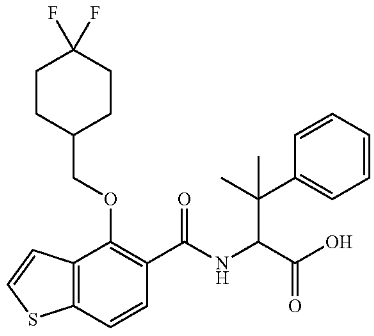 [SMILES: CC(C)(c1ccccc1)C(NC(=O)c1ccc2sccc2c1OCC1CCC(F)(F)CC1)C(=O)O] |
| 2 | 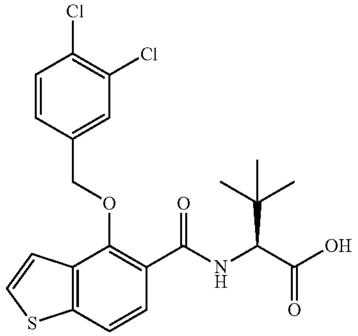 [SMILES: CC(C)(C)[C@H](NC(=O)c1ccc2sccc2c1OCc1ccc(Cl)c(Cl)c1)C(=O)O] |
| 3 | 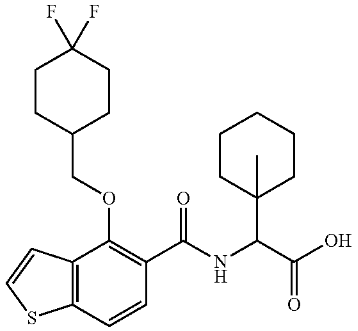 |
| 4 | 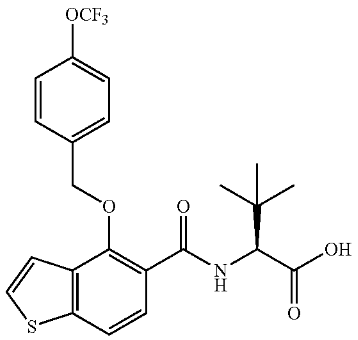 |
TABLE 1-continued
| Compound | Structure |
| --- | --- |
| 5 | 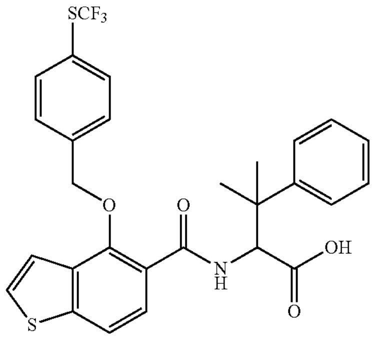 |
| 6 | 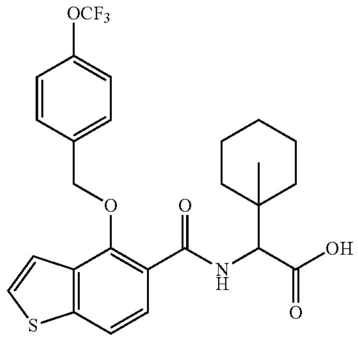 |
| 7 | 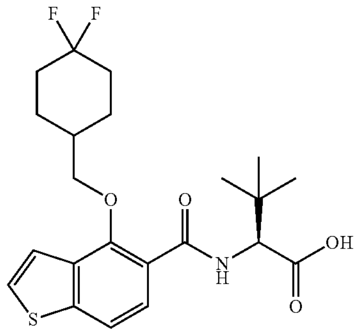 [SMILES: CC(C)(C)[C@H](NC(=O)c1ccc2sccc2c1OCC1CCC(F)(F)CC1)C(=O)O] |
| 8 | 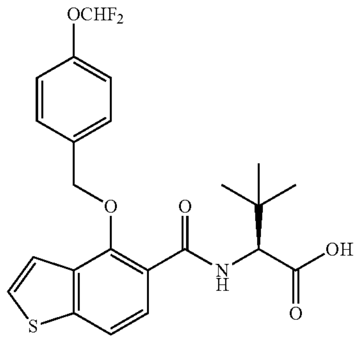 |

TABLE 1-continued
| Compound | Structure |
| --- | --- |
| 9 | 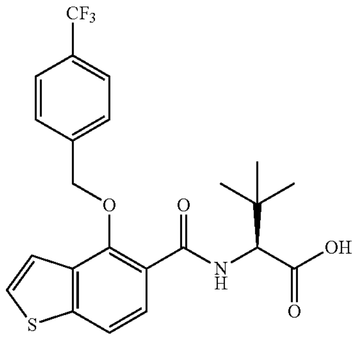 |
| 10 | 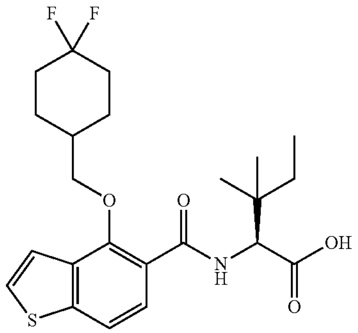 |
| 11 | 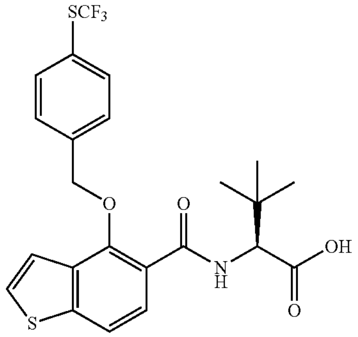 |
| 12 | 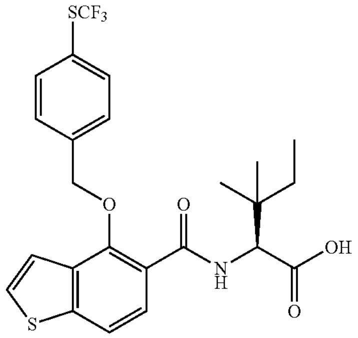 |
TABLE 1-continued
| Compound | Structure |
| --- | --- |
| 13 | 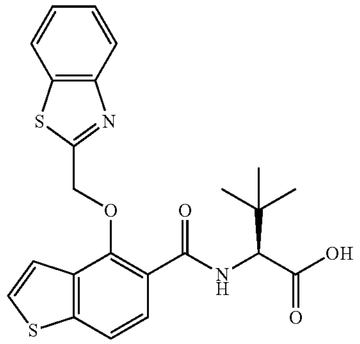 [SMILES: CC(C)(C)[C@H](NC(=O)c1ccc2sccc2c1OCc1nc2ccccc2s1)C(=O)O] |
| 14 | 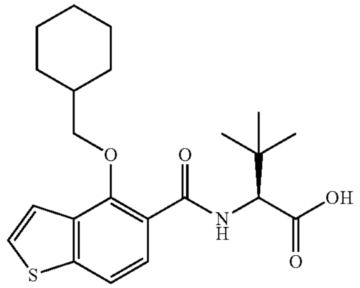 [SMILES: CC(C)(C)[C@H](NC(=O)c1ccc2sccc2c1OCC1CCCCC1)C(=O)O] |
| 15 | 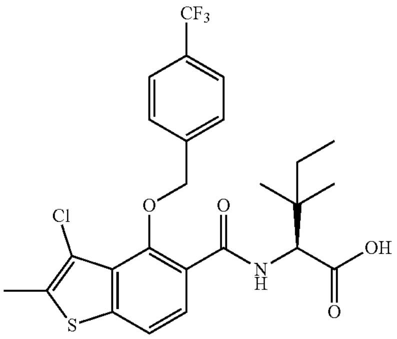 [SMILES: CCC(C)(C)[C@H](NC(=O)c1ccc2sc(C)c(Cl)c2c1OCc1ccc(C(F)(F)F)cc1)C(=O)O] |
| 16 | 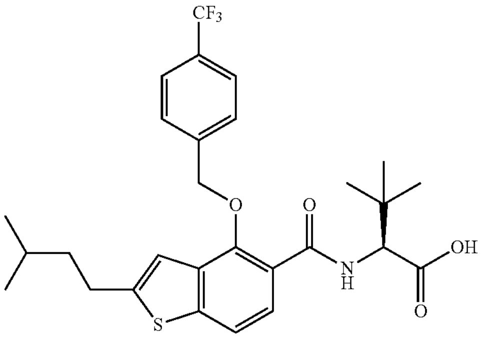 [SMILES: CC(C)CCc1cc2c(OCc3ccc(C(F)(F)F)cc3)c(C(=O)N[C@H](C(=O)O)C(C)(C)C)ccc2s1] |

TABLE 1-continued
| Compound | Structure |
|---|---|
| 17 | 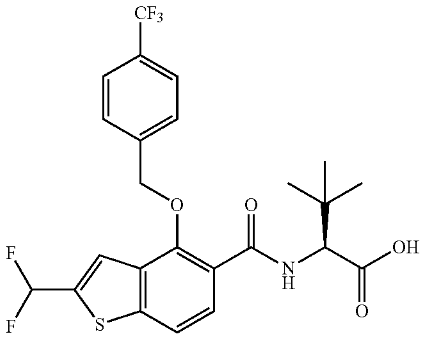 [SMILES: CC(C)(C)[C@H](NC(=O)c1ccc2sc(C(F)F)cc2c1OCc1ccc(C(F)(F)F)cc1)C(=O)O] |
| 18 | 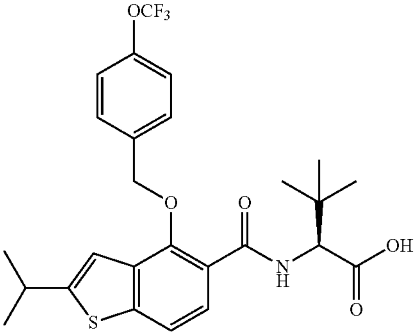 |
| 19 | 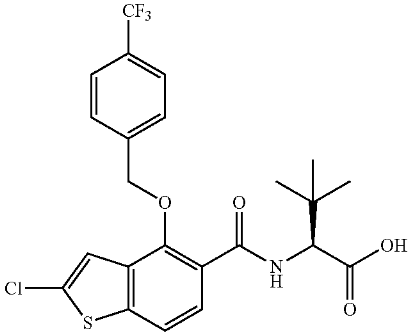 [SMILES: CC(C)(C)[C@H](NC(=O)c1ccc2sc(Cl)cc2c1OCc1ccc(C(F)(F)F)cc1)C(=O)O] |
| 20 | 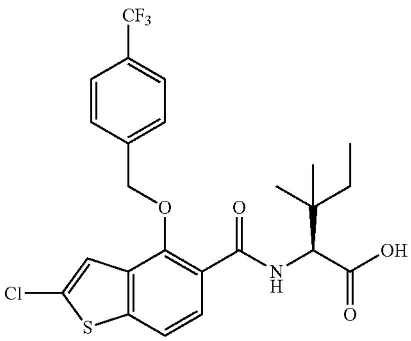 [SMILES: CCC(C)(C)[C@H](NC(=O)c1ccc2sc(Cl)cc2c1OCc1ccc(C(F)(F)F)cc1)C(=O)O] |
TABLE 1-continued
| Compound | Structure |
|---|---|
| 21 | 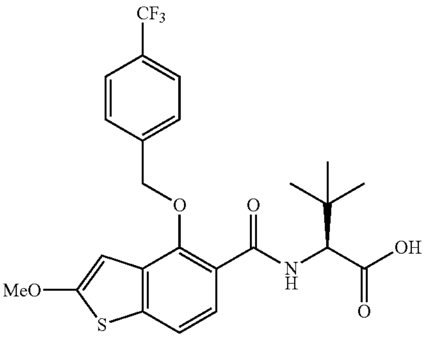 [SMILES: COc1cc2c(OCc3ccc(C(F)(F)F)cc3)c(C(=O)N[C@H](C(=O)O)C(C)(C)C)ccc2s1] |
| 22 | 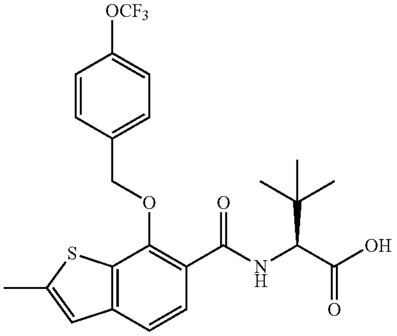 [SMILES: Cc1cc2ccc(C(=O)N[C@H](C(=O)O)C(C)(C)C)c(OCc3ccc(OC(F)(F)F)cc3)c2s1] |
| 23 | 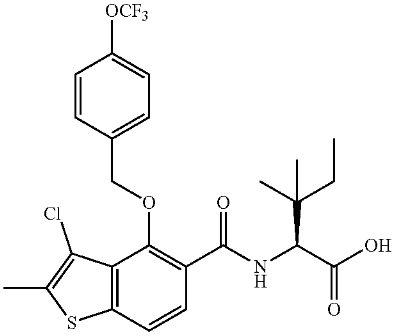 [SMILES: CCC(C)(C)[C@H](NC(=O)c1ccc2sc(C)c(Cl)c2c1OCc1ccc(OC(F)(F)F)cc1)C(=O)O] |
| 24 | 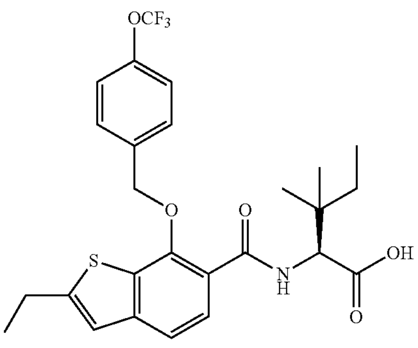 [SMILES: CCc1cc2ccc(C(=O)N[C@H](C(=O)O)C(C)(C)CC)c(OCc3ccc(OC(F)(F)F)cc3)c2s1] |

TABLE 1-continued
| Compound | Structure |
| --- | --- |
| 25 | 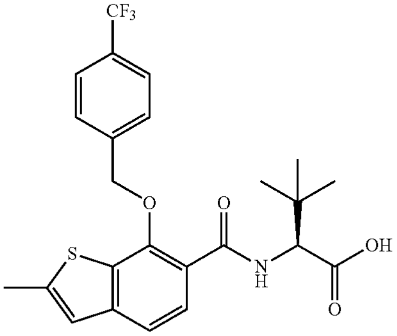 [SMILES: Cc1cc2ccc(C(=O)N[C@H](C(=O)O)C(C)(C)C)c(OCc3ccc(C(F)(F)F)cc3)c2s1] |
| 26 | 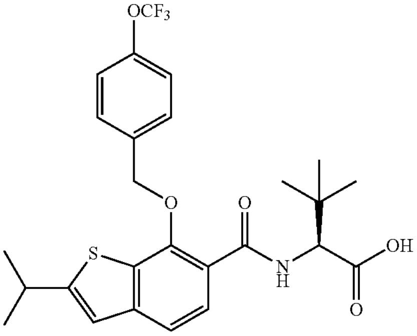 [SMILES: CC(C)c1cc2ccc(C(=O)N[C@H](C(=O)O)C(C)(C)C)c(OCc3ccc(OC(F)(F)F)cc3)c2s1] |
| 27 | 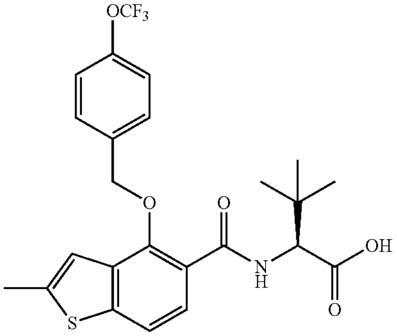 [SMILES: Cc1cc2c(OCc3ccc(OC(F)(F)F)cc3)c(C(=O)N[C@H](C(=O)O)C(C)(C)C)ccc2s1] |
| 28 | 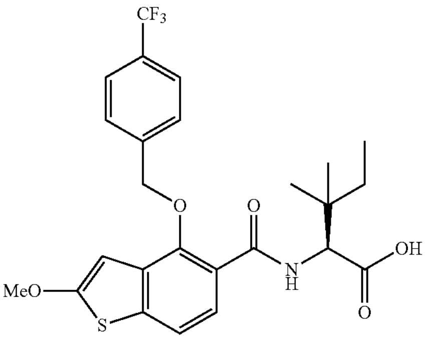 [SMILES: CCC(C)(C)[C@H](NC(=O)c1ccc2sc(OC)cc2c1OCc1ccc(C(F)(F)F)cc1)C(=O)O] |
TABLE 1-continued
| Compound | Structure |
| --- | --- |
| 29 | 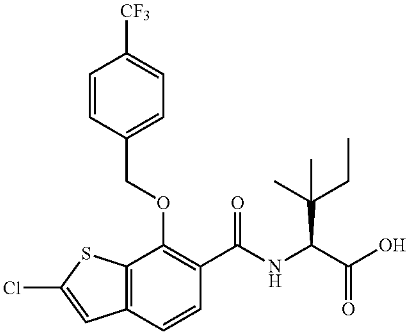 [SMILES: CCC(C)(C)[C@H](NC(=O)c1ccc2cc(Cl)sc2c1OCc1ccc(C(F)(F)F)cc1)C(=O)O] |
| 30 | 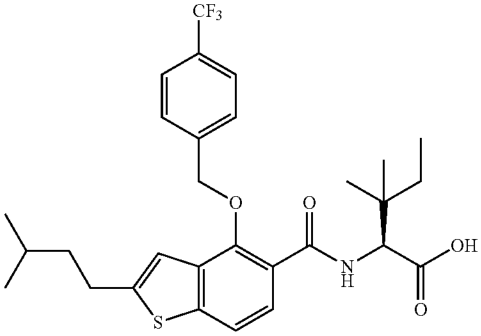 [SMILES: CCC(C)(C)[C@H](NC(=O)c1ccc2sc(CCC(C)C)cc2c1OCc1ccc(C(F)(F)F)cc1)C(=O)O] |
| 31 | 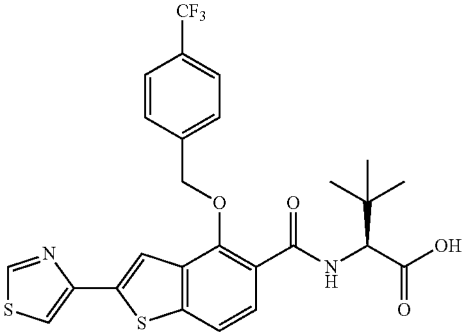 [SMILES: CC(C)(C)[C@H](NC(=O)c1ccc2sc(-c3cscn3)cc2c1OCc1ccc(C(F)(F)F)cc1)C(=O)O] |
| 32 | 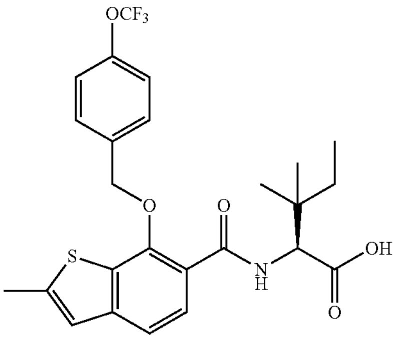 [SMILES: CCC(C)(C)[C@H](NC(=O)c1ccc2cc(C)sc2c1OCc1ccc(OC(F)(F)F)cc1)C(=O)O] |

16
TABLE 1-continued
| Compound | Structure |
|---|---|
| 33 | 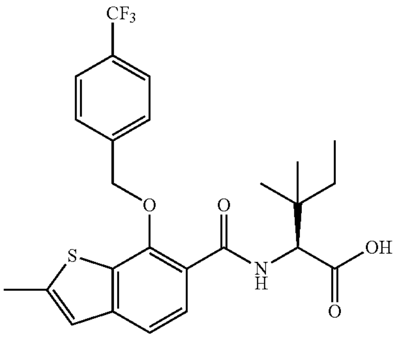 [SMILES: CCC(C)(C)[C@H](NC(=O)c1ccc2cc(C)sc2c1OCc1ccc(C(F)(F)F)cc1)C(=O)O] |
| 34 | 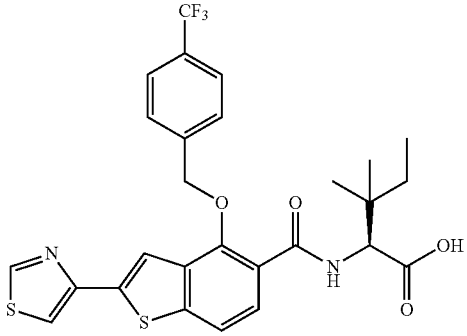 [SMILES: CCC(C)(C)[C@H](NC(=O)c1ccc2sc(-c3cscn3)cc2c1OCc1ccc(C(F)(F)F)cc1)C(=O)O] |
| 35 | 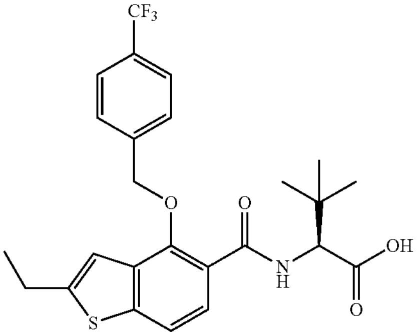 [SMILES: CCc1cc2c(OCc3ccc(C(F)(F)F)cc3)c(C(=O)N[C@H](C(=O)O)C(C)(C)C)ccc2s1] |
| 36 | 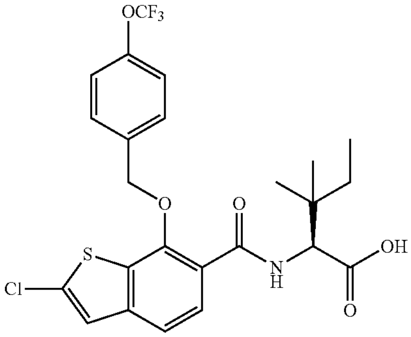 [SMILES: CCC(C)(C)[C@H](NC(=O)c1ccc2cc(Cl)sc2c1OCc1ccc(OC(F)(F)F)cc1)C(=O)O] |
| 37 | 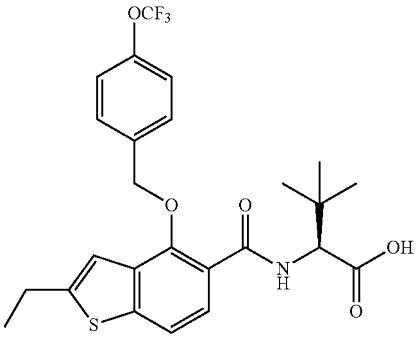 [SMILES: CCc1cc2c(OCc3ccc(OC(F)(F)F)cc3)c(C(=O)N[C@H](C(=O)O)C(C)(C)C)ccc2s1] |
| 38 | 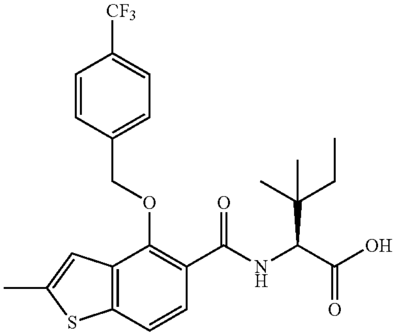 [SMILES: CCC(C)(C)[C@H](NC(=O)c1ccc2sc(C)cc2c1OCc1ccc(C(F)(F)F)cc1)C(=O)O] |
| 39 | 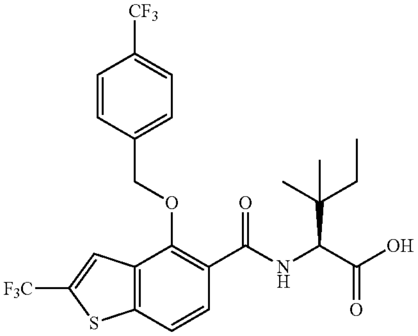 [SMILES: CCC(C)(C)[C@H](NC(=O)c1ccc2sc(C(F)(F)F)cc2c1OCc1ccc(C(F)(F)F)cc1)C(=O)O] |
| 40 | 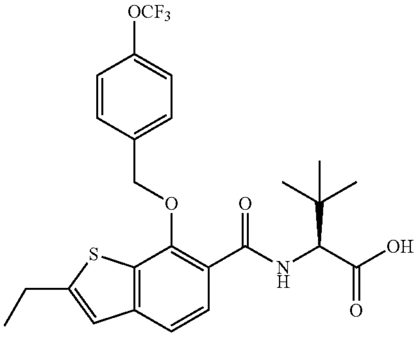 [SMILES: CCc1cc2ccc(C(=O)N[C@H](C(=O)O)C(C)(C)C)c(OCc3ccc(OC(F)(F)F)cc3)c2s1] |

TABLE 1-continued
| Compound | Structure |
| --- | --- |
| 41 | 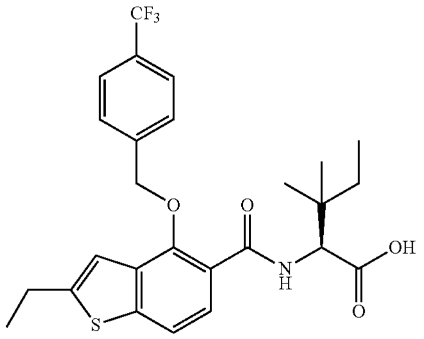 [SMILES: CCc1cc2c(OCc3ccc(C(F)(F)F)cc3)c(C(=O)N[C@H](C(=O)O)C(C)(C)CC)ccc2s1] |
| 42 | 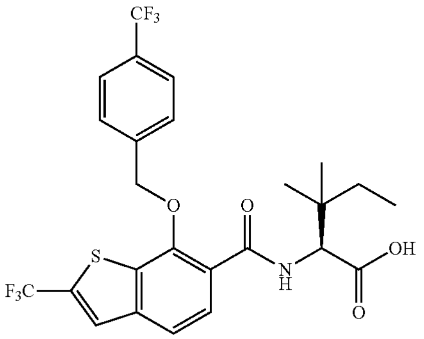 [SMILES: CCC(C)(C)[C@H](NC(=O)c1ccc2cc(C(F)(F)F)sc2c1OCc1ccc(C(F)(F)F)cc1)C(=O)O] |
| 43 | 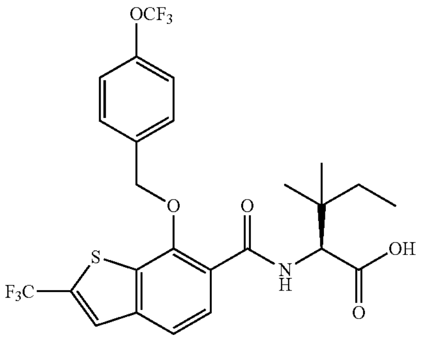 [SMILES: CCC(C)(C)[C@H](NC(=O)c1ccc2cc(C(F)(F)F)sc2c1OCc1ccc(OC(F)(F)F)cc1)C(=O)O] |
| 44 | 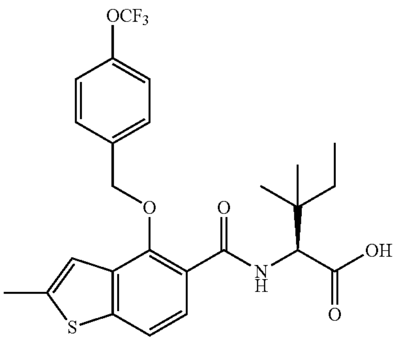 |
TABLE 1-continued
| Compound | Structure |
| --- | --- |
| 45 | 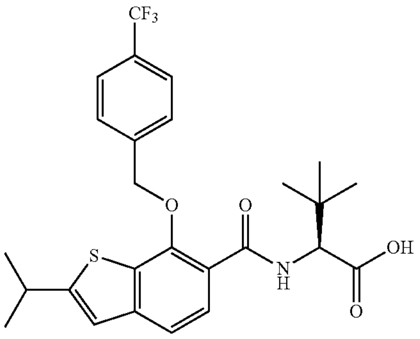 |
| 46 | 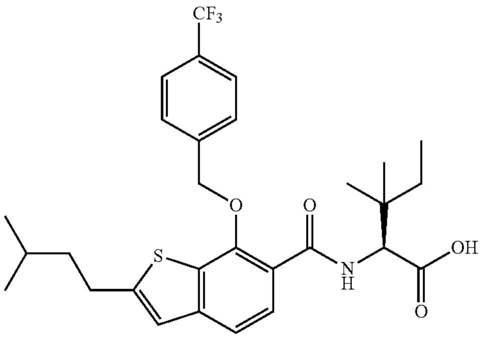 [SMILES: CCC(C)(C)[C@H](NC(=O)c1ccc2cc(CCC(C)C)sc2c1OCc1ccc(C(F)(F)F)cc1)C(=O)O] |
| 47 | 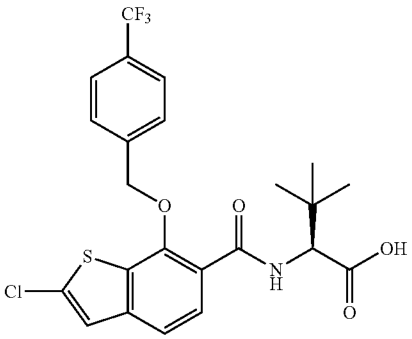 [SMILES: CC(C)(C)[C@H](NC(=O)c1ccc2cc(Cl)sc2c1OCc1ccc(C(F)(F)F)cc1)C(=O)O] |
| 48 | 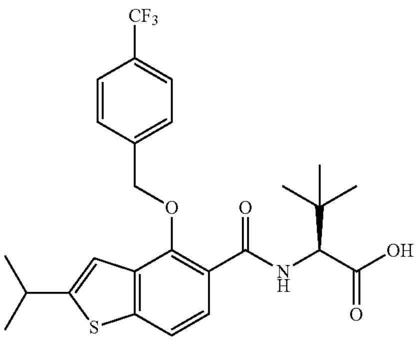 [SMILES: CC(C)c1cc2c(OCc3ccc(C(F)(F)F)cc3)c(C(=O)N[C@H](C(=O)O)C(C)(C)C)ccc2s1] |

TABLE 1-continued
| Compound | Structure |
| --- | --- |
| 49 | 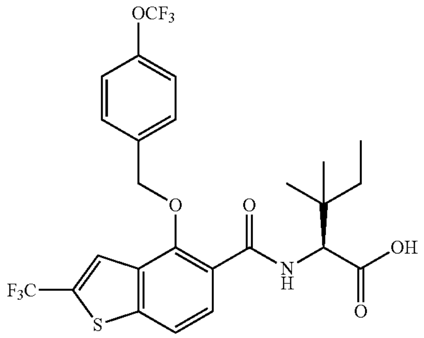 [SMILES: CCC(C)(C)[C@H](NC(=O)c1ccc2sc(C(F)(F)F)cc2c1OCc1ccc(OC(F)(F)F)cc1)C(=O)O] |
| 50 | 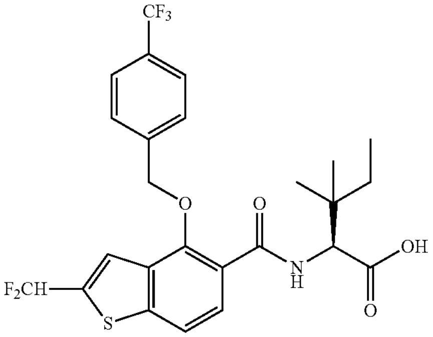 |
| 51 | 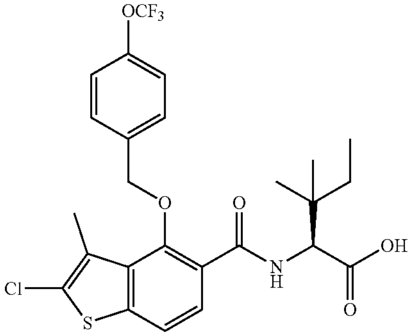 [SMILES: CCC(C)(C)[C@H](NC(=O)c1ccc2sc(Cl)c(C)c2c1OCc1ccc(OC(F)(F)F)cc1)C(=O)O] |
| 52 | 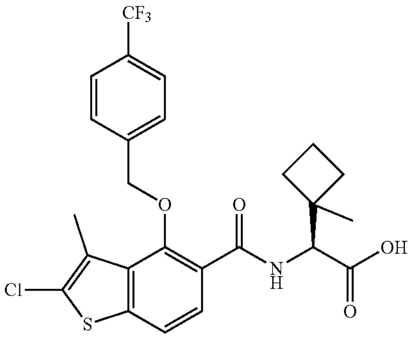 [SMILES: Cc1c(Cl)sc2ccc(C(=O)N[C@H](C(=O)O)C3(C)CCC3)c(OCc3ccc(C(F)(F)F)cc3)c12] |
TABLE 1-continued
| Compound | Structure |
| --- | --- |
| 53 | 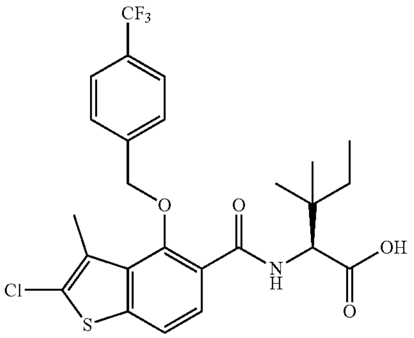 [SMILES: CCC(C)(C)[C@H](NC(=O)c1ccc2sc(Cl)c(C)c2c1OCc1ccc(C(F)(F)F)cc1)C(=O)O] |
| 54 | 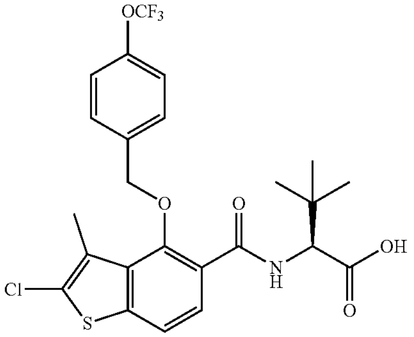 [SMILES: Cc1c(Cl)sc2ccc(C(=O)N[C@H](C(=O)O)C(C)(C)C)c(OCc3ccc(OC(F)(F)F)cc3)c12] |
| 55 | 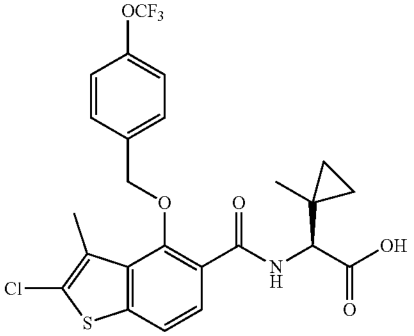 [SMILES: Cc1c(Cl)sc2ccc(C(=O)N[C@H](C(=O)O)C3(C)CC3)c(OCc3ccc(OC(F)(F)F)cc3)c12] |
| 56 | 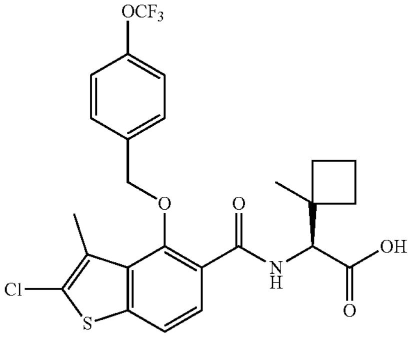 [SMILES: Cc1c(Cl)sc2ccc(C(=O)N[C@H](C(=O)O)C3(C)CCC3)c(OCc3ccc(OC(F)(F)F)cc3)c12] |

TABLE 1-continued
| Compound | Structure |
|---|---|
| 57 | 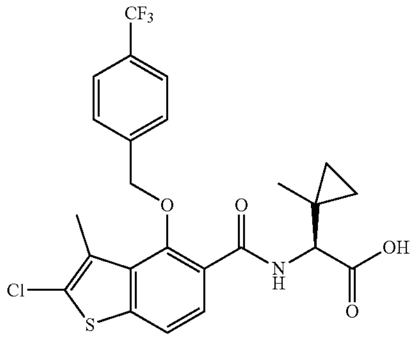 [SMILES: Cc1c(Cl)sc2ccc(C(=O)N[C@H](C(=O)O)C3(C)CC3)c(OCc3ccc(C(F)(F)F)cc3)c12] |
| 58 | 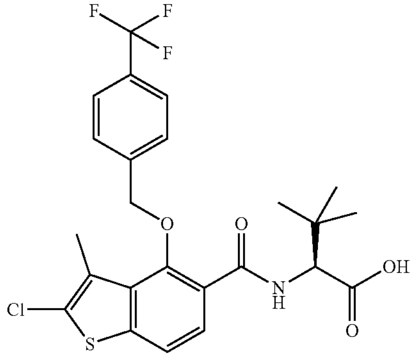 [SMILES: Cc1c(Cl)sc2ccc(C(=O)N[C@H](C(=O)O)C(C)(C)C)c(OCc3ccc(C(F)(F)F)cc3)c12] |
| 59 | 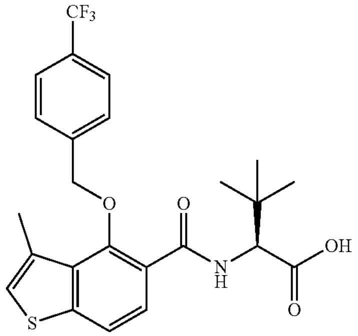 [SMILES: Cc1csc2ccc(C(=O)N[C@H](C(=O)O)C(C)(C)C)c(OCc3ccc(C(F)(F)F)cc3)c12] |
| 60 | 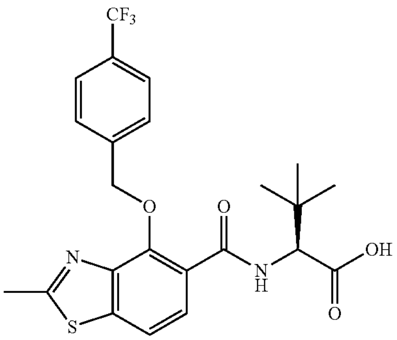 [SMILES: Cc1nc2c(OCc3ccc(C(F)(F)F)cc3)c(C(=O)N[C@H](C(=O)O)C(C)(C)C)ccc2s1] |
TABLE 1-continued
| Compound | Structure |
|---|---|
| 61 | 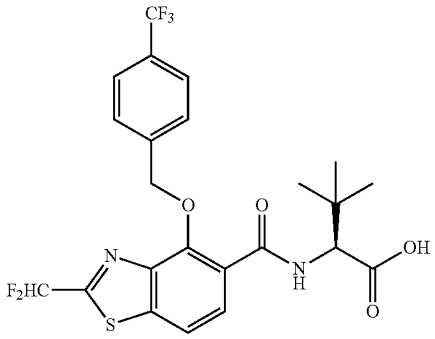 |
| 62 | 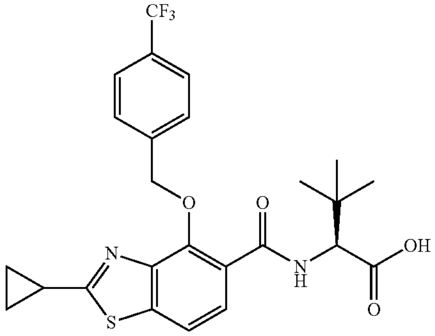 [SMILES: CC(C)(C)[C@H](NC(=O)c1ccc2sc(C3CC3)nc2c1OCc1ccc(C(F)(F)F)cc1)C(=O)O] |
| 63 | 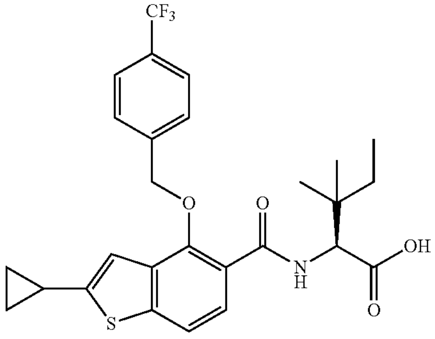 |
| 64 | 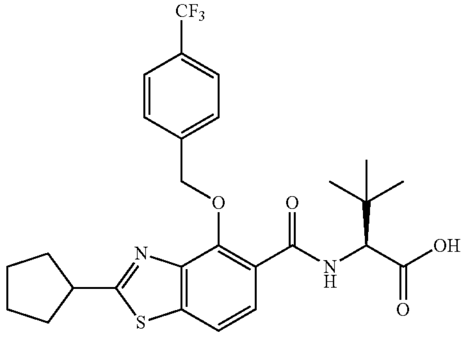 [SMILES: CC(C)(C)[C@H](NC(=O)c1ccc2sc(C3CCCC3)nc2c1OCc1ccc(C(F)(F)F)cc1)C(=O)O] |

TABLE 1-continued

| Compound | Structure |
|---|---|
| 65 | 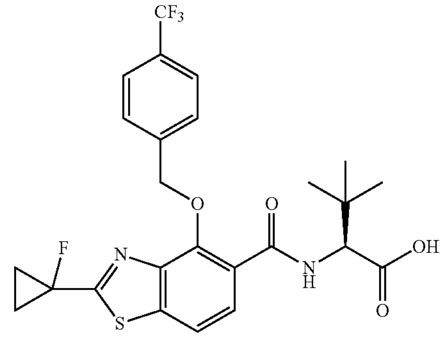 [SMILES: CC(C)(C)[C@H](NC(=O)c1ccc2sc(C3(F)CC3)nc2c1OCc1ccc(C(F)(F)F)cc1)C(=O)O] |
| 66 | 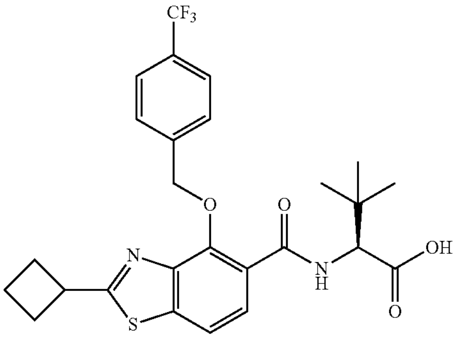 [SMILES: CC(C)(C)[C@H](NC(=O)c1ccc2sc(C3CCC3)nc2c1OCc1ccc(C(F)(F)F)cc1)C(=O)O] |

In certain embodiments, the present invention provides a pharmaceutical preparation suitable for use in a subject, comprising any of the compounds shown above (e.g., a compound of the invention, such as a compound of formula (I), and one or more pharmaceutically acceptable excipients. In certain embodiments, the pharmaceutical preparations may be for use in treating or preventing cystic fibrosis.

Any of the disclosed compounds may be used in the manufacture of medicaments for the treatment of any diseases or conditions disclosed herein.

DEFINITIONS

Unless defined otherwise, all technical and scientific terms used herein have the meaning commonly understood by a person skilled in the art of the present disclosure. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Unless specifically stated or obvious from context, as used herein, the term "or" is understood to be inclusive. Unless specifically stated or obvious from context, as used herein, the terms "a", "an", and "the" are understood to be singular or plural.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to a straight chained or branched aliphatic group containing at least one double bond. Typically, an alkenyl group has from 2 to about 20 carbon atoms, preferably from 2 to about 10, more preferably from 2-6 or 2-4. unless otherwise defined. The term "alkenyl" is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10, more preferably from 1-6 or 1-4. unless otherwise defined. Examples of straight chained and branched alkyl groups include methyl, ethyl, n-propyl, isopropyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "haloalkyl", as used herein, refers to an alkyl group in which at least one hydrogen has been replaced with a halogen, such as fluoro, chloro, bromo, or iodo. Exemplary haloalkyl groups include trifluoromethyl, difluoromethyl, fluoromethyl, 2-fluoroethyl, 2,2-difluoroethyl, and 2,2,2-trifluoroethyl.

The term "alkynyl", as used herein, refers to a straight chained or branched aliphatic group containing at least one triple bond. Typically, an alkenyl group has from 2 to about 20 carbon atoms, preferably from 2 to about 10, more preferably from 2-6 or 2-4. unless otherwise defined. The term "alkynyl" is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

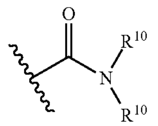

wherein each $R^{10}$ independently represents a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

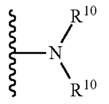

or

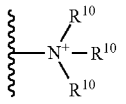

wherein each $R^{10}$ independently represents a hydrogen or a hydrocarbyl group, or two $R^{10}$ are taken together with the N atom to which they are attached complete a heterocycle having from 4 to 8 atoms in the ring structure. The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably, the ring is a 6- to 10-membered ring, such as a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

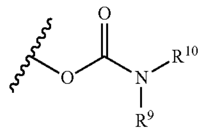

or

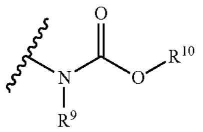

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 9 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings.

A "cycloalkenyl" group is a cyclic hydrocarbon containing one or more double bonds. The cycloalkenyl ring may have 3 to 10 carbon atoms, such as 4 to 9 carbon atoms. As such, cycloalkenyl groups can be monocyclic or multicyclic. Individual rings of such multicyclic cycloalkenyl groups can have different connectivities, e.g., fused, bridged, spiro, etc. in addition to covalent bond substitution. Exemplary cycloalkenyl groups include cyclopropenyl, cyclobutenyl, cyclopentyl, cyclohexenyl, cycloheptenyl, 1,3-cyclohexadienyl, 1,4-cyclohexadienyl and 1,5-cyclooctadienyl.

Exemplary cycloalkyl groups include cyclopropyl, cyclobutyl, cyclopentyl, cyclohexyl, norbornanyl, bicyclo [3.2.1]octanyl, octahydro-pentalenyl, spiro[4.5]decanyl, cyclopropyl, and adamantyl.

The term "carbocyclylalkyl", as used herein, refers to an alkyl group substituted with a carbocycle group.

The term "carbonate" is art-recognized and refers to a group —$OCO_2$—$R^{10}$, wherein $R^{10}$ represents a hydrocarbyl group.

The term "carboxy", as used herein, refers to a group represented by the formula —$CO_2H$.

The term "ester", as used herein, refers to a group —$C(O)OR^{10}$ wherein $R^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 3- to 10-membered rings, more preferably 5- to 9-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

Individual rings of such multicyclic heteroaryl groups can have different connectivities, e.g., fused, etc. in addition to covalent bond substitution. Exemplary heteroaryl groups include furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3, 5-thiadiazolyl, 1,2,3-thiadiazolyl, 1,2,4-thiadiazolyl, pyridyl, pyrimidyl, pyrazinyl, pyridazinyl, 1 ,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl and benzoxazinyl, etc. In general, the heteroaryl group typically is attached to the main structure via a carbon atom.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

Individual rings of such multicyclic heterocycloalkyl groups can have different connectivities, e.g., fused, bridged, spiro, etc. in addition to covalent bond substitution. Exemplary heterocycloalkyl groups include pyrrolidinyl, tetrahydrofuranyl, dihydrofuranyl, tetrahydropyranyl, pyranyl, thiopyranyl, azindinyl, azetidinyl, oxiranyl, methylenedioxyl, chromenyl, barbituryl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, piperizin-2-onyl, piperizin-3-onyl, chromanyl, 2-pyrrolinyl, 3-pyrrolinyl, imidazolidinyl, 2-imidazolidinyl, 1,4-dioxanyl, 8-azabicyclo[3.2.1]octanyl, 3-azabicyclo[3.2.1] octanyl, 3,8-diazabicyclo[3.2.1]octanyl, 2,5-diazabicyclo [2.2.1]heptanyl, 2,5-diazabicyclo[2.2.2]octanyl, octahydro-2H-pyrido[1,2-a]pyrazinyl, 3-azabicyclo[4.1.0]heptanyl, 3-azabicyclo[3.1.0]hexanyl 2-azaspiro[4.4]nonanyl, 7-oxa-1-aza-spiro[4.4]nonanyl, 7-azabicyclo[2.2.2]heptanyl, octahydro-1H-indolyl, etc. In general, the heterocycloalkyl group typically is attached to the main structure via a carbon atom or a nitrogen atom.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group $-OSO_3H$, or a pharmaceutically acceptable salt thereof.

The term "sulfonamide" is art-recognized and refers to the group represented by the general formulae

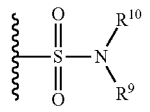

or

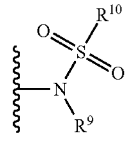

wherein $R^9$ and $R^{10}$ independently represents hydrogen or hydrocarbyl, such as alkyl, or $R^9$ and $R^{10}$ taken together with the intervening atom(s) complete a heterocycle having from 4 to 8 atoms in the ring structure.

The term "sulfoxide" is art-recognized and refers to the group $-S(O)-R^{10}$, wherein $R^{10}$ represents a hydrocarbyl.

The term "sulfonate" is art-recognized and refers to the group $SO_3H$, or a pharmaceutically acceptable salt thereof.

The term "sulfone" is art-recognized and refers to the group $-S(O)_2-R^{10}$, wherein $R^{10}$ represents a hydrocarbyl.

The term "thioalkyl", as used herein, refers to an alkyl group substituted with a thiol group.

The term "thioester", as used herein, refers to a group $-C(O)SR^{10}$ or $-SC(O)R^{10}$ wherein $R^{10}$ represents a hydrocarbyl.

The term "thioether", as used herein, is equivalent to an ether, wherein the oxygen is replaced with a sulfur.

The term "urea" is art-recognized and may be represented by the general formula

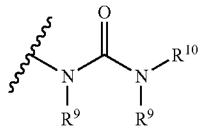

wherein $R^9$ and $R^{10}$ independently represent hydrogen or a hydrocarbyl, such as alkyl, or either occurrence of $R^9$ taken together with $R^{10}$ and the intervening atom(s) complete a heterocycle having from 4 to 8 atoms in the ring structure.

The term "protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3rd Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC")

and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

The invention also includes various isomers and mixtures thereof. Certain of the compounds of the present invention may exist in various stereoisomeric forms. Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. "R" and "S" represent the configuration of substituents around one or more chiral carbon atoms. When a chiral center is not defined as R or S, either a pure enantiomer or a mixture of both configurations is present.

"Racemate" or "racemic mixture" means a compound of equimolar quantities of two enantiomers, wherein such mixtures exhibit no optical activity; i.e., they do not rotate the plane of polarized light. In certain embodiments, compounds of the invention may be racemic.

In certain embodiments, compounds of the invention may be enriched in one enantiomer. For example, a compound of the invention may have greater than about 30% ee, about 40% ee, about 50% ee, about 60% ee, about 70% ee, about 80% ee, about 90% ee, or even about 95% or greater ee. In certain embodiments, compounds of the invention may have more than one stereocenter. In certain such embodiments, compounds of the invention may be enriched in one or more diastereomer. For example, a compound of the invention may have greater than about 30% de, about 40% de, about 50% de, about 60% de, about 70% de, about 80% de, about 90% de, or even about 95% or greater de.

In certain embodiments, the therapeutic preparation may be enriched to provide predominantly one enantiomer of a compound (e.g., of Formula (I)). An enantiomerically enriched mixture may comprise, for example, at least about 60 mol percent of one enantiomer, or more preferably at least about 75, about 90, about 95, or even about 99 mol percent. In certain embodiments, the compound enriched in one enantiomer is substantially free of the other enantiomer, wherein substantially free means that the substance in question makes up less than about 10%, or less than about 5%, or less than about 4%, or less than about 3%, or less than about 2%, or less than about 1% as compared to the amount of the other enantiomer, e.g., in the composition or compound mixture. For example, if a composition or compound mixture contains about 98 grams of a first enantiomer and about 2 grams of a second enantiomer, it would be said to contain about 98 mol percent of the first enantiomer and only about 2% of the second enantiomer.

In certain embodiments, the therapeutic preparation may be enriched to provide predominantly one diastereomer of a compound (e.g., of Formula (I)). A diastereomerically enriched mixture may comprise, for example, at least about 60 mol percent of one diastereomer, or more preferably at least about 75, about 90, about 95, or even about 99 mol percent.

The compounds of the invention may be prepared as individual isomers by either isomer specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least about 60%, about 70%, about 80%, about 90%, about 99% or about 99.9% by weight pure relative to the other stereoisomers. When a single enantiomer is named or depicted by structure, the depicted or named enantiomer is at least about 60%, about 70%, about 80%, about 90%, about 99% or about 99.9% by weight optically pure. Percent optical purity by weight is the ratio of the weight of the enantiomer that is present divided by the combined weight of the enantiomer that is present and the weight of its optical isomer.

In the pictorial representation of the compounds given through this application, a thickened tapered line () indicates a substituent which is above the plane of the ring to which the asymmetric carbon belongs and a dotted line () indicates a substituent which is below the plane of the ring to which the asymmetric carbon belongs.

As used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

An isotope-labelled form of a disclosed compound has one or more atoms of the compound replaced by an atom or atoms having an atomic mass or mass number different that which usually occurs in greater natural abundance. Examples of isotopes which are readily commercially available and which can be incorporated into a disclosed compound by well-known methods include isotopes of hydrogen, carbon, nitrogen, oxygen, phosphorus, fluorine and chlorine, for example, 2H, 3H, 13C, 14C, 15N, 18O, 17O, 31P, 32P, 35S, 18F and 36Cl, respectively. An isotope-labelled compound provided herein can usually be prepared by carrying out the procedures disclosed herein, replacing a non-isotope-labelled reactant by an isotope-labelled reactant.

The concentration of such a heavier isotope, specifically deuterium, may be defined by the isotopic enrichment factor. The term "isotopic enrichment factor" as used herein means the ratio between the isotopic abundance and the natural abundance of a specified isotope. If a hydrogen atom in a compound of this invention is replaced with deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

An isotope-labelled compound as provided herein can be used in a number of beneficial ways. Compounds having 14C incorporated are suitable for medicament and/or substrate tissue distribution assays. Tritium (3H) and carbon-14 (14C), are preferred isotopes owing to simple preparation and excellent detectability. Heavier isotopes, for example deuterium (2H), has therapeutic advantages owing to the higher metabolic stability. Metabolism is affected by the primary kinetic isotope effect, in which the heavier isotope has a lower ground state energy and causes a reduction in the rate-limiting bond breakage. Slowing the metabolism can lead to an increased in vivo half-life or reduced dosage requirements or an improvement in therapeutic index.

For a further discussion, see S. L. Harbeson and R. D. Tung, Deuterium In Drug Discovery and Development, Ann. Rep. Med. Chem. 2011, 46, 403-417, Foster, A. B., "Deuterium Isotope Effects in Studies of Drug Metabolism," Trends in Pharmacological Sciences, 5: 524-527 (1984) AND Foster, A. B., "Deuterium Isotope Effects in the Metabolism of Drugs and Xenobiotics: Implications for Drug Design," Advances in Drug Research, 14: 1-40 (1985).

Metabolic stability can be affected by the compound's processing in different organs of the body. For example, compounds with poor pharmacokinetic profiles are susceptible to oxidative metabolism. In vitro liver microsomal assays currently available provide valuable information on the course of oxidative metabolism of this type, which in turn assists in the rational design of deuterated compounds as disclosed herein. Improvements can be measured in a number of assays known in the art, such as increases in the in vivo half-life (t1/2), concentration at maximum therapeutic effect (Cmax), area under the dose response curve (AUC), and bioavailability; and in terms of reduced clearance, dose and materials costs.

Another effect of deuterated compounds can be diminishing or eliminating undesired toxic metabolites. For example, if a toxic metabolite arises through oxidative carbon-hydrogen (C—H) bond cleavage, the deuterated analogue will have a slower reaction time and slow the production of the unwanted metabolite, even if the particular oxidation is not a rate-determining step. See, e.g., Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

The term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys. Preferred subjects are humans.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" means to decrease, suppress, attenuate, diminish, arrest, or stabilize the development or progression of a disease (e.g., a disease or disorder delineated herein), lessen the severity of the disease or improve the symptoms associated with the disease. Treatment includes treating a symptom of a disease, disorder or condition. Without being bound by any theory, in some embodiments, treating includes augmenting deficient CFTR activity. If it is administered prior to clinical manifestation of the unwanted condition (e.g., disease or other unwanted state of the subject) then the treatment is prophylactic (i.e., it protects the subject against developing the unwanted condition), whereas if it is administered after manifestation of the unwanted condition, the treatment is therapeutic, (i.e., it is intended to diminish, ameliorate, or stabilize the existing unwanted condition or side effects thereof).

As used herein, the term "prodrug" means a pharmacological derivative of a parent drug molecule that requires biotransformation, either spontaneous or enzymatic, within the organism to release the active drug. For example, prodrugs are variations or derivatives of the compounds of the invention that have groups cleavable under certain metabolic conditions, which when cleaved, become the compounds of the invention. Such prodrugs then are pharmaceutically active in vivo, when they undergo solvolysis under physiological conditions or undergo enzymatic degradation. Prodrug compounds herein may be called single, double, triple, etc., depending on the number of biotransformation steps required to release the active drug within the organism, and the number of functionalities present in a precursor-type form. Prodrug forms often offer advantages of solubility, tissue compatibility, or delayed release in the mammalian organism (See, Bundgard, Design of Prodrugs, pp. 7-9, 21-24, Elsevier, Amsterdam 1985 and Silverman, The Organic Chemistry of Drug Design and Drug Action, pp. 352-401, Academic Press, San Diego, CA, 1992). Prodrugs commonly known in the art include well-known acid derivatives, such as, for example, esters prepared by reaction of the parent acids with a suitable alcohol, amides prepared by reaction of the parent acid compound with an amine, basic groups reacted to form an acylated base derivative, etc. Of course, other prodrug derivatives may be combined with other features disclosed herein to enhance bioavailability.

As such, those of skill in the art will appreciate that certain of the presently disclosed compounds having free amino, amido, hydroxy or carboxylic groups can be converted into prodrugs. Prodrugs include compounds having an amino acid residue, or a polypeptide chain of two or more (e.g., two, three or four) amino acid residues which are covalently joined through peptide bonds to free amino, hydroxy or carboxylic acid groups of the presently disclosed compounds. The amino acid residues include the 20 naturally occurring amino acids commonly designated by three letter symbols and also include 4-hydroxyproline, hydroxylysine, demosine, isodemosine, 3-methylhistidine, norvalin, beta-alanine, gamma-aminobutyric acid, citrullinehomocysteine, homoserine, ornithine and methionine sulfone. Prodrugs also include compounds having a carbonate, carbamate, amide or alkyl ester moiety covalently bonded to any of the above substituents disclosed herein.

A "therapeutically effective amount", as used herein refers to an amount that is sufficient to achieve a desired therapeutic effect. For example, a therapeutically effective amount can refer to an amount that is sufficient to improve at least one sign or symptom of cystic fibrosis.

A "response" to a method of treatment can include a decrease in or amelioration of negative symptoms, a decrease in the progression of a disease or symptoms thereof, an increase in beneficial symptoms or clinical outcomes, a lessening of side effects, stabilization of disease, partial or complete remedy of disease, among others.

As used herein, "CFTR" means cystic fibrosis transmembrane conductance regulator. Defects in the function of the CFTR ion channel result from loss of function mutations of CFTR. Such mutations lead to exocrine gland dysfunction, abnormal mucociliary clearance, and cause cystic fibrosis. The most common CFTR mutation in Cystic Fibrosis (CF) patients leads to the specific deletion of three nucleotides of the codon for phenylalanine at position 508. This mutation, which is found in ~70% of CF patients worldwide, is referred to as "ΔF508". The ΔF508 mutation decreases the stability of the CFTR NBD1 domain and limits CFTR interdomain assembly. Since CF is an autosomal recessive disease, a CF patient harboring the ΔF508 CFTR mutation must also carry a second defective copy of CFTR. Approximately 2000 different CF-causing CFTR mutations have been identified in CF patients. CF patients harboring the ΔF508 CFTR mutation can be homozygous for that mutation (ΔF508/ΔF508). CF patients can also be ΔF508 heterozygous, if the second CFTR allele such patients carry instead contains a different CFTR loss of function mutation. Such CFTR mutations include, but are not limited to, G542X, G551D, N1303K, W1282X, R553X, R117H, R1162X, R347P, G85E, R560T, A455E, ΔI507, G178R, S549N, S549R, G551S, G970R, G1244E, S1251N, S1255P, and G1349D.

As used herein, the term "CFTR modulator" refers to a compound that increases the activity of CFTR. In certain aspects, a CFTR modulator is a CFTR corrector or a CFTR potentiator or a dual-acting compound having activities of a corrector and a potentiator. These dual acting agents are useful when the mutations result in absence or reduced amount of synthesized CFTR protein.

As used herein, the term "CFTR corrector" refers to a compound that increases the amount of functional CFTR protein at the cell surface, thus enhancing ion transport through CFTR. CFTR correctors partially "rescue" misfolding of CFTR protein, particularly such misfolding that results from mutations within CFTR, thereby permitting CFTR maturation and functional expression on the cell surface. CFTR correctors may modify the folding environment of the cell in a way that promotes CFTR folding, and include compounds that interact directly with CFTR protein to modify its folding, conformational maturation or stability. Examples of correctors include, but are not limited to, VX-809, VX-661, VX-152, VX-440, VX-445, VX-659, VX-121, VX-983, compounds described in US20190248809A1, GLPG2222, GLPG2737, GLPG3221, GLPG2851, FDL169, FDL304, FDL2052160, FD2035659, and PTI-801. As used herein, the term "CFTR potentiator" refers to a compound that increases the ion channel activity of CFTR protein located at the cell surface, resulting in enhanced ion transport. CFTR potentiators restore the defective channel functions that results from CFTR mutations, or that otherwise increase the activity of CFTR at the cell surface. Examples of potentiators include, but are not limited to, ivacaftor (VX770), deuterated ivacaftor (CPT 656, VX-561), PTI-808, QBW251, GLPG1837, GLPG2451, ABBV-3067, ABBV-974, ABBV-191, FDL176, and genistein.

As used herein, "CFTR disease or condition" refers to a disease or condition associated with deficient CFTR activity, for example, cystic fibrosis, congenital bilateral absence of vas deferens (CBAVD), acute, recurrent, or chronic pancreatitis, disseminated bronchiectasis, asthma, allergic pulmonary aspergillosis, congenital pneumonia, intestinal malabsorption, celiac disease, nasal polyposis, non-tuberculous mycobacterial infection, pancreatic steatorrhea, intestinal atresia, smoking-related lung diseases, such as chronic obstructive pulmonary disease (COPD), rhinosinusitis, dry eye disease, protein C deficiency, A.beta.-lipoproteinemia, lysosomal storage disease, type 1 chylomicronemia, mild pulmonary disease, lipid processing deficiencies, type 1 hereditary angioedema, coagulation-fibrinolyis, hereditary hemochromatosis, CFTR-related metabolic syndrome, chronic bronchitis, constipation, pancreatic insufficiency, hereditary emphysema, and Sjogren's syndrome.

Methods of Use

Disclosed herein are methods of treating deficient CFTR activity in a cell, comprising contacting the cell with a compound of formula (I), or a pharmaceutically acceptable salt thereof. In certain embodiments, contacting the cell occurs in a subject in need thereof, thereby treating a disease or disorder mediated by deficient CFTR activity.

Also, disclosed herein are methods of treating a disease or a disorder mediated by deficient CFTR activity comprising administering a compound of Formula (I) or a pharmaceutically acceptable salt thereof. In some embodiments, the subject is a mammal, preferably a human. In some embodiments, the disease is associated with the regulation of fluid volumes across epithelial membranes, particularly an obstructive airway disease such as CF or COPD.

Such diseases and conditions include, but are not limited to, cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), congenital pneumonia, intestinal malabsorption, celiac disease, nasal polyposis, non-tuberculous mycobacterial infection, pancreatic steatorrhea, intestinal atresia, rhinosinusitis, liver disease, hereditary emphysema, hereditary hemochromatosis, coagulation-fibrinolysis deficiencies, protein C deficiency, Type 1 hereditary angioedema, lipid processing deficiencies, familial hypercholesterolemia, Type 1 chylomicronemia, abetalipoproteinemia, lysosomal storage diseases, I-cell disease/pseudo-Hurler, mucopolysaccharidoses, Sandhoff/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases, Alzheimer's disease, Parkinson's disease, amyotrophic lateral sclerosis, progressive supranuclear palsy, Pick's disease, several polyglutamine neurological disorders, Huntington's, spinocerebullar ataxia type I, spinal and bulbar muscular atrophy, dentatorubal pallidoluysian, myotonic dystrophy, spongiform encephalopathies, hereditary Creutzfeldt-Jakob disease, Fabry disease, Straussler-Scheinker syndrome, COPD, dry-eye disease, Sjogren's disease, Osteoporosis, Osteopenia, bone healing and bone growth, bone repair, bone regeneration, reducing bone resorption, increasing bone deposition, Gorham's Syndrome, chloride channelopathies, myotonia congenita, Bartter's syndrome type III, Dent's disease, hyperekplexia, epilepsy, hyperekplexia, lysosomal storage disease, Angelman syndrome, Primary Ciliary Dyskinesia (PCD), PCD with situs inversus, PCD without situs inversus and ciliary aplasia.

Such diseases and conditions include, but are not limited to, cystic fibrosis, congenital bilateral absence of vas deferens (CBAVD), acute, recurrent, or chronic pancreatitis, disseminated bronchiectasis, asthma, allergic pulmonary aspergillosis, congenital pneumonia, intestinal malabsorption, celiac disease, nasal polyposis, non-tuberculous mycobacterial infection, pancreatic steatorrhea, intestinal atresia, rhinosinusitis, chronic obstructive pulmonary disease (COPD), chronic sinusitis, dry eye disease, protein C deficiency, Abetalipoproteinemia, lysosomal storage disease, type 1 chylomicronemia, mild pulmonary disease, lipid processing deficiencies, type 1 hereditary angioedema, coagulation-fibrinolyis, hereditary hemochromatosis, CFTR-related metabolic syndrome, chronic bronchitis, constipation, pancreatic insufficiency, hereditary emphysema, and Sjogren's syndrome. In some embodiments, the disease is cystic fibrosis.

Provided herein are methods of treating cystic fibrosis, comprising administering to a subject in need thereof, a compound as disclosed herein or a pharmaceutically acceptable salt thereof. Also provided herein are methods of lessening the severity of cystic fibrosis, comprising administering to a subject in need thereof, a compound as disclosed herein or a pharmaceutically acceptable salt thereof. In some embodiments, the subject is a human. In some embodiments, the subject is at risk of developing cystic fibrosis, and administration is carried out prior to the onset of symptoms of cystic fibrosis in the subject.

Provided herein are compounds as disclosed herein for use in treating a disease or condition mediated by deficient CFTR activity. Also provided herein are uses of a compound as disclosed herein for the manufacture of a medicament for treating a disease or condition mediated by deficient CFTR activity.

The compounds and methods described herein can be used to treat subjects who have deficient CFTR activity and harbor CFTR mutations like ΔF508. The ΔF508 mutation impedes normal CFTR folding, stability, trafficking, and function by decreasing the stability of CFTR's NBD1 domain, the competency of CFTR domain-domain assembly, or both. Due their impact on the ICL4 interface, a CFTR corrector with an ICL4-directed mechanism can be effective in subjects harboring the following mutations: ΔF508-CFTR (>70% of all CF patients harbor at least one copy) and mutations that cause ICL4 interface instability for example: G85E, H139R, H1054D, L1065P, L1077P, R1066C and other CFTR mutations where ICL4 interface stability is compromised.

Provided herein are kits for use in measuring the activity of CFTR or a fragment thereof in a biological sample in vitro or in vivo. The kit can contain: (i) a compound as disclosed herein, or a pharmaceutical composition comprising the disclosed compound, and (ii) instructions for: a) contacting the compound or composition with the biological sample; and b) measuring activity of said CFTR or a fragment thereof. In some embodiments, the biological sample is biopsied material obtained from a mammal or extracts thereof; blood, saliva, urine, feces, semen, tears, other body fluids, or extracts thereof. In some embodiments, the mammal is a human.

Combination Treatments

As used herein, the term "combination therapy" means administering to a subject (e.g., human) two or more CFTR modulators, or a CFTR modulator and an agent such as antibiotics, ENaC inhibitors, GSNO (S-nitrosothiol s-nitroglutanthione) reductase inhibitors, and a CRISPR Cas correction therapy or system (as described in US 2007/0022507 and the like).

In certain embodiments, the method of treating or preventing a disease or condition mediated by deficient CFTR activity comprises administering a compound as disclosed herein conjointly with one or more other therapeutic agent (s). In some embodiments, one other therapeutic agent is administered. In other embodiments, at least two other therapeutic agents are administered.

Additional therapeutic agents include, for example, ENaC inhibitors, mucolytic agents, modulators of mucus rheology, bronchodilators, antibiotics, anti-infective agents, anti-inflammatory agents, ion channel modulating agents, therapeutic agents used in gene or mRNA therapy, agents that reduce airway surface liquid and/or reduce airway surface PH, CFTR correctors, and CFTR potentiators, or other agents that modulate CFTR activity. Other therapeutics include liposomal composition components such as those described in WO2012/170889, hybrid oligonucleotides that facilitate RNA cleavage such as those described in WO2016/130943, and single stranded oligonucleotides that modulate gene expression as described in WO2016/130929.

In some embodiments, at least one additional therapeutic agent is selected from one or more CFTR modulators, one or more CFTR correctors and one or more CFTR potentiators.

Non-limiting examples of additional CFTR modulators, correctors and potentiators include VX-770 (Ivacaftor), VX-809 (Lumacaftor, 3-(6-(I-(2,2-5 difluorobenzo[d][1,3]dioxol-5-yl)cyclopropanecarboxamido)-3-methylpyridin-2-yl) benzoic acid, VX-661 (Tezacaftor, I-(2,2-difluoro-1,3-benzodioxol-5-yl)-N—[I-[(2R)-2,3-dihydroxypropyl]-6-fluoro-2-(2-hydroxy-1, I-dimethylethyl)-IH-indol-5-yl]-cyclopropanecarboxamide), VX-983, VX-152, VX-440, VX-445, VX-659, VX-371, VX-121, Orkambi, compounds described in US20190248809A1, Ataluren (PTC 124) (3-[5-(2-fluorophenyl)-1, 2,4-oxadiazol-3-yl]benzoic acid), PTI-130 (Proteostasis), PTI-801, PTI-808, PTI-428, N91115.74 (cavosonstat), QBW251 (Novartis) compounds described in WO2011113894, compounds N30 Pharmaceuticals (e.g., WO 2014/186704), deuterated ivacaftor (e.g., CTP-656 or VX-561), GLPG2222, GLPG3221, GLPG2451, GLPG3067, GLPG2851, GLPG2737, GLPG1837 (N-(3-carbamoyl-5,5,7,7-tetramethyl-5,7-dihydro-4H-thieno[2,3-c]pyran-2-yl)-1H-pyrazole-5-carboxamide), GLPG2665 (Galapagos), ABBV-191 (Abbvie), ABBV-974, FDL 169 (Flatley Discovery lab), FDL 176, FDL438, FDL304, FD2052160, FD1881042, FD2027304, FD2035659, FD2033129, FD1860293, CFFT-Pot01, CFFT-Pot-02, P-1037, glycerol, phenylbutyrate, and the like.

Non-limiting examples of anti-inflammatory agents are N6022 (3-(5-(4-(IH-imidazol-I-yl)10 phenyl)-I-(4-carbamoyl-2-methylphenyl)-'H-pyrrol-2-yl) propanoic acid), Ibuprofen, Lenabasum (anabasum), Acebilustat (CTX-4430), LAU-7b, POL6014, docosahexaenoic acid, alpha-1 antitrypsin, sildenafil. Additional therapeutic agents also include, but are not limited to a mucolytic agent, a modifier of mucus rheology (such as hypertonic saline, mannitol, and oligosaccharide based therapy), a bronchodilator, an anti-infective (such as tazobactam, piperacillin, rifampin, meropenum, ceftazidime, aztreonam, tobramycin, fosfomycin, azithromycin, vancomycin, gallium and colistin), an anti-infective agent, an anti-inflammatory agent, a CFTR modulator other than a compound of the present invention, and a nutritional agent. Additional therapeutic agents can include treatments for comorbid conditions of cystic fibrosis, such as exocrine pancreatic insufficiency which can be treated with Pancrelipase or Liprotamase.

Examples of CFTR potentiators include, but are not limited to, Ivacaftor (VX-770), CTP-656, NVS-QBW251, PTI-808, ABBV-3067, ABBV-974, ABBV-191, FDL176, FD1860293, GLPG2451, GLPG1837, and N-(3-carbamoyl-5,5,7,7-tetramethyl-5,7-dihydro-4H-thieno[2,3-c]pyran-2-yl)-1H-pyrazole-5-carboxamide examples of potentiators are also disclosed in publications: WO2005120497, WO2008147952, WO2009076593, WO2010048573, WO2006002421, WO2008147952, WO2011072241, WO2011113894, WO2013038373, WO2013038378, WO2013038381, WO2013038386, WO2013038390, WO2014180562, WO2015018823, and U.S. patent application Ser. Nos. 14/271,080, 14/451,619 and 15/164,317.

Non-limiting examples of correctors include. Lumacaftor (VX-809), 1-(2,2-difluoro-1,3-benzodioxol-5-yl)-N-{1-[(2R)-2,3-dihydroxypropyl]-6-fluoro-2-(1-hydroxy-2-methylpropan-2-yl)-1H-indol-5-yl}cyclopropane carboxamide (VX-661), VX-983, GLPG2222 GL_PG2665, GLPG2737, GLPG3221, GLPG2851, VX-152, VX-440, VX-121, VX-445, VX-659, compounds described in US20190248809A 1, PTI-801, FDL169, FDL304, FD2052160, and FD2035659. Examples of correctors are also disclosed in US20160095858A1, and U.S. application Ser, Nos. 14/925,649 and 14/926,727.

In certain embodiments, the additional therapeutic agent is a CFTR amplifier. CFTR amplifiers enhance the effect of known CFTR modulators, such as potentiators and correctors. Examples of CFTR amplifier include PTI130 and PTT-428. Examples of amplifiers are also disclosed in publications: WO2015138909 and WO2015138934.

In certain embodiments, the additional therapeutic agent is an agent that reduces the activity of the epithelial sodium channel blocker (ENaC) either directly by blocking the channel or indirectly by modulation of proteases that lead to an increase in ENaC activity (e.g., serine proteases, channel-activating proteases). Exemplary of such agents include camostat (a trypsin-like protease inhibitor), QAU145, 552-02, GS-9411, INO-4995. Aerolytic, amiloride, AZD5634, and VX-371. Additional agents that reduce the activity of the epithelial sodium channel blocker (ENaC) can be found, for example, in PCT Publication No. WO02009074575 and WO2013043720; and U.S. Pat. No. 8,999,976.

In one embodiment, the ENaC inhibitor is VX-371.

In one embodiment, the ENaC inhibitor is SPX-101 (S18).

In certain embodiments, the additional therapeutic agent is an agent that modulates the activity of the non-CFTR Cl— channel TMEM16A Non-limiting examples of such agents include TMEM16A activators, denufosol, Melittin, Cinnamaldehyde, 3,4,5-Trimethoxy-N-(2-methoxyethyl)-N-(4-phenyl-2-thiazolyl)benzamide, INO-4995, CLCA1, ETX001, ETD002 and phosphatidylinositol diC8-PIP2, and TMEM16A inhibitors, 10 bm, Arctigenin, dehydroandrographolide, Ani9, Niclosamide, and benzbromarone.

In certain embodiments, the combination of a compound of Formula (I), with a second therapeutic agent may have a synergistic effect in the treatment of cancer and other diseases or disorders mediated by adenosine. In other embodiments, the combination may have an additive effect.

Pharmaceutical Compositions

The compositions and methods of the present invention may be utilized to treat a subject in need thereof. In certain embodiments, the subject is a mammal such as a human, or a non-human mammal. When administered to subject, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of a subject without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the subject. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11)

polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the subject being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the subject being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the subject's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

In certain embodiments, the dosing follows a 3+3 design. The traditional 3+3 design requires no modeling of the dose-toxicity curve beyond the classical assumption for cytotoxic drugs that toxicity increases with dose. This rule-based design proceeds with cohorts of three patients; the first cohort is treated at a starting dose that is considered to be safe based on extrapolation from animal toxicological data, and the subsequent cohorts are treated at increasing dose levels that have been fixed in advance. In some embodiments, the three doses of a compound of formula (I) range from about 100 mg to about 1000 mg orally, such as about 200 mg to about 800 mg, such as about 400 mg to about 700 mg, such as about 100 mg to about 400 mg, such as about 500 mg to about 1000 mg, and further such as about 500 mg to about 600 mg. Dosing can be three times a day when taken with without food, or twice a day when taken with food. In certain embodiments, the three doses of a compound of formula (I) range from about 400 mg to about 800 mg, such as about 400 mg to about 700 mg, such as about 500 mg to about 800 mg, and further such as about 500 mg to about 600 mg twice a day. In certain preferred embodiments, a dose of greater than about 600 mg is dosed twice a day.

If none of the three patients in a cohort experiences a dose-limiting toxicity, another three patients will be treated at the next higher dose level. However, if one of the first three patients experiences a dose-limiting toxicity, three more patients will be treated at the same dose level. The dose escalation continues until at least two patients among a cohort of three to six patients experience dose-limiting toxicities (i.e., ≥ about 33% of patients with a dose-limiting toxicity at that dose level). The recommended dose for phase II trials is conventionally defined as the dose level just below this toxic dose level.

In certain embodiments, the dosing schedule can be about 40 $mg/m^2$ to about 100 $mg/m^2$, such as about 50 $mg/m^2$ to about 80 $mg/m^2$, and further such as about 70 $mg/m^2$ to about 90 $mg/m^2$ by IV for 3 weeks of a 4 week cycle.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the subject, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, a subject who receives such treatment can benefit from a combined effect of different therapeutic compounds.

In certain embodiments, conjoint administration of compounds of the invention with one or more additional therapeutic agent(s) (e.g., one or more additional chemotherapeutic agent(s)) provides improved efficacy relative to each individual administration of the compound of the invention (e.g., compound of formula I or Ia) or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s).

This invention includes the use of pharmaceutically acceptable salts of compounds of the invention in the compositions and methods of the present invention. A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Although specific embodiments of the present disclosure will now be described with reference to the preparations and schemes, it should be understood that such embodiments are by way of example only and merely illustrative of but a small number of the many possible specific embodiments which can represent applications of the principles of the present disclosure. Various changes and modifications will be obvious to those of skill in the art given the benefit of the present disclosure and are deemed to be within the spirit and scope of the present disclosure as further defined in the appended claims.

Unless defined otherwise, all technical and scientific terms used herein have the same meaning as commonly understood by one having ordinary skill in the art to which this disclosure belongs. Although other compounds or methods can be used in practice or testing, certain preferred methods are now described in the context of the following preparations and schemes.

A number of synthetic protocols were used to produce the compounds described herein. These synthetic protocols (see schemes below) have common intersections and can be used alternatively for synthesis of the compounds described herein.

EXAMPLES

General Schemes

Scheme 1

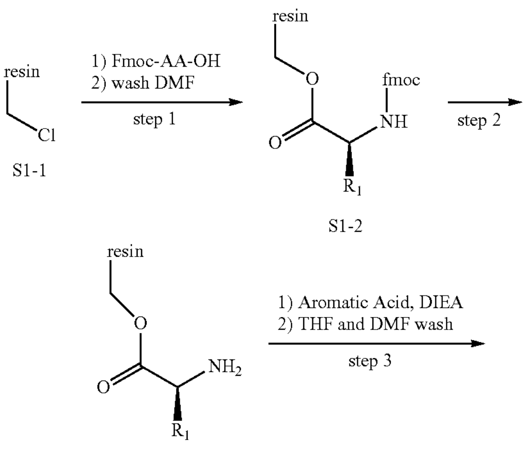

S1-1

S1-2

S1-3

-continued

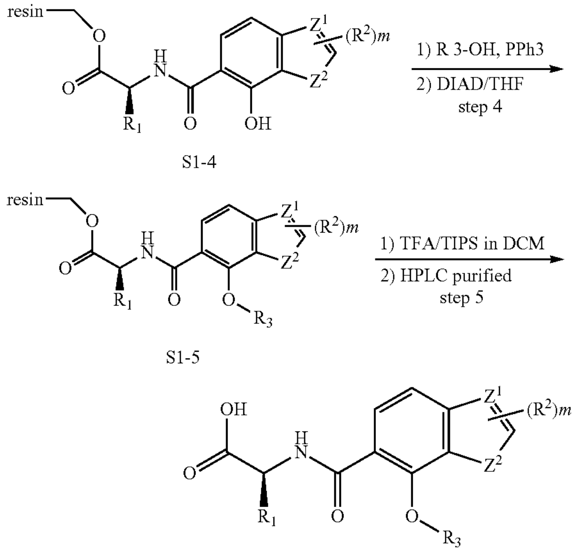

S1-4

S1-5

S1-6

Scheme 1 provides a general scheme when using solid phase chemistry to derive the compounds described herein through a 5-step process. In step 1, resin supported chloride S1-1 is coupled with an appropriate Fmoc protected amino acid to yield compound S1-2. Removal of the Fmoc protection gives rise to S1-3. This is followed by further coupling of an appropriate aromatic acid with DIEA, followed by washing with THF and DMF to provide amide S1-4. Derivatization of phenol of the amide (step 4) is carried out with reaction with R30H, triphenylphosphine and DIAD to produce compound S1-5. Lastly, removal of the resin is accomplished via treatment with TFA/TIPS followed by HPLC purification to produce final product S1-6.

Scheme 2

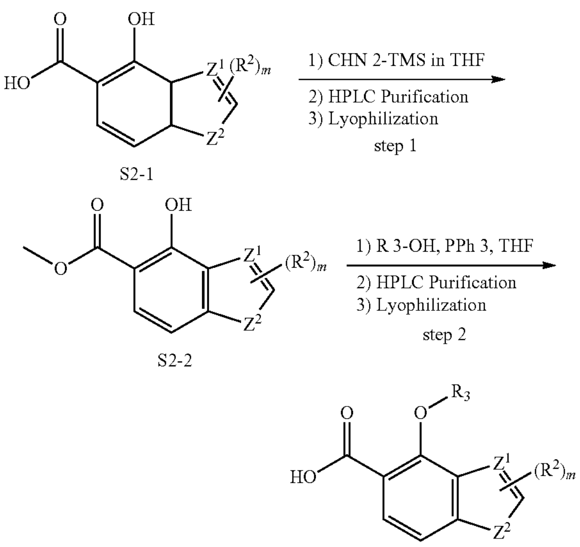

S2-1

S2-2

S2-3

-continued

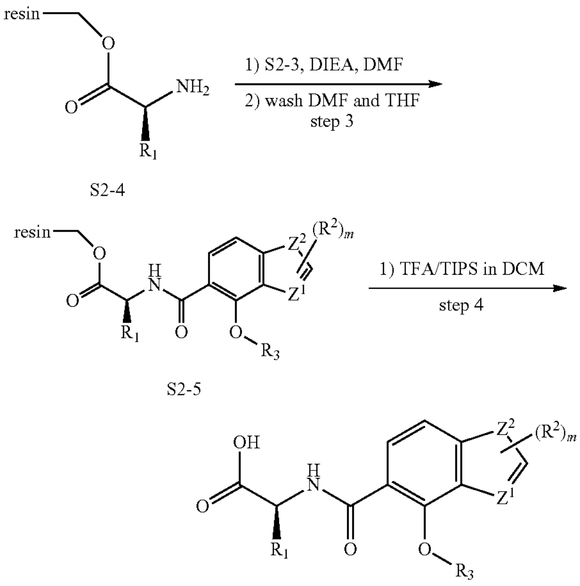

S2-4

S2-5

S2-6

Scheme 2 provides a general scheme to illustrate an alternate solid phase synthetic procedure to arrive at the compounds described herein through a 4-step process. In step 1, aromatic carboxylic acid S2-1 is reacted with TMS-$CHN_2$ followed by purification and lyophilization to provide ester S2-2. Reaction of ester S2-2 with an appropriate alcohol in the presence of triphenylphosphine in THF is carried out to produce compound S2-3. Coupling of carboxylic acid S2-3 with resin containing compound S2-4 in the presence of DIEA in DMF produced aryl amide of amino acid S2-5. Removal of the resin is carried via treatment of S2-5 with TFA/TIPS followed by HPLC purification to produce final product S2-6.

Scheme 3

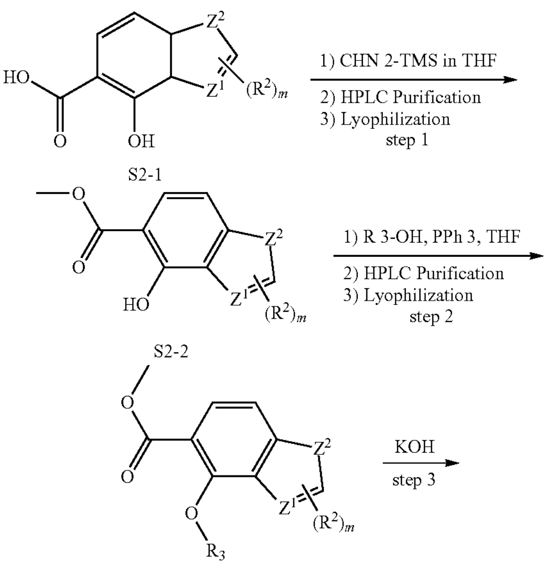

S2-1

S2-2

S3-1

-continued

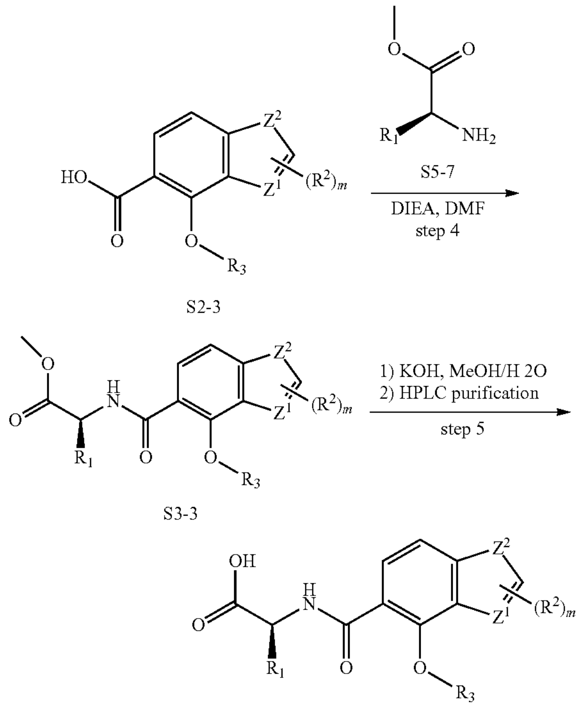

S5-7

S2-3

S3-3

S1-6

Scheme 3 provides a further general scheme for the solution phase synthesis to arrive at the compounds described herein through a 4-step process. In step 1, aromatic carboxylic acid S2-1 is reacted with TMS-$CHN_2$ followed by purification and lyophilization to provide methyl ester S2-2. Reaction of ester S2-2 with an appropriate alcohol in the presence of triphenylphosphine in THF is carried out to produce compound S3-1. Hydrolysis of S3-1 gave rise to the acid S2-3. Coupling of carboxylic acid S2-3 with amino acid methyl ester S5-7 in the presence of DIEA in DMF produced the ester S3-3. Removal of the methyl ester is carried via treatment of S3-3 with KOH in a mixture methanol and water followed by HPLC purification to produce final product S1-6.

Scheme 4

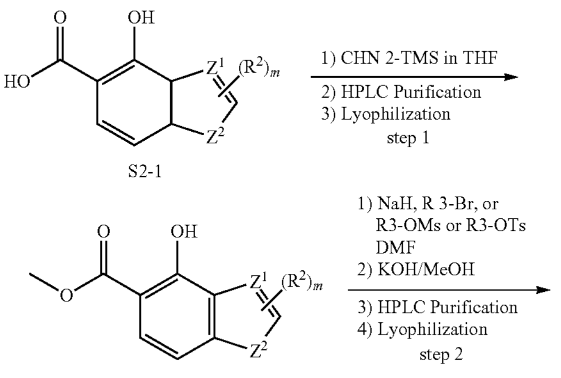

S2-1

S2-2

-continued

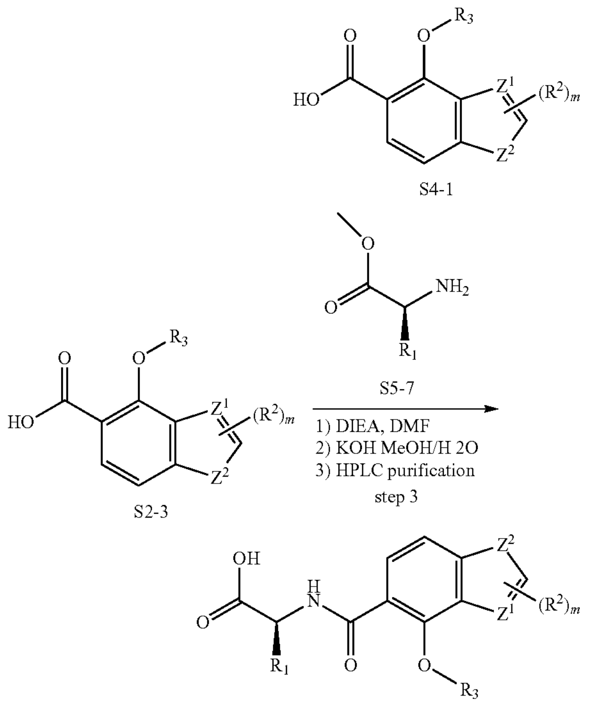

S4-1

S5-7

S2-3

S1-6

Scheme 4 provides a further general scheme to arrive at the compounds described herein through a 3-step process. In step 1, aromatic carboxylic acid S2-1 was reacted with TMS-$CHN_2$ followed by purification and lyophilization to provide ester S2-2. Reaction of ester S2-2 with sodium hydride and an appropriate bromide, mesylate, or tosylate, followed by treatment with KOH/MeOH and was carried out to produce carboxylic acid S4-1. Coupling of S4-1 with amino acid methyl ester S5-7 in the presence of DIEA in DMF produced the methyl ester. Removal of the methyl ester is carried via treatment with KOH in a mixture methanol and water followed by HPLC purification to produce final product S1-6.

Scheme 5

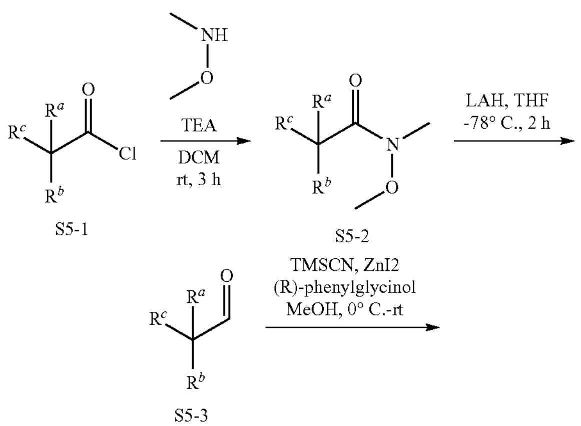

S5-1

S5-2

S5-3

-continued

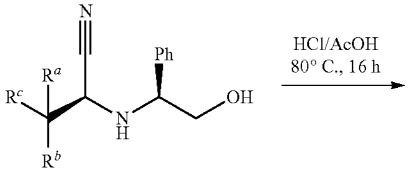

S5-3

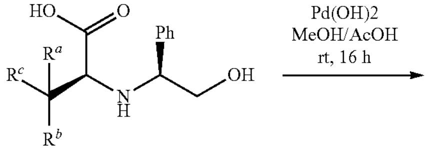

S5-5

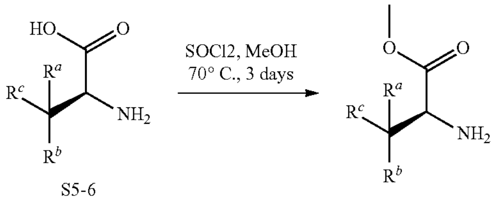

S5-6

S5-7

Scheme 5 illustrates the synthesis of the commercially un-available amino acid methyl ester S5-7. In step 1, the acid chloride S5-1 is condensed with O,N-Dimethyl-hydroxylamine to form an amide S5-2, which was reduced into aldehyde S5-3. The aldehyde S6-3 is treated with a proper agent of cyano source, such as TMS-CN, and chiral auxiliary, such as (R)-phenylglycinol, in methanol or ethanol to form a key intermediate S6-4. After hydrolysis catalyzed by an acid, such as hydrochloric acid, and removal of the auxiliary, the desired amino acid S5-6 is obtained. This amino acid is converted into an ester, such as methyl ester S5-7, and is ready for use as a coupling partner.

Analytical Procedures $^1$H NMR spectra were recorded with Bruker AC 400 MHz apparatus. Chemical shifts (δ) are quoted in parts per million (ppm) and coupling constants (J) in hertz (Hz).

LC-MS spectra were obtained with UPLC Acquity device of Waters for liquid chromatography part, coupling with mass spectrometer ZMD of Waters. This system was piloted by MassLynx v4.1 software. Detection was made in UV at 220 nm.

Operational conditions for liquid chromatography part are the following:

Column: Assentis Express $C_{18}$ 50×2.1 mm, 2.7μ Supelco

Eluent: Way A: $H_2O$+0.02% TFA;

Way B: $CH_3CN$+0.014% TFA;

Gradient: $T_0$ min: 2% B, $T_1$ min: 98% B, $T_{1.3}$ min: 98% B, $T_{1.33}$ min: 2% B, $T_{1.5}$ min: following injection;

Flow: 1 mL/min;

Temperature: 55° C.

SQD: ESI+30V

UV: 220 nm

Injection: 0.2 μl.

Data reported as retention time in min. ($t_R$).

MS data was reported as m/z values.

Preparation of Intermediates

Intermediate Example 1: Preparation of (S)-methyl 2-amino-3,3-dimethyl-pentanoate Step 1. Preparation of N-methoxy-2,2,N-trimethyl-butyramide

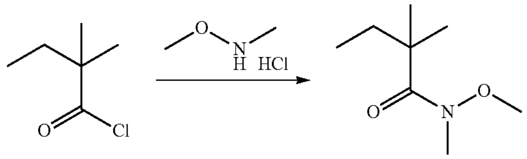

To a solution of methyl 3,3-dimethyl-pentanoyl chloride (10.0 g, 70 mmol) in $CH_2Cl_2$ (67 mL) was added of N,O-dimethyl hydroxylamine hydrochloride (7.8 g, 80 mmol), then TEA (22.3 g, 0.22 mol) was added slowly at 0° C. The resulting mixture was stirred at the same temperature for 2 h until the disappearance of starting material as checked by LCMS. Then, the solid was filtered out. The solvent was concentrated in vacuo and purified by silica gel column chromatography (petroleum ether/ethyl acetate=3/1) to afford N-methoxy-2,2,N-trimethyl-butyramide as a yellow oil (10.3 g, yield 88%). LCMS: Purity: 100%, $t_R$=1.94 min, MS: m/z (ES+)=160 (M+H$^+$).

Step 2. Preparation of 2,2-dimethylbutanal

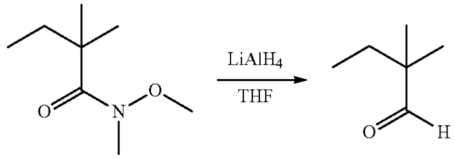

To a solution of N-methoxy-2,2,N-trimethyl-butyramide (10.0 g, 62.9 mmol) in 100 mL anhydrous THF was added 94 mL $LiAlH_4$ (1 M in THF) slowly at −78° C. under $N_2$ protection, and the resulting mixture was stirred at the same temperature for 2 h. Then 3.6 mL water, 3.6 mL 15% aqueous NaOH and 11 mL water were added to this mixture slowly at 0° C. in sequence.

The mixture was stirred at room temperature for 30 minutes and filtered out the solid. The solvent was dried over $Na_2SO_4$ and the solution of the crude title compound was used in the next step directly without concentration. GCMS: $t_R$=4.86 min, MS: m/z (ES+)=100 (M+H$^+$).

Step 3. Preparation of (2S)-2-[[(1R)-2-hydroxy-1-phenyl-ethyl]amino]-3,3-dimethyl-pentanenitrile

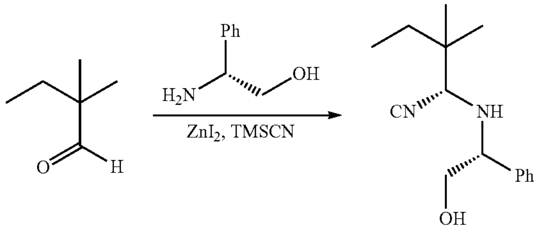

To a solution of 2,2-dimethylbutanal obtained in the previous step was added 90 mL methanol, $ZnI_2$ (0.996 g, 3.12 mmol) and (R)-2-amino-2-phenylethanol (9.48 g, 69.1 mmol) in sequence. The mixture was stirred at room temperature for 30 min. TMSCN (9.34 g, 94.14 mmol) was added dropwise at 0° C., and the mixture was stirred for 16 h at room temperature. The solvent was concentrated and purified by silica gel column chromatography (petroleum ether/ethyl acetate=5/1) to obtain 8.8 g (2S)-2-[[(1R)-2-hydroxy-1-phenyl-ethyl]amino]-3,3-dimethyl-pentanenitrile as a yellow oil, yield 57% (two steps). LCMS: $t_R$=2.13 min, MS: m/z (ES+)=247 (M+$H^+$).

Step 4. Preparation of (2S)-2-[[(1R)-2-hydroxy-1-phenyl-ethyl]amino]-3,3-dimethyl-pentanoic acid

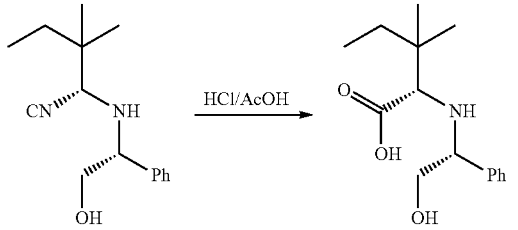

To a solution of (2S)-2-[[(1R)-2-hydroxy-1-phenyl-ethyl]amino]-3,3-dimethyl-pentanenitrile (8.5 g, 34.6 mmol) in 29.7 mL acetic acid was added 67.8 mL conc. HCl and the mixture was stirred at 80° C. overnight. Solvent was removed in vacuo and the residue was slurried with water (2 mL×3) to remove the other isomer and afford (2S)-2-[[(1R)-2-hydroxy-1-phenyl-ethyl]amino]-3,3-dimethyl-pentanoic acid as a white solid. (3.74 g, yield: 40.8%).

LCMS: Purity: 100%, $t_R$=1.45 min, MS: m/z (ES+)=266 (M+$H^+$).

Step 5. Preparation of (2S)-2-amino-3,3-dimethyl-pentanoic acid

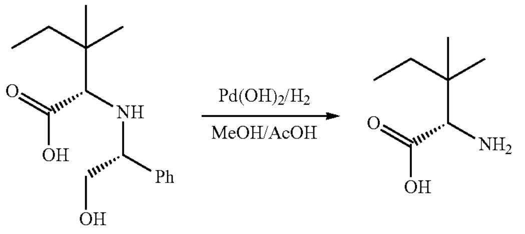

To a suspension of $Pd(OH)_2$ (1.12 g, 0.81 mmol) in 18.6 mL acetic acid and 93 mL methanol was added of (2S)-2-[[(1R)-2-hydroxy-1-phenyl-ethyl]amino]-3,3-dimethyl-pentanoic acid (3.7 g, 13.9 mmol) and the mixture was stirred at room temperature under the hydrogen overnight. $Pd(OH)_2$ was filtered out and the solvent was removed in vacuo to afford the crude target product, which was washed with ethyl ether to give (2S)-2-amino-3,3-dimethyl-pentanoic acid as a white solid (1.92 g, yield: 94.8%). LCMS: MS: m/z (ES+) =146 (M+$H^+$).

Step 6. Preparation of (2S)-methyl 2-amino-3,3-dimethyl-pentanoate

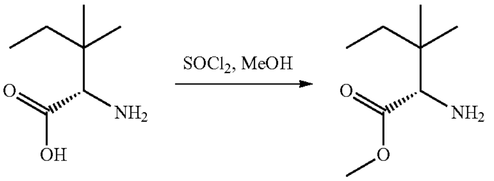

To a solution of (2S)-2-amino-3,3-dimethyl-pentanoic acid (1.72 g, 11.85 mmol) in 30 mL methanol was added 6 mL thionyl chloride ($SOCl_2$) and the mixture was stirred at 70° C. for 24 h. Next 6 mL $SOCl_2$ and 6 mL methanol were added to this mixture which was reacted at 70° C. for another 24 h. Finally, 6 mL $SOCl_2$ and 6 mL methanol were added again to this mixture. The reaction mixture was stirred at the same temperature for 24 h. Then solvent removed in vacuo. The residue was dissolved in ethyl acetate and washed with saturated sodium bicarbonate aqueous solution. The organic phases were concentrated and purified by silica gel column chromatography (ethyl acetate, 100%) to give compound methyl 2-amino-3,3-dimethyl-pentanoate as a yellow liquid (1.404 g, yield: 74.5%). The target product was dissolved in ethyl acetate and added 6 mL hydrochloric acid solution (4M in 1,4-dioxane), then solvent removed in vacuo to provide the corresponding hydrochloride as a white solid.

1H NMR (400 MHz, CDCl3) δ 8.53 (br s, 3H), 3.75 (s, 3H), 3.74-3.72 (m, 1H), 1.41-1.29 (m, 2H), 0.96 (s, 3H), 0.92 (s, 3H), 0.84-0.81 (m, 3H).

LCMS: $t_R$=1.03 min., MS: m/z (ES+)=160 (M+$H^+$).

Intermediate Example 2: Preparation of methyl (2S)-2-amino-2-(1-methylcyclopropyl)acetate hydrochloride

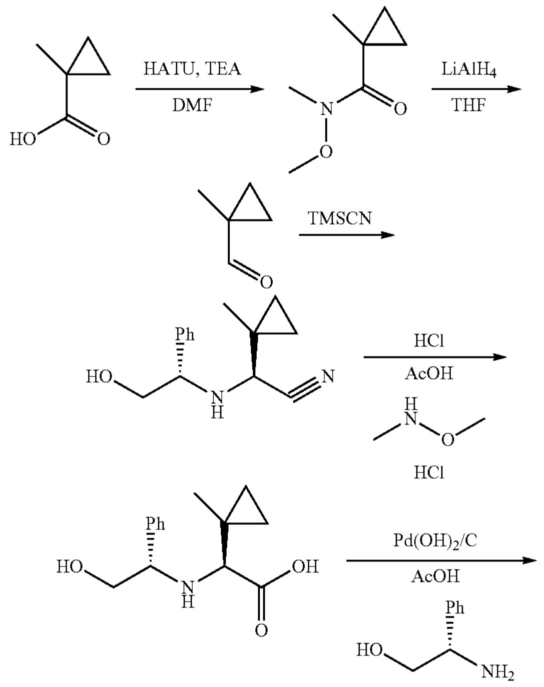

-continued

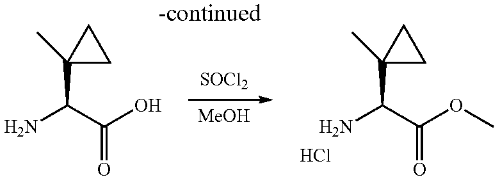

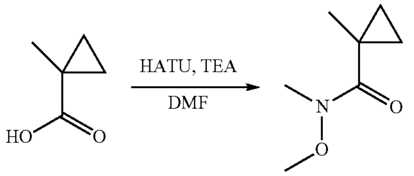

Step 1. To a solution of 1-methylcyclopropanecarboxylic acid (8.03 g, 80.2 mmol) in DMF (150 mL) was added N,O-dimethyl hydroxylamine hydrochloride (9.36 g, 96.5 mmol) and HATU (45.3 g, 119.2 mmol), then TEA (24.7 g, 244.1 mmol) was added slowly at room temperature. The resulting mixture was stirred at the same temperature for 2 h until the disappearance of starting material as checked by LCMS. The solvent was concentrated in vacuo and purified by silica gel column chromatography (petroleum ether/ethyl acetate=3/1) to afford N-methoxy-N,1-dimethyl-cyclopropanecarboxamide as a yellow oil (8.7 g, yield 75.6%). LCMS Purity: 99%; MS: m/z (ES+)=144 (M+H$^+$).

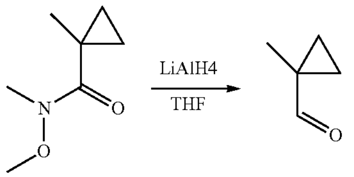

Step 2. To a solution of N-methoxy-N,1-dimethyl-cyclopropanecarboxamide (8.7 g, 60.84 mmol) in 250 mL anhydrous THF was added 100 mL $LiAlH_4$ (1 M in THF) slowly at −78° C. under $N_2$ protection, and the resulting mixture was stirred at the same temperature for 2 h. Next 3.6 mL water, 3.6 mL 15% aqueous NaOH and 11 mL water were added to this mixture slowly at 0° C. in sequence. The mixture was stirred at room temperature for 30 min and filtered out the solid. The solvent was dried over $Na_2SO_4$ to afford the crude 1-methylcyclopropanecarbaldehyde which was utilized for the next step directly.

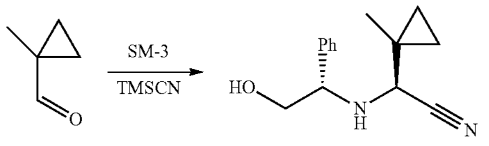

Step 3. To a solution of 1-methylcyclopropanecarbaldehyde obtained in the previous step was added 90 mL methanol, $ZnI_2$ (1 g, 3.1 mmol) and (R)-2-amino-2-phenylethanol (SM-3, 10 g, 72.9 mmol) in sequence. The mixture was stirred at room temperature for 30 min. Next the TMSCN (9.1 g, 91.7 mmol) was added dropwise at 0° C., and the mixture was stirred for 16 h at room temperature. The solvent was concentrated and purified by silica gel column chromatography (petroleum ether/ethyl acetate=5/1) to obtain 8.0 g (2S)-2-[[(1S)-2-hydroxy-1-phenyl-ethyl]amino]-2-(1-methylcyclopropyl)acetonitrile as a yellow oil. (Two steps yield 57%).

LCMS Purity: 94%; MS: m/z (ES+)=231 (M+H$^+$).

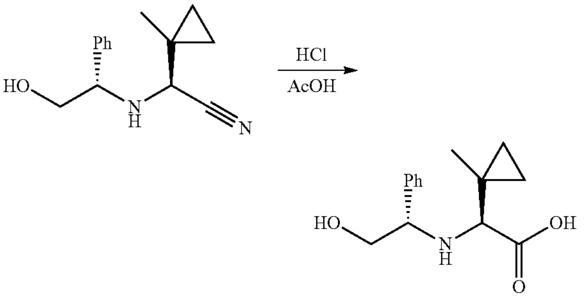

Step 4. To a solution of (2S)-2-[[(1S)-2-hydroxy-1-phenyl-ethyl]amino]-2-(1-methylcyclopropyl)acetonitrile (8.0 g, 34.8 mmol) in 20 mL acetic acid was added 60 mL conc. HCl and the mixture was stirred at 80° C. overnight. Next, solvent was removed in vacuo and the residue was washed with water (2 mL×3) to afford (2S)-2-[[(1S)-2-hydroxy-1-phenyl-ethyl]amino]-2-(1-methylcyclopropyl)acetic acid as a white solid. (5.3 g, yield: 61.2%).

LCMS Purity: 96%; MS: m/z (ES+)=250 (M+H$^+$).

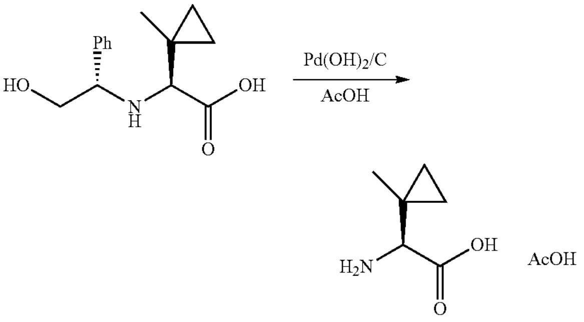

Step 5. To a suspension of $Pd(OH)_2$ (215 mg) in 15 mL acetic acid was added (2S)-2-[[(1S)-2-hydroxy-1-phenyl-ethyl]amino]-2-(1-methylcyclopropyl)acetic acid (1.2 g, 4.8 mmol) and the mixture was stirred at room temperature under hydrogen overnight. Next the $Pd(OH)_2$ was filtered out and the solvent was removed in vacuo to afford the crude target product, which was washed with ethyl ether to give (2S)-2-amino-2-(1-methylcyclopropyl)acetic acid acetic acid salt as a white solid (700 mg, yield: 77%)

LCMS Purity: 97%; MS: m/z (ES+)=130 (M+H$^+$).

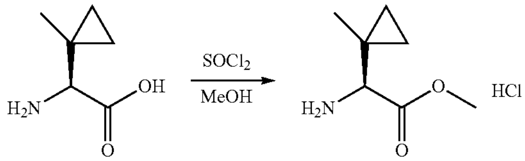

Step 6. To a solution of (2S)-2-amino-2-(1-methylcyclopropyl)acetic acid acetic acid salt (450 mg, 3.5 mmol) in 15 mL methanol was added 3 mL thionyl chloride ($SOCl_2$) and the mixture was stirred at 70° C. for 24 h, then solvent removed in vacuo. The residue was dissolved in ethyl acetate and washed with saturated sodium bicarbonate aqueous solution. The organic phase was concentrated and purified by silica gel column chromatography (ethyl acetate, 100%) to give compound as a yellow liquid. The target product was dissolved in ethyl acetate and 6 mL hydrochloric acid solution added (4M in 1,4-dioxane), then removed the solvent in vacuo to provide the corresponding hydrochloride of methyl (2S)-2-amino-2-(1-methylcyclopropyl)acetate; hydrochloride (500 mg) as a white solid.

$^1H$ NMR (400 MHz, DMSO-$d_6$) (8.58 (s, 3H), 3.78 (s, 3H), 3.49 (s, 1H), 0.99 (s, 3H), 0.78-0.77 (m, 2H), 0.50-0.47 (m, 2H) ppm.

LCMS Purity: >95%, $t_R$=1.18 min; MS: m/z ($ES^+$)=144 ($M+H^+$).

Intermediate Example 3. Preparation of methyl (2S)-2-amino-2-(1-methylcyclobutyl)acetate

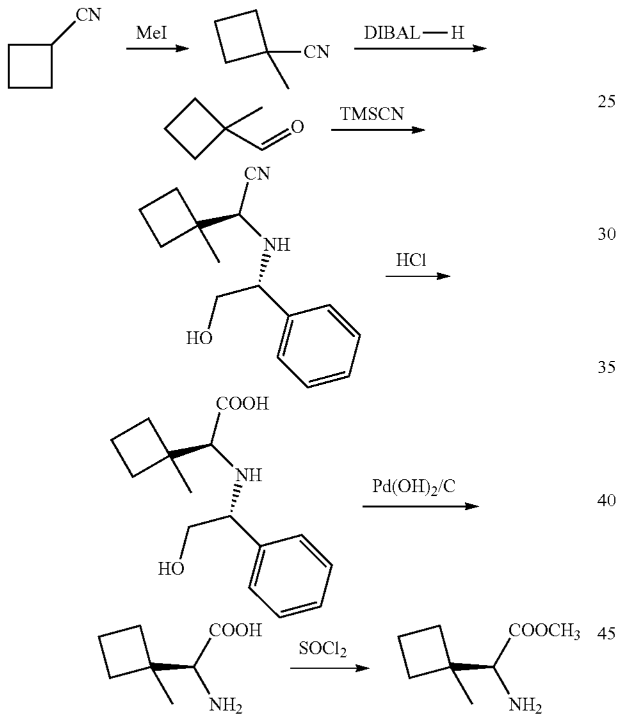

Step 1

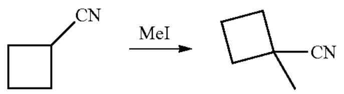

To a stirred solution of cyclobutanecarbonitrile (2.67 g, 32.96 mmol) in anhydrous THF (150 mL) was added LiHMDS (66 mL, 66.0 mmol, 1.0 N in THF) at −78° C. The resulting mixture was stirred at 0° C. for 30 minutes and then MeI (7.02 g, 49.44 mmol) was added at −78° C. The resulting reaction mixture was stirred at room temperature overnight, quenched with aq. sat. $NH_4Cl$ (100 mL) and the aqueous layer was extracted with DCM (50 mL×3). The combined organic layer was washed with brine (20 mL), dried over anhydrous $Na_2SO_4$, filtered and concentrated to afford 1-methylcyclobutanecarbonitrile (3.13 g, crude) as yellow oil, which was used directly in the next step without further purification. GCMS MS: m/z (ES+)=96 ($M+H^+$).

Step 2

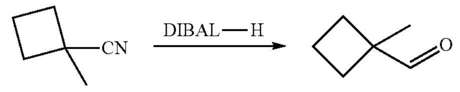

To a stirred solution of 1-methylcyclobutanecarbonitrile (3.13 g, crude) in anhydrous THF (100 mL) was added DIBAL-H (82.4 mL, 82.4 mmol, 1 N in toluene) slowly at −78° C. under $N_2$, and the resulting mixture was stirred at −78° C. for 2 h. Next, the mixture was diluted with water (50 mL) and extracted with DCM (50 mL×3), washed with brine (30 mL), dried over anhydrous $Na_2SO_4$, filtered and concentrated to afford 1-methylcyclobutanecarbaldehyde (3.23 g, crude) as yellow oil. GCMS MS: m/z (ES+)=99 ($M+H^+$).

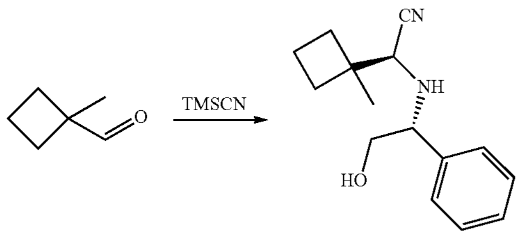

To a stirred solution of 1-methylcyclobutanecarbaldehyde (3.23 g, crude) in MeOH (30 mL), $ZnI_2$ (0.996 g, 3.12 mmol) and (R)-2-amino-2-phenylethanol (5.43 g, 39.55 mmol) were added. The mixture was stirred at room temperature for 30 min. Next TMSCN (4.89 g, 49.44 mmol) was added dropwise at 0° C., and the mixture was stirred for 16 h at room temperature. The solvent was concentrated and purified by silica gel column chromatography (PE/EA=5/1) to afford (2S)-2-[[(1R)-2-hydroxy-1-phenyl-ethyl]amino]-2-(1-methylcyclobutyl)acetonitrile (3.69 g, 46% for three steps) as yellow oil. LCMS: MS: m/z (ES+)=245 ($M+H^+$).

Step 4

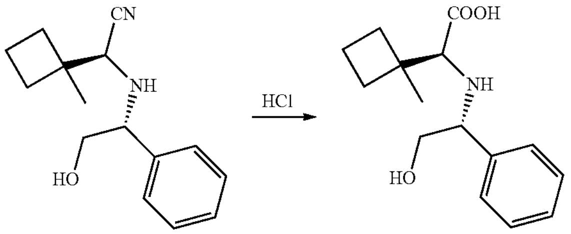 [SMILES: CC1([C@@H](C#N)N[C@@H](CO)c2ccccc2)CCC1 ; Cl ; CC1([C@H](N[C@@H](CO)c2ccccc2)C(=O)O)CCC1]

To a stirred solution of (2S)-2-[[(1R)-2-hydroxy-1-phenyl-ethyl]amino]-2-(1-methylcyclobutyl)acetonitrile (3.69 g, 15.1 mmol) in AcOH (20 mL) was added HCl (20 mL), the mixture was stirred at 80° C. overnight, and then concentrated to afford (2S)-2-[[(1R)-2-hydroxy-1-phenylethyl]amino]-2-(1-methylcyclobutyl)acetic acid (1.9 g, 48%) as a white solid, which was used directly in the next step without further purification. LCMS: MS: m/z (ES+)=264 (M+H$^+$).

Step 5

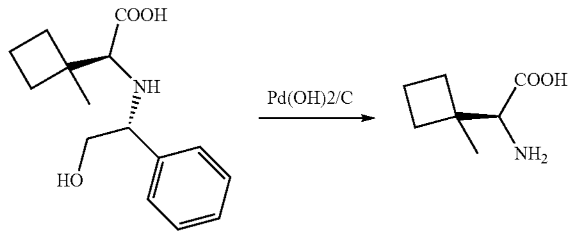

To a stirred solution of (2S)-2-[[(1R)-2-hydroxy-1-phenyl-ethyl]amino]-2-(1-methylcyclobutyl)acetic acid (1.8 g, 6.84 mmol) in AcOH (30 mL), $Pd(OH)_2/C$ (1.12 g, 0.81 mmol) was added. Next the mixture was stirred at room temperature under hydrogen overnight. Next the $Pd(OH)_2/C$ was filtered out and the solvent was removed in vacuo to afford (2S)-2-amino-2-(1-methylcyclobutyl)acetic acid (539 mg, 55%) as a white solid, which was used directly in the next step without further purification. LCMS: MS: m/z (ES+)=144 (M+H$^+$).

Step 6

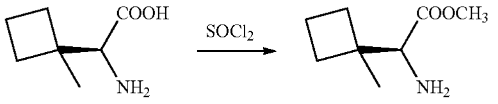

To a stirred solution of (2S)-2-amino-2-(1-methylcyclobutyl)acetic acid (539 mg, 3.77 mmol) in MeOH (20 mL) was added $SOCl_2$ (890 mg, 7.54 mmol). This mixture was stirred at 60° C. for 16 hours, concentrated and purified by prep-HPLC to afford methyl (2S)-2-amino-2-(1-methylcyclobutyl)acetate (551 mg, 93%) as a white solid.

LCMS: MS: m/z (ES+)=158.1 (M+H$^+$).

$^1$H NMR (400 MHz, $CDCl_3$) δ 8.76 (br s, 3H), 4.10 (s, 1H), 3.82 (s, 3H), 2.44-2.32 (m, 2H), 2.04-1.78 (m, 4H), 1.33 (s, 3H) ppm.

Intermediate Example 4. Preparation of 2-Methyl-7-(4-trifluoromethyl-benzyloxy)-benzo[b]thiophene-6-carboxylic acid 2-Methyl-7-(4-trifluoromethyl-benzyloxy)-benzo[b]thiophene-6-carboxylic acid was prepared according to the following scheme.

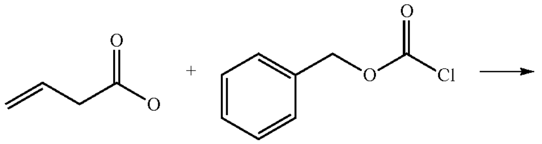

-continued

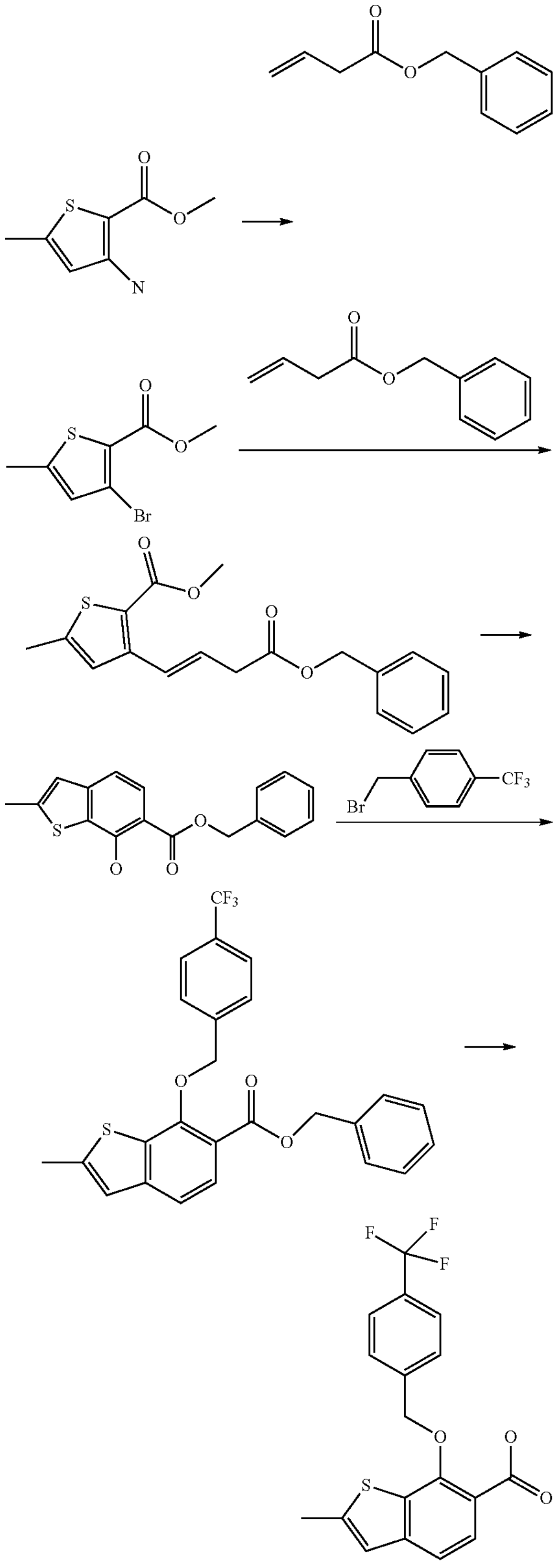

Step 1

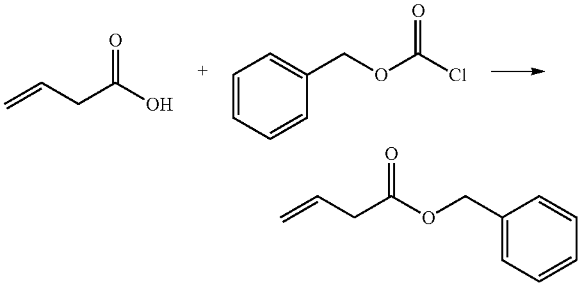

A mixture of but-3-enoic acid (3 g, 34.9 mmol) and pyridine (6.8 g, 86.3 mmol) was dissolved in the DCM (50 ml), benzyl carbonochloridate (6.5 g, 38.4 mmol) was added slowly at 0° C., the reaction mixture was stirred at RT for 2 hrs, the reaction mixture was monitored by LC-MS, then 1 N HCl was added, and then extracted with EA (50 ml×3), the organic layer was concentrated in vacuo and was purified by silica gel column chromatography (EA/PE=5/95) to get the desired product benzyl but-3-enoate (3.5 g, 57%) as a colourless oil.

LCMS Purity: 89%; MS: m/z (ES+)=177 ($M+H^+$).

Step 2

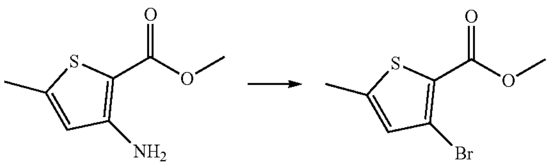

A mixture of $CuBr_2$ (1300 mg, 6.0 mmol) and tert-butylnitrite (772 mg, 7.5 mmol) was dissolved in the MeCN (20 ml), methyl 3-amino-5-methyl-thiophene-2-carboxylate (850 mg, 5.0 mmol) was added slowly at 0° C., the reaction mixture stirred at RT for 2 hrs. Next the reaction mixture was diluted with 1N HCl and extracted with EA (20 ml×3), washed with water brine and dried by $Na_2SO_4$ to yield the desired product methyl 3-bromo-5-methyl-thiophene-2-carboxylate (750 mg, 64%) as a colorless oil.

LCMS Purity: 75%; MS: m/z (ES+)=235 ($M+H^+$).

Step 3

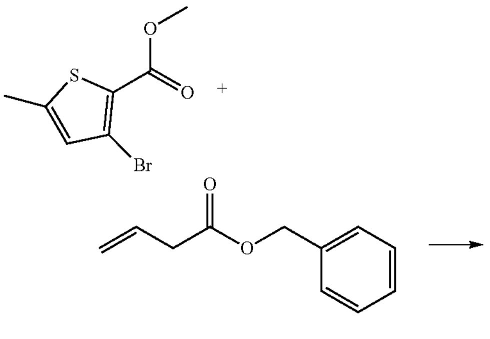

-continued

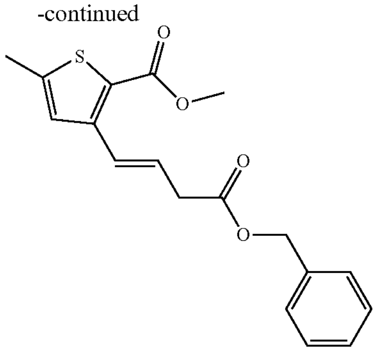

A mixture of methyl 3-bromo-5-methyl-thiophene-2-carboxylate (650 mg, 2.8 mmol) and benzyl but-3-enoate (733 mg, 4.2 mmol) was dissolved in dioxane (15 ml), N,N-dicyclohexylmethylamine (1.2 g, 6.2 mmol) was added and bis(tri-tert-butylphosphine)palladium(0) (14.3 mg, 0.028 mmol) was added under $N_2$ stream. The reaction mixture was stirred at 110° C. for 16 hrs, then the reaction mixture was monitored by LC-MS, the organic was concentrated in vacuo to yield the crude desired product methyl 3-[(E)-4-benzyloxy-4-oxo-but-1-enyl]-5-methyl-thiophene-2-carboxylate (700 mg, purity: 50%) as a yellow oil.

LCMS Purity: 50%; MS: m/z (ES+)=331 ($M+H^+$).

Step 4

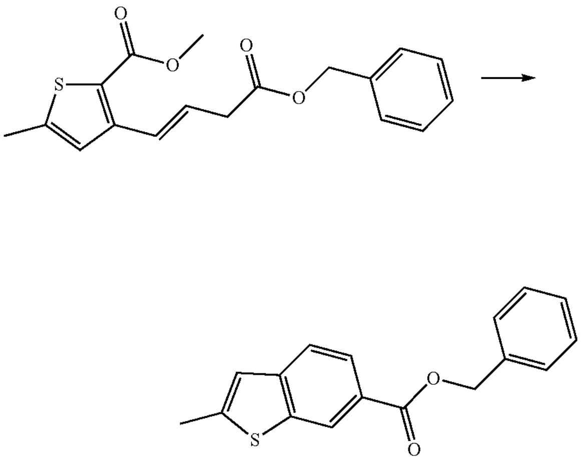 [SMILES: COC(=O)c1sc(C)cc1/C=C/CC(=O)OCc1ccccc1 ; Cc1cc2ccc(C(=O)OCc3ccccc3)cc2s1]

A mixture of methyl 3-[(E)-4-benzyloxy-4-oxo-but-1-enyl]-5-methyl-thiophene-2-carboxylate (100 mg, 0.30 mmol) was dissolved in THF (10 ml), t-BuOK (50 mg, 0.45 mmol) was added at 0° C., and the reaction mixture was stirred at RT for 16 hrs. The reaction mixture was monitored by LC-MS, then water was added and extracted with EA (20 ml×3), the organic layer was concentrated and purified by silica gel column chromatography (EA/PE=5/95) to yield the desired product benzyl 7-hydroxy-2-methyl-benzothiophene-6-carboxylate (200 mg, 30%) as a white solid. LCMS Purity: 70%; MS: m/z ($ES^+$)=299 ($M+H^+$).

Step 5

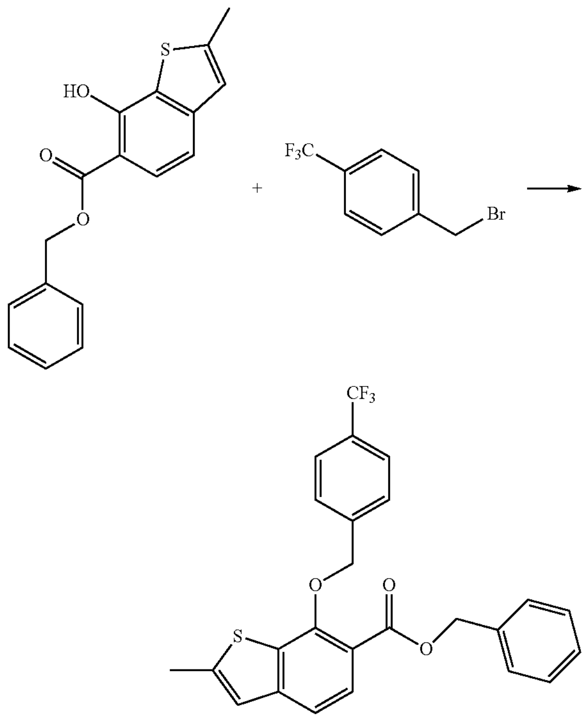

A mixture of benzyl 7-hydroxy-2-methyl-benzothiophene-6-carboxylate (50 mg, 0.23 mmol) was dissolved in the DMF (5 ml), then $Cs_2CO_3$ (150 mg, 0.46 mmol) and 1-(bromomethyl)-4-(trifluoromethyl) benzene (61 mg, 0.25 mmol) were added separately, then the reaction mixture was stirred at RT for 1 hr. The reaction mixture was analyzed by LC-MS to determine the presence of the desired product, then water was added and extracted with EA (20 ml×3), the organic layer was concentrated to yield the crude desired product benzyl 2-methyl-7-[[4-(trifluoromethyl)phenyl]methoxy]benzothiophene-6-carboxylate (300 mg, purity: 50%) as a yellow oil. LCMS Purity: 50%; MS: m/z (ES+)=457 (M+H$^+$).

Step 6

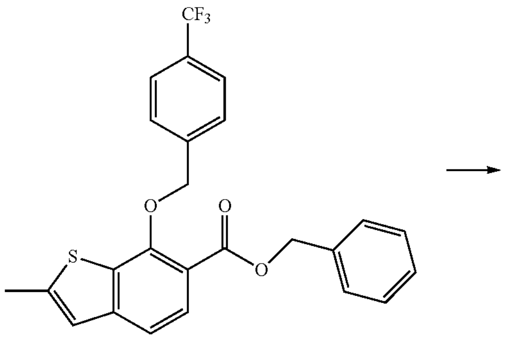

-continued

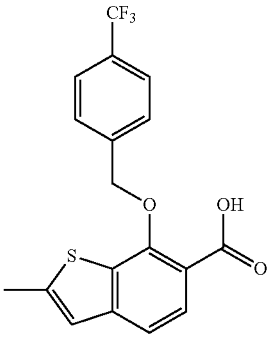

A mixture of benzyl 2-methyl-7-[[4-(trifluoromethyl)phenyl]methoxy]benzothiophene-6-carboxylate (300 mg, 0.78 mmol) was dissolved in THF (25 ml) and $H_2O$ (5 ml), NaOH (126.3 mg, 3.16 mmol) was added, and the reaction mixture was stirred at 50° C. for 16 hrs. The reaction mixture was analyzed by LC-MS to determine the presence of the desired product, then the reaction mixture was adjusted to ~pH 5 with 1 N HCl, and then extracted with EA (20 ml×3), the organic layer was concentrated and purified by silica gel column chromatography (EA/PE=20/80) to get yield desired 2-Methyl-7-(4-trifluoromethyl-benzyloxy)-benzo[b]thiophene-6-carboxylic acid (200 mg, 90%) as a white solid. LCMS Purity: 97%; MS: m/z (ES+)=367 (M+H$^+$).

Intermediate Example 5. Preparation of 2-Methyl-7-(4-trifluoromethyl-benzyloxy)-benzo[b]thiophene-6-carboxylic acid

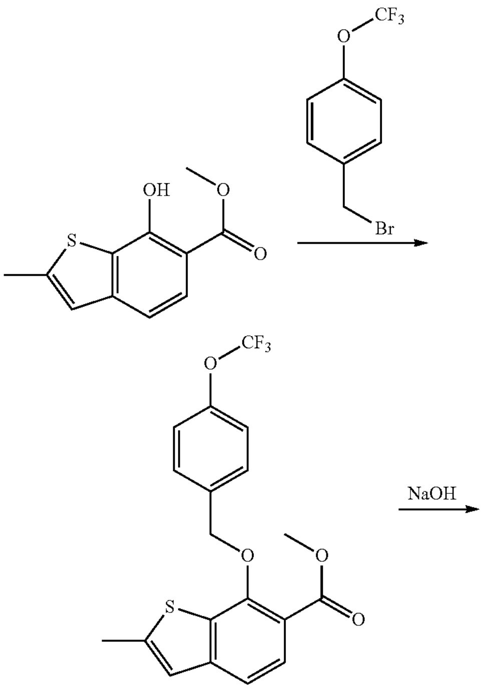

-continued

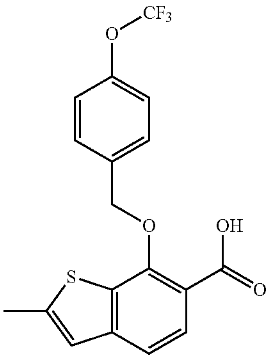

2-Methyl-7-(4-trifluoromethyl-benzyloxy)-benzo[b]thiophene-6-carboxylic acid can be synthesized by coupling of methyl 7-hydroxy-2-methyl-benzothiophene-6-carboxylate with 1-(bromomethyl)-4-(trifluoromethoxy)benzene to obtain an ester. Hydrolysis of the ester yielded the desired acid as brown oil. LCMS Purity: 89%; MS: m/z (ES+)=382 ($M+H^+$).

Intermediate Example 6A. Preparation of 2-ethyl-7-[[4-(trifluoromethoxy)phenyl]methoxy]benzothiophene-6-carboxylic acid 2-Ethyl-7-[[4-(trifluoromethoxy)phenyl]methoxy]benzothiophene-6-carboxylic acid was prepared according to the following scheme:

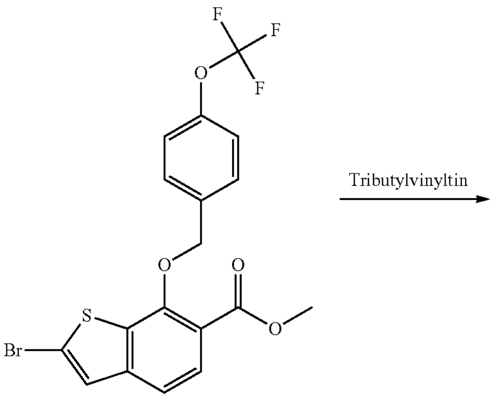

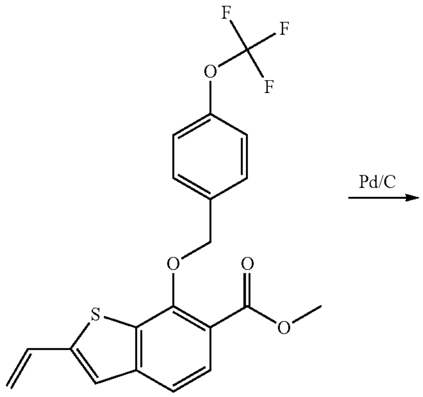

-continued

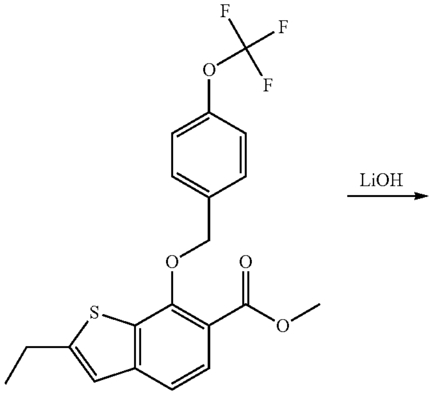

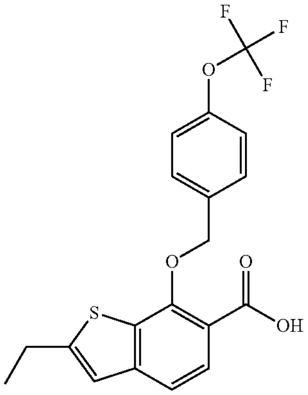

Step 1

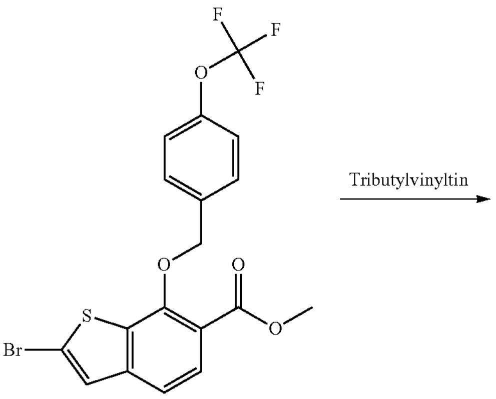

-continued

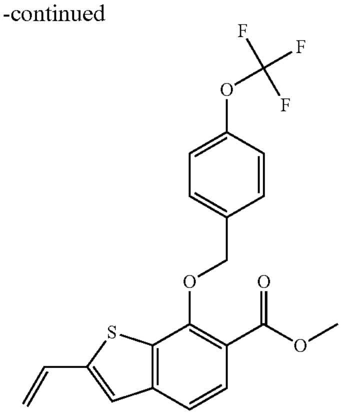

A solution of methyl 2-bromo-7-[[4-(trifluoromethoxy) phenyl]methoxy]-benzothiophene-6-carboxylate (350 mg, 0.76 mmol), tributylvinyltin (482 mg, 1.52 mmol), $(PPh_3)_4Pd$ (88 mg, 0.08 mmol) in DMF (5 mL) was stirred at 90° C. for 3 hours under $N_2$. Next, the mixture was diluted with aqueous KF (50 mL) and extracted with EA (50 mL), washed with brine (50 mL), dried over anhydrous $Na_2SO_4$, filtered and concentrated in vacuo, and the residue was purified by silica gel chromatography (PE/EA=1/10) to afford methyl 7-[[4-(trifluoromethoxy)phenyl]methoxy]-2-vinyl-benzothiophene-6-carboxylate (220 mg, 71%) as white solid. LCMS Purity: 94%; MS: m/z (ES+)=409 ($M+H^+$).

Step 2

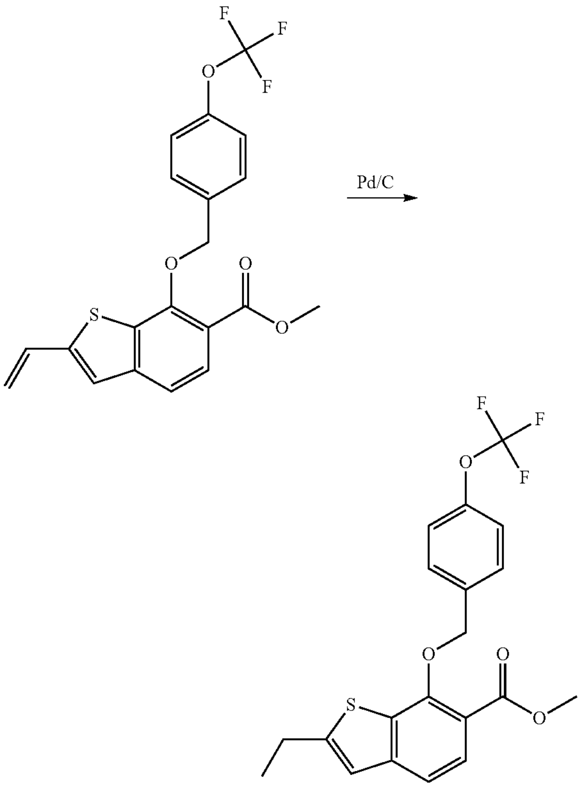

To a solution of methyl 7-[[4-(trifluoromethoxy)phenyl] methoxy]-2-vinyl-benzothiophene-6-carboxylate (220 mg, 0.54 mmol) in MeOH (10 mL) was added 10% Pd/C (50 mg), and the reaction mixture was stirred at room temperature under $H_2$ atmosphere overnight. The resulting mixture was filtered and concentrated in vacuo to afford methyl 2-ethyl-7-[[4-(trifluoromethoxy)phenyl]methoxy]benzothiophene-6-carboxylate (220 mg, crude) as yellow solid. LCMS Purity: 89%; MS: m/z (ES+)=411 ($M+H^+$).

Step 3

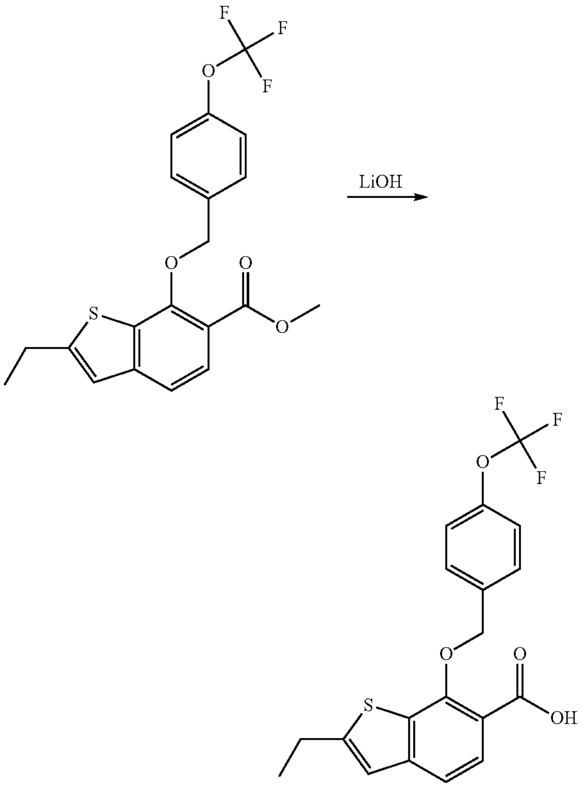

To a stirred solution of methyl 2-ethyl-7-[[4-(trifluoromethoxy)phenyl]methoxy]-benzothiophene-6-carboxylate (220 mg, crude) in MeOH/THF/$H_2O$ (10 mL/10 mL/1 mL) was added $LiOH \cdot H_2O$ (113 mg, 2.70 mmol). The solution was stirred at 70° C. overnight. The solution was concentrated and then acidified with aqueous hydrochloric acid (2 N) to pH=4-5, extracted with EA (50 mL) and washed with brine (50 mL), dried over anhydrous $Na_2SO_4$, filtered and concentrated in vacuo to afford 2-ethyl-7-[[4-(trifluoromethoxy)phenyl]methoxy]benzothiophene-6-carboxylic (197 mg, crude) as yellow solid. LCMS Purity: 96%; MS: m/z (ES+)=397 ($M+H^+$).

Intermediate Example 6B. Preparation of 2-(trifluoromethyl)-7-[[4-(trifluoromethyl)phenyl]methoxy] benzothiophene-6-carboxylic acid

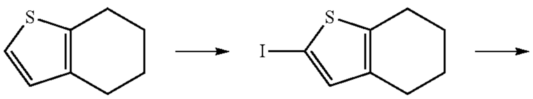

-continued

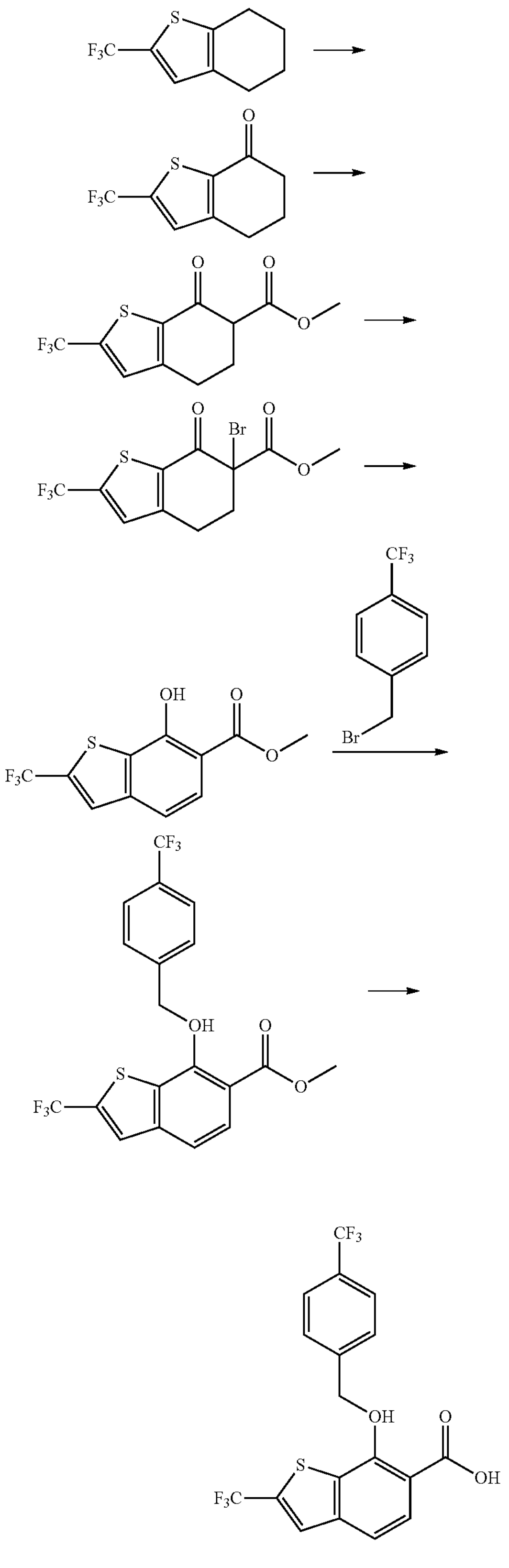

Step 1

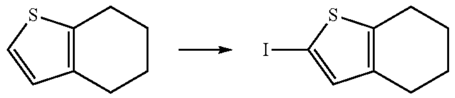 [SMILES: c1cc2c(s1)CCCC2 ; Ic1cc2c(s1)CCCC2]

To a stirred solution of 4,5,6,7-tetrahydrobenzothiophene (1380 mg, 10 mmol) in DCM/AcOH was added NIS (2230 mg, 10.0 mmol). The solution was stirred at 20° C. overnight. The solution was extracted with EA (55 mL), washed with brine (5 mL), dried over anhydrous $Na_2SO_4$, filtered and concentrated in vacuo, and the residue was purified by SGC (PE) to afford 2-iodo-4,5,6,7-tetrahydrobenzothiophen (1.97 g, 75%) as black oil. $^1$H NMR (400 MHz, $CDCl_3$) δ 6.88 (s, 1H), 2.70-2.47 (m, 4H), 1.81-1.74 (m, 4H) ppm.

Step 2

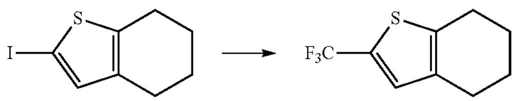 [SMILES: Ic1cc2c(s1)CCCC2 ; FC(F)(F)c1cc2c(s1)CCCC2]

An oven-dried test tube with a septum cap and a stir bar was charged with copper (I) iodide (170 mg, 0.9 mmol), 1,10-phenanthroline (160 mg, 0.9 mmol), KF (530 mg, 9.0 mmol). The reaction vessel was closed, then evacuated and refilled with argon or nitrogen three times. DMSO (8.0 mL) and 2-iodo-4,5,6,7-tetrahydrobenzothiophen (792 mg, 3 mmol), $B(OMe)_3$ (930 mg, 9.0 mmol), $TMSCF_3$ (1300 mg, 9.0 mmol) were added via syringe. The resulting orange-brown suspension was stirred for 20 h at 65° C. The mixture was extracted with ether (3×20 mL). The organic layers were combined, washed with brine, dried and concentrated to give 2-(trifluoromethyl)-4,5,6,7-tetrahydrobenzothiophene (741 mg, 90%) as black oil.

Step 3

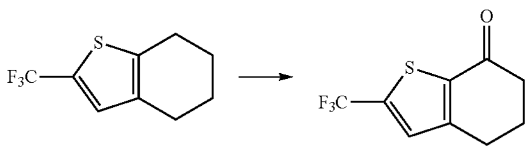 [SMILES: FC(F)(F)c1cc2c(s1)CCCC2 ; O=C1CCCc2cc(C(F)(F)F)sc21]

To a solution of 2-(trifluoromethyl)-4,5,6,7-tetrahydrobenzothiophene (500 mg, 2.43 mmol) in HOAc (20 mL) and water (20 mL) was added ceric ammonium nitrate (6.65 g, 12.15 mmol) at 0° C., then the reaction mixture was stirred at room temperature overnight. 60 mL of water was added, extracted with EA (20 mL×3), washed with aqueous $NaHCO_3$ (30 mL) and brine (30 mL), dried over $Na_2SO_4$, filtered and concentrated in vacuo, and purified by silica gel column chromatography (EA/PE=1/20) to afford 2-(trifluoromethyl)-5,6-dihydro-4H-benzothiophen-7-one (160 mg, 30%) as yellow oil. MS: m/z (ES+)=221 (M+H$^+$).

Step 4

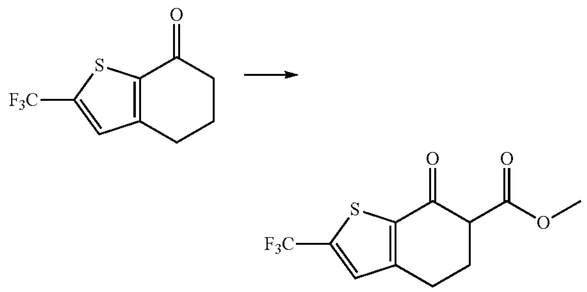

To a stirred solution of NaH (58 mg, 1.45 mmol, 60% in oil) in $Me_2CO_3$ (10 mL) was added MeOH (0.1 mL) and 2-(trifluoromethyl)-5,6-dihydro-4H-benzothiophen-7-one (160 mg, 0.73 mmol) at room temperature. The resulting solution was heated at 70° C. for 4 hours. The mixture was cooled in ice, treated with HCl (2 N) to pH=7, extracted with EA (20 mL×3), washed with sat. aqueous $NaHCO_3$ (10 mL), brine (10 mL) and $H_2O$ (10 mL), dried over $Na_2SO_4$, filtered and concentrated to afford methyl 7-oxo-2-(trifluoromethyl)-5,6-dihydro-4H-benzothiophene-6-carboxylate (200 mg, crude) as yellow oil, which was used directly in the next step without further purification. MS: m/z (ES+)=279 ($M+H^+$).

Step 5

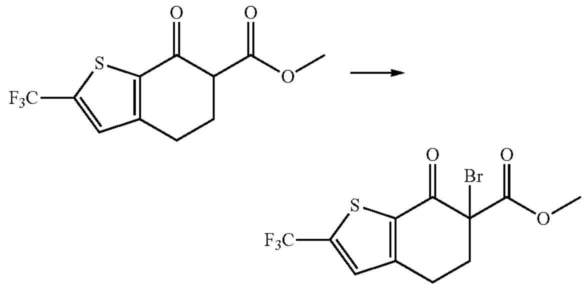

To a solution of methyl 7-oxo-2-(trifluoromethyl)-5,6-dihydro-4H-benzothiophene-6-carboxylate (200 mg, crude) in $CHCl_3$ (20 mL) was added NBS (143 mg, 0.8 mmol) and AIBN (cat.) at room temperature, and the reaction mixture was stirred under reflux for 1 hour, and concentrated to afford methyl 6-bromo-7-oxo-2-(trifluoromethyl)-4,5-dihydrobenzothiophene-6-carboxylate (260 mg, crude) as yellow oil, which was used directly in the next step without further purification. MS: m/z (ES+)=357 ($M+H^+$).

Step 6

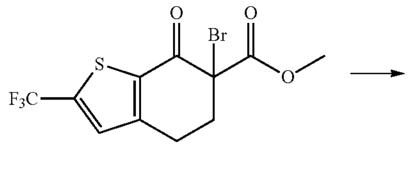

-continued

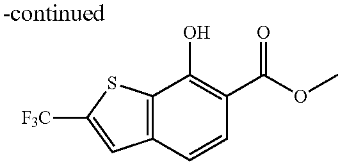

To a solution of methyl 6-bromo-7-oxo-2-(trifluoromethyl)-4,5-dihydrobenzothiophene-6-carboxylate (260 mg, crude) in THF (20 mL) was added DBU (333 mg, 2.19 mmol) at room temperature, and the reaction was stirred at room temperature for 4 hours, adjusted pH to 6 with 1 N HCl, extracted with EA (20 mL×3), washed with brine (20 mL), dried over $Na_2SO_4$, filtered and concentrated, and finally purified by silica gel chromatography (PE/EA=30/1) to afford methyl 7-hydroxy-2-(trifluoromethyl)benzothiophene-6-carboxylate (120 mg, 60% for three steps) as a white solid. MS: m/z (ES+)=277 ($M+H^+$).

Step 7

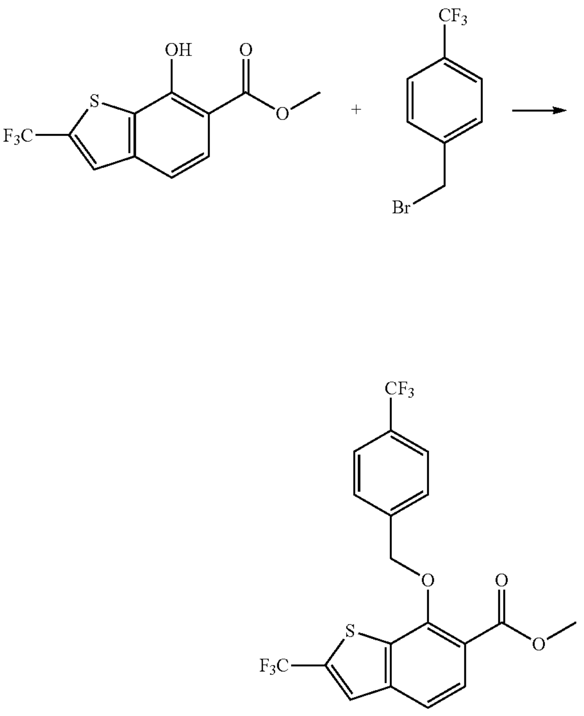

To a stirred solution of methyl 7-hydroxy-2-(trifluoromethyl)benzothiophene-6-carboxylate (60 mg, 0.22 mmol) in DMF (10 mL) were added 1-(bromomethyl)-4-(trifluoromethyl)benzene (62 mg, 0.26 mmol) and $Cs_2CO_3$ (143 mg, 0.44 mmol). The resulting mixture was stirred at room temperature for 4 hours, diluted with water (30 mL), and extracted with EA (20 mL×3), washed with brine (20 mL×2), dried over anhydrous sodium sulfate, filtered and concentrated in vacuo to afford methyl 2-(trifluoromethyl)-7-[[4-(trifluoromethyl)phenyl]methoxy]benzothiophene-6-carboxylate (84 mg, 89%) as a yellow oil, which was used directly in the next step without further purification. MS: m/z (ES+)=435 ($M+H^+$).

Step 8

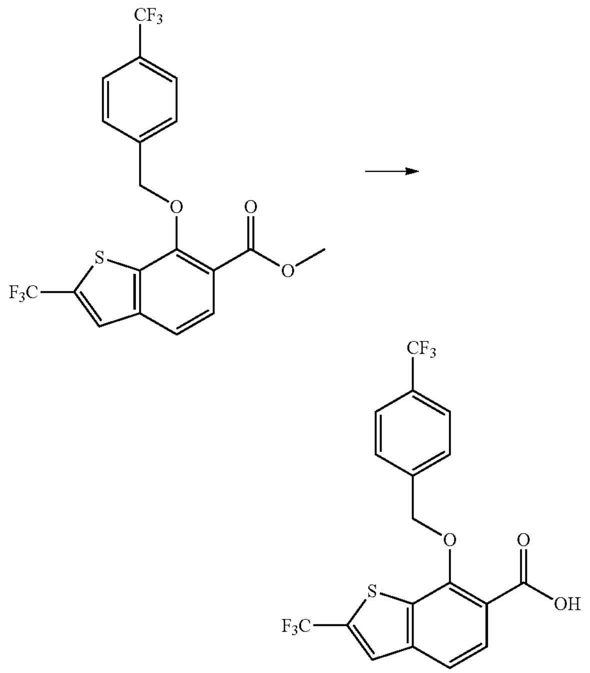

To a stirred solution of methyl 2-(trifluoromethyl)-7-[[4-(trifluoromethyl)phenyl]methoxy]benzothiophene-6-carboxylate (84 mg, 0.19 mmol) in MeOH/THF/$H_2O$ (10 mL/10 mL/1 mL) was added LiOH·$H_2O$ (24 mg, 0.58 mmol). The solution was stirred at 70° C. overnight. The solution was concentrated and then acidified with aqueous hydrochloric acid (2 N) to pH=4-5 and extracted with EA (20 mL×3). The combined organic phases were washed with brine (20 mL), dried over anhydrous sodium sulfate, filtered and concentrated in vacuo, and purified by silica gel column chromatography (PE/EA=1/1) to afford 2-(trifluoromethyl)-7-[[4-(trifluoromethyl)phenyl]methoxy]benzothiophene-6-carboxylic acid (77 mg, 95%) as a white solid. MS: m/z (ES+)=421 (M+$H^+$).

Intermediate Example 6C. Preparation of 7-[[4-(trifluoromethoxy)phenyl]methoxy]-2-(trifluoromethyl)-benzothiophene-6-carboxylic acid Similarly, 7-[[4-(trifluoromethoxy)phenyl]methoxy]-2-(trifluoromethyl)benzothiophene-6-carboxylic acid was prepared by coupling of methyl 7-hydroxy-2-(trifluoromethyl)benzothiophene-6-carboxylate with 1-(bromomethyl)-4-(trifluoromethoxy)benzene, followed by hydrolysis.

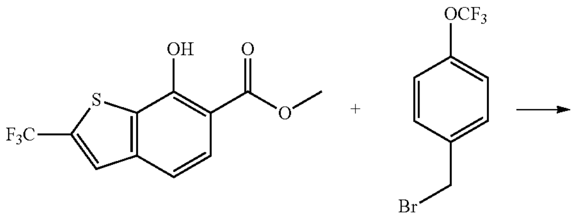

-continued

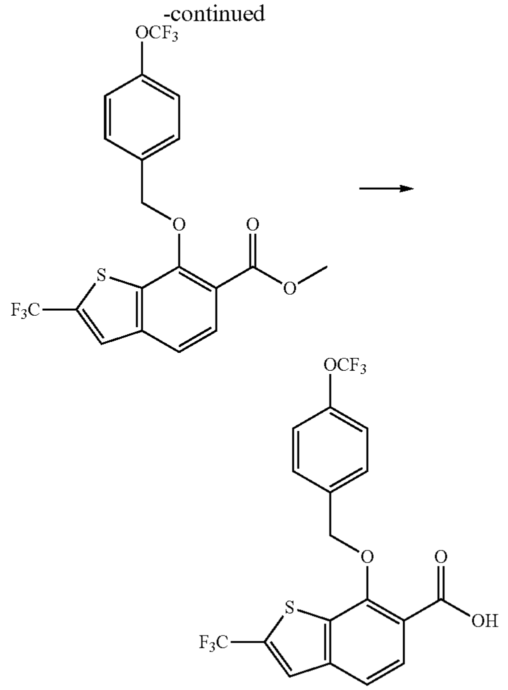

To a stirred solution of methyl 7-hydroxy-2-(trifluoromethyl)benzothiophene-6-carboxylate (60 mg, 0.22 mmol) in DMF (10 mL) were added 1-(bromomethyl)-4-(trifluoromethoxy)benzene (66 mg, 0.26 mmol) and $Cs_2CO_3$ (143 mg, 0.44 mmol). The resulting mixture was stirred at room temperature for 4 hours, diluted with water (50 mL), and extracted with EA (20 mL×3), washed with brine (20 mL×2), dried over anhydrous sodium sulfate, filtered and concentrated in vacuo to afford the ester (75 mg, 80%) as a yellow oil, which was used directly in the next step without further purification. MS: m/z (ES+)=451 (M+$H^+$).

To a stirred solution of the ester obtained above (75 mg, 0.17 mmol) in MeOH/THF/$H_2O$ (10 mL/10 mL/1 mL) was added LiOH·$H_2O$ (21 mg, 0.51 mmol). The solution was stirred at 70° C. overnight. The solution was concentrated and then acidified with aqueous hydrochloric acid (2 N) to pH=4-5 and extracted with EA (20 mL×3). The combined organic phase was washed with brine (20 mL), dried over anhydrous sodium sulfate, filtered and concentrated in vacuo, and purified by silica gel column chromatography (PE/EA=1/1) to afford 7-[[4-(trifluoromethoxy)phenyl]methoxy]-2-(trifluoromethyl)benzothiophene-6-carboxylic acid (69 mg, 95%) as a white solid. MS: MS: m/z (ES+)=437 (M+$H^+$).

Intermediate Example 7. Preparation of 2-isopropyl-7-[[4-(trifluoromethyl)phenyl]methoxy]benzothiophene-6-carboxylic acid

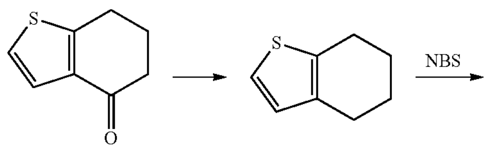

-continued

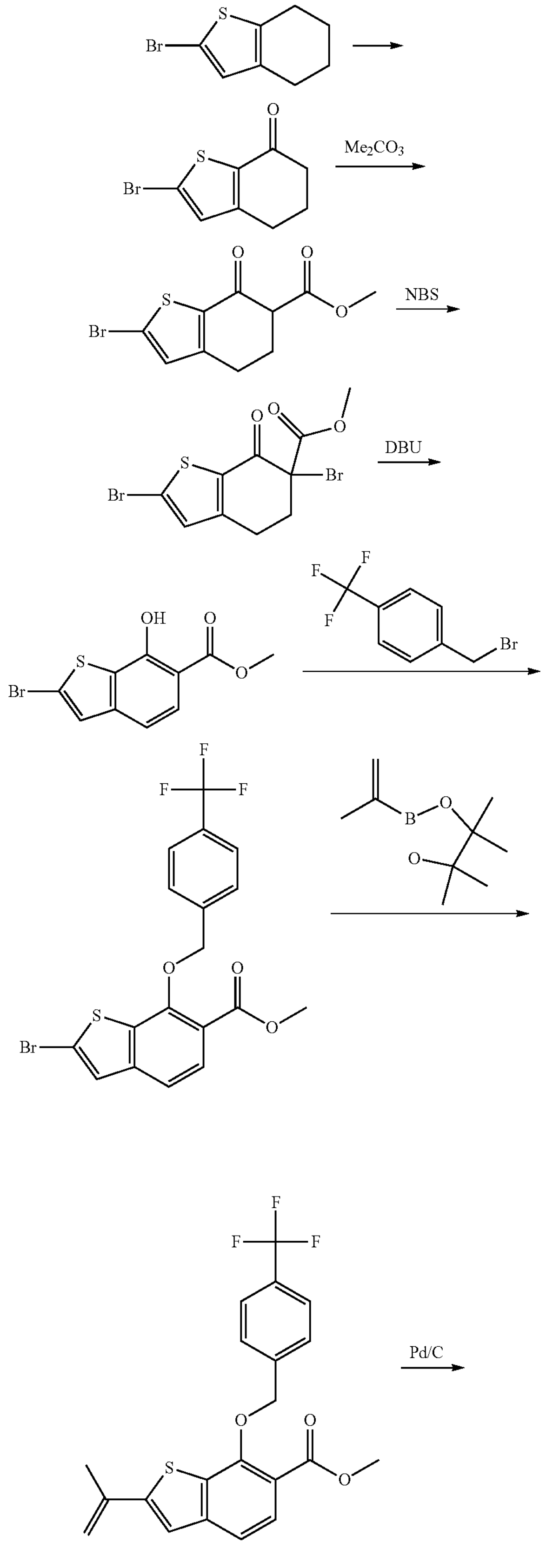

-continued

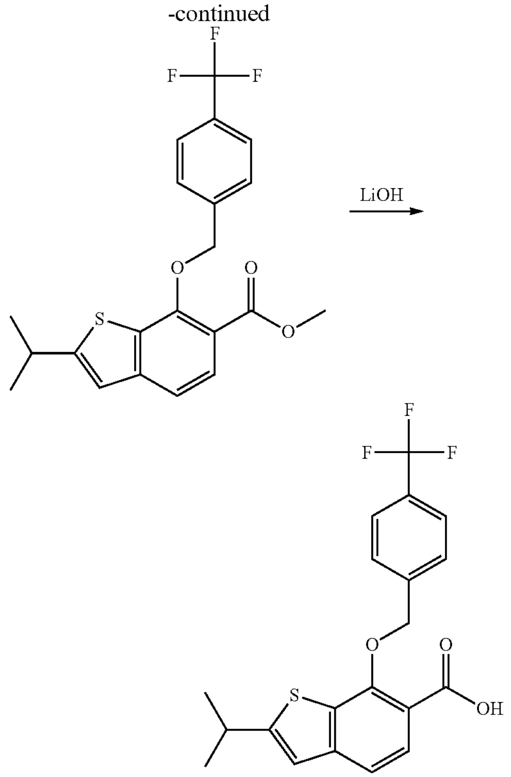

Step 1

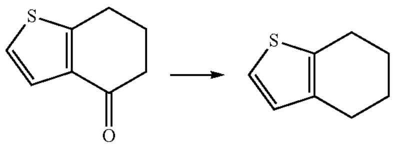 [SMILES: O=C1CCCc2sccc21 ; c1cc2c(s1)CCCC2]

To a solution of 6,7-dihydro-5H-benzothiophen-4-one (10.0 g, 65.8 mmol) in diethylene glycol (100 mL) were added hydrazine monohydrate (13.5 g, 230.3 mmol, 85% in water) and KOH (12.9 g, 230.3 mmol), and the solution was stirred at 180° C. overnight. Next, the reaction was cooled to room temperature and diluted with water (100 mL), the aqueous phase was adjusted to pH 6 with HCl (2 N), extracted with EA (100 mL), washed with brine (100 mL) and dried over $Na_2SO_4$, filtered and concentrated in vacuo to afford 4,5,6,7-tetrahydrobenzothiophene (9.0 g, crude) as a yellow oil, which used directly for the next step.

LCMS Purity: 95%; MS: m/z $(ES^+)$=139 $(M+H^+)$.

Step 2

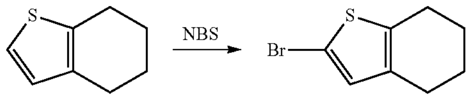

To a solution of 4,5,6,7-tetrahydrobenzothiophene (9.0 g, crude) in DCM (100 mL) was added NBS (12.2 g, 68.5 mmol) at room temperature, and the reaction mixture was stirred at room temperature for 2 hours. Following, the reaction was concentrated in vacuo and 50 mL of water was added, extracted with EA (50 mL), washed with brine (50 mL) and dried over $Na_2SO_4$, filtered and concentrated in vacuo to afford 2-bromo-4,5,6,7-tetrahydrobenzothiophene (11.2 g, crude) as yellow oil, which used directly for the next step. LCMS Purity: 95%; MS: m/z ($ES^+$)=217 ($M+H^+$).

Step 3

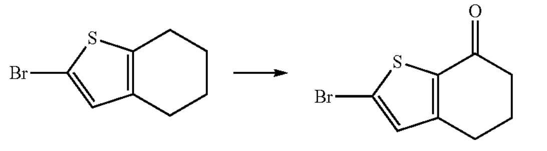 [SMILES: Brc1cc2c(s1)CCCC2 ; O=C1CCCc2cc(Br)sc21]

To a solution of 2-bromo-4,5,6,7-tetrahydrobenzothiophene (11.2 g, crude) in HOAc (100 mL) and water (100 mL) was added ceric ammonium nitrate (113.1 g, 206.4 mmol) at 0° C., then the reaction mixture was stirred at room temperature overnight. 100 mL of water was added, extracted with EA (100 mL), washed with aqueous $NaHCO_3$ (100 mL) and brine (100 mL), dried over $Na_2SO_4$, filtered and concentrated in vacuo, and purified by silica gel column chromatography (EA/PE=1/20) to afford 2-bromo-5,6-dihydro-4H-benzothiophen-7-one (6.8 g, 45% of three steps) as yellow oil. LCMS Purity: 85%; MS: m/z ($ES^+$)=231 ($M+H^+$).

Step 4

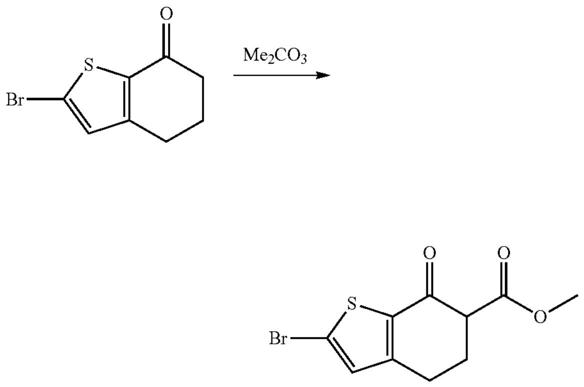

To a stirred solution of NaH (3.3 g, 81.81 mmol, 60% in oil) in $Me_2CO_3$ (70 mL) was added ST1-2-bromo-5,6-dihydro-4H-benzothiophen-7-one (6.3 g, 27.27 mmol) at room temperature, and the solution was heated at 70° C. for 2 hours. The reaction was next cooled and adjusted to pH 4 with HCl (2 N), extracted with EA (100 mL), washed with brine (100 mL) and dried over anhydrous $Na_2SO_4$, filtered and concentrated in vacuo, and finally purified by silica gel column chromatography (EA/PE=1/10) to afford methyl 2-bromo-7-oxo-5,6-dihydro-4H-benzothiophene-6-carboxylate (6.2 g, 79%) as a yellow oil. LCMS Purity: 92%; MS: m/z ($ES^+$)=289 ($M+H^+$).

Step 5

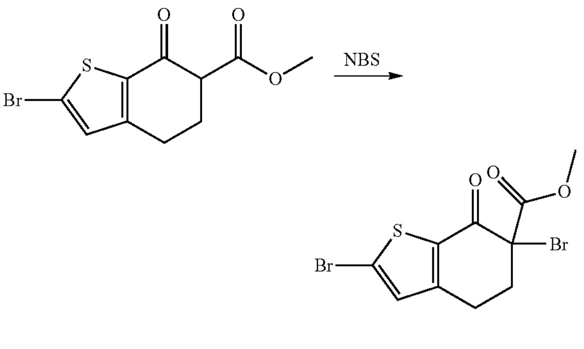

To a solution of methyl 2-bromo-7-oxo-5,6-dihydro-4H-benzothiophene-6-carboxylate (5.1 g, 18.0 mmol) in $CHCl_3$ (50 mL) was added NBS (3.5 g, 19.8 mmol) and AIBN (148 mg, 0.9 mmol) at room temperature, and the reaction mixture was stirred under reflux for 1 hours, concentrated in vacuo to afford methyl 2,6-dibromo-7-oxo-4,5-dihydrobenzothiophene-6-carboxylate (9.0 g, crude) as a red oil, which was used directly for the next step. LCMS Purity: 94%; MS: m/z ($ES^+$)=369 ($M+H^+$).

Step 6

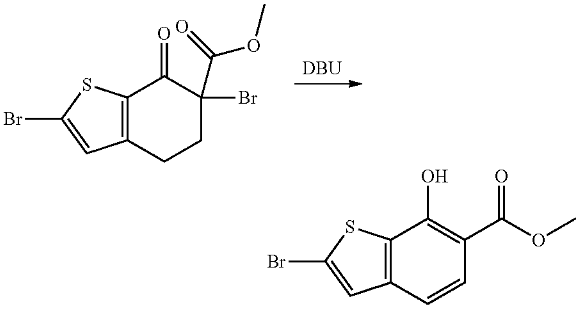

To a solution of methyl 2,6-dibromo-7-oxo-4,5-dihydrobenzothiophene-6-carboxylate (9.0 g, crude) in THF (100 mL) was added DBU (8.2 g, 54.0 mmol) at room temperature, the solution was stirred at room temperature for 2 hours, adjusted pH to 6 with 1 N HCl, extracted with EA (100 mL), washed with brine (100 mL), dried over anhydrous $Na_2SO_4$, filtered and concentrated in vacuo, and finally the residue was purified by silica gel chromatography (PE/EA=1/50) to afford methyl 2-bromo-7-hydroxy-benzothiophene-6-carboxylate (3.0 g, 60% of two steps) as a white solid. LCMS Purity: 54%; MS: m/z ($ES^+$)=288 ($M+H^+$).

Step 7

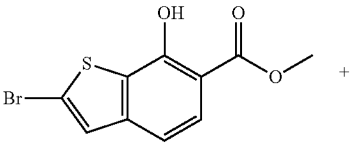

-continued

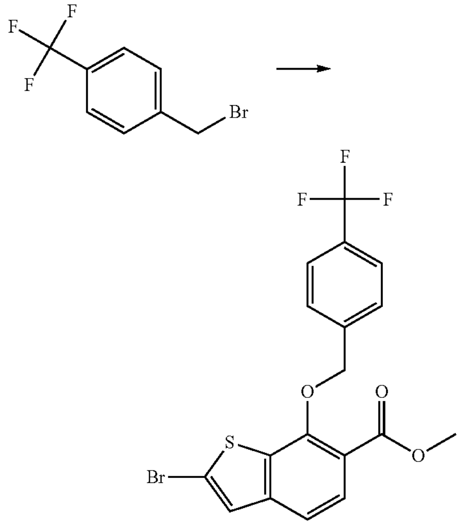

To a stirred solution of methyl 2-bromo-7-hydroxy-benzothiophene-6-carboxylate (200 mg, 0.77 mmol) in DMF (10 mL) were added the bromide (184 mg, 0.77 mmol) and $Cs_2CO_3$ (456 mg, 1.40 mmol). The resulting mixture was stirred at room temperature for 1 h, diluted with water (50 mL) and extracted with EA (50 mL), washed with brine (50 mL), dried over anhydrous $Na_2SO_4$, filtered and concentrated in vacuo, and the residue was purified by silica gel chromatography (EA/PE=1/10) to afford methyl 2-bromo-7-[[4-(trifluoromethyl)phenyl]methoxy]benzothiophene-6-carboxylate (310 mg, crude) as a yellow oil.

LCMS Purity: 86%; MS: m/z ($ES^+$)=446 ($M+H^+$).

Step 8

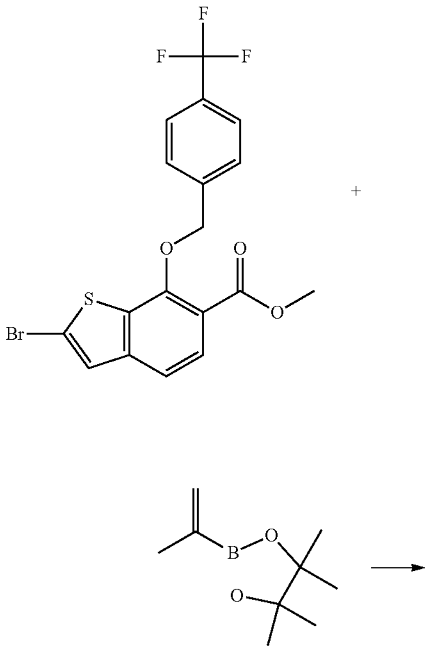

-continued

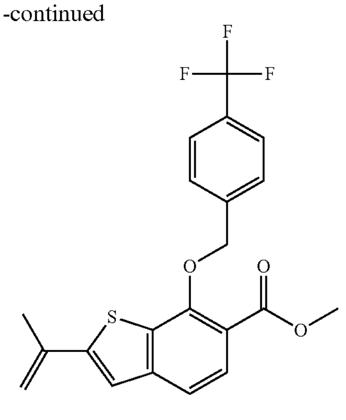

A solution of methyl 2-bromo-7-[[4-(trifluoromethyl)phenyl]methoxy]-benzothiophene-6-carboxylate (310 mg, crude), 2-isopropenyl-4,4,5,5-tetramethyl-1,3,2-dioxaborolane (129 mg, 0.77 mmol), $(PPh_3)_4Pd$ (24 mg, 0.02 mmol), $K_2CO_3$ (290 mg, 2.10 mmol) in 1,4-dioxane (10 mL) and $H_2O$ (10 mL) was stirred at 85° C. for 1 hour under $N_2$. Next, the reaction was diluted with water (50 mL) and extracted with EA (50 mL), washed with brine (50 mL), dried over anhydrous $Na_2SO_4$, filtered and concentrated in vacuo to afford methyl 2-isopropenyl-7-[[4-(trifluoromethyl)phenyl]methoxy]benzothiophene-6-carboxylate (150 mg, crude) as a yellow oil.

LCMS Purity: 91%; MS: m/z ($ES^+$)=407 ($M+H^+$).

Step 9

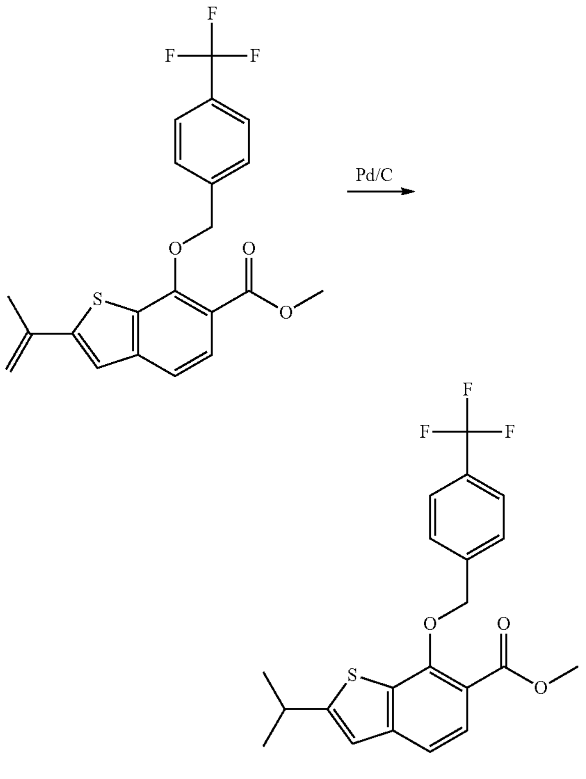

To a solution of methyl 2-isopropenyl-7-[[4-(trifluoromethyl)phenyl]methoxy]benzothiophene-6-carboxylate (150 mg, crude) in MeOH (10 mL) was added 10% Pd/C (30 mg), and the reaction mixture was stirred at room temperature under $H_2$ atmosphere overnight. The resulting mixture was filtered and concentrated in vacuo, and the residue was purified by prep-TLC to afford methyl 2-isopropyl-7-[[4-(trifluoromethyl)phenyl]methoxy]benzothiophene-6-carboxylate (100 mg, 35% of three steps) as white solid. LCMS Purity: 89%; MS: m/z ($ES^+$)=409 ($M+H^+$).

Step 10

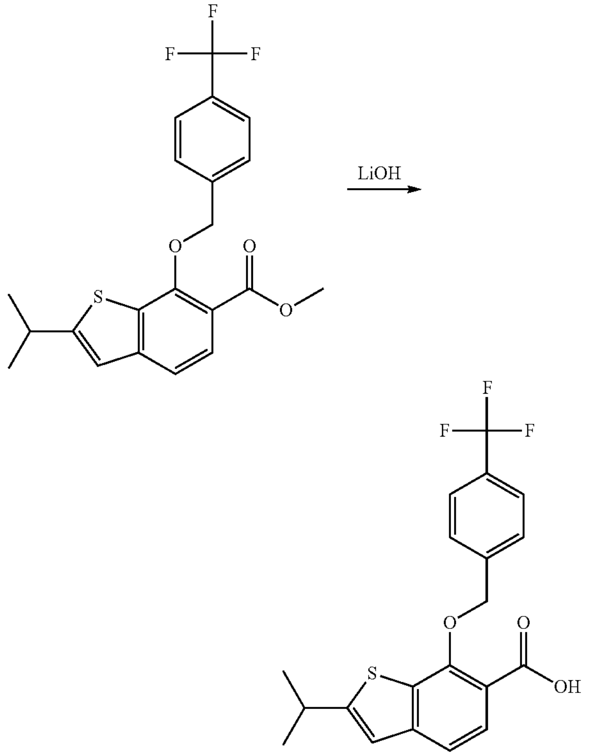

To a stirred solution of methyl 2-isopropyl-7-[[4-(trifluoromethyl)phenyl]methoxy]-benzothiophene-6-carboxylate (100 mg, 0.25 mmol) in MeOH/THF/$H_2O$ (10 mL/10 mL/1 mL) was added LiOH·$H_2O$ (53 mg, 1.25 mmol). The solution was stirred at 70° C. overnight. The solution was concentrated and then acidified with aqueous hydrochloric acid (2 N) to pH=4-5, extracted with EA (50 mL) and washed with brine (50 mL), dried over anhydrous $Na_2SO_4$, filtered and concentrated in vacuo to afford 2-isopropyl-7-[[4-(trifluoromethyl)phenyl]methoxy]benzothiophene-6-carboxylic acid (90 mg, crude) as white solid. LCMS Purity: 96%; MS: m/z ($ES^+$)=395 ($M+H^+$).

Intermediate Example 8. Preparation of 2-isopropyl-7-[[4-(trifluoromethoxy)phenyl]methoxy]benzothiophene-6-carboxylic acid 2-isopropyl-7-[[4-(trifluoromethoxy)phenyl]methoxy] benzothiophene-6-carboxylic acid was prepared similarly by coupling of methyl 2-bromo-7-hydroxy-benzothiophene-6-carboxylate with 1-(bromomethyl)-4-(trifluoromethoxy) benzene.

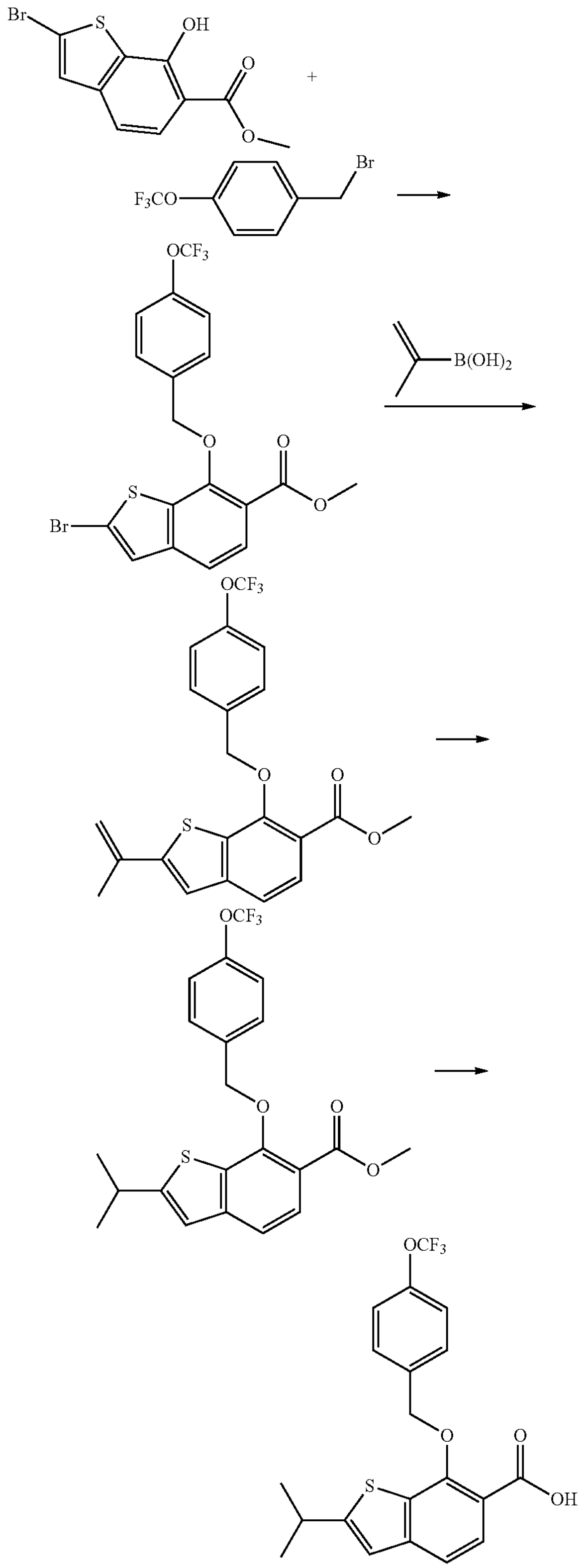

Step 1

To a solution of methyl 2-bromo-7-hydroxy-benzothiophene-6-carboxylate (1.5 g, 5.2 mmol) in DMF (15 mL)

was added 1-(bromomethyl)-4-(trifluoromethoxy)benzene (1.3 g, 5.2 mmol) and $Cs_2CO_3$ (3.4 g, 10.4 mmol). The mixture was stirred at room temperature overnight. Then the mixture was diluted with $H_2O$ (50 mL), extracted with EA (3×50 mL), the combined organic phase was washed with brine (50 mL), dried over anhydrous sodium sulphate, filtered, concentrated in vacuo, and the residue was purified by silica gel chromatography (PE/EA=10/1) to afford methyl 2-bromo-7-[[4-(trifluoromethoxy)phenyl]methoxy]benzothiophene-6-carboxylate (940 mg, 39%) as a light yellow solid. LCMS Purity: 84%; MS: m/z (ES+)=460 (M+$H^+$).

Step 2

To a solution of methyl 2-bromo-7-[[4-(trifluoromethoxy)phenyl]methoxy]benzothiophene-6-carboxylate (100 mg, 0.2 mmol) in dioxane/$H_2O$ (2 mL, v/v=1/1) was added prop-1-en-2-ylboronic acid (17 mg, 0.2 mmol), $K_2CO_3$ (54 mg, 0.4 mmol) and $Pd(PPh_3)_4$ (12 mg, 0.01 mmol). The mixture was stirred at 80° C. overnight under $N_2$. Next the mixture was diluted with $H_2O$ (50 mL), and extracted with EA (3×20 mL). The combined organic phase was washed with brine (50 mL), dried over anhydrous sodium sulphate, filtered, concentrated in vacuo, and the residue was purified by silica gel chromatography (PE/EA=10/1) to afford methyl 2-isopropenyl-7-[[4-(trifluoromethoxy) phenyl]methoxy] benzothiophene-6-carboxylate (250 mg, crude) as a yellow oil. LCMS Purity: 76%; MS: m/z (ES+)=422 (M+$H^+$).

Step 3

To a solution of methyl 2-isopropenyl-7-[[4-(trifluoromethoxy)phenyl]methoxy]-benzothiophene-6-carboxylate (250 mg, 0.6 mmol) in methanol (5 mL) was added 10% Pd/C (50 mg) and stirred at room temperature overnight under $H_2$. Next the reaction mixture was filtered through celite with the aid of methanol (50 mL), and the filtrate was concentrated in vacuo to afford methyl 2-isopropyl-7-[[4-(trifluoromethoxy)phenyl]-methoxy]benzothiophene-6-carboxylate (200 mg, crude) as a brown oil, which was used directly for the next step. LCMS Purity: 68%; MS: m/z (ES+)=425 (M+$H^+$).

Step 4

To a solution of methyl 2-isopropyl-7-[[4-(trifluoromethoxy) phenyl]methoxy]-benzothiophene-6-carboxylate (200 mg, 0.5 mmol) in THF/$H_2O$ (3 mL, v/v=2/1) was added $LiOH \cdot H_2O$ (42 mg, 1.0 mmol). The resulting solution was stirred at room temperature overnight. The reaction mixture was diluted with water (40 mL) and acidified with 2N HCl to pH 7-6, and the mixture was extracted with EA (3×40 mL). The combined organic phase was washed with brine (50 ml), treated with anhydrous sodium sulfate, filtered and concentrated in vacuo to afford 2-isopropyl-7-[[4-(trifluoromethoxy)phenyl]methoxy]benzothiophene-6-carboxylic acid (200 mg, crude) as white solid. LCMS Purity: 82%; MS: m/z ($ES^+$)=411 (M+$H^+$)

Intermediate Example 9. Preparation of 2-chloro-7-[[4-(trifluoromethyl)phenyl]methoxy]benzothiophene-6-carboxylic acid

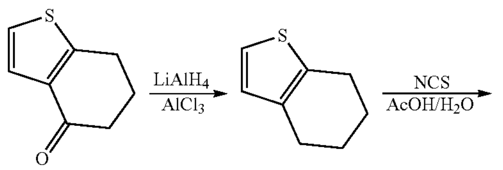

-continued

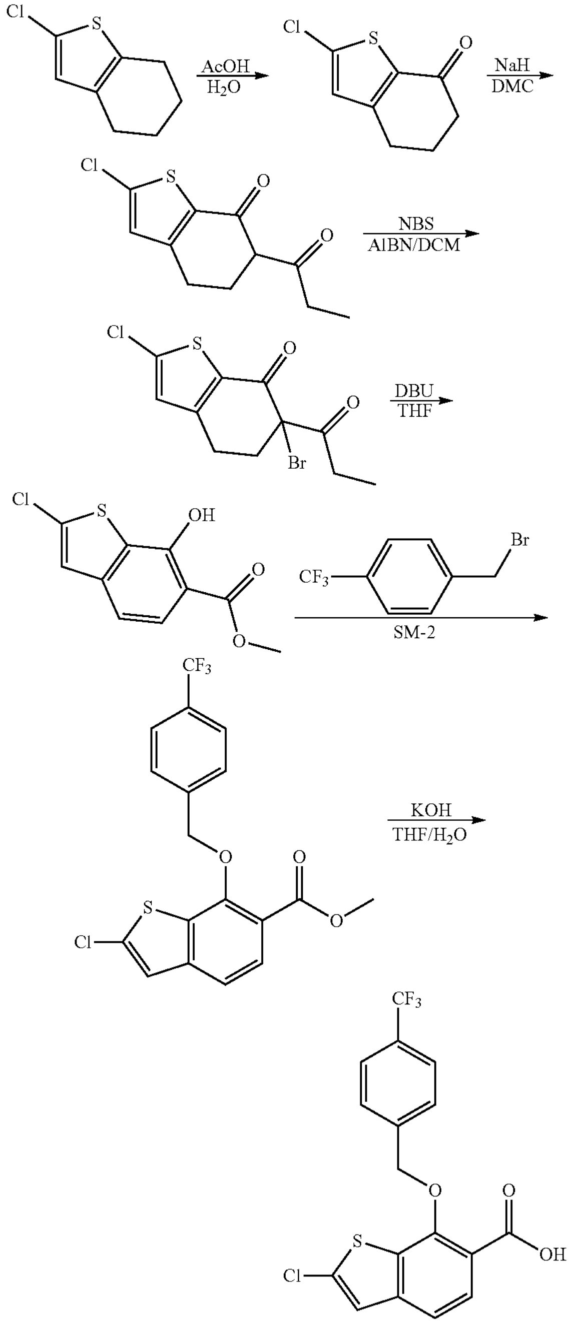

Step 1

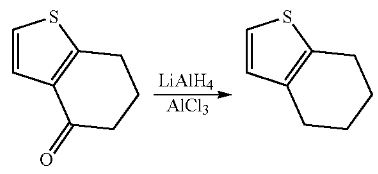

Aluminum trichloride (6340 mg, 47.6 mmol) in anhydrous diethyl ether (50 mL) was placed under an atmosphere of argon and lithium aluminum hydride (1900 mg, 50 mmol) was added dropwise. The resultant solution was stirred for 2 minutes and then a solution of S 6,7-dihydro-5H-benzothiophen-4-one (6020 mg, 39.6 mmol) in diethyl ether (20 mL) was added dropwise. The reaction mixture was stirred at ambient temperature for 2 h then was quenched with water (30 mL) followed by 6M sulfuric acid (50 mL) before being extracted into diethyl ether (4×15 mL). The combined organic phase was washed with water (20 mL) and brine, dried over sodium sulfate, filtered and evaporated to afford the title compound of 4,5,6,7-tetrahydrobenzothiophene (5.3 g, 97.1 percent) as a white oil. LCMS: $t_R$=2.21 min., purity 77.4% at 254 nm. MS: m/z ($ES^+$)=139 ($M+H^+$).

Step 2

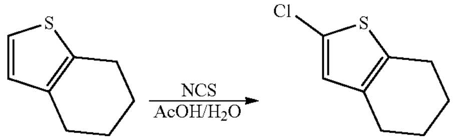

A solution of 4,5,6,7-tetrahydrobenzothiophene (1.8 g, 13 mmol) in $CHCl_3$ (15 mL) and AcOH (10 ml) was added NCS (2.7 g, 20.2 mmol) at room temperature, then the reaction mixture was stirred under the same temperature for 2 h, concentrated in vacuo and purified by silica gel column chromatography (PE) to afford 2 g (89.3%) of 2-chloro-4,5,6,7-tetrahydrobenzothiophene as white oil. LCMS: $t_R$=1.96 min., purity 72% at 254 nm. MS: m/z ($ES^+$)=173 ($M+H^+$).

Step 3

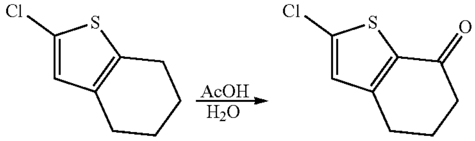

A solution of 2-chloro-4,5,6,7-tetrahydrobenzothiophene (2.5 g, 14.5 mmol) in AcOH (25 mL) and water (25 mL) was added ceric ammonium nitrate (31.8 g, 58 mmol) at 0° C., the reaction mixture was stirred at room temperature overnight, 50 mL water was added, extracted with EA (50 mL), washed with aqueous $NaHCO_3$ (50 mL) and brine (50 mL), dried over $Na_2SO_4$, filtered and concentrated in vacuo, and finally purified by silica gel column chromatography (EA/PE=1/20) to afford 2 g (74%) of 2-chloro-5,6-dihydro-4H-benzothiophen-7-one as yellow oil. LCMS: $t_R$=1.96 min., purity 82% at 254 nm. MS: m/z ($ES^+$)=187 ($M+H^+$).

Step 4

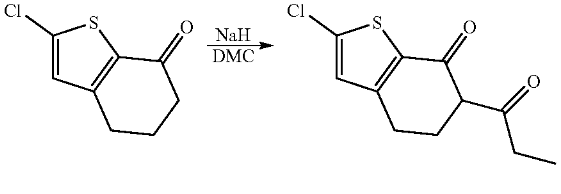

To a solution of 2-chloro-5,6-dihydro-4H-benzothiophen-7-one (2515 mg, 10.4 mmol) in $CHCl_3$ (15 mL) was added NBS (2000 mg, 11.2 mmol) and AIBN (135 mg, 0.82 mmol) at room temperature, then the reaction mixture was stirred under reflux for 20 h, concentrated in vacuo to afford 3346 mg (100%) of 2-chloro-6-propanoyl-5,6-dihydro-4H-benzothiophen-7-one as a yellow oil. LCMS: $t_R$=1.62 min., purity 91.3% at 254 nm. MS: m/z ($ES^+$)=245 ($M+H^+$).

Step 5

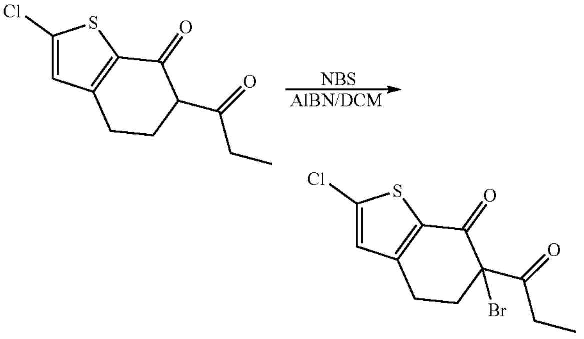

A solution of 2-chloro-6-propanoyl-5,6-dihydro-4H-benzothiophen-7-one (3346 mg, 10.4 mmol) in THF (20 mL) was added DBU (4800 mg, 31.6 mmol) at room temperature, the solution was stirred at room temperature for 2 hours, adjusted pH to 6 with 1 N HCl, extracted with EA (150 mL), washed with brine (150 mL), dried over anhydrous $Na_2SO_4$, filtered and concentrated in vacuo, and finally purified by silica gel column chromatography (EA/PE=1/50) to afford 1600 mg (63.6%) of 6-bromo-2-chloro-6-propanoyl-4,5-dihydrobenzothiophen-7-one as a yellow solid. LCMS: $t_R$=2.04 min., purity 54% at 254 nm. MS: m/z ($ES^+$)=323 ($M+H^+$).

Step 6

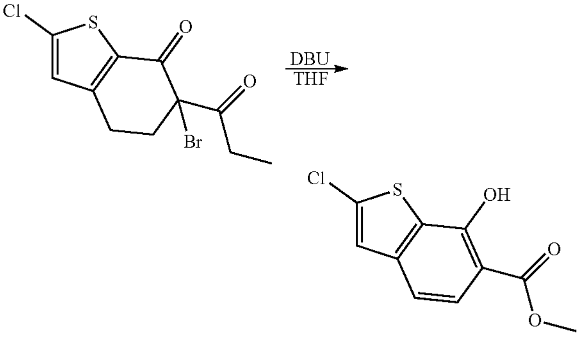

To a solution of 6-bromo-2-chloro-6-propanoyl-4,5-dihydrobenzothiophen-7-one (3346 mg, 10.4 mmol) in THF (20 mL) was added DBU (4800 mg, 31.6 mmol) at room temperature. The solution was stirred at room temperature for 2 hours, adjusted pH to 6 with 1 N HCl, extracted with EA (150 mL), washed with brine (150 mL), dried over anhydrous $Na_2SO_4$, filtered and concentrated in vacuo, and then purified by silica gel column chromatography (EA/PE=1/50) to afford 1600 mg (63.6%) of methyl 2-chloro-7- hydroxy-benzothiophene-6-carboxylate as yellow solid. LCMS: $t_R$=2.29 min., purity 97% at 254 nm. MS: m/z $(ES^+)$=243 $(M+H^+)$.

Step 7

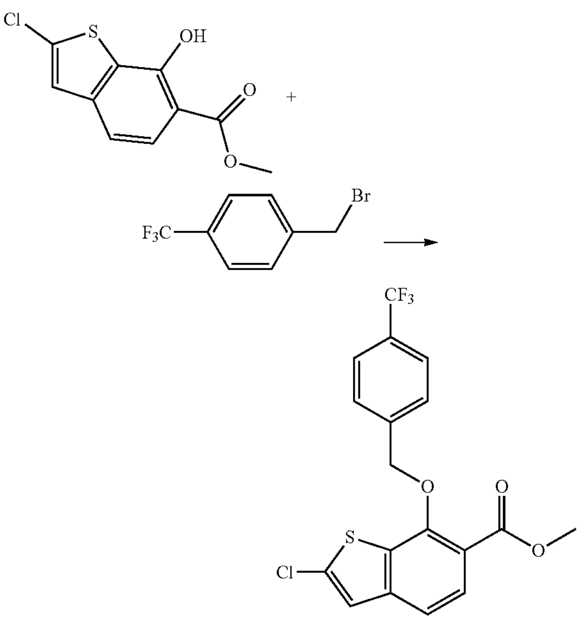

To a stirred solution of methyl 2-chloro-7-hydroxy-benzothiophene-6-carboxylate (160 mg, 0.66 mmol) in DMF (2 mL) were added 1-(bromomethyl)-4-(trifluoromethyl)benzene (170 mg, 0.71 mmol) and $Cs_2CO_3$ (485 mg, 1.49 mmol). The resulting mixture was stirred at room temperature for 20 h, diluted with water (10 mL), and extracted with EA (20 mL×2), washed with brine (20 mL), dried over anhydrous $Na_2SO_4$, filtered and concentrated in vacuo and purified by silica gel column chromatography (EA/PE=1/20) to afford 235 mg (89%) of methyl 2-chloro-7-[[4-(trifluoromethyl)phenyl]methoxy]benzothiophene-6-carboxylate as a white solid. LCMS: $t_R$=2.41 min., purity 100% at 214 nm. MS: m/z $(ES^+)$=423 (M+Na+).

Step 8

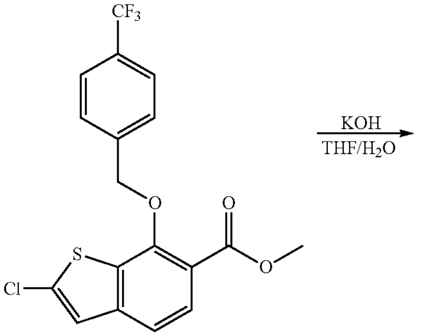

-continued

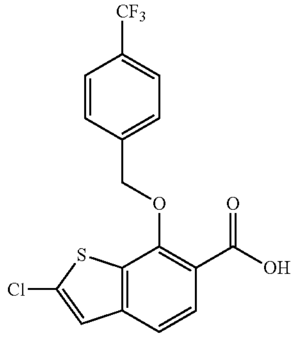

To a mixture of 235 mg (0.59 mmol) of methyl 2-chloro-7-[[4-(trifluoromethyl)phenyl]methoxy]benzothiophene-6-carboxylate and 170 mg of KOH (3.03 mmol) in 0.5 mL of $H_2O$, 2 mL of THF and 2 mL of MeOH were added and vigorously stirred at room temperature for 3 h and then concentrated. The residue was acidified with 10% citric acid and extracted with EA (40 mL). The extract was washed twice with brine (10 mL) and dried over $Na_2SO_4$, concentrated and the crude product thus obtained was purified by silica gel column chromatography on silica gel (DCM/MeOH=10:1) to give 200 mg of 2-chloro-7-[[4-(trifluoromethyl)phenyl]methoxy]benzothiophene-6-carboxylic acid (88.1 percent) as a white solid LCMS: $t_R$=1.47 min., purity 97.3% at 214 nm. MS: m/z $(ES^+)$=386 $(M+H^+)$.

Intermediate Example 10. Preparation of 2-chloro-7-[[4-(trifluoromethoxy)phenyl]methoxy]benzothiophene-6-carboxylic acid

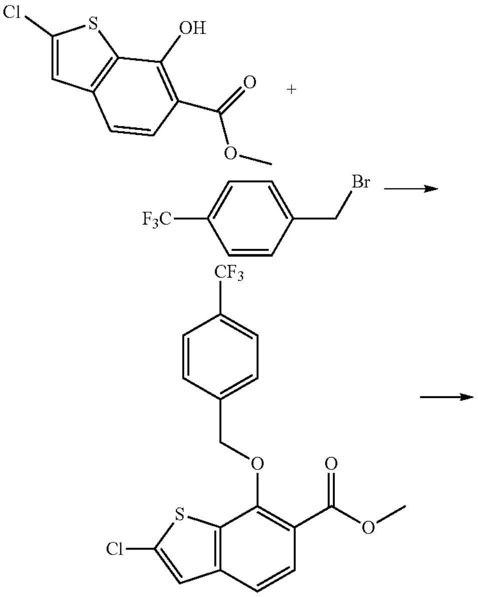

-continued

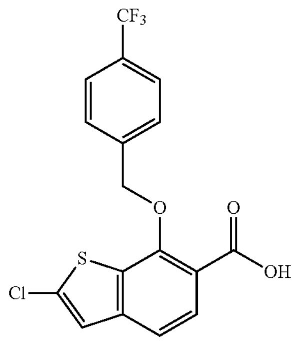

To a solution of methyl 2-chloro-7-hydroxy-benzothiophene-6-carboxylate (150 g, 0.6 mmol) in DMF (15 mL) was added 1-(bromomethyl)-4-(trifluoromethoxy)benzene (152 mg, 0.6 mmol) and $Cs_2CO_3$ (391 mg, 1.2 mmol). The mixture was stirred at room temperature overnight. Then the mixture was diluted with $H_2O$ (50 mL), extracted with EA (3×50 mL), the combined organic phase was washed with brine (50 mL), dried over anhydrous sodium sulphate, filtered, concentrated in vacuo, and the residue was purified by silica gel chromatography (PE/EA=10/1) to afford methyl 2-chloro-7-[[4-(trifluoromethoxy)phenyl]methoxy]benzothiophene-6-carboxylate (150 mg, crude) as a light yellow solid. LCMS Purity: 74%; MS: m/z (ES+)=417 (M+H$^+$).

To a solution of methyl 2-chloro-7-[[4-(trifluoromethoxy)phenyl]methoxy]benzothiophene-6-carboxylate (150 mg, 0.4 mmol) in THF/$H_2O$ (3 mL, v/v=2/1) was added LiOH·$H_2O$ (34 mg, 0.8 mmol). The resulting solution was stirred at room temperature overnight. The reaction mixture was diluted with water (40 mL) and acidified with 2N HCl to pH 7-6. The mixture was extracted with EA (3×40 mL), the combined organic phase was washed with brine (50 ml), dried over anhydrous sodium sulfate, filtered and concentrated in vacuo and purified by silica gel chromatography (PE/EA=10/1) to afford 2-chloro-7-[[4-(trifluoromethoxy)phenyl]methoxy]benzothiophene-6-carboxylic acid (100 mg, crude) as a light yellow oil. LCMS Purity: 85%; MS: m/z (ES+)=402 (M+H$^+$).

Intermediate Example 11. Preparation of 2-isopentyl-7-[[4-(trifluoromethyl)phenyl]methoxy]benzothiophene-6-carboxylic acid

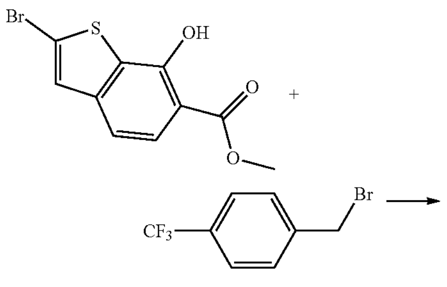

-continued

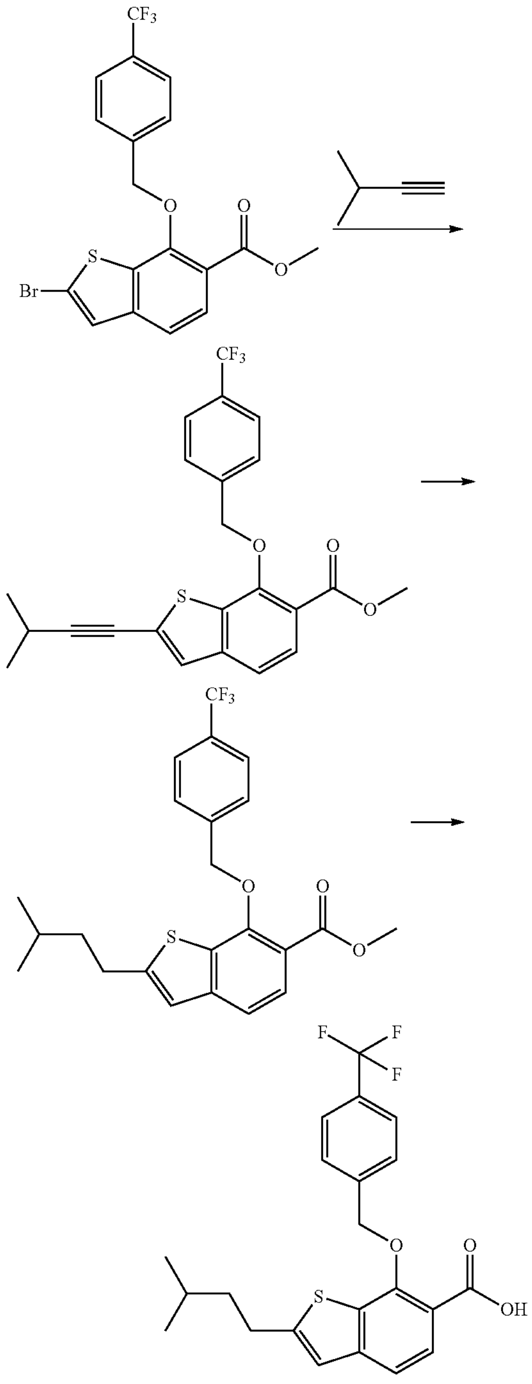

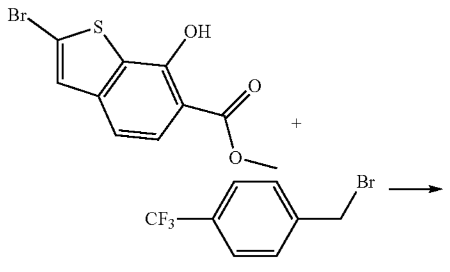

-continued

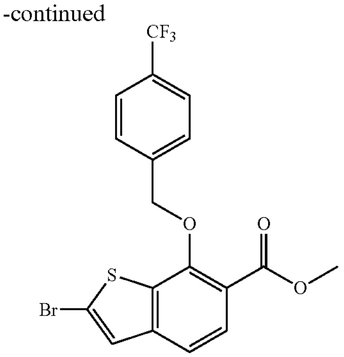

To a solution of methyl 2-bromo-7-hydroxy-benzothiophene-6-carboxylate (200 mg, 0.7 mmol) in DMF (4 mL) was added 1-(bromomethyl)-4-(trifluoromethyl)benzene (167 mg, 0.7 mmol) and $Cs_2CO_3$ (456 mg, 1.4 mmol). The mixture was stirred at room temperature overnight. Then the mixture was diluted with $H_2O$ (50 mL), extracted with EA (3×50 mL), the combined organic phase was washed with brine (50 mL), dried over anhydrous sodium sulphate, filtered, concentrated in vacuo, and the residue was purified by silica gel chromatography (PE/EA=10/1) to afford methyl 2-bromo-7-[[4-(trifluoromethyl)phenyl]methoxy]benzothiophene-6-carboxylate (270 mg, crude) as a light yellow solid. LCMS Purity: 85%; MS: m/z (ES+)=445 (M+$H^+$).

Step 2

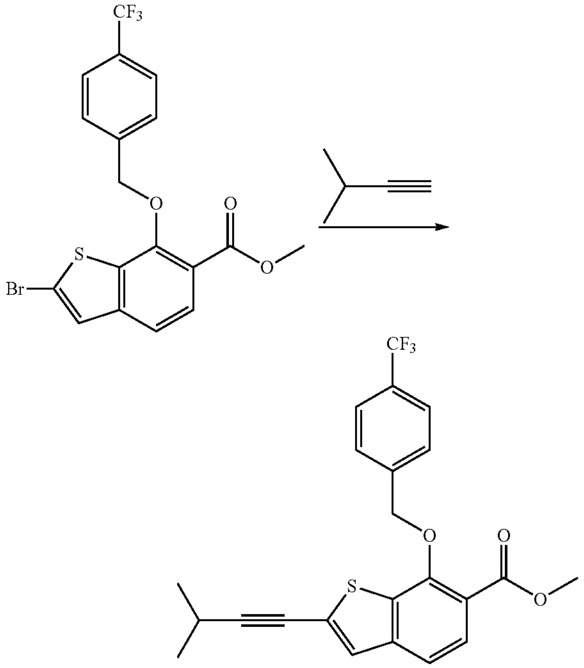

To a solution of methyl 2-bromo-7-[[4-(trifluoromethyl)phenyl]methoxy]benzothiophene-6-carboxylate (270 mg, 0.6 mmol) in $Et_2NH$ (5 mL) was added 3-methylbut-1-yne (82 mg, 1.2 mmol), CuI (12 mg, 0.06 mmol) and $Pd(PPh_3)_4$ (35 mg, 0.03 mmol). The mixture was stirred at 70° C. overnight under $N_2$. Then the mixture was diluted with $H_2O$ (50 mL), extracted with EA (3×20 mL), and the combined organic phase was washed with brine (50 mL), dried over anhydrous sodium sulphate, filtered, concentrated in vacuo, and the residue was purified by silica gel chromatography (PE/EA=10/1) to afford methyl 2-(3-methylbut-1-ynyl)-7-[[4-(trifluoromethyl)phenyl]methoxy]benzothiophene-6-carboxylate (250 mg, crude) as a yellow oil. LCMS Purity: 77%; MS: m/z (ES+)=432 (M+$H^+$).

Step 3

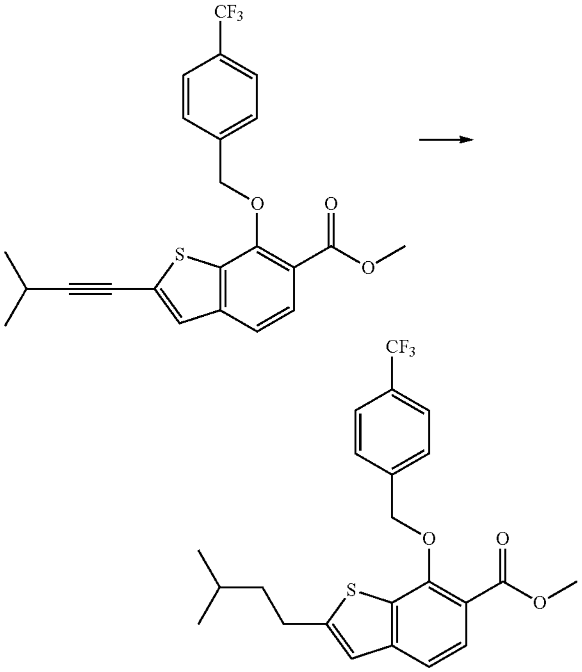

To a solution of 2-(3-methylbut-1-ynyl)-7-[[4-(trifluoromethyl)phenyl]methoxy]-benzothiophene-6-carboxylate (250 mg, 0.6 mmol) in methanol (5 mL) was added 10% Pd/C (50 mg) and stirred at room temperature overnight under $N_2$, then the reaction mixture was filtered through celite with the aid of methanol (50 mL). The filtrate was concentrated in vacuo to afford methyl 2-isopentyl-7-[[4-(trifluoromethyl)phenyl]methoxy]benzothiophene-6-carboxylate (200 mg, crude) as a brown oil, which was used directly for the next step. LCMS Purity: 73%; MS: m/z (ES+)=437 (M+$H^+$).

Step 4

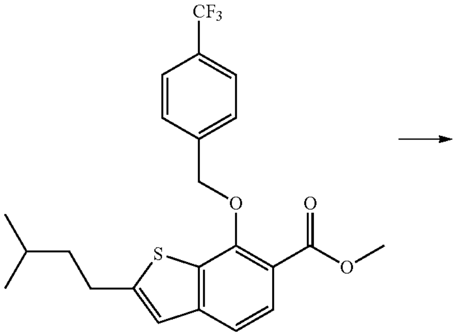

-continued

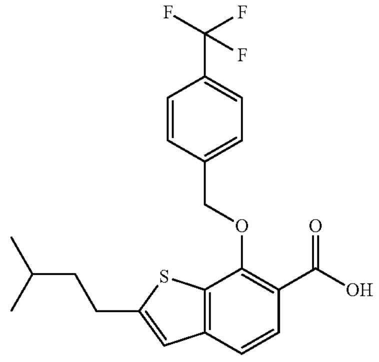

To a solution of methyl 2-isopentyl-7-[[4-(trifluoromethyl)phenyl]methoxy]benzothiophene-6-carboxylate (200 mg, 0.46 mmol) in THF/$H_2O$ (3 mL, v/v=2/1) was added LiOH·$H_2O$ (39 mg, 0.92 mmol). The resulting solution was stirred at room temperature overnight. The reaction mixture was diluted with water (40 mL) and acidified with 2N HCl to pH 7-6. The mixture was extracted with EA (3×40 mL), the combined organic phase was washed with brine (50 ml), dried over anhydrous sodium sulfate, filtered and concentrated in vacuo to afford 2-isopentyl-7-[[4-(trifluoromethyl)phenyl]methoxy]benzothiophene-6-carboxylic acid (164 mg, 61%) as a light yellow solid. LCMS Purity: 87%; MS: m/z (ES+)=423 (M+H$^+$).

Intermediate Example 12. Preparation of 3-Methyl-4-(4-trifluoromethyl-benzyloxy)-benzo[b]thiophene-5-carboxylic acid

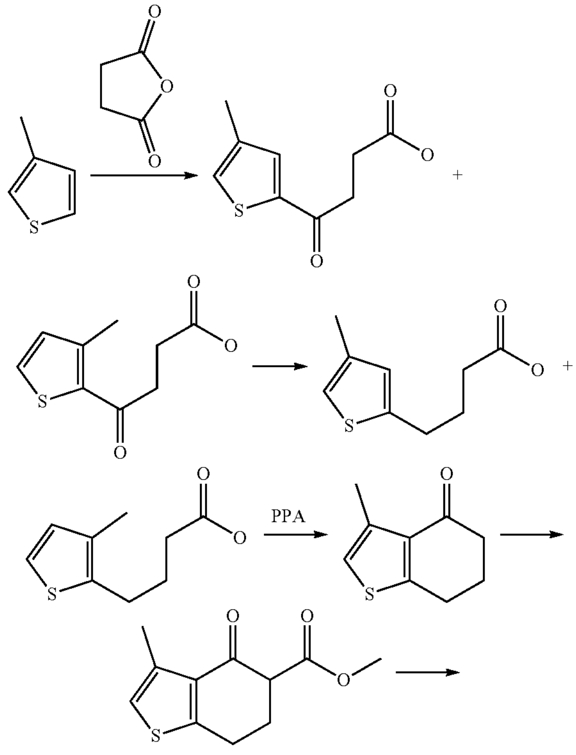

-continued

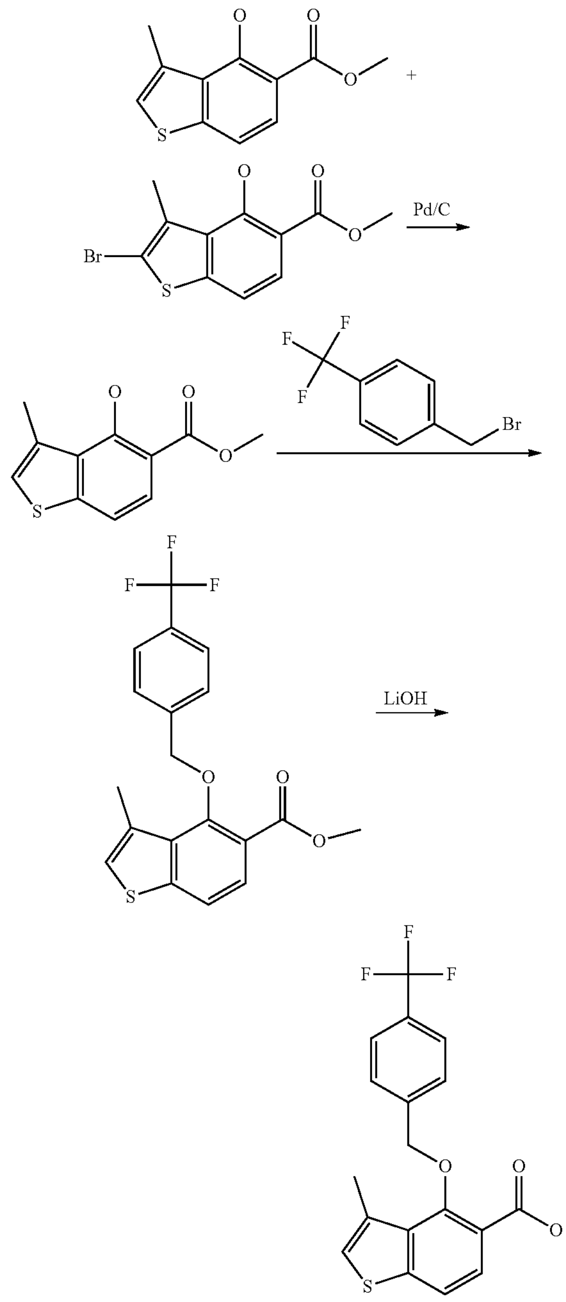

Step 1

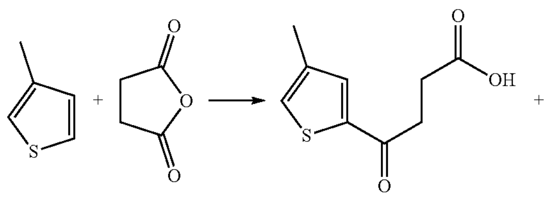

-continued

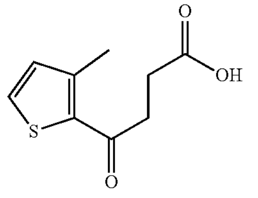

To a stirred solution of 3-methylthiophene (20.0 g, 204.1 mmol) and tetrahydrofuran-2,5-dione (24.5 g, 244.9 mmol) in DCM (200 mL) at room temperature was added $AiCl_3$ (59.7 g, 449.0 mmol) slowly, then the solution was stirred at 50° C. for 2 hours, cooled and adjusted pH to 2 with HCl (6 N), extracted with DCM (100 mL) twice, washed with brine (100 mL) and dried over $Na_2SO_4$, filtered and concentrated to afford the mixture of 4-(4-methyl-2-thienyl)-4-oxo-butanoic acid and 4-(3-methyl-2-thienyl)-4-oxo-butanoic acid (41.8 g) as a yellow solid. LCMS Purity: 97%; MS: m/z (ES+)=199 (M+H$^+$).

Step 2

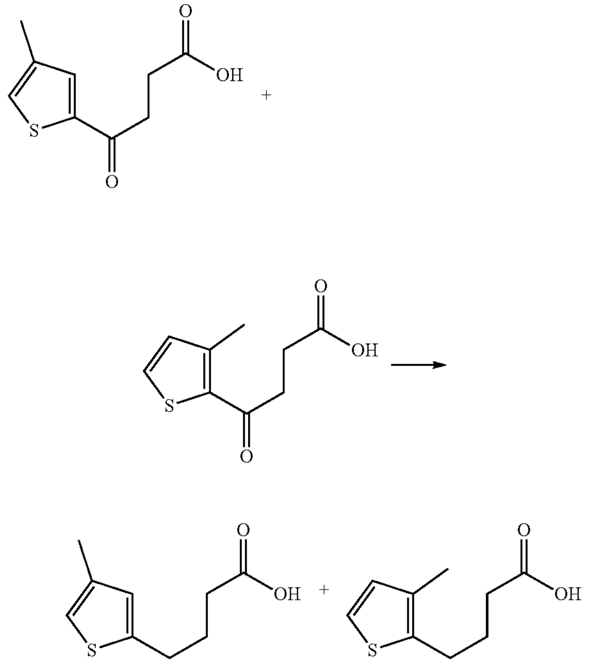

To a solution of 4-(4-methyl-2-thienyl)-4-oxo-butanoic acid and 4-(3-methyl-2-thienyl)-4-oxo-butanoic acid (41.8 g, 211 mmol) in ethylene glycol (200 mL) was added hydrazine monohydrate (26.4 g, 422 mmol, 80% in water) and KOH (23.6 g, 422 mmol), the solution was stirred at 200° C. for 17 hours, then cooled and adjusted pH to 2 with HCl (6 N), extracted with DCM (100 mL) twice, washed with brine (100 mL) and dried over $Na_2SO_4$, filtered and concentrated, and purified by silica gel column chromatography (EA/PE=1/5) to afford the mixture of the desired product 4-(4-methyl-2-thienyl)butanoic acid and a by-product 4-(3-methyl-2-thienyl)butanoic acid (30.1 g) as a yellow oil. LCMS Purity: 54%; MS: m/z (ES$^+$)=185 (M+H$^+$).

Step 3

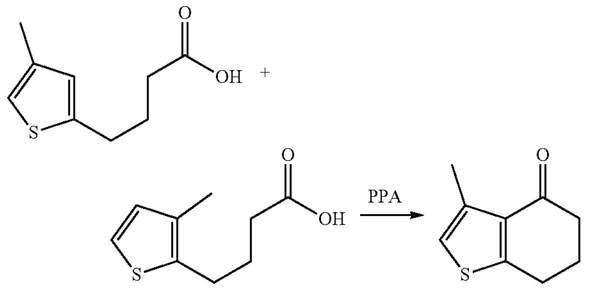

A solution of 4-(4-methyl-2-thienyl)butanoic acid and a by-product 4-(3-methyl-2-thienyl)butanoic acid (30.1 g, 16.6 mmol) in PPA (150 mL) was stirred at 90° C. for 1 hr, poured into 300 mL ice-cold water, extracted with DCM (100 mL) twice, washed with brine (100 mL) and dried over $Na_2SO_4$, filtered and concentrated, and purified by silica gel column chromatography (EA/PE=1/15) to afford 3-methyl-6,7-dihydro-5H-benzothiophen-4-one (4.0 g, 12% over three steps) as a yellow oil. LCMS Purity: 62%; MS: m/z (ES$^+$)=167 (M+H$^+$).

Step 4

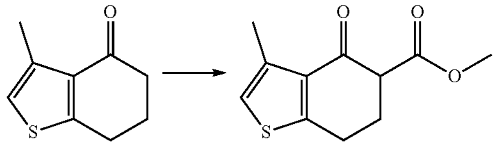

To a stirred solution of NaH (2.0 g, 50.6 mmol, 60% in oil) in $Me_2CO_3$ (40 mL) was added 3-methyl-6,7-dihydro-5H-benzothiophen-4-one (4.2 g, 25.3 mmol) at room temperature, and the solution was heated at 70° C. for 3 hours, then cooled and adjusted pH to 4 with HCl (2 N), extracted with EA (100 mL) twice, washed with brine (100 mL) and dried over $Na_2SO_4$, filtered and concentrated, and finally purified by silica gel column chromatography (EA/PE=1/10) to afford methyl 3-methyl-4-oxo-6,7-dihydro-5H-benzothiophene-5-carboxylate (4.3 g, 76%) as a yellow solid.

LCMS Purity: 97%; MS: m/z (ES$^+$)=226 (M+H$^+$).

Step 5

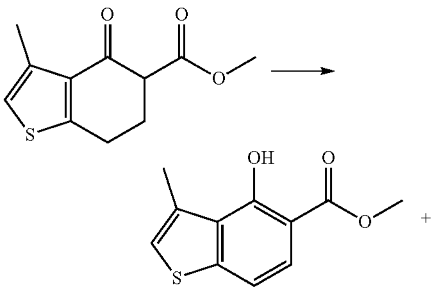

-continued

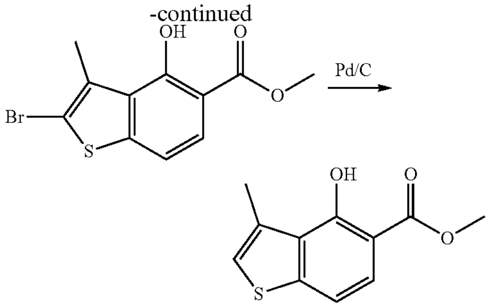

To a solution of methyl 3-methyl-4-oxo-6,7-dihydro-5H-benzothiophene-5-carboxylate (4.2 g, 19.6 mmol) in $CHCl_3$ (100 mL) was added NBS (3.8 g, 21.6 mmol) and AIBN (160 mg, 0.98 mmol) at room temperature, then the reaction mixture was stirred under reflux for 1 hr, and concentrated to afford a residue. THF (100 mL) and DBU (8.9 g, 58.8 mmol) were added at room temperature, the solution was stirred at room temperature for 2 hours, adjusted pH to 6 with 1 N HCl, extracted with EA (100 mL) twice, washed with brine (100 mL), dried over $Na_2SO_4$, filtered and concentrated, then purified by silica gel chromatography (PE) to afford the mixture of methyl 4-hydroxy-3-methyl-benzothiophene-5-carboxylate and a by-product, methyl 2-bromo-4-hydroxy-3-methyl-benzothiophene-5-carboxylate (4.0 g) as a white solid. The mixture was dissolved in MeOH (100 mL), 10% Pd/C (0.9 g) was added, and the reaction mixture was stirred at room temperature under $H_2$ atmosphere for 3 hours. The resulting mixture was filtered, concentrated, purified by silica gel column chromatography (PE) to afford methyl 4-hydroxy-3-methyl-benzothiophene-5-carboxylate (2.5 g, 57% of two steps) as a white solid.

Step 6

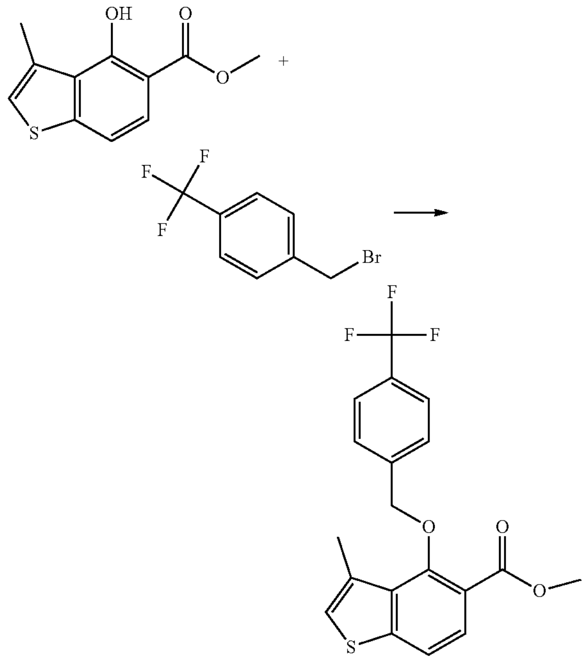

To a stirred solution of methyl 4-hydroxy-3-methyl-benzothiophene-5-carboxylate (600 mg, 2.7 mmol) in DMF (10 mL) were added bromide (710 mg, 2.98 mmol) and $Cs_2CO_3$ (1.8 g, 5.4 mmol). The resulting mixture was stirred at room temperature for 1 h, diluted with water (50 mL), and extracted with EA (50 mL×2), washed with brine (50 mL), dried over anhydrous sodium sulfate, filtered and concentrated in vacuo to afford methyl 3-methyl-4-[[4-(trifluoromethyl) phenyl]methoxy]benzothiophene-5-carboxylate (1.2 g, crude) as a yellow oil, which used directly for the next step. LCMS Purity: 97%; MS: m/z $(ES^+)$=381 $(M+H^+)$.

Step 7

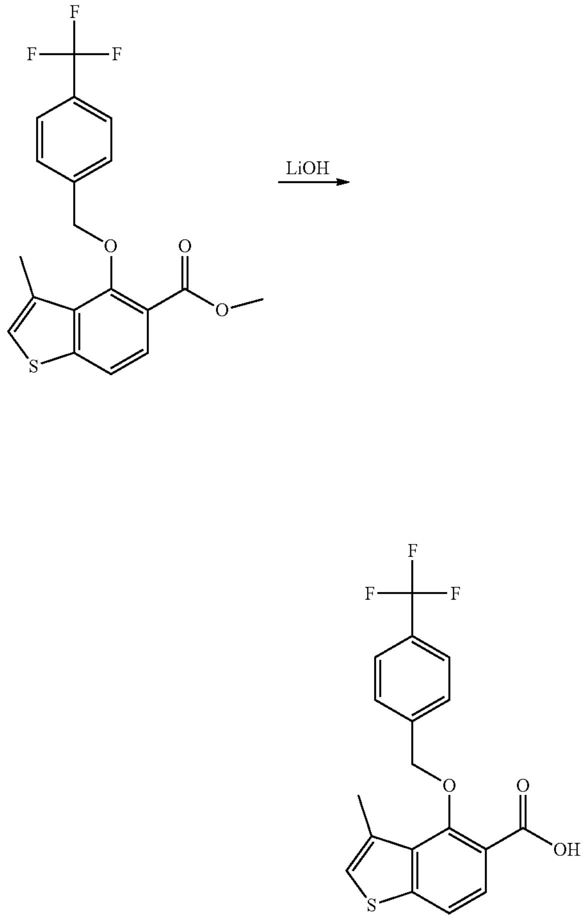

To a stirred solution of methyl 3-methyl-4-[[4-(trifluoromethyl) phenyl]methoxy]-benzothiophene-5-carboxylate (1.2 g, crude) in $MeOH/THF/H_2O$ (10 mL/10 mL/1 mL) was added LiOH. $H_2O$ (400 mg, 9.6 mmol). The solution was stirred at 70° C. overnight. The solution was concentrated and then acidified with aqueous hydrochloric acid (2 N) to pH=4-5 and extracted with EA (50 mL×2). The combined organic phase was washed with brine (50 mL), dried over anhydrous sodium sulfate, filtered and concentrated in vacuo, purified by silica gel column chromatography (PE/EA=1/5) to afford 3-Methyl-4-(4-trifluoromethyl-benzyloxy)-benzo[b]thiophene-5-carboxylic acid (940 mg, 95% of two steps) as a white solid.

$^1H$ NMR (400 MHz, $CDCl_3$) δ 8.03 (d, J=8.4 Hz, 1H), 7.74 (d, J=8.8 Hz, 1H), 7.68 (d, J=2.0 Hz, 4H), 7.12 (s, 1H), 5.20 (s, 2H), 2.61 (s, 3H) ppm. LCMS purity: >95%; $t_R$=2.08 min; MS: m/z $(ES^+)$=367 $(M+H^+)$.

Intermediate Example 13. Preparation of 2-chloro-3-methyl-4-[[4-(trifluoromethyl)phenyl]methoxy]benzothiophene-5-carboxylic acid

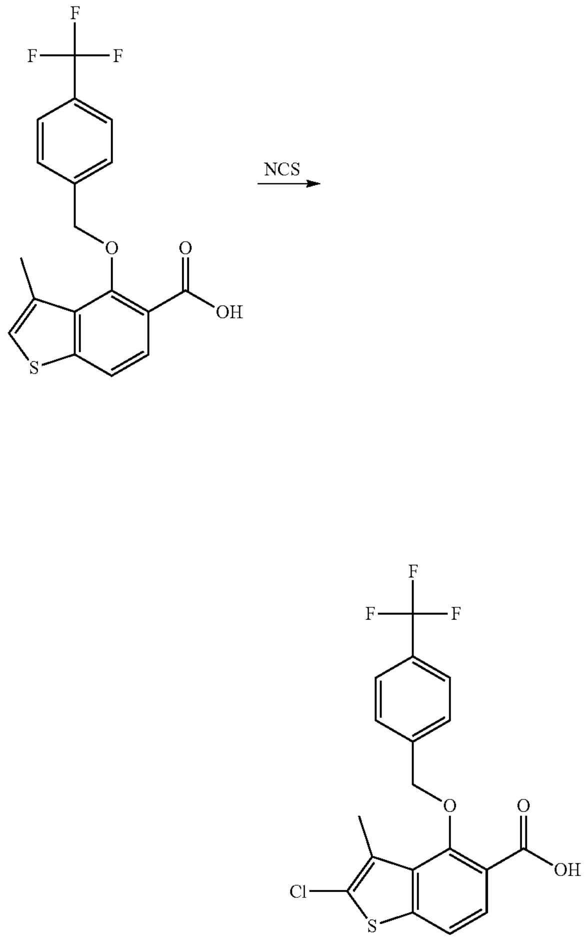

To a stirred solution of 3-methyl-4-[[4-(trifluoromethyl)phenyl]methoxy]benzothiophene-5-carboxylic acid (300 mg, 0.82 mmol) in $THF/H_2O$ (10 mL/1 mL) was added NCS (328 mg, 2.46 mmol), the solution was stirred at 70° C. for 2 hours, next diluted with water (50 mL) and extracted with EA (50 mL), washed with brine (50 mL), dried over $Na_2SO_4$, filtered and concentrated, and purified by silica gel chromatography (PE/EA=1/3) to afford the mixture of 2-chloro-3-methyl-4-[[4-(trifluoromethyl)phenyl]methoxy]benzothiophene-5-carboxylic acid (168 mg, 51%) as a white solid.

$^1H$ NMR (400 MHz, $CDCl_3$) δ 8.02 (d, J=8.4 Hz, 1H), 7.69 (dd, J=19.6 Hz & 8.0 Hz, 4H), 7.62 (d, J=8.8 Hz, 1H), 5.16 (s, 2H), 2.57 (s, 3H) ppm.

LCMS purity: >95%; $t_R$=1.32 min; MS: m/z ($ES^+$)=400 ($M+H^+$).

Intermediate Example 14. Preparation of 2-chloro-3-methyl-4-[[4-(trifluoromethoxy)phenyl]methoxy]-benzothiophene-5-carboxylic acid

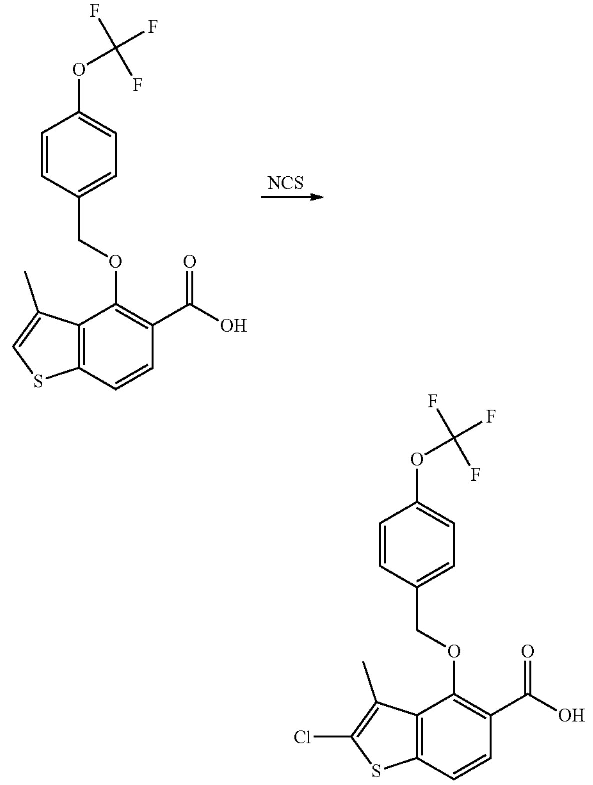

To a stirred solution of 3-methyl-4-[[4-(trifluoromethoxy)phenyl]methoxy]benzothiophene-5-carboxylic acid (260 mg, 0.68 mmol) in $THF/H_2O$ (10 mL/1 mL) was added NCS (273 mg, 2.04 mmol), the solution was stirred at 70° C. for 2 hr, then diluted with water (50 mL) and extracted with EA (50 mL), washed with brine (50 mL), dried over $Na_2SO_4$, filtered and concentrated, and purified by silica gel chromatography (PE/EA=1/3) to afford the mixture of 2-chloro-3-methyl-4-[[4-(trifluoromethoxy)phenyl]methoxy]benzothiophene-5-carboxylic acid (130 mg, 46%) as a white solid.

$^1H$ NMR (400 MHz, $CDCl_3$) δ 8.02 (d, J=8.4 Hz, 1H), 7.61 (d, J=8.4 Hz, 1H), 7.57 (d, J=8.8 Hz, 2H), 7.29 (d, J=4.8 Hz, 2H), 5.10 (s, 2H), 2.59 (s, 3H) ppm.

LCMS purity: >95%; $t_R$=1.36 min; MS: m/z ($ES^+$)=416 ($M+H^+$).

Intermediate Example 15. Preparation of 3-Methyl-4-(4-trifluoromethyl-benzyloxy)-benzo[b]thiophene-5-carboxylic acid

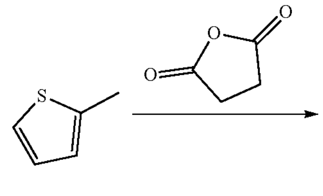

-continued

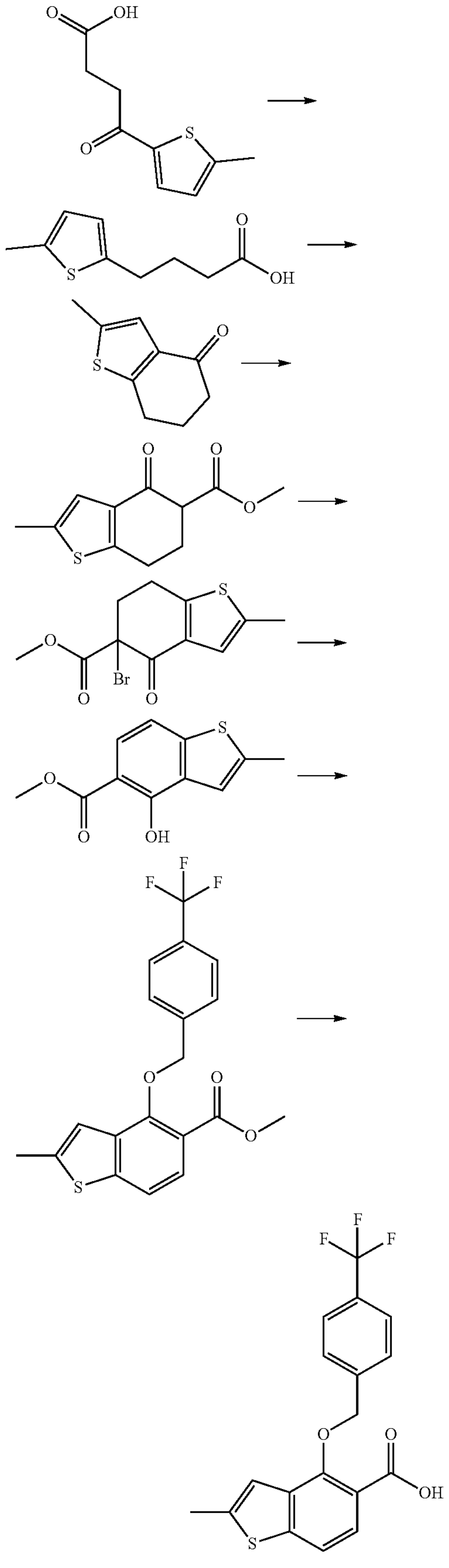

Step 1

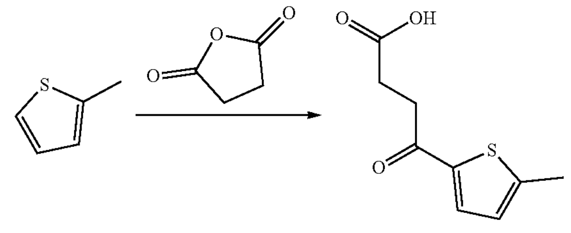

$AiCl_3$ (13.3 g, 100.0 mmol) was added into a solution of 2-methylthiophene (4.9 g, 50 mmol) and tetrahydrofuran-2,5-dione (6.0 g, 60 mmol) in DCM (150 mL) at 0° C. After addition, the mixture was stirred at 50° C. for 3 hours. Then, the mixture was diluted with $H_2O$ (150 mL). The organic phase was washed with $H_2O$ and brine, dried over $Na_2SO_4$, filtered and concentrated to yield 4-(5-methyl-2-thienyl)-4-oxo-butanoic acid as a yellow solid (9.4 g, 95% yield). LCMS purity: 98%; MS: m/z $(ES^+)$=199 $(M+H^+)$.

Step 2

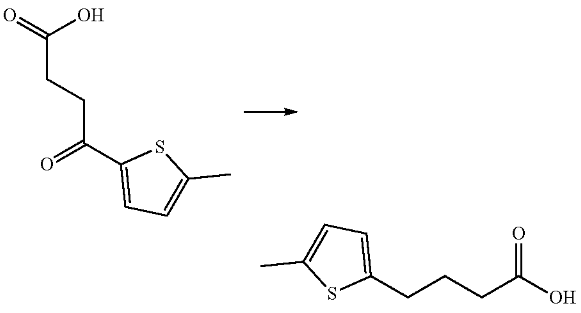

To a solution of 4-(5-methyl-2-thienyl)-4-oxo-butanoic acid (6.1 g, 30.8 mmol), KOH (3.5 g, 61.6 mmol) in ethylene diglycol (100 mL) was added hydrazine hydrate (3.1 g, 61.6 mmol). The mixture was stirred at 180° C. for 16 hours. The mixture was quenched with 4N HCl to pH 2-3 and filtered, the solid cake was washed with water, and dried to give 4-(5-methyl-2-thienyl)butanoic acid (4.5 g, 80% yield). LCMS purity: 95%; MS: m/z $(ES^+)$=185 $(M+H^+)$.

Step 3

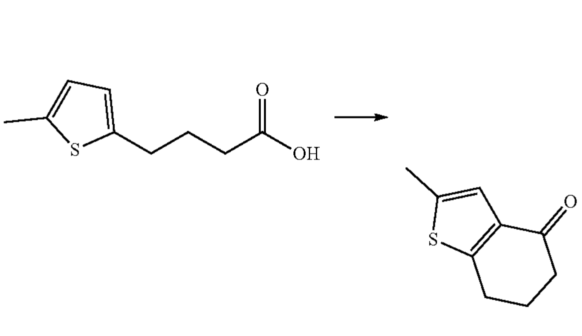

A solution of 4-(5-methyl-2-thienyl)butanoic acid (4.7 g, 25.5 mmol) in TFA/TFAA (40 mL, v/v: 1/1) was stirred at rt for 16 h. The reaction was concentrated and the residue was treated with saturated $NaHCO_3$ solution, extracted with EA (50 mL×2) and the combined organic phase was washed with $H_2O$ and brine, dried over $Na_2SO_4$, filtered and concentrated. The residue was purified by SGC (PE/EA=10:1) to give 2-methyl-6,7-dihydro-5H-benzothiophen-4-one (2.9 g, 69% yield) as a yellow oil. LCMS purity: 92%; MS: m/z ($ES^+$)=167 ($M+H^+$).

Step 4

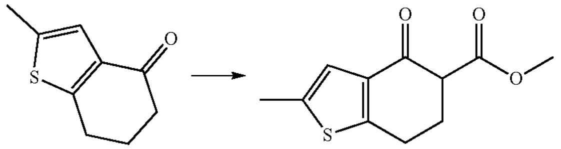

To a solution of 2-methyl-6,7-dihydro-5H-benzothiophen-4-one (2.9 g, 17.5 mmol) in $Me_2CO_3$ (30 mL) was added NaH (60% in oil, 2.1 g, 52.5 mmol). After stirring at 70° C. for 5 h, the mixture was quenched with water and extracted with EA (100 mL×2). The organic phase was washed with brine, dried over $Na_2SO_4$, filtered and concentrated. The residue was purified by SGC (PE/EA=10:1) to give methyl 2-methyl-4-oxo-6,7-dihydro-5H-benzothiophene-5-carboxylate (3.5 g, 88% yield) as a yellow solid. LCMS purity: 93%; MS: m/z ($ES^+$)=225 ($M+H^+$).

Step 5

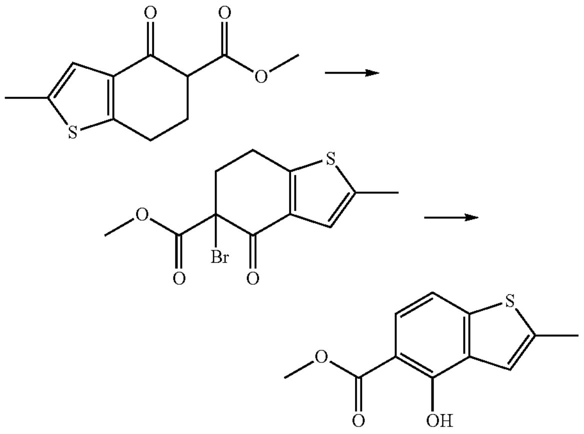

To a solution of methyl 2-methyl-4-oxo-6,7-dihydro-5H-benzothiophene-5-carboxylate (3.0 g, 13.3 mmol) in $CHCl_3$ (60 mL) was added NBS (2.8 g, 16.0 mmol) and AIBN (cat.) at room temperature, and the reaction mixture was stirred under reflux for 1 hour, concentrated to afford a residue. The residue was dissolved in THF (50 mL), DBU (6.1 g, 40.0 mmol) was added at room temperature, the solution was stirred at room temperature for 4 hours, adjusted pH to 6 with 1 N HCl, extracted with EA (80 mL×3), washed with brine (80 mL), dried over $Na_2SO_4$, filtered and concentrated, then purified by silica gel chromatography (PE) to afford methyl 4-hydroxy-2-methyl-benzothiophene-5-carboxylate (2.0 g, 68% yield) as a white solid. LCMS purity: 91%; MS: m/z ($ES^+$)=223 ($M+H^+$).

Step 6

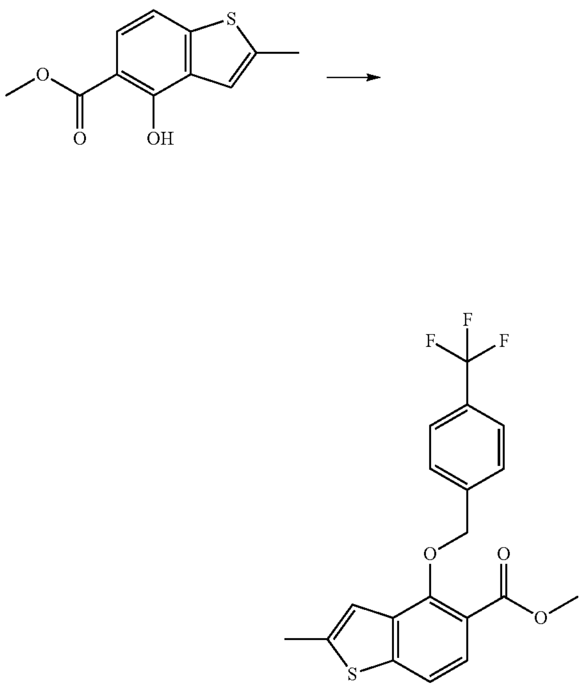

To a stirred solution of methyl 4-hydroxy-2-methyl-benzothiophene-5-carboxylate (200 mg, 0.9 mmol) in DMF (10 mL) were added 1-(bromomethyl)-4-(trifluoromethyl)benzene (236 mg, 1.0 mmol) and $Cs_2CO_3$ (587 mg, 1.8 mmol). The resulting mixture was stirred at room temperature for 1 h, diluted with water (50 mL), and extracted with EA (50 mL×2), washed with brine (50 mL), dried over anhydrous sodium sulfate, filtered and concentrated in vacuo to afford methyl 2-methyl-4-[[4-(trifluoromethyl)phenyl]methoxy]benzothiophene-5-carboxylate (330 mg, crude) as yellow oil, which used directly for the next step. LCMS purity: 98%; MS: m/z ($ES^+$)=381 ($M+H^+$).

Step 7

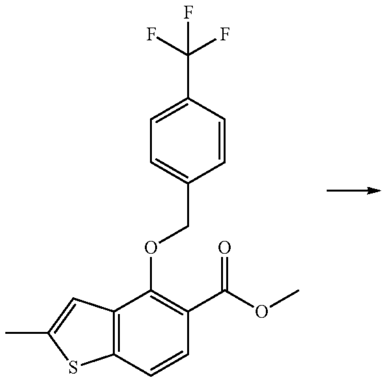

-continued

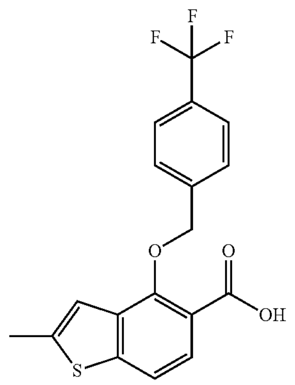

To a stirred solution of methyl 2-methyl-4-[[4-(trifluoromethyl)phenyl]methoxy]-benzothiophene-5-carboxylate (330 mg, crude) in MeOH/THF/$H_2O$ (10 mL/10 mL/1 mL) was added LiOH. $H_2O$ (364 mg, 8.68 mmol). The solution was stirred at 70° C. overnight, concentrated and then acidified with aqueous hydrochloric acid (2 N) to pH=4-5, extracted with EA (50 mL×2). The combined organic phase was washed with brine (50 mL), dried over anhydrous sodium sulfate, filtered and concentrated in vacuo, and purified by silica gel column chromatography (PE/EA=1/5) to afford 2-methyl-4-[[4-(trifluoromethyl) phenyl]methoxy] benzothiophene-5-carboxylic acid (260 mg, 79% of two steps) as a white solid. LCMS purity: 90%; MS: m/z ($ES^+$)=367 ($M+H^+$)

Intermediate Example 16. Preparation of 2-methyl-4-[[4-(trifluoromethoxy)phenyl]methoxy]benzothiophene-5-carboxylic acid 2-Methyl-4-[[4-(trifluoromethoxy)phenyl]methoxy]benzothiophene-5-carboxylic acid was prepared similarly by coupling of methyl 4-hydroxy-2-methyl-benzothiophene-5-carboxylate with 1-(bromomethyl)-4-(trifluoromethoxy) benzene, followed by hydrolysis.

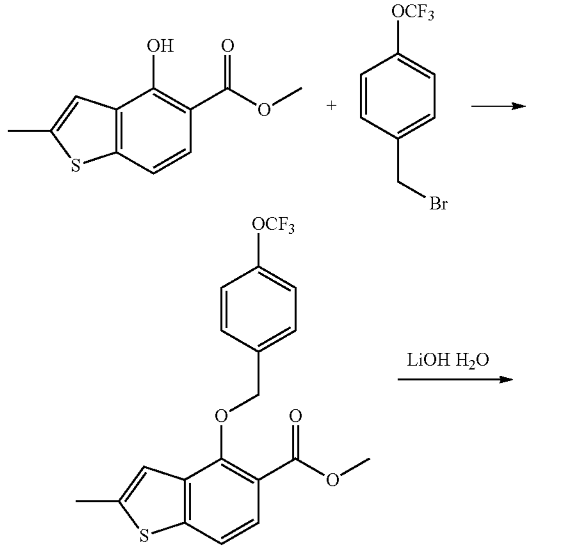

-continued

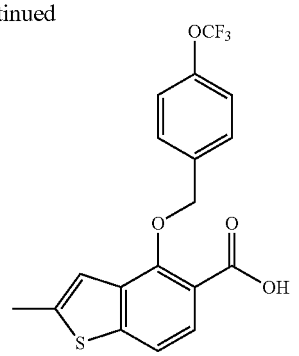

To a stirred solution of methyl 4-hydroxy-2-methyl-benzothiophene-5-carboxylate (400 mg, 1.8 mmol) in DMF (9.0 mL) were added 1-(bromomethyl)-4-(trifluoromethoxy)benzene (551 mg, 2.16 mmol) and $Cs_2CO_3$ (1.174 g, 3.6 mmol). The resulting mixture was stirred at room temperature for 1.5 h, diluted with water (15 mL), and extracted with EA (20 mL×3), washed with brine (50 mL), dried over anhydrous sodium sulfate, filtered and concentrated in vacuo, and the residue was purified by silica gel column (PE:EA=10:1) to afford methyl 2-methyl-4-[[4-(trifluoromethoxy)phenyl] methoxy]benzothiophene-5-carboxylate (726 mg, 100% yield) as a white solid. LCMS purity: 98%; MS: m/z ($ES^+$)=396 ($M+H^+$).

To a stirred solution of methyl 2-methyl-4-[[4-(trifluoromethoxy)phenyl]methoxy]-benzothiophene-5-carboxylate (726 mg, 1.8 mmol) in MeOH/THF/$H_2O$ (10 mL/10 mL/2 mL) was added LiOH·$H_2O$ (378 mg, 9.0 mmol). The solution was stirred at 70° C. for 3 h. The solution was concentrated and then acidified with aqueous hydrochloric acid (2 N) to pH=4-5 and extracted with EA (10 mL×3). The combined organic phase was washed with brine (20 mL), dried over anhydrous sodium sulfate, filtered and concentrated in vacuo to afford 2-Methyl-4-[[4-(trifluoromethoxy) phenyl]methoxy]benzothiophene-5-carboxylic acid (600 mg, 87% yield) as a white solid. LCMS purity: >95%; MS: m/z ($ES^+$)=383 ($M+H^+$).

Intermediate Example 17. Preparation of 3-chloro-2-methyl-4-[[4-(trifluoromethoxy)phenyl]methoxy] benzothiophene-5-carboxylic acid

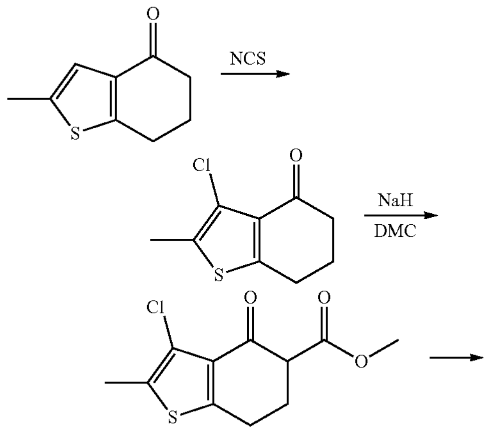

-continued

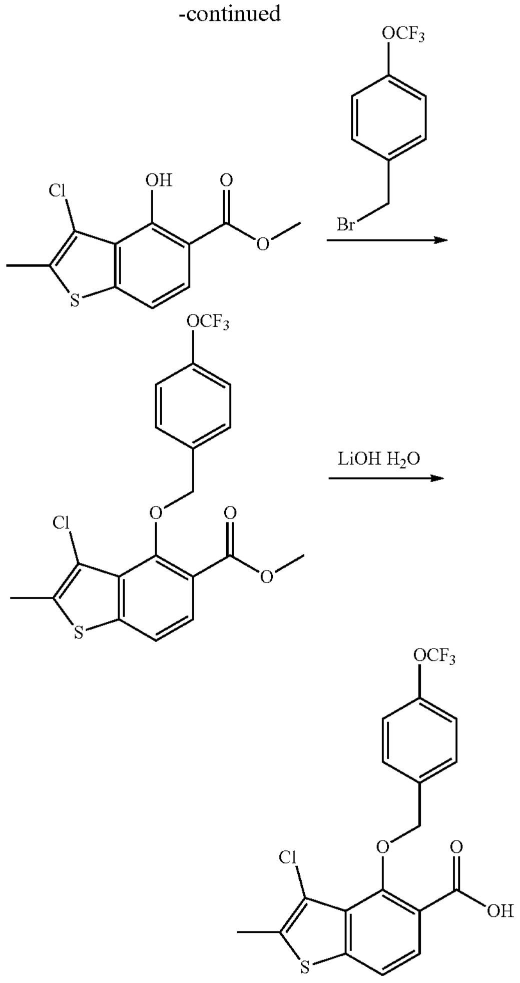

Step 1

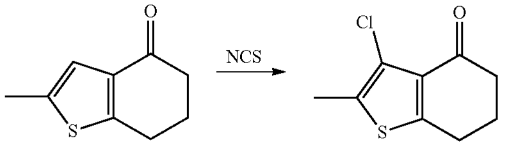

A mixture of 2-methyl-6,7-dihydro-5H-benzothiophen-4-one (1.286 g, 7.75 mmol) and N-chlorosuccinimide (1.448 g, 10.85 mmol) in 1,2-dichloroethane (40 mL) and acetic acid glacial (40 mL) was stirred at 90° C. for 4 h. The mixture was cooled to room temperature, concentrated, and diluted with saturated sodium bicarbonate (50 mL), extracted with ethyl acetate (3×50 mL), the combined organic layers were washed with brine (100 mL), dried over sodium sulfate and concentrated, the residue was purified by flash column chromatography (7% ethyl acetate in petroleum ether) to give 3-chloro-2-methyl-6,7-dihydro-5H-benzothiophen-4-one (389 mg, 25% yield) as a white solid. LCMS purity: 95%; MS: m/z ($ES^+$)=200 ($M+H^+$).

Step 2

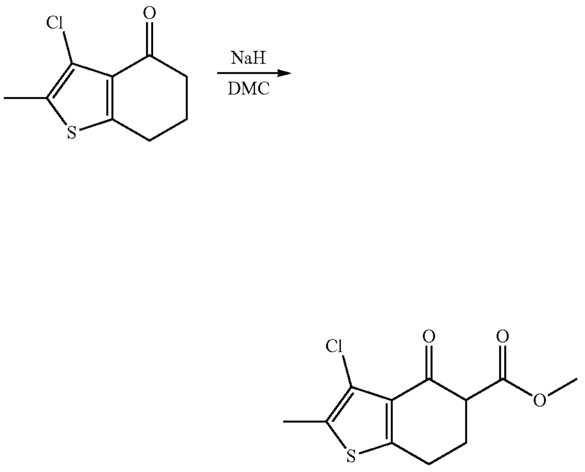

To a mixture of 3-chloro-2-methyl-6,7-dihydro-5H-benzothiophen-4-one (425 mg, 2.125 mmol) in dimethyl carbonate (15 mL) was added NaH (1.7 g, 42.5 mmol) at room temperature, and the resulting mixture was heated at 70° C. for 2 h, then cooled and adjusted pH to 4 with HCl (2 N), extracted with EA (3×20 mL), washed with brine (50 mL) and dried over $Na_2SO_4$, filtered and concentrated to afford methyl 3-chloro-2-methyl-4-oxo-6,7-dihydro-5H-benzothiophene-5-carboxylate as red oil which was used directly for the next step without further purification. LCMS purity: 90%; MS: m/z ($ES^+$)=259 ($M+H^+$).

Step 3

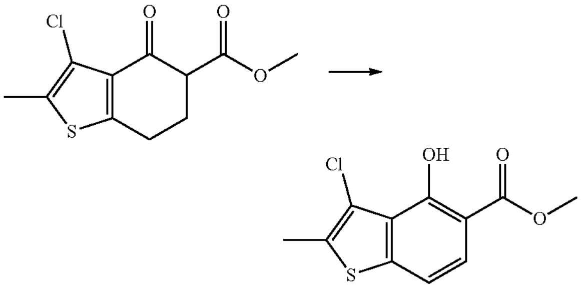

A mixture of methyl 3-chloro-2-methyl-4-oxo-6,7-dihydro-5H-benzothiophene-5-carboxylate (crude), N-Bromo succinimide (454 mg, 2.55 mmol) and AIBN (35 mg, 0.213 mmol) was dissolved in $CHCl_3$ (12 mL) at room temperature, then the mixture was stirred under reflux for 1 h. After concentration, the residue was dissolved in THF (12 mL), and DBU (1.27 mL, 8.5 mmol) was added at room temperature, the resulting solution was stirred at room temperature overnight. Next the pH was adjusted to ~6 with 1 N HCl, solution extracted with ethyl acetate (3×50 mL), washed with brine (80 mL), dried over $Na_2SO_4$, concentrated, and the residue was purified by silica gel chromatography (2% ethyl acetate in petroleum ether) to give methyl 3-chloro-4-hydroxy-2-methyl-benzothiophene-5-carboxylate (367 mg, two steps: 67% yield) as a white solid. LCMS purity: 95%; MS: m/z ($ES^+$)=257 ($M+H^+$).

Step 4

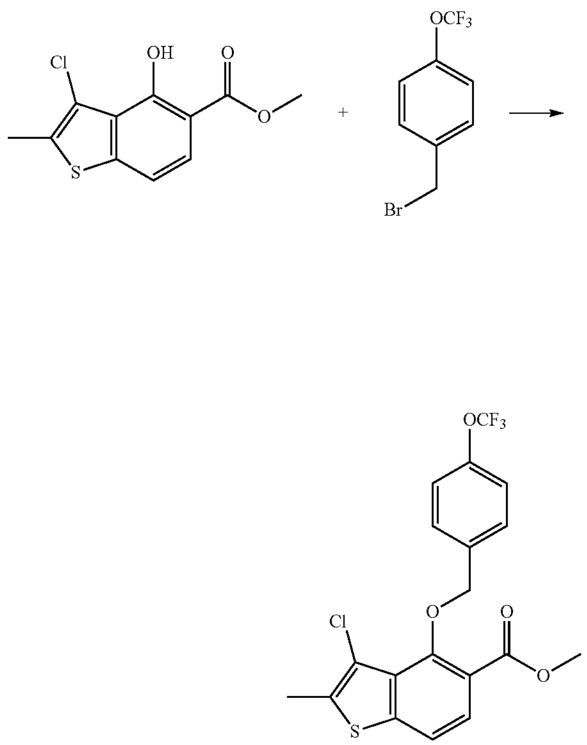

To a stirred solution of methyl 3-chloro-4-hydroxy-2-methyl-benzothiophene-5-carboxylate (125 mg, 0.489 mmol) in DMF (8.0 mL) were added bromide (149 mg, 0.586 mmol) and $Cs_2CO_3$ (318 mg, 0.977 mmol). The resulting mixture was stirred at room temperature for 2 h, diluted with water (20 mL), and extracted with EA (25 mL×3), washed with brine (50 mL), dried over anhydrous sodium sulfate, filtered and concentrated in vacuo, and the residue was purified by thin-layer chromatography (PE: $Et_2O$:DCM=35:1:1) to afford methyl 3-chloro-2-methyl-4-[[4-(trifluoromethoxy)phenyl]methoxy]benzothiophene-5-carboxylate (141 mg, 67% yield) as a white solid. LCMS purity: 98%; MS: m/z $(ES^+)$=431 $(M+H^+)$.

Step 5

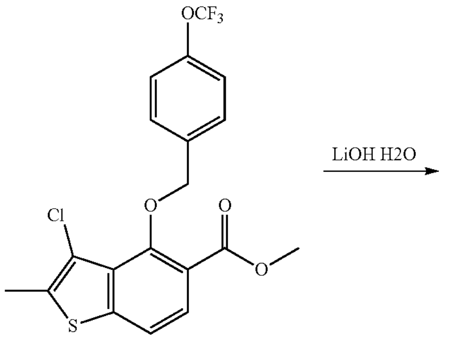

-continued

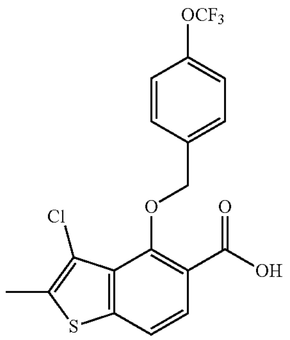

To a stirred solution of methyl 3-chloro-2-methyl-4-[[4-(trifluoromethoxy)phenyl]methoxy]benzothiophene-5-carboxylate (141 mg, 0.415 mmol) in MeOH/THF/$H_2O$ (5 mL/10 mL/2 mL) was added $LiOH \cdot H_2O$ (697 mg, 16.6 mmol). The solution was stirred at 70° C. for 3 h. The solution was concentrated and then acidified with aqueous hydrochloric acid (2 N) to pH=4-5 and extracted with EA (20 mL×3). The combined organic phase was washed with brine (50 mL), dried over anhydrous sodium sulfate, filtered and concentrated in vacuo to afford 3-chloro-2-methyl-4-[[4-(trifluoromethoxy)phenyl]methoxy]-benzothiophene-5-carboxylic acid (137 mg, 100% yield) as a white solid. LCMS purity: >95%; MS: m/z $(ES^+)$=417 $(M+H^+)$.

Intermediate Example 18. Preparation of 3-chloro-2-methyl-4-[[4-(trifluoromethyl)phenyl]methoxy]benzothiophene-5-carboxylic acid

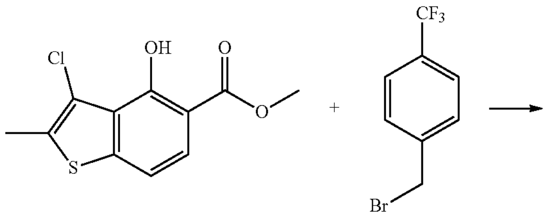

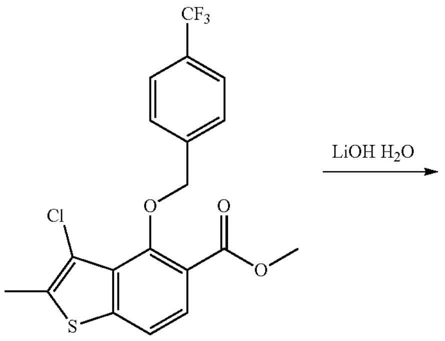

-continued

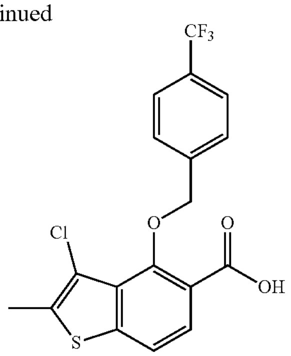

A mixture of methyl 3-chloro-4-hydroxy-2-methyl-benzothiophene-5-carboxylate (71 mg, 0.277 mmol), the bromide (80 mg, 0.333 mmol) and $Cs_2CO_3$ (181 mg, 0.554 mmol) in DMF (10.0 mL) was stirred at room temperature for 3 h, diluted with water (20 mL), and extracted with EA (15 mL×3), washed with brine (50 mL×2), dried over anhydrous sodium sulfate, filtered and concentrated in vacuo, and the residue was purified by thin-layer chromatography (PE:$Et_2O$ :DCM=60:1:2) to afford the ester (67 mg, 58%) as a white solid. LCMS purity: 95%; MS: m/z ($ES^+$)=415 ($M+H^+$).

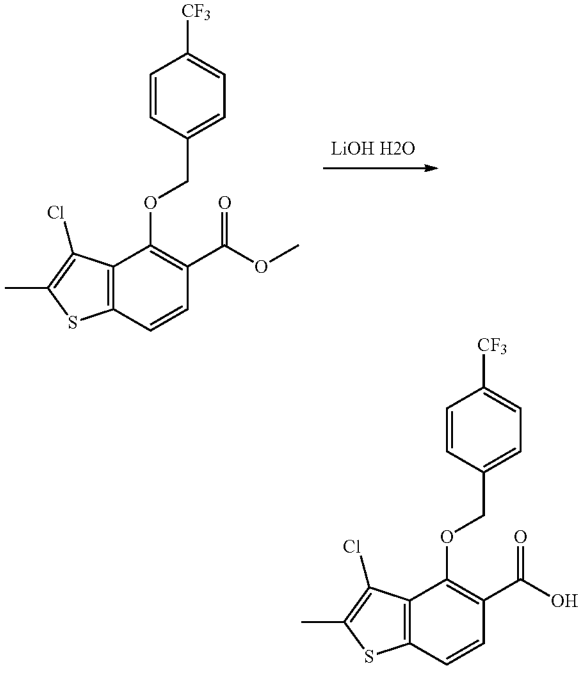

To a stirred solution of the ester (67 mg, 0.162 mmol) in MeOH/THF/$H_2O$ (5 mL/12 mL/2 mL) was added LiOH.$H_2O$ (272 mg, 6.48 mmol). The solution was stirred at 70° C. for 3 h. The solution was concentrated and then acidified with aqueous hydrochloric acid (2 N) to pH=4-5 and extracted with EA (15 mL×3). The combined organic phase was washed with brine (30 mL), dried over anhydrous sodium sulfate, filtered and concentrated in vacuo to afford 3-chloro-2-methyl-4-[[4-(trifluoromethyl)phenyl]methoxy] benzothiophene-5-carboxylic acid (65 mg, 100%) as a white solid. LCMS purity: 95%; MS: m/z ($ES^+$)=401 ($M+H^+$).

Intermediate Example 19. Preparation of 2-isopropyl-4-[[4-(trifluoromethyl)phenyl]methoxy]benzothiophene-5-carboxylic acid

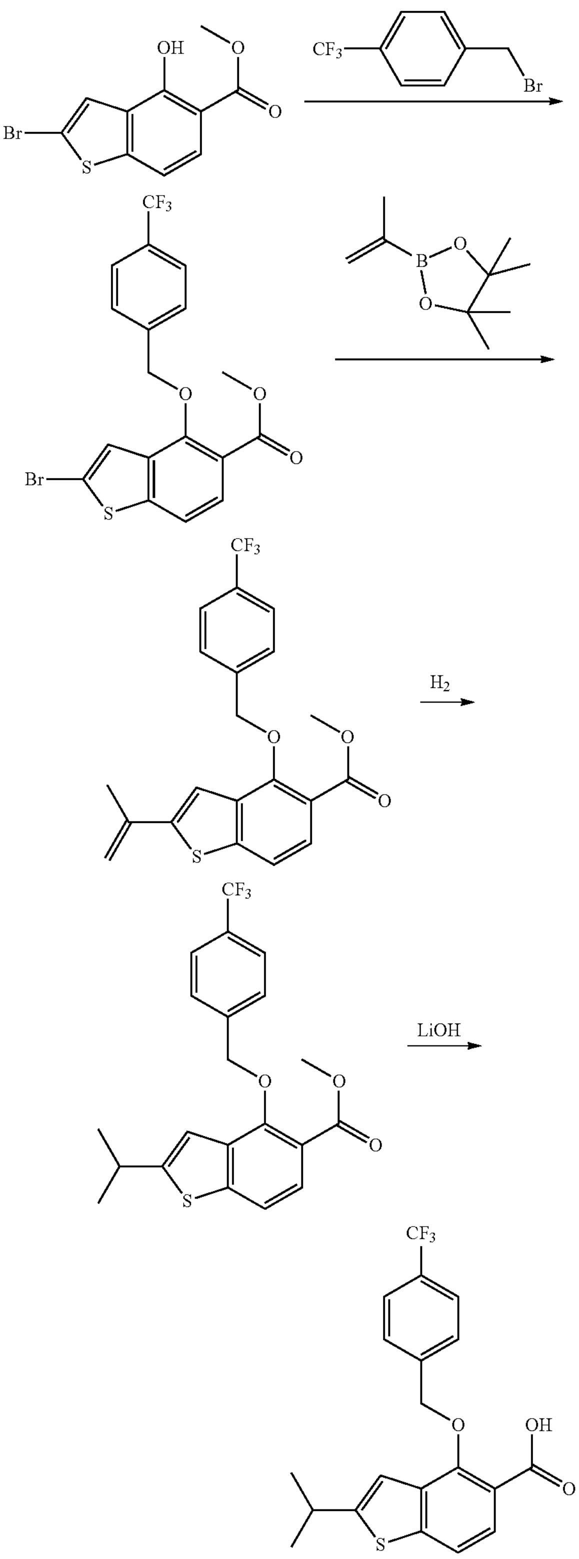

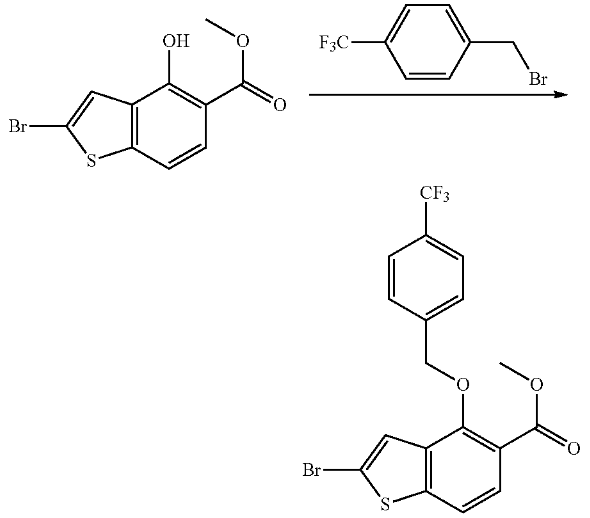

To a stirred solution of methyl 2-bromo-4-hydroxy-benzothiophene-5-carboxylate (100 mg, 0.35 mmol) in DMF (20 mL) was added 1-(bromomethyl)-4-(trifluoromethyl) benzene (92 mg, 0.38 mmol) and $K_2CO_3$ (97 mg, 0.7 mmol). The resulting mixture was stirred at room temperature for 1 h, diluted with water (30 mL), and extracted with EA (20 mL×3), washed with brine (20 mL×2), dried over anhydrous sodium sulfate, filtered and concentrated in vacuo to afford methyl 2-bromo-4-[[4-(trifluoromethyl)phenyl]methoxy] benzothiophene-5-carboxylate (140 mg, 90%) as a yellow oil, which was used directly in the next step without further purification. MS: m/z (ES+)=445 (M+H+).

Step 2

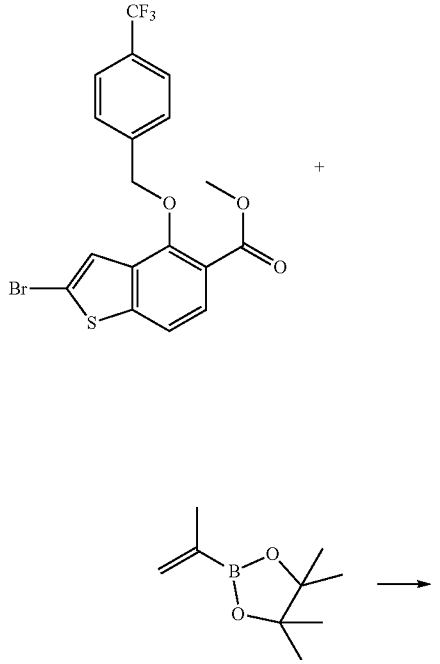

-continued

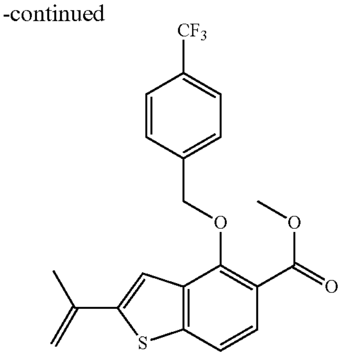

To a stirred solution of methyl 2-bromo-4-[[4-(trifluoromethyl) phenyl]methoxy]-benzothiophene-5-carboxylate (140 mg, 0.32 mmol) in 1,4-dioxane/$H_2O$ (20 mL/5 mL) was added 2-isopropenyl-4,4,5,5-tetramethyl-1,3,2-dioxaborolane (58 mg, 0.35 mmol), $Pd(dppf)_2Cl_2$ (14 mg, 10% w/w) and $K_2CO_3$ (88 mg, 0.64 mmol). The resulting mixture was stirred at 90° C. for 16 hours under $N_2$, diluted with water (30 mL), and extracted with EA (20 mL×3), washed with brine (20 mL×2), dried over anhydrous sodium sulfate, filtered and purified by silica gel chromatography (PE/EA=10/1) to afford methyl 2-isopropenyl-4-[[4-(trifluoromethyl)phenyl]methoxy]benzothiophene-5-carboxylate (100 mg, 83%) as a yellow oil. MS: m/z (ES+)=407 (M+H+).

Step 3

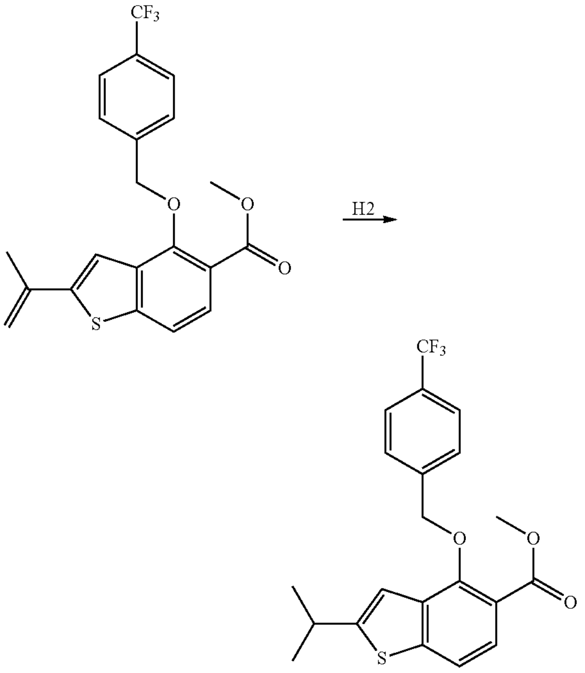

A solution of methyl 2-isopropenyl-4-[[4-(trifluoromethyl) phenyl]methoxy]benzothiophene-5-carboxylate (100 mg, 0.24 mmol) in MeOH (20 mL) was added Pd/C (10 mg, 10% w/w). The solution was stirred under $H_2$ at room temperature for 16 hours. The catalyst was filtered off, and the filtrate was condensed in vacuo to give methyl 2-isopropyl-4-[[4-(trifluoromethyl)phenyl]methoxy]benzothiophene-5-carboxylate (90 mg, 91%) as a yellow oil, which was directly used in the next step without further purification. MS: m/z (ES+)=409 (M+H$^+$).

Step 4

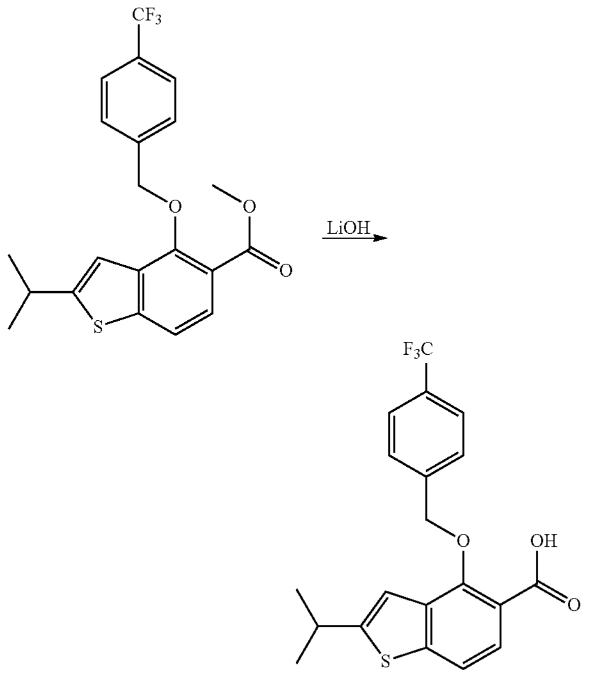

To a stirred solution of methyl 2-isopropyl-4-[[4-(trifluoromethyl) phenyl]methoxy]-benzothiophene-5-carboxylate (90 mg, 0.22 mmol) in MeOH/THF/$H_2O$ (8 mL/8 mL/1 mL) was added LiOH. $H_2O$ (28 mg, 066 mmol). The solution was stirred at 50° C. for 3 hours. The solution was concentrated and then acidified with aqueous hydrochloric acid (2 N) to pH=4-5 and extracted with EA (20 mL×2). The combined organic phase was washed with brine (20 mL), dried over anhydrous sodium sulfate, filtered and concentrated in vacuo to afford 2-isopropyl-4-[[4-(trifluoromethyl)phenyl]methoxy]benzothiophene-5-carboxylic acid (80 mg, 92%) as a white solid, which was used directly in the next step without further purification. MS: m/z (ES+)=395 (M+H$^+$).

Intermediate Example 20. Preparation of 2-isopropyl-4-[[4-(trifluoromethoxy)phenyl]methoxy]benzothiophene-5-carboxylic acid

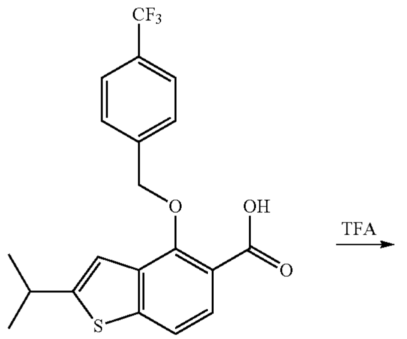

-continued

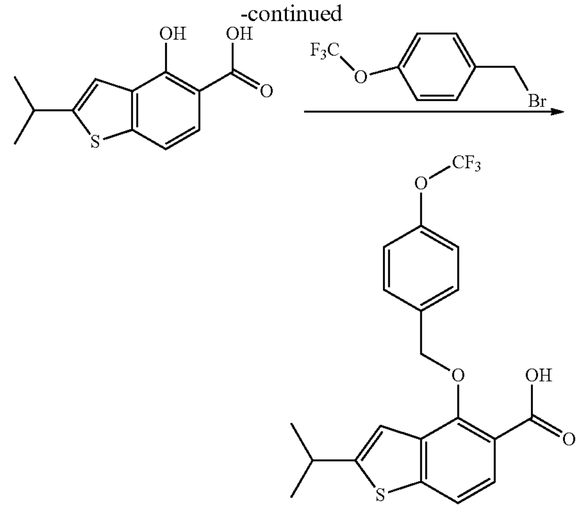

Step 1

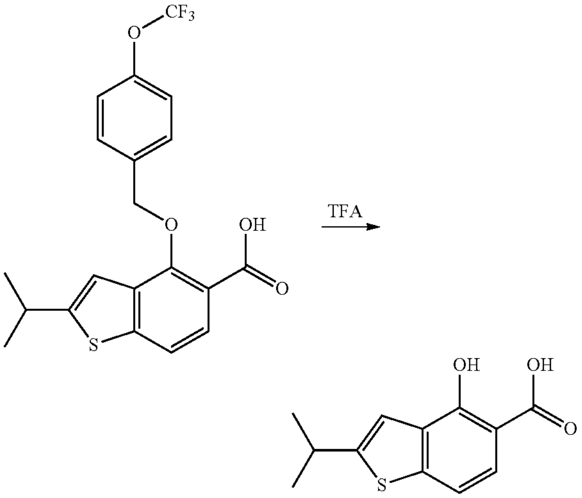

To a stirred solution of TFA (10 mL) was added 2-isopropyl-4-[[14-(trifluoromethyl)phenyl]methoxy]-benzothiophene-5-carboxylic acid (80 mg, 0.2 mmol), the solution was stirred at 80° C. for 16 hours, diluted with water (30 mL) and extracted with DCM (20 mL×3), washed with brine (20 mL), dried over anhydrous $Na_2SO_4$, filtered and concentrated in vacuo to afford 4-hydroxy-2-isopropyl-benzothiophene-5-carboxylic acid (40 mg, crude) as a yellow oil, which was used directly in the next step without further purification. MS: m/z (ES+)=237 (M+H$^+$).

Step 2

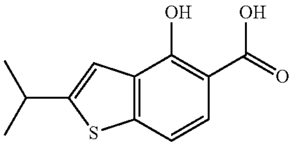

+

-continued

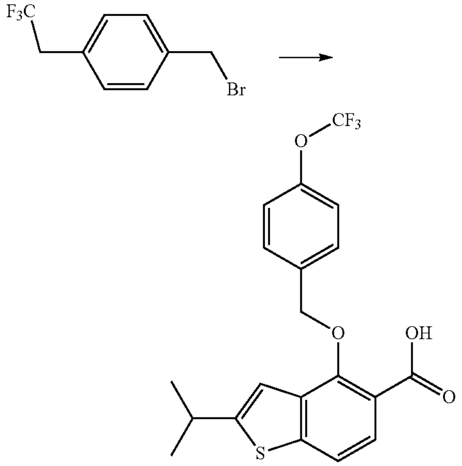

To a stirred solution of 4-hydroxy-2-isopropyl-benzothiophene-5-carboxylic acid (40 mg, crude) in DMF (10 mL) were added 1-(bromomethyl)-4-(trifluoromethoxy)benzene (56 mg, 0.22 mmol) and KOH (22 mg, 0.4 mmol). The resulting mixture was stirred at room temperature for 16 hours, diluted with water (20 mL), acidified with aqueous hydrochloric acid (2 N) to pH=4-5, and extracted with EA (20 mL×2), washed with brine (20 mL), dried over anhydrous sodium sulfate, filtered and concentrated in vacuo to afford 2-isopropyl-4-[[4-(trifluoromethoxy) phenyl] methoxy]benzothiophene-5-carboxylic acid (75 mg, crude) as a yellow oil, which was used directly in the next step without further purification. MS: m/z (ES+)=411 (M+H$^+$).

Intermediate Example 21. Preparation of 4-[[4-(trifluoromethoxy)phenyl]methoxy]-2-(trifluoromethyl) benzothiophene-5-carboxylic acid

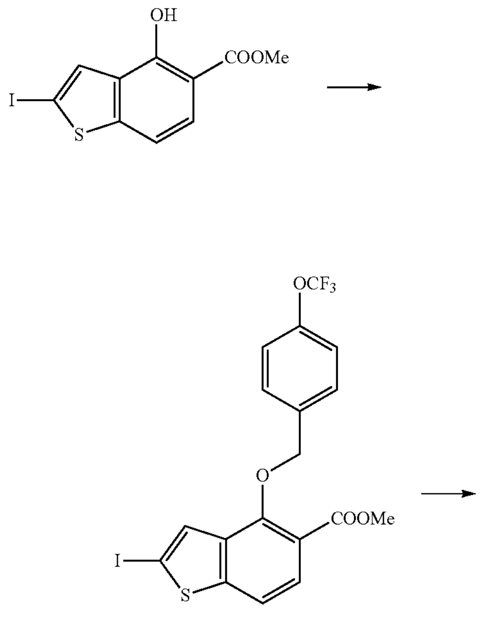

-continued

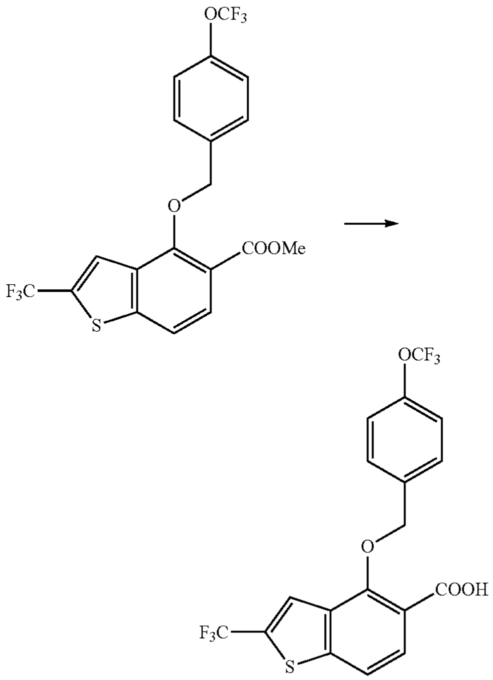

Step 1

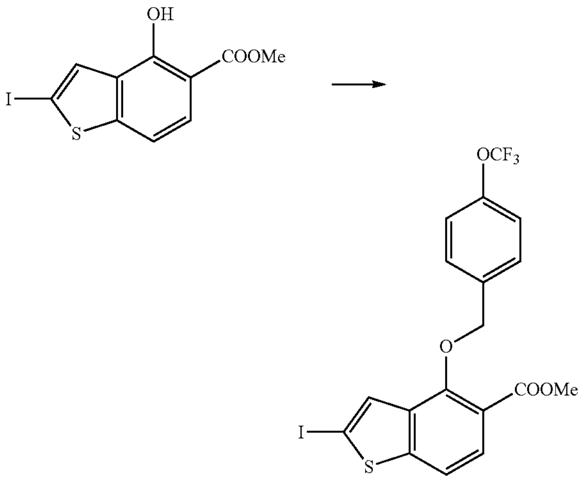

To a stirred solution of methyl 4-hydroxy-2-iodo-benzothiophene-5-carboxylate (200 mg, 0.60 mmol) in DMF (10 mL) were added 1-(bromomethyl)-4-(trifluoromethoxy)benzene (184 mg, 0.72 mmol) and $Cs_2CO_3$ (391 mg, 1.20 mmol). The resulting mixture was stirred at room temperature for 1 h, diluted with water (50 mL), and extracted with EA (50 mL×2), washed with brine (50 mL), dried over anhydrous sodium sulfate, filtered and concentrated in vacuo. The crude material was purified by silica gel chromatography (PE/EA=20:1) to afford methyl 2-iodo-4-[[4-(trifluoromethoxy)phenyl]methoxy]benzothiophene-5-carboxylate (275 mg, 90% yield) as a white solid. LCMS purity: 90%; MS: m/z (ES$^+$)=509 (M+H$^+$).

Step 2

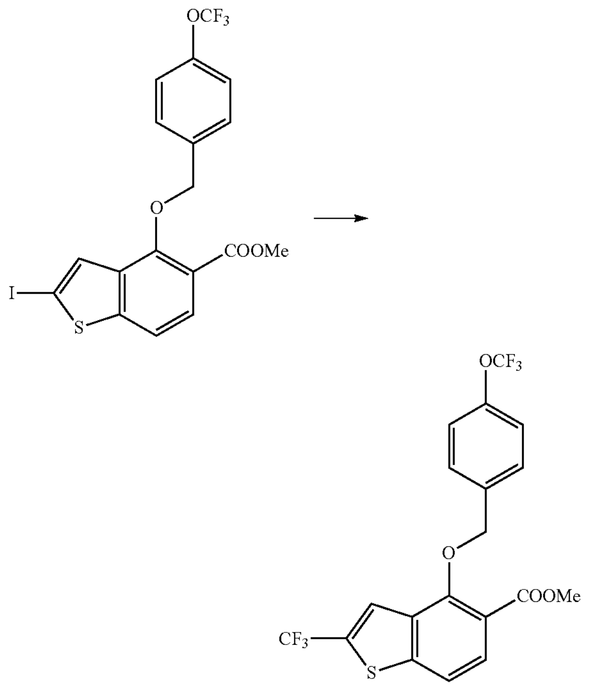

To a stirred solution of methyl 2-iodo-4-[[4-(trifluoromethoxy)phenyl]methoxy]-benzothiophene-5-carboxylate (258 mg, 0.507 mmol), CuI (19 mg, 0.10 mmol), 1,10-phenanthroline (18 mg, 0.10 mmol), B(OMe)3 (152 mg, 1.50 mmol), $TMSCF_3$ (215 mg, 1.50 mmol), KF (90 mg, 1.50 mmol) were added in DMSO (10 mL). The mixture was stirred at 60° C. for 20 hours and then, the mixture was quenched with water (50 mL), and extracted with EA (50 mL×2), washed with brine (50 mL), dried over anhydrous sodium sulfate, filtered and concentrated in vacuo. The crude material was purified by silica gel chromatography (PE/EA=50:1) to afford methyl 4-[[4-(trifluoromethoxy)phenyl]methoxy]-2-(trifluoromethyl)benzothiophene-5-carboxylate (142 mg, 62% yield) as a yellow solid. LCMS purity: 90%; MS: m/z ($ES^+$)=451 (M+Na+).

Step 3

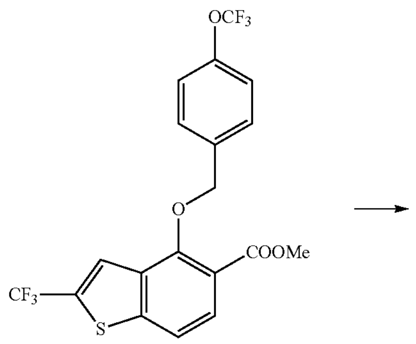

-continued

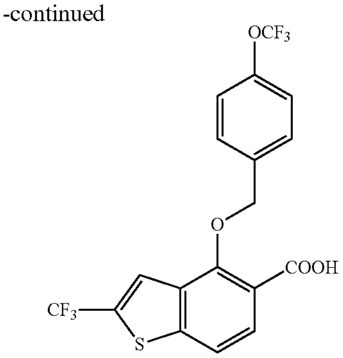

To a stirred solution of methyl 4-[[4-(trifluoromethoxy)phenyl]methoxy]-2-(trifluoromethyl)benzothiophene-5-carboxylate (135 mg, 0.30) in MeOH/THF/$H_2O$ (10 mL/10 mL/1 mL) was added $LiOH·H_2O$ (126 mg, 3.00 mmol). The solution was stirred at 70° C. overnight. The solution was concentrated and then acidified with aqueous hydrochloric acid (2 N) to pH=4-5 and extracted with EA (50 mL×2). The combined organic phase was washed with brine (50 mL), dried over anhydrous sodium sulfate, filtered and concentrated in vacuo, purified by silica gel column chromatography (PE/EA=1/5) to afford 4-[[4-(trifluoromethoxy)phenyl]methoxy]-2-(trifluoromethyl)-benzothiophene-5-carboxylic acid (106 mg, 81% yield) as a white solid. LCMS purity: 90%; MS: m/z ($ES^+$)=437 ($M+H^+$).

Intermediate Example 22. Preparation of 2-chloro-4-[[4-(trifluoromethyl)phenyl]methoxy]benzothiophene-5-carboxylic acid

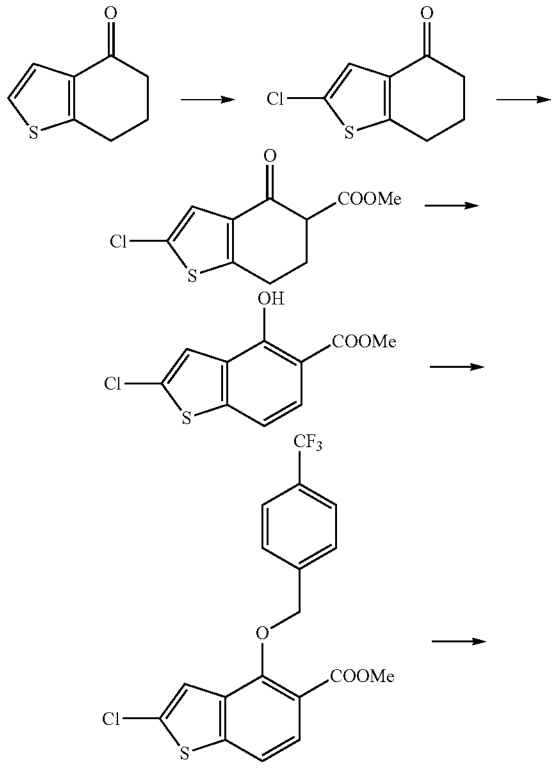

-continued

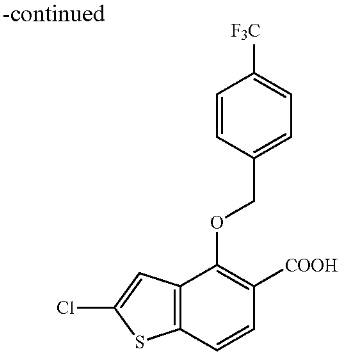

Step 1

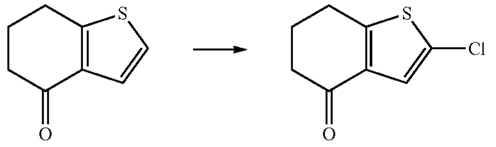 [SMILES: O=C1CCCc2sccc21 ; O=C1CCCc2sc(Cl)cc21]

To a solution of 6,7-dihydro-5H-benzothiophen-4-one (1.0 g, 6.6 mmol) in glacial acetic acid (5 ml), NCS (1.1 g, 7.92 mmol) was added and the reaction mixture was kept under reflux and stirring for 1 h. Then the solvent was removed under reduced pressure. The residue was treated with a 10% aqueous solution of $NaHCO_3$ and it was extracted with ethyl acetate. The organic phase was washed with water and dried over $Na_2SO_4$. It was concentrated under reduced pressure. The residue was purified by SGC (PE/EA=10:1) to give 2-chloro-6,7-dihydro-5H-benzothiophen-4-one (730 mg, 60% yield) as a yellow solid. LCMS purity: 93%; MS: m/z ($ES^+$)=186 ($M+H^+$).

Step 2

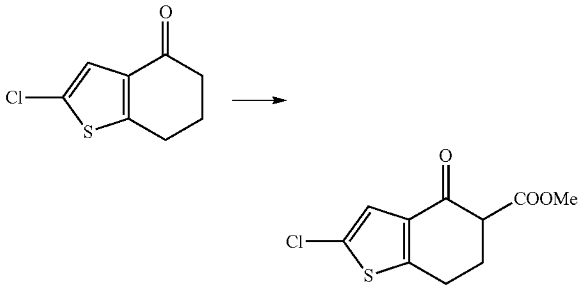

To a solution of 2-chloro-6,7-dihydro-5H-benzothiophen-4-one (500 mg, 2.7 mmol) in $Me_2CO_3$ (10 mL) was added NaH (60% in oil, 215 mg, 5.38 mmol). After stirring at 70° C. for 5 h, the mixture was quenched with water and extracted with EA (50 mL×2). The organic phase was washed with brine, dried over $Na_2SO_4$, filtered and concentrated. The residue was purified by SGC (PE/EA=10:1) to give methyl 2-chloro-4-oxo-6,7-dihydro-5H-benzothiophene-5-carboxylate (477 mg, 55% yield) as a yellow oil. LCMS purity: 95%; MS: m/z ($ES^+$)=245 ($M+H^+$).

Step 3

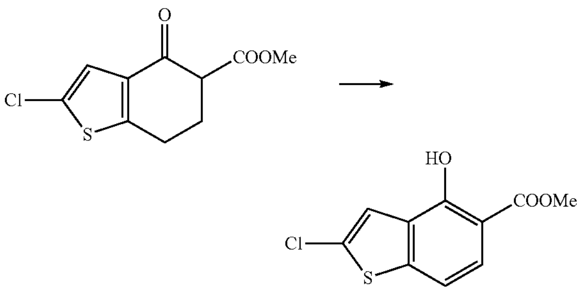

A solution of methyl 2-chloro-4-oxo-6,7-dihydro-5H-benzothiophene-5-carboxylate (400 mg, 1.64 mmol) in $CHCl_3$ (10 mL) was added NBS (310 mg, 1.81 mmol) and AIBN (cat.) at room temperature, then the reaction mixture was stirred under reflux for 1 hour, concentrated to afford a residue. The residue was dissolved in THF (20 mL), DBU (565 mg, 3.72 mmol) was added at room temperature, the solution was stirred at room temperature for 4 hours, adjusted pH to 6 with 1 N HCl, extracted with EA (40 mL×3), washed with brine (80 mL), dried over $Na_2SO_4$, filtered and concentrated, then purified by silica gel chromatography (PE) to afford methyl 2-chloro-4-hydroxy-benzothiophene-5-carboxylate (345 mg, 87% yield) as a white solid. LCMS purity: 90%; MS: m/z ($ES^+$)=243 ($M+H^+$).

Step 4

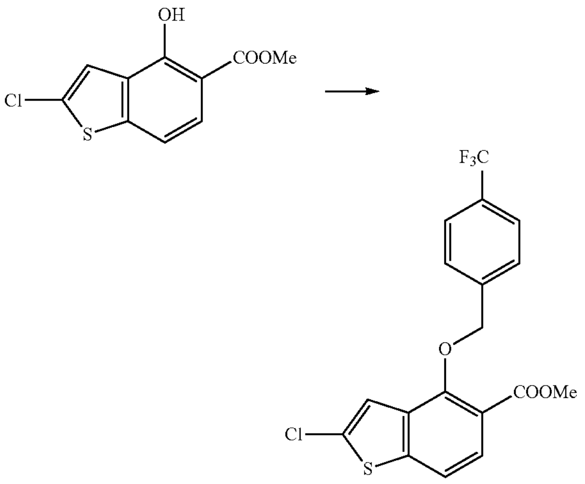

To a stirred solution of methyl 2-chloro-4-hydroxy-benzothiophene-5-carboxylate (220 mg, 0.91 mmol) in DMF (10 mL) were added 1-(bromomethyl)-4-(trifluoromethyl) benzene (239 mg, 1.00 mmol) and $Cs_2CO_3$ (593 mg, 1.82 mmol). The resulting mixture was stirred at room temperature for 1 h, diluted with water (50 mL), and extracted with EA (50 mL×2), washed with brine (50 mL), dried over anhydrous sodium sulfate, filtered and concentrated in vacuo. The crude was purified by silica gel chromatography (PE/EA=20:1) to afford methyl 2-chloro-4-[[4-(trifluoromethyl)phenyl]methoxy]benzothiophene-5-carboxylate (250 mg, 70% yield) as a white solid. LCMS purity: 94%; MS: m/z ($ES^+$)=401 ($M+H^+$).

Step 5

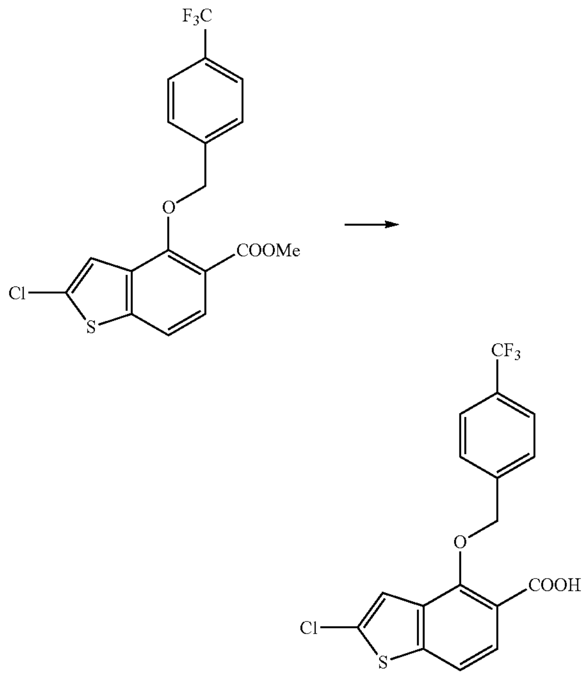

To a stirred solution of methyl 2-chloro-4-[[4-(trifluoromethyl) phenyl]methoxy]-benzothiophene-5-carboxylate (250 mg, 0.625 mmol) in MeOH/THF/$H_2O$ (10 mL/10 mL/1 mL) was added LiOH·$H_2O$ (105 mg, 2.5 mmol). The solution was stirred at 70° C. overnight. The solution was concentrated and then acidified with aqueous hydrochloric acid (2 N) to pH=4-5 and extracted with EA (50 mL×2). The combined organic phase was washed with brine (50 mL), dried over anhydrous sodium sulfate, filtered and concentrated in vacuo, purified by silica gel column chromatography (PE/EA=1/5) to afford 2-chloro-4-[[4-(trifluoromethyl)phenyl]methoxy]benzothiophene-5-carboxylic acid (230 mg, 96% yield) as a white solid. LCMS purity: 96%; MS: m/z ($ES^+$)=387 ($M+H^+$).

Intermediate Example 23. Preparation of 2-methoxy-4-[[4-(trifluoromethyl)phenyl]methoxy]benzothiophene-5-carboxylic acid 2-methoxy-4-[[4-(trifluoromethyl)phenyl]methoxy]benzothiophene-5-carboxylic acid was prepared according to the following scheme.

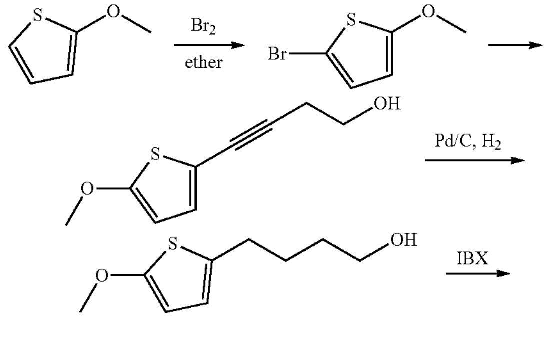

-continued

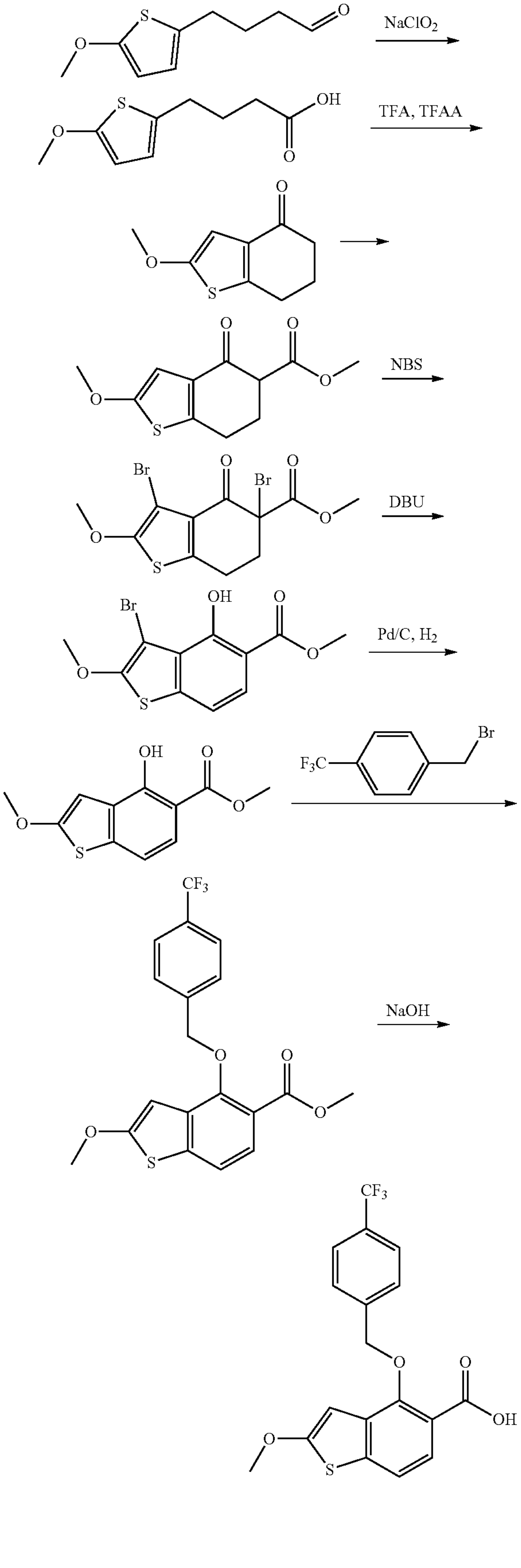

Step 1

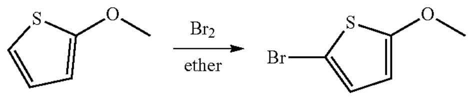

To a solution of 2-methoxythiophene (5.0 g, 43.9 mmol) in $Et_2O$ (200 mL) at −70° C. was added a solution of $Br_2$ (7.02 g, 43.9 mmol) in $Et_2O$ (100 mL). The resulting mixture was stirred at −70° C. for 1 h. The resulting mixture was poured into sat. aq. $NaHCO_3$ (500 mL) and extracted with $Et_2O$ (3×200 mL). The organic layers were combined, dried over anhydrous $Na_2SO_4$, filtered, and concentrated in vacuo to afford 2-bromo-5-methoxy-thiophene (5.0 g, 58%) as a light yellow oil. $^1H$ NMR (400 MHz, $CDCl_3$, ppm) δ 6.71 (d, J=4.0 Hz, 1H), 5.99 (d, J=4.0 Hz, 1H), 3.88 (s, 3H).

Step 2

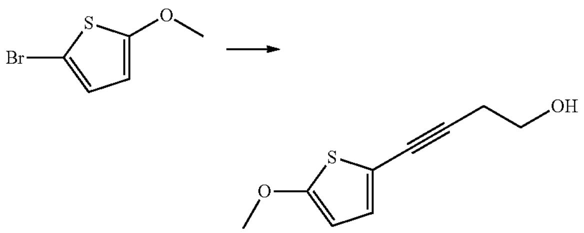

A mixture of 2-bromo-5-methoxy-thiophene (5.0 g, 25.9 mmol), but-3-yn-1-ol (5.44 g, 77.7 mmol), $Pd(PPh_3)_2Cl_2$ (1.82 g, 2.59 mmol), and CuI (246 mg, 1.30 mmol) in $Et_3N$ (20.0 mL) and DMF (20.0 mL) was stirred under $N_2$ at 80° C. overnight. On cooling, the reaction mixture was poured into water (200 mL) and the mixture extracted with EA (3×100 mL). The combined extracts were dried over $Na_2SO_4$, concentrated. The residue was purified by silica gel column chromatography (PE/EA=15/1 to 4/1) to afford 4-(5-methoxy-2-thienyl)but-3-yn-1-ol (3.0 g, 64%) as a light yellow oil. LCMS purity: 87%; MS: m/z ($ES^+$)=183 ($M+H^+$).

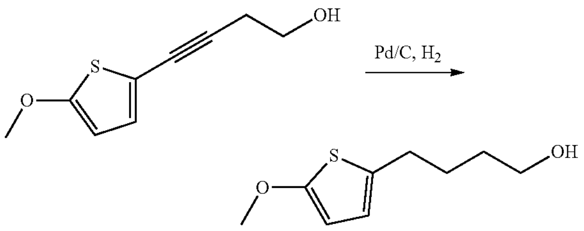

To a solution of 4-(5-methoxy-2-thienyl)but-3-yn-1-ol (3.0 g, 16.5 mmol) in MeOH (20.0 mL) was added 10% Pd/C (800 mg). The resultant mixture was stirred at room temperature under hydrogen for 5 days. The mixture was filtered, and the filtrate was concentrated in vacuo to afford 4-(5-methoxy-2-thienyl)butan-1-ol (2.6 g, 85%) as a light yellow oil. LCMS purity: 88%; MS: m/z ($ES^+$)=187 ($M+H^+$).

Step 4

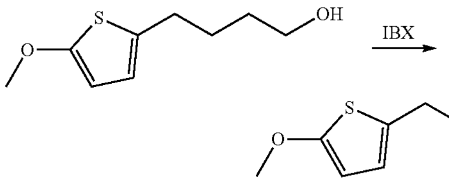

To a solution of 4-(5-methoxy-2-thienyl)butan-1-ol (2.6 g, 14.0 mmol) in EA (100 mL) was added IBX (11.8 g, 42.0 mmol). The resultant mixture was stirred at reflux for 5 h. The mixture was filtered, and the filtrate was concentrated in vacuo. The residue was purified by silica gel column chromatography (PE/EA=10/1) to afford 4-(5-methoxy-2-thienyl)butanal (1.5 g, 58%) as a light yellow oil. LCMS purity: 95%; MS: m/z ($ES^+$)=460 ($M+H^+$).

Step 5

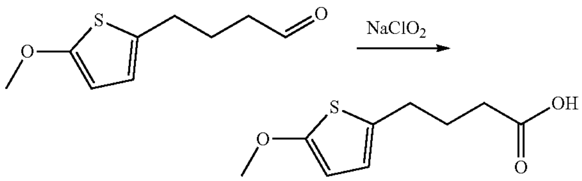

To a mixture of 4-(5-methoxy-2-thienyl)butanal (1.5 g, 8.15 mmol), $KH_2PO_4$ (4.43 g, 32.6 mmol) in 1,4-dioxane (16.0 mL) and $H_2O$ (8.0 mL) was added $NaClO_2$ (3.67 g, 40.75 mmol) and 2-methyl-2-butene (8.0 mL), and the resulting mixture was stirred at room temperature for 16 hours. The mixture was diluted with water (50 mL) and extracted with EA (50 mL), washed with brine (50 mL), dried over anhydrous $Na_2SO_4$, filtered and concentrated in vacuo, and the residue was purified by silica gel column chromatography (PE/EA=10/1) to afford 4-(5-methoxy-2-thienyl)butanoic acid (1.0 g, 62%) as a light yellow oil. LCMS purity: 84%; MS: m/z ($ES^+$)=200 ($M+H^+$).

Step 6

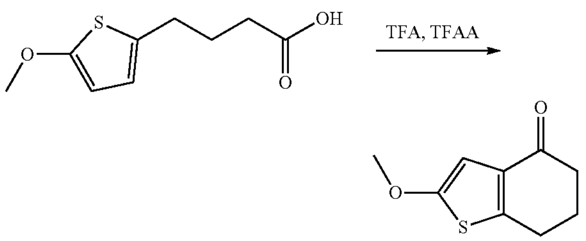

The mixture of 4-(5-methoxy-2-thienyl)butanoic acid (1.0 g, 5.43 mmol) in TFA (10.0 mL) and TFAA (5.0 mL) was stirred at room temperature for 2 hours. The mixture was diluted with water (50 mL) and extracted with $Et_2O$ (3×30 mL), washed with brine (50 mL), dried over anhydrous $Na_2SO_4$, filtered and concentrated in vacuo, and the residue was purified by silica gel column chromatography ($Et_2O$/

PE=1/3) to afford 2-methoxy-6,7-dihydro-5H-benzothiophen-4-one (500 mg, 55%) as a light yellow oil. LCMS purity: 83%; MS: m/z ($ES^+$)=183 ($M+H^+$).

Step 7

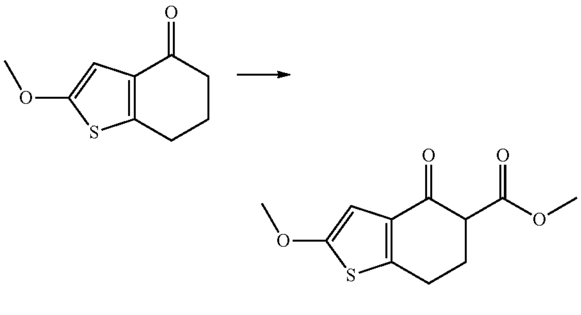

To a stirred solution of NaH (88 mg, 2.20 mmol, 60% in oil) in dimethyl carbonate (2.0 mL) was added 2-methoxy-6,7-dihydro-5H-benzothiophen-4-one (100 mg, 0.549 mmol) at room temperature. The resulting solution was heated at 25° C. for 2 hours. The mixture was cooled in ice, treated with HCl (2 N) to pH=4, extracted with EA (3×10 mL). The combined organic phases were dried over anhydrous sodium sulfate, filtered, and concentrated in vacuo to afford methyl 2-methoxy-4-oxo-6,7-dihydro-5H-benzothiophene-5-carboxylate (100 mg, 76%) as a light yellow oil. LCMS purity: 84%; MS: m/z ($ES^+$)=240 ($M+H^+$).

Step 8

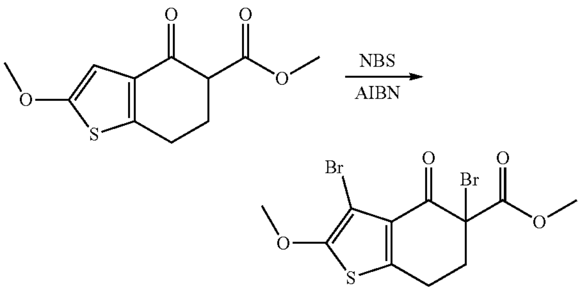

To a stirred solution of methyl 2-methoxy-4-oxo-6,7-dihydro-5H-benzothiophene-5-carboxylate (100 mg, 0.417 mmol) in $CHCl_3$ (2.0 mL) was added NBS (148 mg, 0.834 mmol) and AIBN (20.5 mg, 0.125 mmol) at room temperature. The reaction mixture was stirred at room temperature, concentrated to afford methyl 3,5-dibromo-2-methoxy-4-oxo-6,7-dihydrobenzothiophene-5-carboxylate (200 mg, crude) as a light yellow oil. LCMS purity: 74%; MS: m/z ($ES^+$)=398 ($M+H^+$).

Step 9

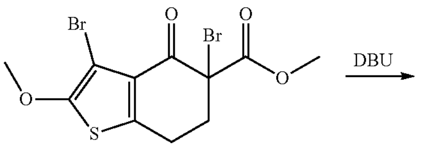

-continued

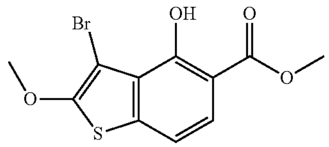

To a stirred solution of methyl 3,5-dibromo-2-methoxy-4-oxo-6,7-dihydrobenzothiophene-5-carboxylate (200 mg, 0.503 mmol) in THF (2.0 mL) was added DBU (1.0 mL) at room temperature. The mixture was stirred at room temperature for 1 hr, adjusted pH to 6 with 1 N HCl, extracted with EA (3×10 mL), washed with brine (50 mL), dried over $Na_2SO_4$, filtered and concentrated to afford methyl 3-bromo-4-hydroxy-2-methoxy-benzothiophene-5-carboxylate (120 mg, 75%) as a light yellow oil. LCMS purity: 81%; MS: m/z ($ES^+$)=317 ($M+H^+$).

Step 10

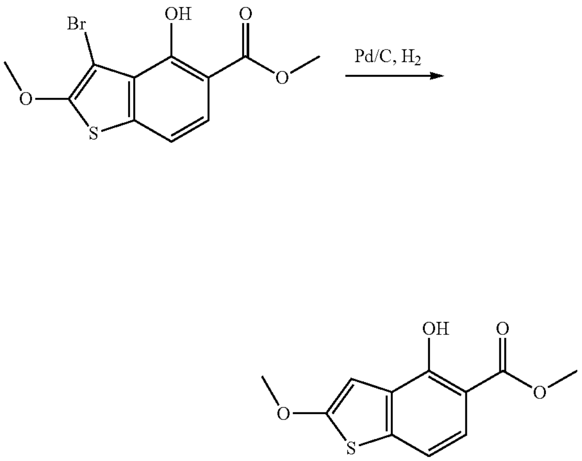

To a solution of methyl 3-bromo-4-hydroxy-2-methoxy-benzothiophene-5-carboxylate (100 mg, 0.315 mmol) in MeOH (5.0 mL) was added 10% Pd/C (100 mg). The resultant mixture was stirred at room temperature under hydrogen overnight. The mixture was filtered, and the filtrate was concentrated in vacuo to afford methyl 4-hydroxy-2-methoxy-benzothiophene-5-carboxylate (100 mg, crude) as a light yellow solid. LCMS purity: 84%; MS: m/z ($ES^+$)=239 ($M+H^+$).

Step 11

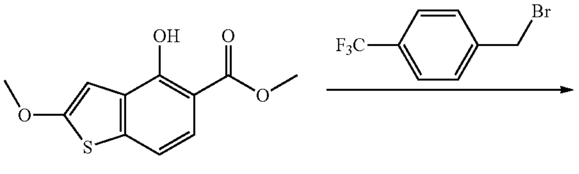

-continued

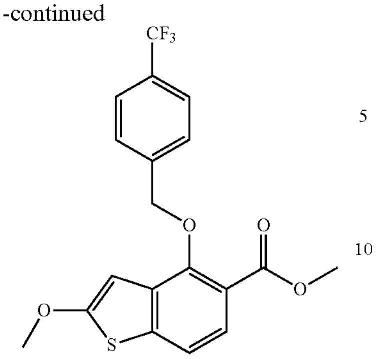

To a solution of methyl 4-hydroxy-2-methoxy-benzothiophene-5-carboxylate (100 mg, crude, 0.315 mmol) in DMF (25.0 mL) was added 1-(bromomethyl)-4-(trifluoromethyl) benzene (151 mg, 0.630 mmol), followed by $K_2CO_3$ (175 mg, 1.26 mmol). The resulting mixture was stirred at rt overnight. The mixture was poured into water (20 mL), extracted with EA (3×20 mL), filtered, and concentrated in vacuo. The residue was purified by prep-TLC (PE/EA=10/1) to afford methyl 2-methoxy-4-[[4-(trifluoromethyl)phenyl] methoxy]benzothiophene-5-carboxylate (40 mg, 24%) as a light yellow oil. LCMS purity: 96%; MS: m/z $(ES^+)$=397 $(M+H^+)$.

Step 12

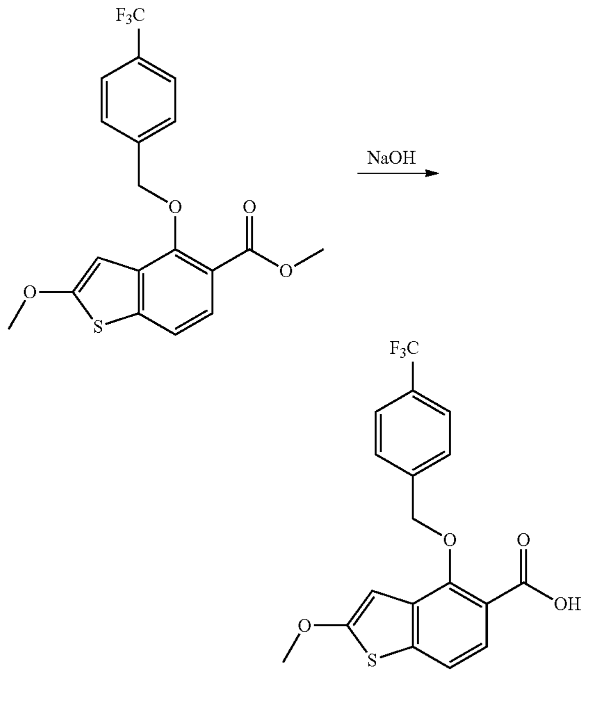

To a solution of methyl 2-methoxy-4-[[4-(trifluoromethyl)phenyl]methoxy]benzothiophene-5-carboxylate (40 mg, 0.101 mmol) in MeOH/$H_2O$ (v/v=2/1, 1.0 mL) was added NaOH (20.2 mg, 0.505 mmol). The mixture was stirred at 30° C. for 5 h. The residue was diluted with $H_2O$ (30 mL), acidified with aqueous HCl (2.0 M) to pH<3, and extracted with ethyl acetate (3×20 mL). The combined organic phases were dried over anhydrous sodium sulfate, filtered, and concentrated in vacuo to afford 2-methoxy-4-[[4-(trifluoromethyl)phenyl]methoxy]benzothiophene-5-carboxylic acid (30 mg, 78%) as a white solid. LCMS purity: 52%; MS: m/z $(ES^+)$=382 $(M+H^+)$.

Intermediate Example 24. Preparation of 2-ethyl-4-[[4-(trifluoromethoxy)phenyl]methoxy]benzothiophene-5-carboxylic acid 2-Ethyl-4-[[4-(trifluoromethoxy)phenyl]methoxy]benzothiophene-5-carboxylic acid was prepared according to the following scheme.

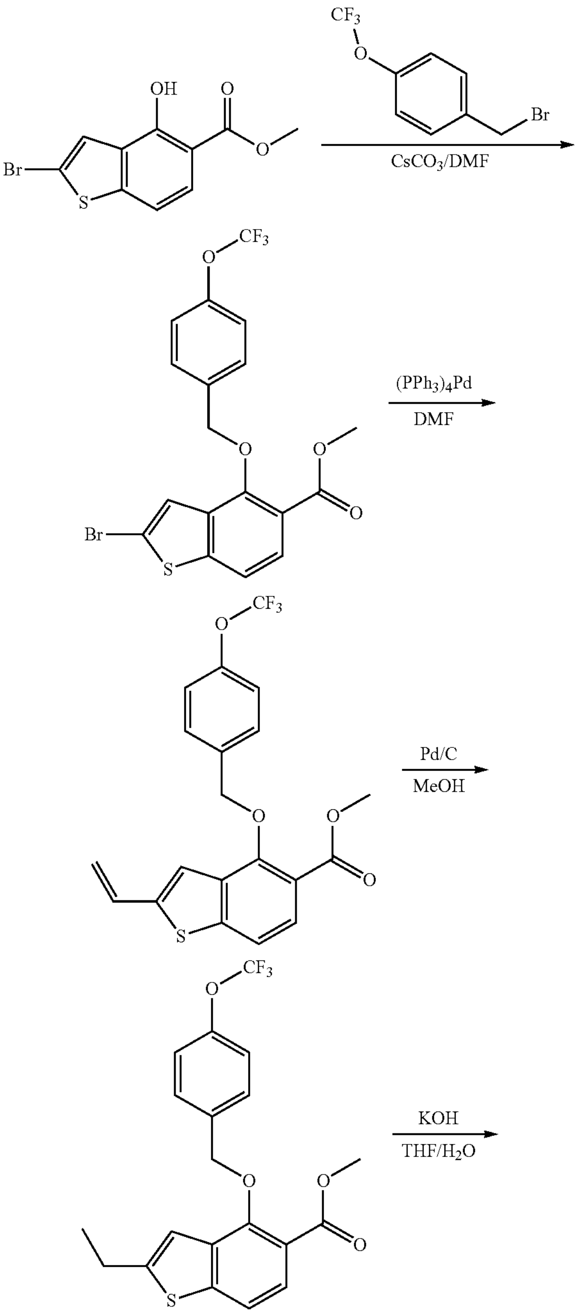

-continued

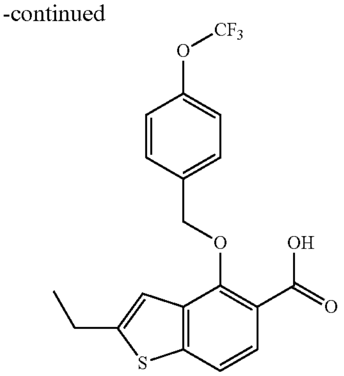

Step 1

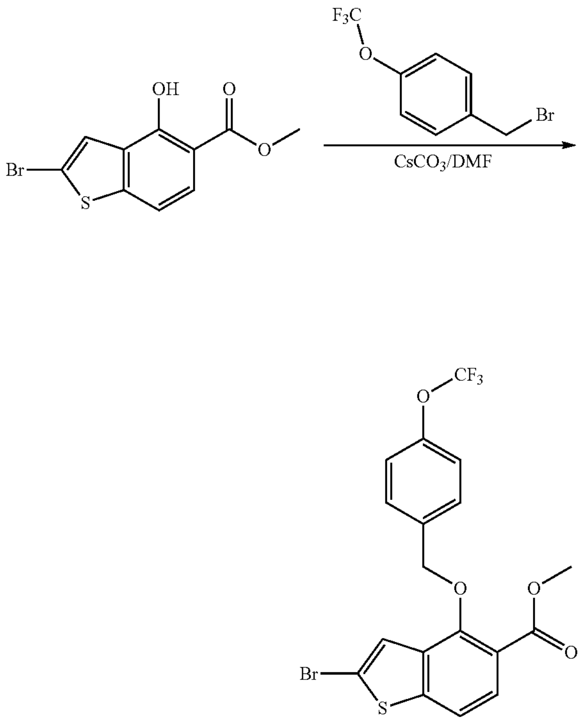

Step 2

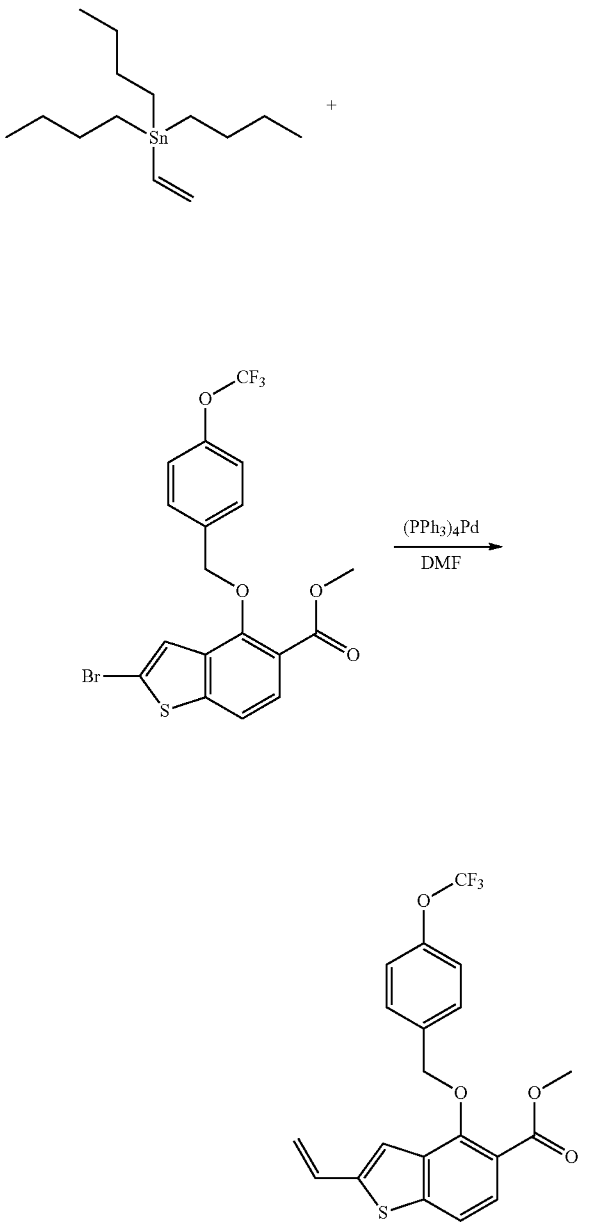

To a stirred solution of methyl 2-bromo-4-hydroxy-benzothiophene-5-carboxylate (270 mg, 0.94 mmol) in DMF (3 mL) were added 1-(bromomethyl)-4-(trifluoromethoxy)benzene (270 mg, 2.69 mmol) and $Cs_2CO_3$ (790 mg, 2.4 mmol). The resulting mixture was stirred at room temperature for 2 h, diluted with water (50 mL), and extracted with EA (50 mL×2), washed with brine (50 mL), dried over anhydrous $Na_2SO_4$, filtered and concentrated in vacuo and purified by silica gel column chromatography (EA/PE=1/20) to afford (414 mg; 95.6%) of methyl 2-bromo-4-[[4-(trifluoromethoxy)phenyl]methoxy]benzothiophene-5-carboxylate as a yellow oil. LCMS purity 79%; MS: m/z ($ES^+$)=484 ($M+H^+$).

A solution of methyl 2-bromo-4-[[4-(trifluoromethoxy)phenyl]methoxy]-benzothiophene-5-carboxylate (414 mg, 0.898 mmol), tributyl(vinyl)stannane (600 mg, 1.893 mmol), $(PPh_3)_4Pd$ (150 mg, 0.13 mmol) in DMF (4 mL) was stirred at 90° C. for 3 hours under $N_2$, diluted with aqueous KF (50 mL) and extracted with EA (50 mL), washed with brine (50 mL), dried over anhydrous $Na_2SO_4$, filtered and concentrated in vacuo, and the residue was purified by silica gel chromatography (PE/EA=1/50) to afford methyl 4-[[4-(trifluoromethoxy)phenyl]methoxy]-2-vinyl-benzothiophene-5-carboxylate (350 mg, 95.6%) as a yellow oil. LCMS: purity 90.7%; MS: m/z ($ES^+$)=409 ($M+H^+$).

Step 3

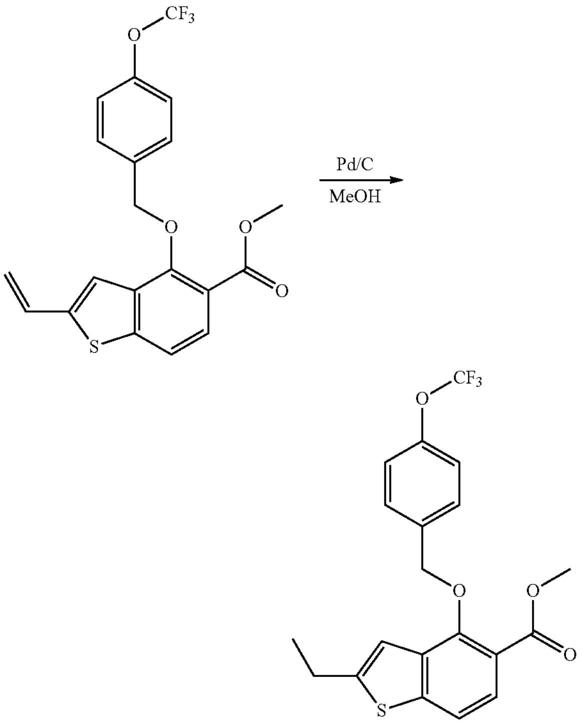

A mixture of 350 mg (0.86 mmol) of methyl 4-[[4-(trifluoromethoxy) phenyl]methoxy]-2-vinyl-benzothiophene-5-carboxylate and 180 mg of 10% Pd—C in 50 mL of MeOH containing 1% water was vigorously stirred under 1 atm of $H_2$ at room temperature for 20 h and then filtered. The filtrate was concentrated to yield methyl 2-ethyl-4-[[4-(trifluoromethoxy)phenyl]methoxy]benzothiophene-5-carboxylate (330 mg; 94%) as a yellow oil. LCMS: purity 92.5%; MS: m/z ($ES^+$)=411 ($M+H^+$).

Step 4

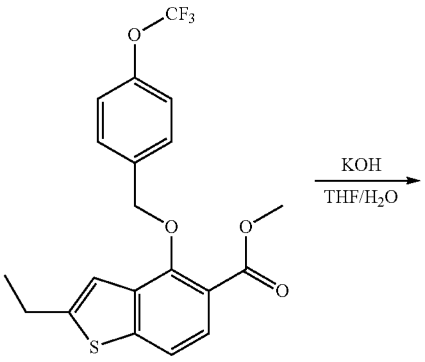

-continued

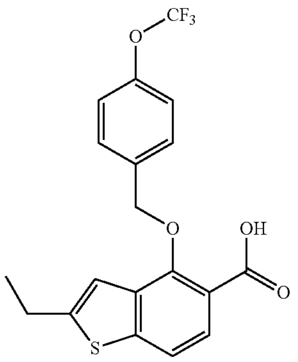

A mixture of 330 mg (0.81 mmol) of methyl 2-ethyl-4-[[4-(trifluoromethoxy)phenyl]methoxy]benzothiophene-5-carboxylate and 220 mg of KOH (3.92 mmol) in 0.5 mL of $H_2O$, 2 mL of THF and 2 mL of MeOH was vigorously stirred at room temperature for 3 h and then concentrated. The residue was acidified with 10% citric acid and extracted with EA (40 mL). The extract was washed twice with brine (10 mL) and dried over $Na_2SO_4$, concentrated and the crude product thus obtained was purified by silica gel column chromatography on silica gel (PE/EA=4:1) to give 2-ethyl-4-[[4-(trifluoromethoxy)phenyl]methoxy]benzothiophene-5-carboxylic acid (250 mg; 78.6%) as a white solid.

LCMS: purity 89.7%; MS: m/z ($ES^+$)=397 ($M+H^+$).

Intermediate Example 25. Preparation of 2-(difluoromethyl)-4-[[4-(trifluoromethyl)phenyl]methoxy]benzothiophene-5-carboxylic acid 2-(difluoromethyl)-4-[[4-(trifluoromethyl)phenyl]methoxy]benzothiophene-5-carboxylic acid was prepared according to the following scheme.

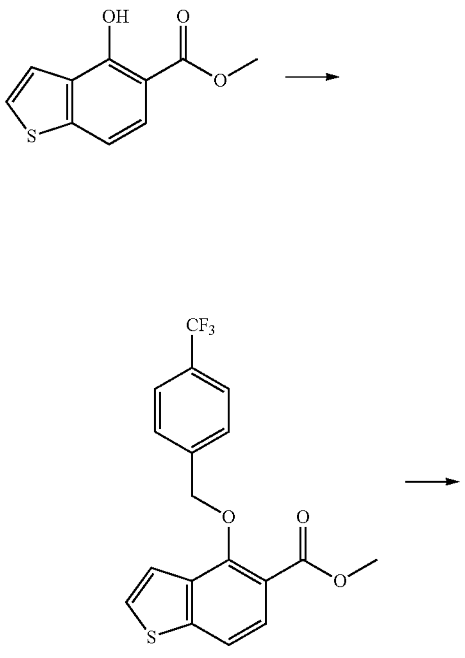

-continued
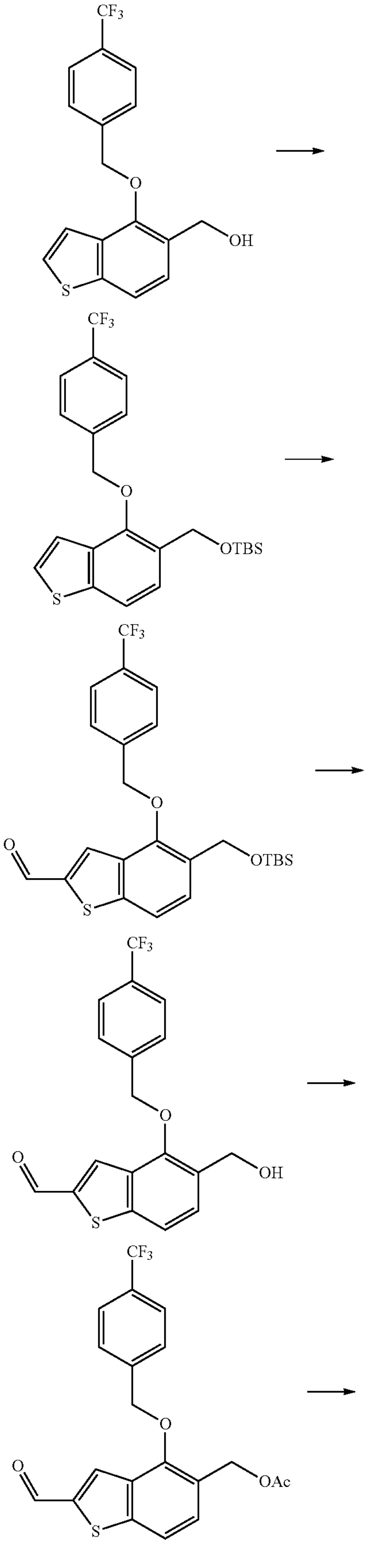
-continued
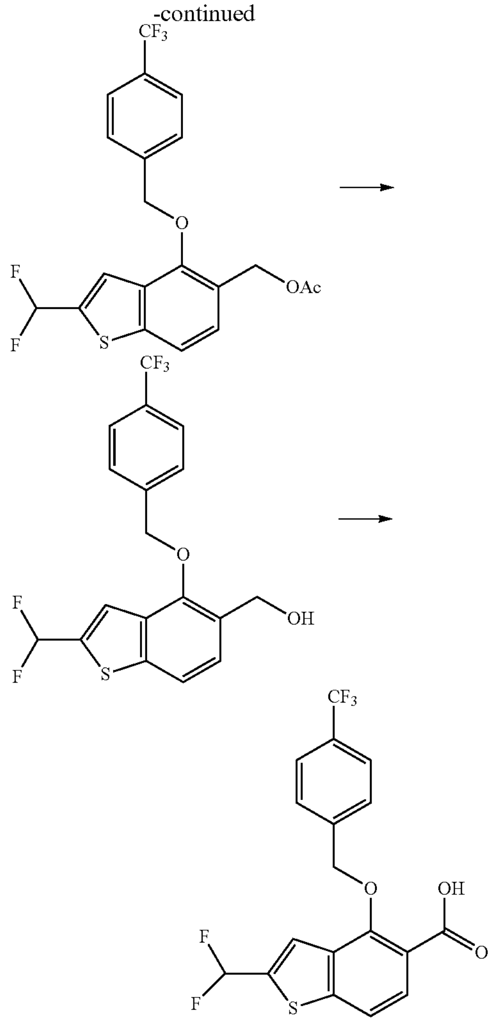
Step 1
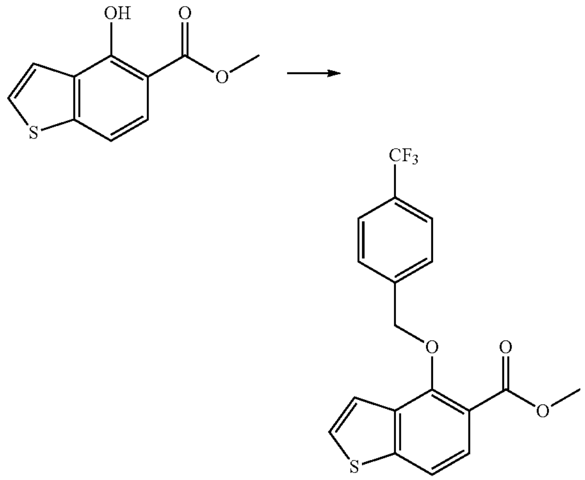
To a solution of methyl 4-hydroxybenzo[b]thiophene-5-carboxylate (500 mg, 2.4 mmol) in DMF (10 mL) was added 1-(bromomethyl)-4-(trifluoromethyl)benzene (571 mg, 2.4 mmol), $Cs_2CO_3$ (1.8 g, 4.8 mmol). The resulting mixture was stirred at room temperature overnight. The mixture was diluted with $H_2O$ (50 mL), extracted with EA (3×30 mL), combined organic phase washed with brine (50 mL), dried over anhydrous sodium sulphate, filtered, concentrated in vacuo to afford methyl 4-[[4-(trifluoromethyl)phenyl] methoxy]benzothiophene-5-carboxylate (500 mg, crude) as a light yellow solid. LCMS purity: 82%; MS: m/z (ES+) =566 ($M+H^+$).

Step 2

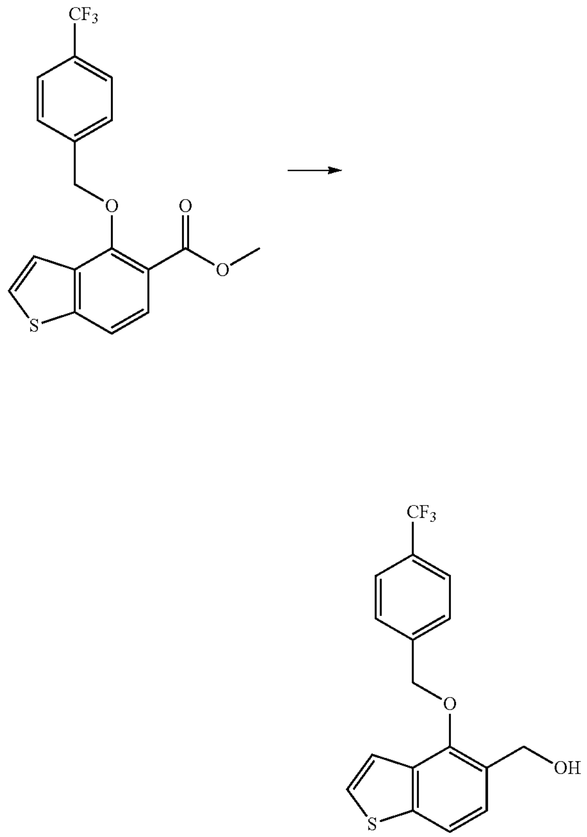

To a solution of methyl 4-[[4-(trifluoromethyl)phenyl] methoxy]benzothiophene-5-carboxylate (500 mg, 1.4 mmol) cooled to 0° C. in THF (10 mL) was added LAH (1.4 mL, 1 M in THF). The resulting solution was stirred at 0° C. for 2 hrs. The reaction mixture was quenched with $NH_4Cl$ aq. (20 mL), diluted with water (40 mL) and the mixture was extracted with EA (3×40 mL). The combined organic phase was washed with brine (50 ml), anhydrous sodium sulfate, filtered and concentrated in vacuo to afford [4-[[4-(trifluoromethyl)phenyl]methoxy]benzothiophen-5-yl]methanol (450 mg, crude) as a light yellow solid. LCMS purity: 81%; MS: m/z (ES+)=339 ($M+H^+$).

Step 3

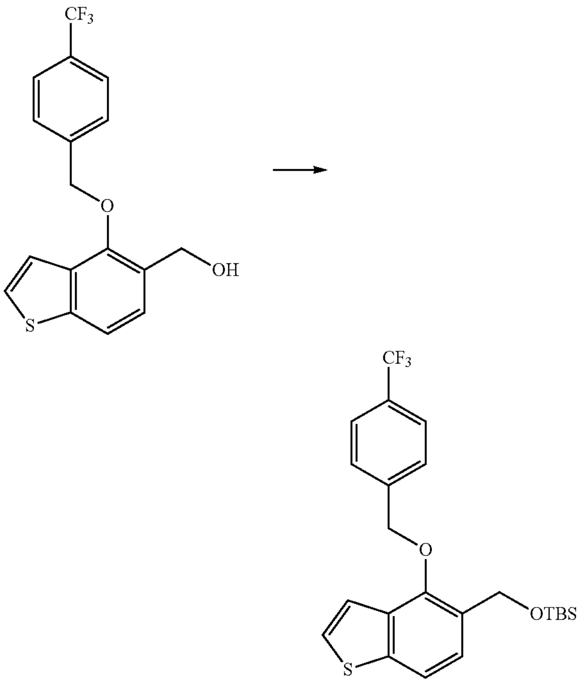

To a solution of [4-[[4-(trifluoromethyl)phenyl]methoxy] benzothiophen-5-yl]methanol (450 mg, 1.3 mmol) in DCM (10 mL) was added imidazole (184 mg, 2.7 mmol), and TBSCl (236 mg, 1.6 mmol). The resulting mixture was stirred at room temperature for 2 hrs. Then the mixture was diluted with $H_2O$ (50 mL), extracted with EA (3×30 mL), the combined organic phase was washed with brine (50 mL), dried over anhydrous sodium sulphate, filtered, concentrated in vacuo to afford tert-butyl-dimethyl-[[4-[[4-(trifluoromethyl)phenyl]methoxy]benzothiophen-5-yl]methoxy]silane (600 mg, crude) as a colorless oil. LCMS purity: 77%; MS: m/z (ES+)=453 ($M+H^+$).

Step 4

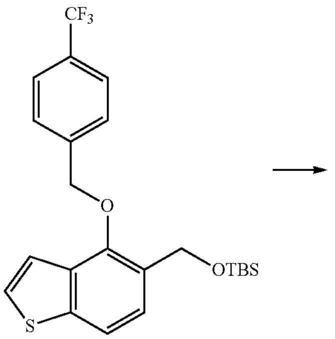

-continued

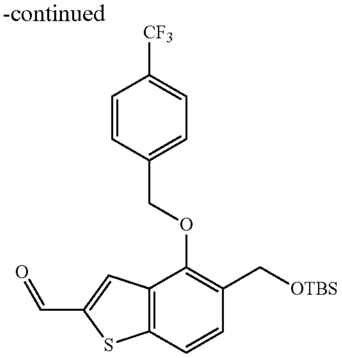

To a solution of DIPA (244 mg, 2.42 mmol) in anhydrous THF (10 mL) cooled to −78° C. was added nBuLi (0.97 mL, 2.5 M in hexane) dropwise, and warmed to room temperature, stirred for 20 min. then cooled to −78° C., tert-butyl-dimethyl-[[4-[[4-(trifluoromethyl)phenyl]methoxy]benzo-thiophen-5-yl]methoxy]silane (500 mg, 1.1 mmol) in anhydrous THF (2 mL) was added dropwise, and stirred for 30 min at −78° C., then anhydrous DMF (161 mg, 2.2 mmol) was added, and reaction stirred for 2 hr at −78° C. The mixture was quenched with $NH_4Cl$ aq. (10 mL) and diluted with $H_2O$ (50 mL), extracted with EA (3×30 mL), and combined organic phase was washed with brine (50 mL), dried over anhydrous sodium sulphate, filtered, concentrated in vacuo to afford 5-[[tert-butyl(dimethyl)silyl]oxymethyl]-4-[[4-(trifluoromethyl)phenyl]methoxy]benzothiophene-2-carbaldehyde (333 mg, crude) as a brown solid. LCMS purity: 74%; MS: m/z (ES+)=481 (M+H$^+$).

Step 5

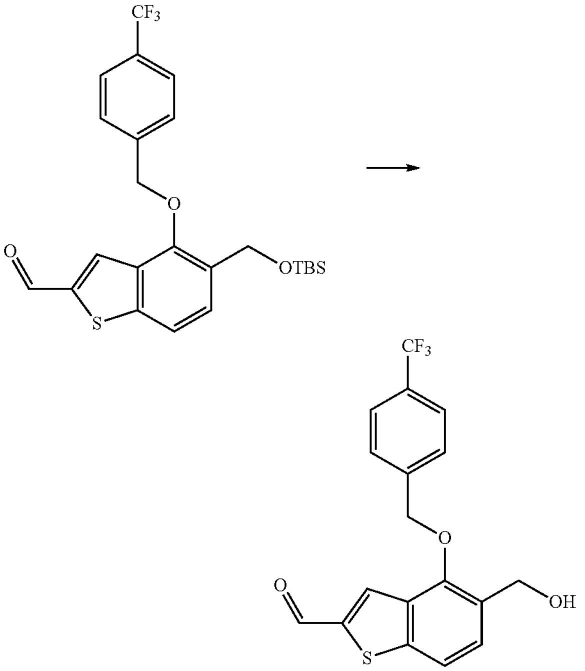

To a solution of 5-[[tert-butyl(dimethyl)silyl]oxymethyl]-4-[[4-(trifluoromethyl)phenyl]methoxy]benzothiophene-2-carbaldehyde (200 mg, 0.42 mmol) in THF (2 mL) was added TBAF (0.42 mL, 1 M in THF). The resulting mixture was stirred at room temperature for 2 h, then diluted with $H_2O$ (50 mL), extracted with EA (3×30 mL), and the combined organic phase was washed with brine (50 mL), dried over anhydrous sodium sulphate, filtered, concentrated in vacuo to afford 5-(hydroxymethyl)-4-[[4-(trifluoromethyl)phenyl]methoxy]benzothiophene-2-carbaldehyde (200 mg, crude) as a light yellow solid. LCMS purity: 69%; MS: m/z (ES+)=367 (M+H$^+$).

Step 6

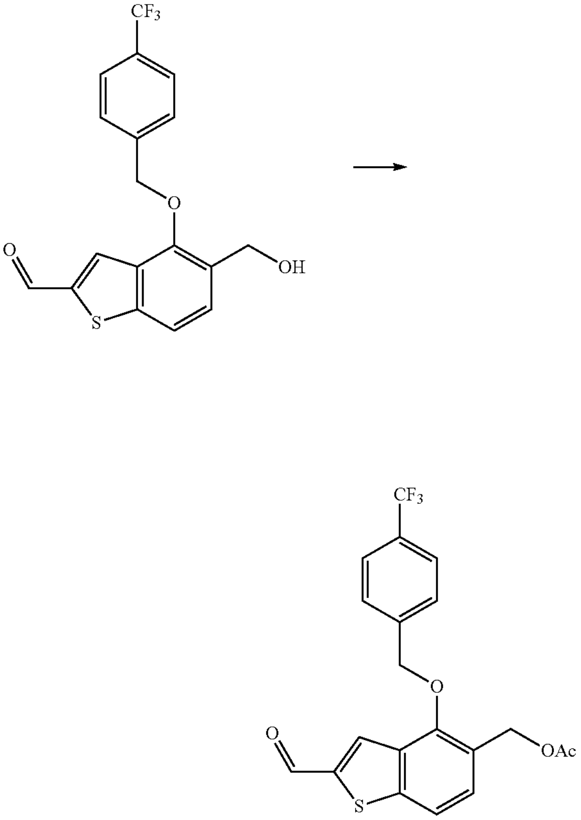

To a solution of 5-(hydroxymethyl)-4-[[4-(trifluoromethyl)phenyl]methoxy]benzothiophene-2-carbaldehyde (200 mg, 0.55 mmol) in DCM (5 mL) was added DCC (131 mg, 0.65 mmol), AcOH (66 mg, 1.1 mmol). The resulting mixture was stirred at room temperature overnight. Then the mixture was diluted with $H_2O$ (20 mL), extracted with EA (3×50 mL), and the combined organic phase was washed with brine (50 mL), dried over anhydrous sodium sulphate, filtered, concentrated in vacuo to afford [2-formyl-4-[[4-(trifluoromethyl)phenyl]methoxy]benzothiophen-5-yl] methyl acetate (200 mg, crude) as a light yellow solid. LCMS purity: 73%; MS: m/z (ES+)=409 (M+H$^+$).

Step 7

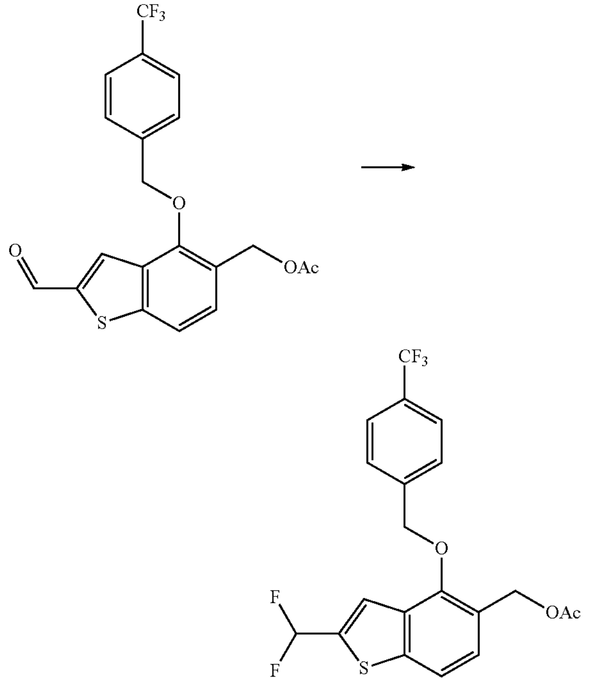

To a solution of [2-formyl-4-[[4-(trifluoromethyl)phenyl]methoxy]benzothiophen-5-yl]methyl acetate (100 mg, 0.25 mmol) in DCM (2 mL) was added BAST (119 mg, 0.54 mmol). The resulting mixture was stirred at room temperature overnight. Then the mixture was diluted with $NaHCO_3$ aqueous (50 mL), extracted with EA (3x30 mL). The combined organic phase was washed with brine (50 mL), dried over anhydrous sodium sulphate, filtered, concentrated in vacuo and purified by SGC (PE/EA=10/1) to afford [2-(difluoromethyl)-4-[[4-(trifluoromethyl)phenyl]methoxy]benzothiophen-5-yl]methyl acetate (63 mg, 60%) as a colorless oil. LCMS purity: 87%; MS: m/z (ES+)=431 (M+H$^+$).

Step 8

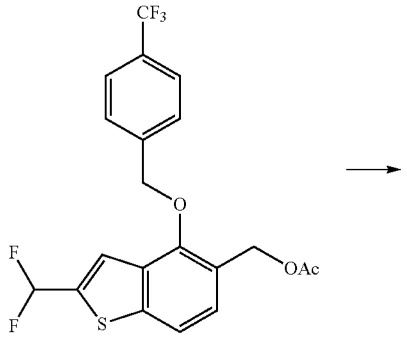

-continued

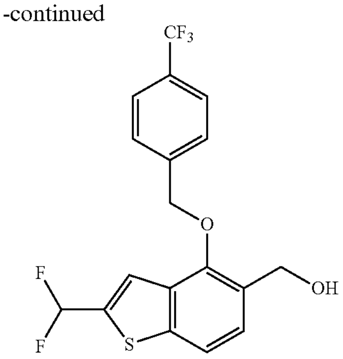

To a solution of [2-(difluoromethyl)-4-[[4-(trifluoromethyl)phenyl]methoxy]benzothiophen-5-yl]methyl acetate (40 mg, 0.09 mmol) in methanol (2 mL) was added $K_2CO_3$ (12 mg, 0.09 mmol). The resulting mixture was stirred at room temperature for 2 hr, diluted with $H_2O$ (20 mL), and extracted with EA (3x20 mL). The combined organic phase was washed with brine (50 mL), dried over anhydrous sodium sulphate, filtered, concentrated in vacuo to afford [2-(difluoromethyl)-4-[[4-(trifluoromethyl)phenyl]methoxy]benzothiophen-5-yl]methanol (37 mg, crude) as a colorless oil. LCMS purity: 89%; MS: m/z (ES+)=389 (M+H$^+$).

Step 9

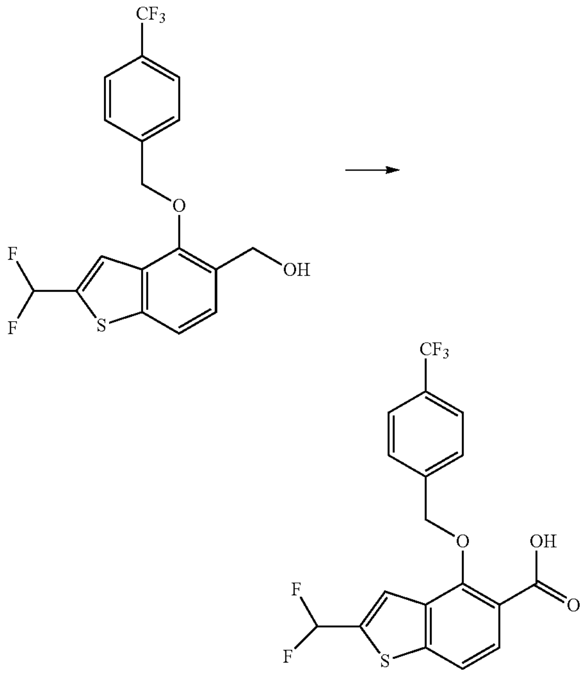

To a solution of [2-(difluoromethyl)-4-[[4-(trifluoromethyl)phenyl]methoxy]benzothiophen-5-yl]methanol (110 mg, 0.28 mmol) in acetone (2 mL) was added Jones' reagent (0.22 mL, 0.56 mmol). The resulting mixture was stirred at room temperature for 2 hr. Then the mixture was diluted with $H_2O$ (40 mL), extracted with EA (3x20 mL), and the combined organic phase was washed with brine (50 mL), dried over anhydrous sodium sulphate, filtered, concentrated in vacuo to afford 2-(difluoromethyl)-4-[[4-(trifluoromethyl)phenyl]methoxy]benzothiophene-5-carboxylic acid (120 mg, crude) as a colorless oil. LCMS purity: 79%; MS: m/z (ES+)=403 (M+H$^+$).

Intermediate Example 26. Preparation of 2-thiazol-4-yl-4-[[4-(trifluoromethyl)phenyl]methoxy]benzothiophene-5-carboxylic acid 2-Thiazol-4-yl-4-[[4-(trifluoromethyl)phenyl]methoxy]benzothiophene-5-carboxylic acid was prepared according to the following sequence.

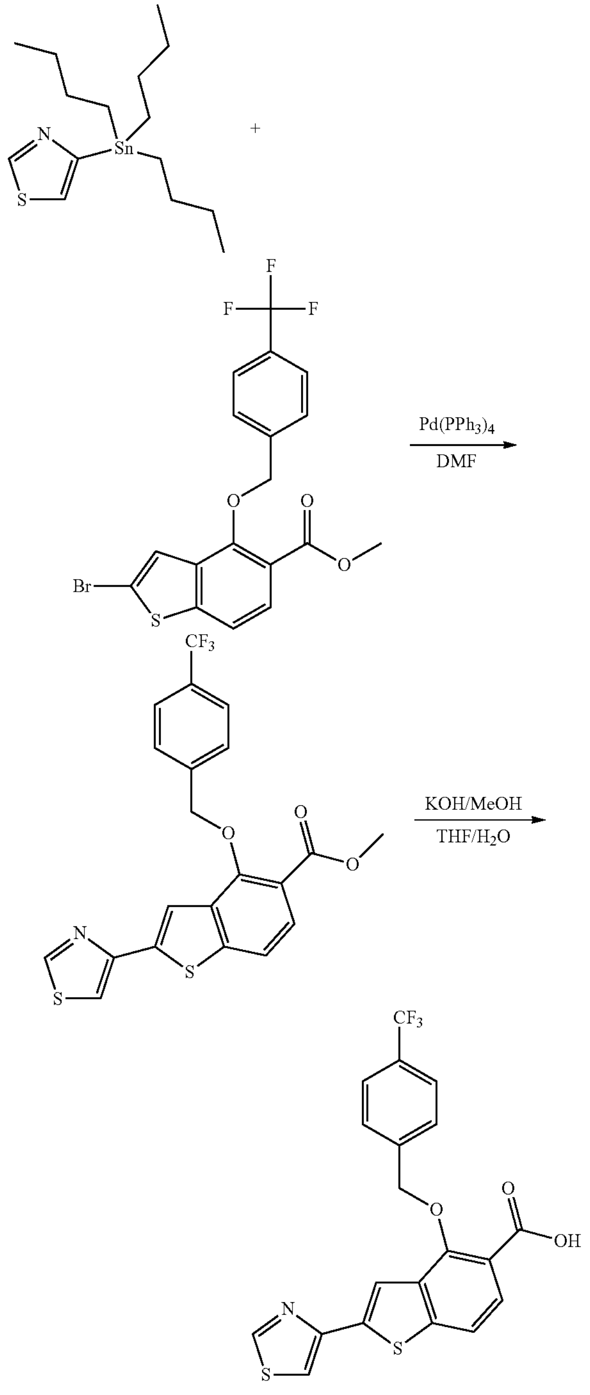

Step 1

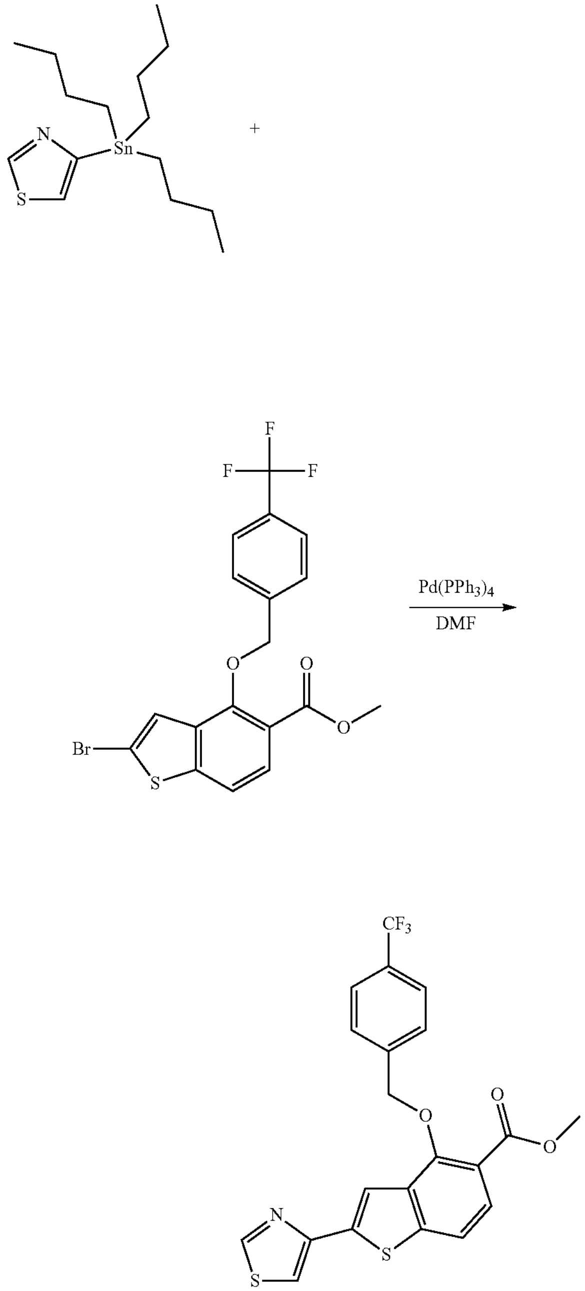

A mixture of methyl 2-bromo-4-[[4-(trifluoromethyl)phenyl]methoxy]-benzothiophene-5-carboxylate (200 mg, 0.45 mmol), tributyl(thiazol-4-yl)stannane (340 mg, 0.91 mmol), $(PPh_3)_4Pd$ (53 mg, 0.045 mmol) in DMF (4 mL) was stirred at 90° C. for 3 hours under $N_2$. Next the mixture was diluted with aqueous KF (50 mL) and extracted with EA (50 mL), washed with brine (50 mL), dried over anhydrous $Na_2SO_4$, filtered and concentrated in vacuo, and the residue was purified by silica gel chromatography (PE/EA=1/10) to afford methyl 2-thiazol-4-yl-4-[[4-(trifluoromethyl)phenyl]methoxy]benzothiophene-5-carboxylate (200 mg, 99%) as a yellow solid. LCMS: purity 90.7%; MS: m/z (ES$^+$)=450 (M+H$^+$).

Step 2

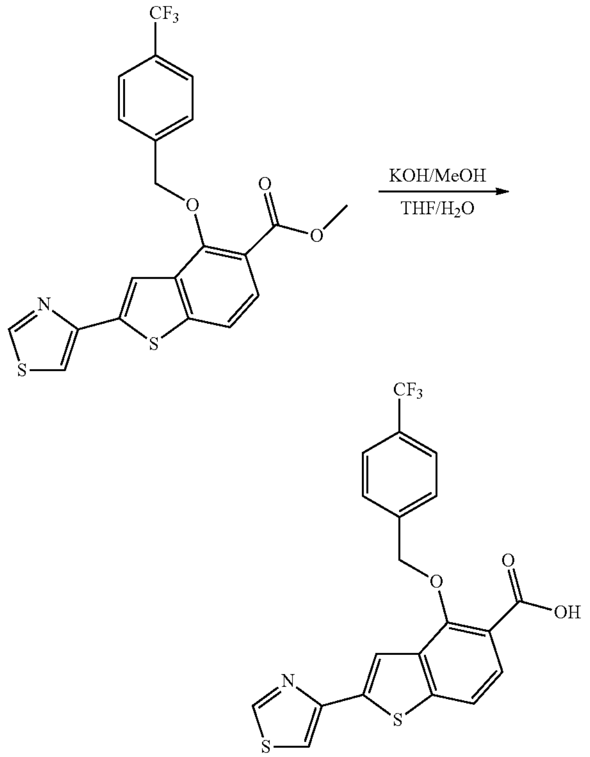

A mixture of 200 mg (0.445 mmol) of 2-thiazol-4-yl-4-[[4-(trifluoromethyl)phenyl]methoxy]-benzothiophene-5-carboxylate and 168 mg of KOH (3.0 mmol) in 0.5 mL of $H_2O$, 2 mL of THF and 2 mL of MeOH was vigorously stirred at room temperature for 3 h and then concentrated. The residue was acidified with 10% citric acid and extracted with EA (40 mL). The extract was washed twice with brine (10 mL) and dried over $Na_2SO_4$ and concentrated. The crude product thus obtained was purified by column chromatography on silica gel (DCM/MeOH=10:1) to give 2-thiazol-4-yl-4-[[4-(trifluoromethyl)phenyl]methoxy]-benzothiophene-5-carboxylic acid (170 mg; 88%) as white solid. LCMS: purity 90.3%; MS: m/z ($ES^+$)=436 ($M+H^+$).

Intermediate Example 27. Preparation of 2-cyclopropyl-4-[[4-(trifluoromethyl)phenyl]methoxy]-1,3-benzothiazole-5-carboxylic acid

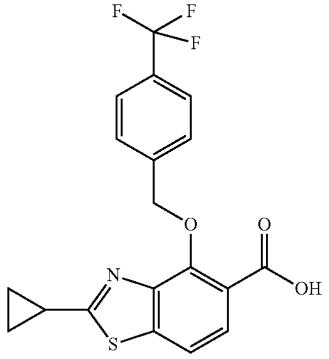 [SMILES: O=C(O)c1ccc2sc(C3CC3)nc2c1OCc1ccc(C(F)(F)F)cc1]

Step 1

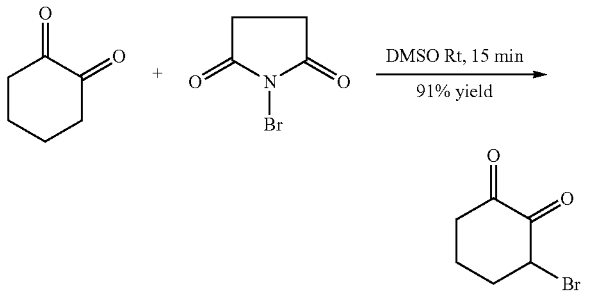

To a solution of 1,2-cyclohexanedione (25 g, 223 mmol) in 100 mL of dimethylsulfoxide was added at 5° C., N-bromosuccinimide (42.86 g, 240.8 mmol). The mixture was stirred at room temperature overnight. Water was added and the mixture was extracted with dichloromethane. The organic layers were collected and washed once with water and once with saturated aqueous solution of NaCl. The organic phases were dried over $MgSO_4$ and concentrated in vacuo. The crude product obtained was a yellow oil (44 g, 100% yield). The product was used without purification. LCMS: $t_R$=0.49 min., MS: m/z (ES+)=191 ($M+H^+$)

Step 2

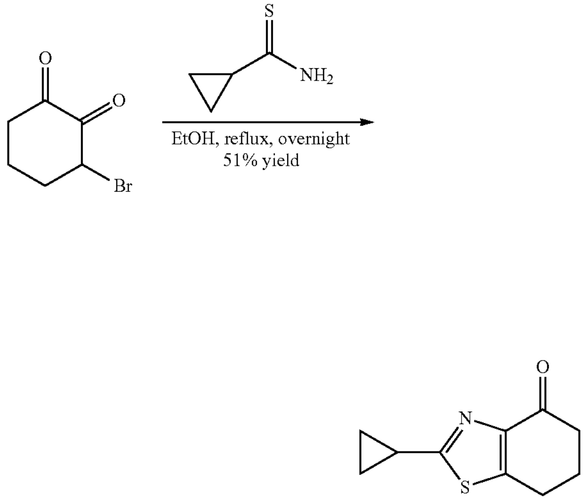

3-bromocyclohexane-1,2-dione (9.47 g, 49.6 mmol) and a cyclopropanecarbothioamide (4.97 g, 49.13 mmol) was mixed in 150 mL of ethanol. The mixture was heated at reflux overnight. Then, the crude was concentrated in vacuo. Dichloromethane and water were added. The solution was extracted and the organic layer was washed once with water and once with saturated aqueous solution of NaCl. The organic layers were collected, dried over $MgSO_4$ and concentrated in vacuo. The crude product obtained was purified by column chromatography on silica gel using a mixture of heptane and ethyl acetate as eluent (gradient: 0% to 80% AcOEt in heptane) to give a yellow oil (4.82 g, 51% yield). LCMS: $t_R$=0.53 min., MS: m/z (ES+)=194 ($M+H^+$).

Step 3

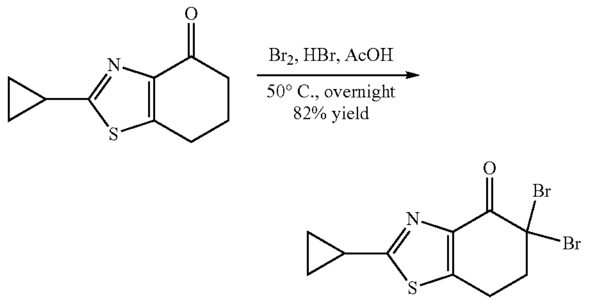

To a solution of 2-cyclopropyl-3,5,6,7-tetrahydro-1,3-benzothiazol-4-one (3.85 g, 19.92 mmol) in 70 mL of acetic acid, was added dropwise hydrobromic acid (2 ml, 11.58 mmol, 33% in AcOH) and dibromine (3 ml, 58.23 mmol). The mixture was stirred at 50° C. overnight. Then 500 mL of dichloromethane was added and the mixture was extracted with 150 mL of water. The organic phrases were washed with water, dried over $MgSO_4$ and concentrated in vacuo. The crude product obtained was a brown oil (5.71 g, 82% yield). The product was used without purification. LCMS: $t_R$=0.73 min., MS: m/z (ES+)=352 (M+H$^+$).

Step 4

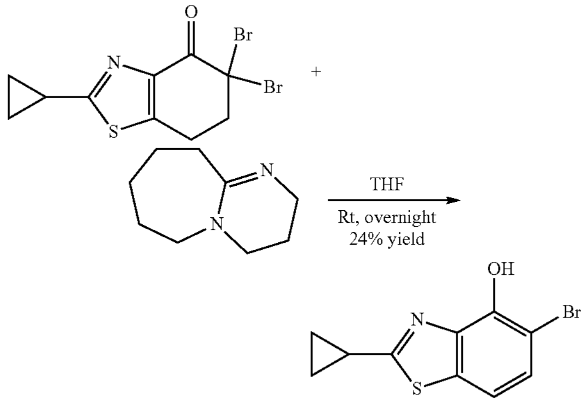

To a solution of 5,5-dibromo-2-cyclopropyl-6,7-dihydro-1,3-benzothiazol-4-one (5.71 g, 16.27 mmol) in 500 mL of tetrahydrofuran was added dropwise 1,8-diazabicyclo[5.4.0]undec-7-ene (12.26 ml, 81.33 mmol). The solution was stirred at room temperature overnight. Then, the crude mixture was poured onto 300 mL of ice water and acidified with hydrochloric acid 1M until pH<3. The crude mixture was extracted twice with ethyl acetate. The organic phases were collected, dried over $MgSO_4$ and concentrated in vacuo. The crude product obtained was purified by column chromatography on silica gel using a mixture of heptane and dichloromethane as eluent (gradient: 0% dichloromethane—30'→100% Dichloromethane) to give a beige powder (1.04 g, 24% yield). LCMS: $t_R$=0.82 min., MS: m/z (ES+)=272 (M+H$^+$).

Step 5

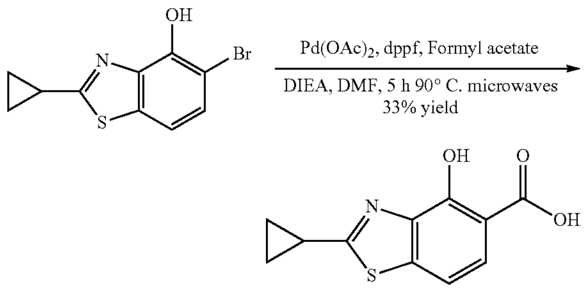

To a solution of 5-bromo-2-cyclopropyl-1,3-benzothiazol-4-ol (250 mg, 925.43 μmol) in 5 mL of anhydrous DMF was added $Pd(OAc)_2$ (83.1 mg, 370.18 μmol) and 1,1'-bis(diphenylphosphino)ferrocene (dppf) (211.56 mg, 370.18 μmol). DIEA (969.8 μl, 5.56 mmol) was added followed by addition of formyl acetate (876 μl, 5.56 mmol) dropwise. The mixture was heated at 90° C. by using microwave irradiation for 5 hours. The crude mixture was concentrated in vacuo. 30 ml of water and 10 ml of HCl 1N were added and the mixture was extracted with ethyl acetate. The organic layer was washed three times with NaOH 1N. The aqueous layers were combined and washed twice with ethyl acetate. The aqueous layer was acidified with HCl 1M solution and washed four times with ethyl acetate. The organic layers were collected and washed once with water and once with saturated aqueous solution of NaCl. The organic phases were dried over $Na_2SO_4$ and concentrated in vacuo. The crude product obtained was a beige powder (143 mg, 33% yield). LCMS: $t_R$=0.63 min., MS: m/z (ES+)=236 (M+H$^+$).

Step 6

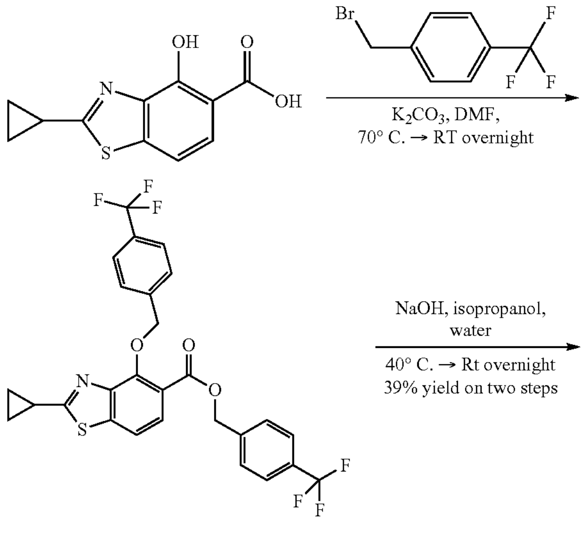

-continued

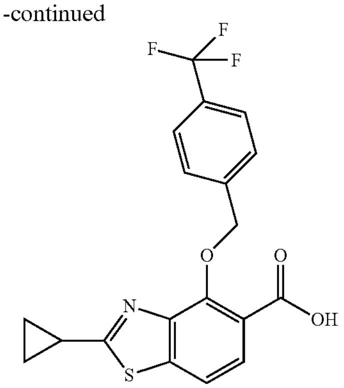

To a solution of 2-cyclopropyl-4-hydroxy-1,3-benzothiazole-5-carboxylic acid (143 mg, 607.85 μmol) in 50 mL of N,N-dimethylformamide was added potassium carbonate (176 mg, 1.28 mmol). The mixture was heated at 70° C. for 15 minutes and then 4-(trifluoromethyl)benzyl bromide (320 mg, 1.34 mmol) was added. Then, the mixture was stirred at room temperature overnight. The crude was concentrated in vacuo and extracted with ethyl acetate. The organic layer was washed once with water and once with saturated aqueous solution of NaCl. The organic layers were collected, dried over $Na_2SO_4$ and concentrated in vacuo. The crude product obtained was a white powder (260 mg).

To a solution of [4-(trifluoromethyl)phenyl]methyl 2-cyclopropyl-4-[[4-(trifluoromethyl)phenyl]methoxy]-1,3-benzothiazole-5-carboxylate (260 mg, 471.44 μmol) in 200 mL of isopropanol was added a solution of sodium hydroxide 1M (2.36 ml, 2.36 mmol), 20 mL of water. The mixture was heated at 40° C. for 30 minutes and then was stirred at room temperature overnight. The crude was concentrated in vacuo. Water and 10 ml of HCl 1N were added and the mixture was extracted three times with ethyl acetate. The organic layers were combined and washed once with water and once with saturated aqueous solution of NaCl. The organic phases were dried over $Na_2SO_4$ and concentrated in vacuo. The crude product obtained was a white powder (184 mg, 39% yield on two steps). LCMS: $t_R$=0.89 min., MS: m/z (ES+)=394 (M+H$^+$).

Intermediate Example 28. Preparation of 2-methyl-4-[[4-(trifluoromethyl)phenyl]methoxy]-1,3-benzothiazole-5-carboxylic acid

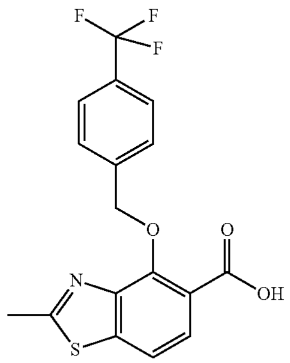 [SMILES: Cc1nc2c(OCc3ccc(C(F)(F)F)cc3)c(C(=O)O)ccc2s1]

Using the appropriate commercially available compounds, the title compound was prepared by analogous procedure used to synthesize the compound 2-cyclopropyl-4-[[4-(trifluoromethyl)phenyl]methoxy]-1,3-benzothiazole-5-carboxylic acid.

LCMS: $t_R$=0.83 min., MS: m/z (ES+)=368 (M+H$^+$).

Intermediate Example 29. Preparation of 2-cyclobutyl-4-[[4-(trifluoromethyl)phenyl]methoxy]-1,3-benzothiazole-5-carboxylic acid

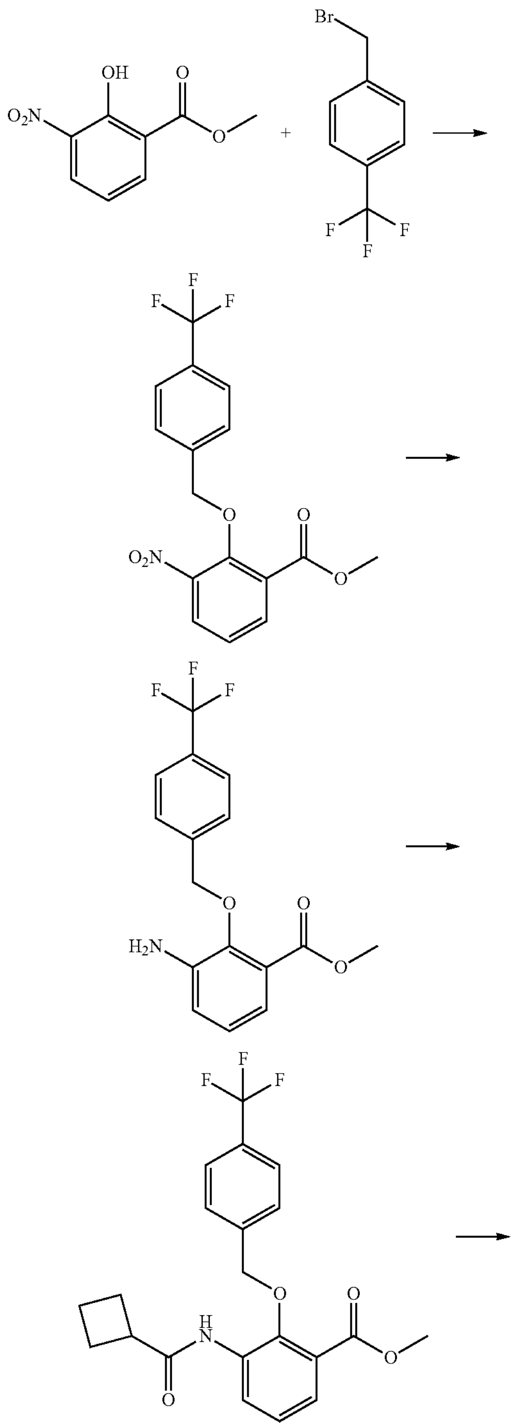

-continued

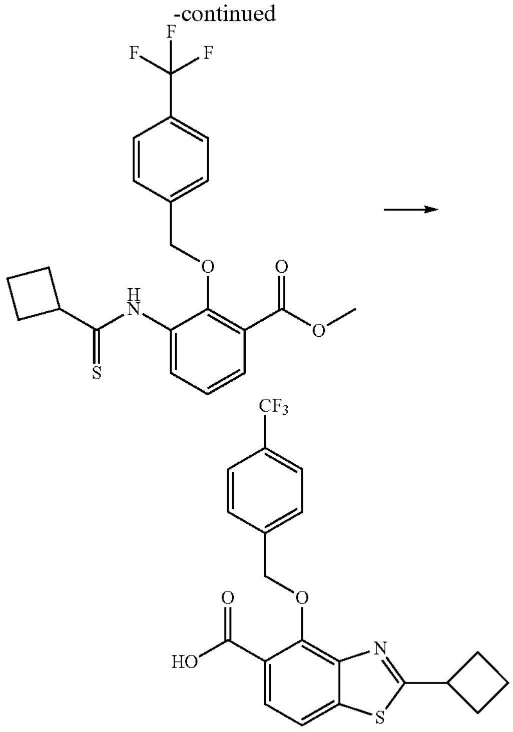

Step 1

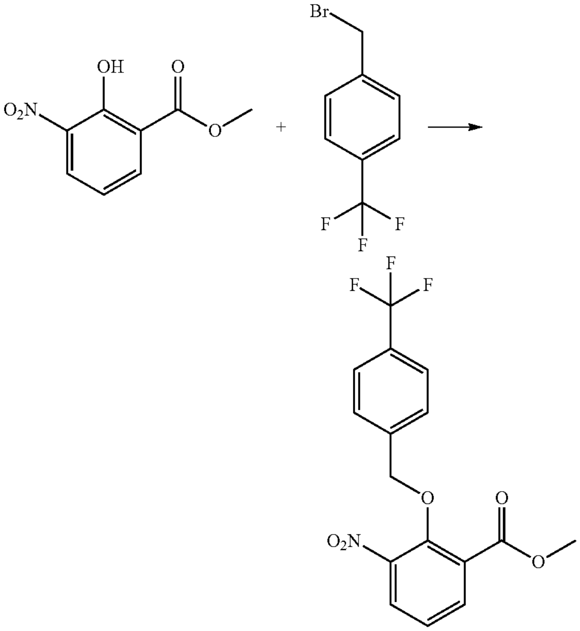

To a stirred solution of methyl 2-hydroxy-3-nitro-benzoate (11.0 g, 0.0558 mol) in DMF (200 mL) was added 1-(bromomethyl)-4-(trifluoromethyl)benzene (14.7 g, 0.0614 mol) and $K_2CO_3$ (23.1 g, 0.167 mol). Then the mixture stirred at 25° C. for 12 hours. LCMS showed desired product was detected. The mixture was added water (100 mL) and extracted with EA (100 mL×3). The combined organic layers were dried over $Na_2SO_4$, purified by silica gel column chromatography (petroleum ether/EA from 100% to 70%) to give 19.0 g (95.9% yield) of methyl 3-nitro-2-[[4-(trifluoromethyl)phenyl]methoxy]benzoate as a yellow oil. LCMS purity: 100%; MS: m/z (ES+)=356 (M+H$^+$).

Step 2

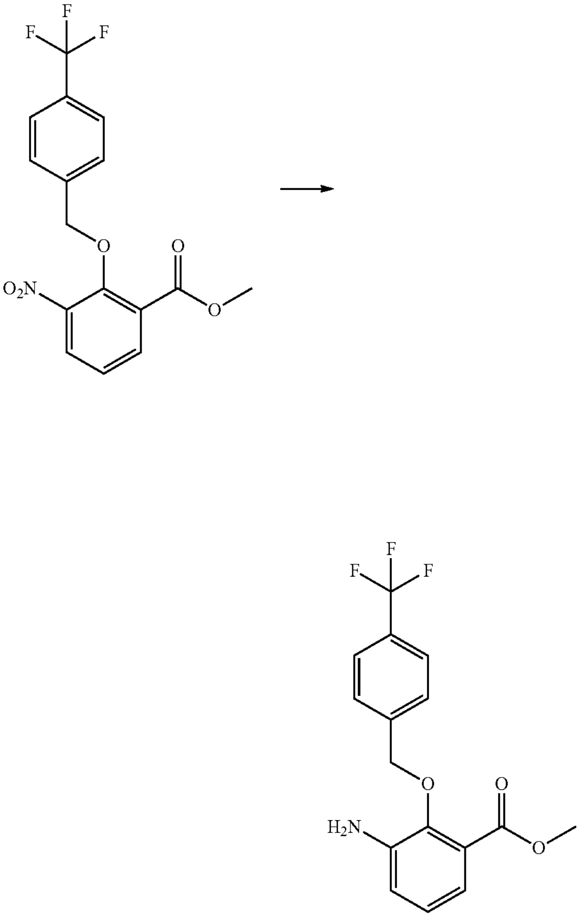

To a stirred solution of methyl 3-nitro-2-[[4-(trifluoromethyl)phenyl]methoxy]benzoate (19.0 g, 0.0535 mol) in a mixed solvents of MeOH/$H_2O$ (300 mL/100 mL) was added Zinc dust (140 g, 2.14 mol) and $NH_4Cl$ (114 g, 2.14 mol). Then the mixture stirred at 60° C. for 2 hours. LCMS showed desired product was detected. The mixture was filtered and evaporated to remove the MeOH, added water (70 mL) and extracted with EA (100 mL×3). The combined organic layers were dried over $Na_2SO_4$, purified by silica gel column chromatography (petroleum ether/EA from 100% to 90%) to give methyl 3-amino-2-[[4-(trifluoromethyl) phenyl]methoxy]benzoate (17.0 g, 0.0523 mol, yield: 97.7%) as brown oil. LCMS purity: 98.7%; MS: m/z (ES+)=326 (M+H$^+$).

Step 3

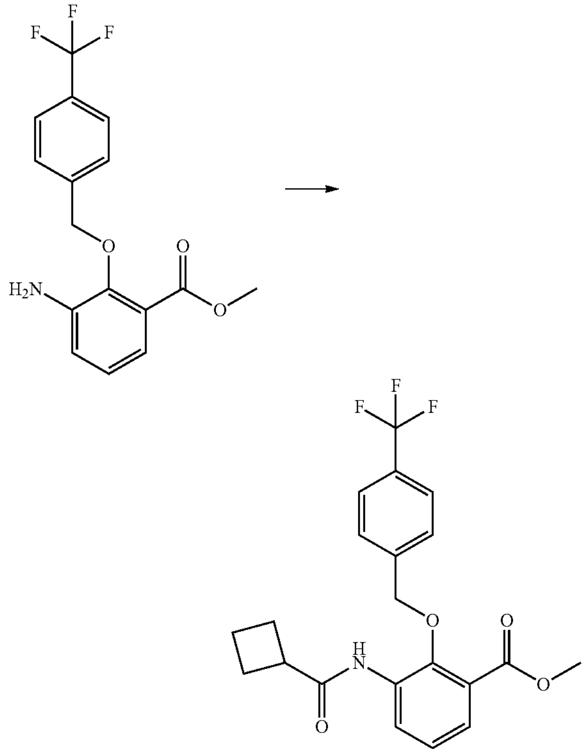

To a stirred solution of cyclobutanecarboxylic acid (0.880 g, 8.79 mmol) in DMF (12 mL) was added TEA (2.05 g, 20.3 mmol)) and HATU (6.43 g, 16.9 mol). Then the mixture stirred at 25° C. for 0.5 hour. Methyl 3-amino-2-[[4-(trifluoromethyl)phenyl]methoxy]benzoate (2.20 g, 6.76 mol) was added to the mixture and stirred at 25° C. for 16 hours. TLC (PE/EA=8/1) showed the starting material was consumed. The mixture was added water (8 mL) and extracted with EA (10 mL×3). The combined organic layers were dried over $Na_2SO_4$, purified by silica gel column chromatography (petroleum ether/EA from 100% to 70%) to give methyl 3-(cyclobutanecarbonylamino)-2-[[4-(trifluoromethyl)phenyl]methoxy]benzoate (2.14 g, 5.25 mmol, yield: 77.7%) as a white solid.

LCMS: $t_R$=2.20 min. MS: m/z ($ES^+$)=408 ($M+H^+$).

Step 4

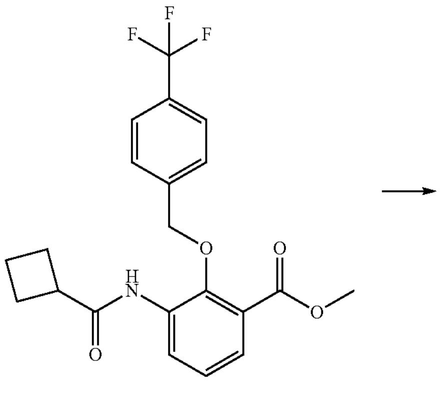

-continued

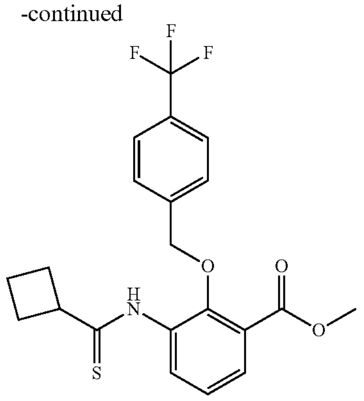

Lawesson's reagent (1.49 g, 3.68 mmol) was added to a suspension of methyl 3-(cyclobutanecarbonylamino)-2-[[4-(trifluoromethyl)phenyl]methoxy]benzoate (2.14 g, 5.25 mmol) in toluene (8 mL) at room temperature, and then the mixture was stirred at 70° C. for 16 hours. TLC (PE/EA=4/1) showed the starting material was consumed. The mixture was evaporated to dryness and purified by silica gel column chromatography (PE/EA=5/1) to give methyl 3-(cyclobutanecarbothioylamino)-2-[[4-(trifluoromethyl) phenyl] methoxy]benzoate (1.89 g, 4.46 mmol, yield: 85%) as yellow solid. LCMS: 100% at UV254; MS: m/z ($ES^+$)=424 ($M+H^+$).

Step 5

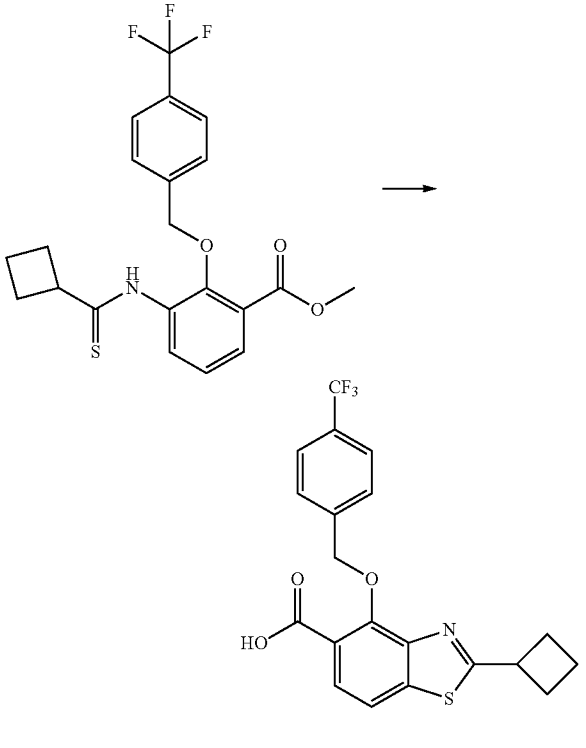

To a solution of methyl 3-(cyclobutanecarbothioylamino)-2-[[4-(trifluoromethyl)phenyl]methoxy]benzoate (1.00 g, 2.36 mmol) in water (10 mL) was added KOH (0.530 g, 9.45 mmol) and $K_3[Fe(CN)_6]$(2.33 g, 7.08 mmol), then the mixture was stirred at 60° C. for 17 hours. LCMS showed the starting material was consumed and desired product was detected. The mixture was adjusted the pH=4 with HCl (2 M), extracted with EA (15 mL×3). The combined organic layers were dried over $Na_2SO_4$, filtered and evaporated to dryness, which was purified by silica gel column chromatography (DCM) to give to give 2-cyclobutyl-4-[[4-(trifluoromethyl)phenyl]methoxy]-1,3-benzothiazole-5-carboxylic acid (0.400 g, 0.000982 mol, yield: 41.6%) as white solid. LCMS: Purity 100% at UV254; MS: m/z ($ES^+$)=408 $(M+H)^+$.

2-cyclopentyl-4-[[4-(trifluoromethyl)phenyl]methoxy]-1,3-benzothiazole-5-carboxylic acid was synthesized similarly as above by using cyclobpentanecarboxylic acid instead of cyclobutanecarboxylic acid in step 3.

Intermediate Example 30. Preparation of 2-(difluoromethyl)-4-[[4-(trifluoromethyl)phenyl]methoxy]-1,3-benzothiazole-5-carboxylic acid

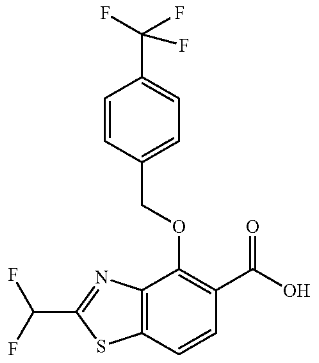 [SMILES: O=C(O)c1ccc2sc(C(F)F)nc2c1OCc1ccc(C(F)(F)F)cc1]

Step 1

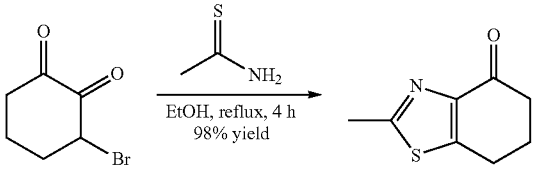

3-bromocyclohexane-1,2-dione (2 g, 10.47 mmol) and ethanethioamide (786 mg, 10.47 mmol) was mixed in 100 mL of ethanol. The mixture was heated at reflux for 2 hours. Then, the crude was concentrated in vacuum. Dichloromethane and water were added. The solution was extracted and the organic layer was washed once with water and once with saturated aqueous solution of NaCl. The organic layers were collected, dried over $MgSO_4$ and concentrated in vacuum. The crude product obtained was a yellow oil (1.71 g, 98% yield). The product was used without purification. LCMS: $t_R$=0.45 min., MS: m/z (ES+)=168 $(M+H^+)$.

Step 2

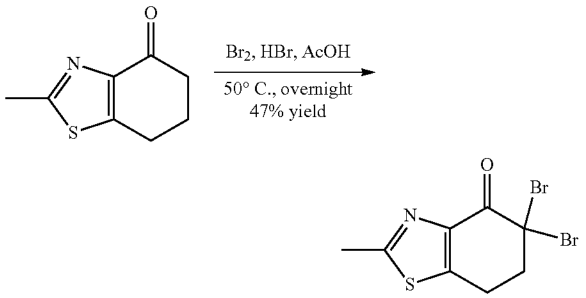

To a solution of 2-methyl-6,7-dihydro-5H-1,3-benzothiazol-4-one (3.97 g, 23.74 mmol) in 50 mL of acetic acid, was added dropwise hydrobromic acid (2 ml, 11.87 mmol, 33% in AcOH) and dibromine (3.06 ml, 59.35 mmol). The mixture was stirred at 50° C. overnight. Then 500 mL of dichloromethane was added and the mixture was extracted with 150 mL of water. The organic phrases were washed with water, dried over $MgSO_4$ and concentrated in vacuum. The crude product obtained was a brown oil (3.63 g, 47% yield). The product was used without purification. LCMS: $t_R$=0.69 min., MS: m/z (ES+)=326 $(M+H^+)$.

Step 3

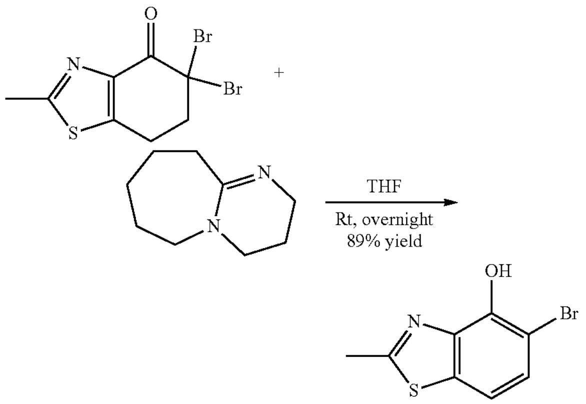

To a solution of 5,5-dibromo-2-methyl-6,7-dihydro-1,3-benzothiazol-4-one (1.94 g, 5.97 mmol) in 500 mL of tetrahydrofuran was added dropwise 1,8-diazabicyclo[5.4.0]undec-7-ene (4.50 ml, 29.84 mmol). The solution was stirred at room temperature overnight. Then, the crude mixture was poured on 250 mL of ice water and acidified with hydrochloric acid 1M until pH<3. The crude mixture was extracted three times with ethyl acetate. The organic phases were collected, dried over $MgSO_4$ and concentrated in vacuum. The crude product obtained was purified by column chromatography on silica gel using a mixture of heptane and dichloromethane as eluent (gradient: 0% dichloromethane—30'→100% Dichloromethane) to give beige powder (1.30 g, 89% yield). LCMS: $t_R$=0.70 min., MS: m/z (ES+)=246 $(M+H^+)$.

Step 4

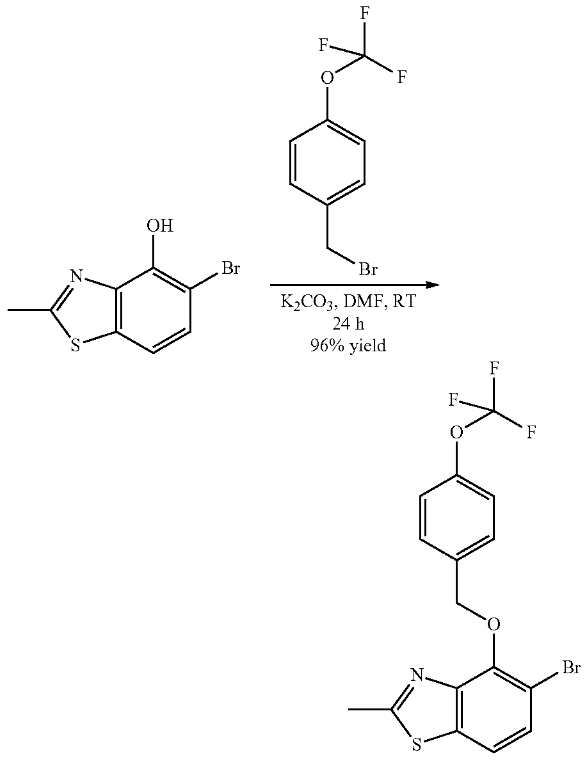

To a solution of 5-bromo-2-methyl-1,3-benzothiazol-4-ol (0.97 g, 3.97 mmol) in 50 mL of N,N-dimethylformamide was added potassium carbonate (1.10 g, 7.95 mmol). The mixture was heated at 70° C. during 15 minutes and then 1-(bromomethyl)-4-(trifluoromethoxy)benzene (1.22 g, 4.77 mmol) was added. Then, the mixture was stirred at room temperature overnight. The crude was concentrated in vacuum and extracted with ethyl acetate. The organic layer was washed once with water and once with saturated aqueous solution of NaCl. The organic layers were collected, dried over $Na_2SO_4$ and concentrated in vacuum. The crude product obtained was a beige powder (1.59 g, 96% yield).

Step 5

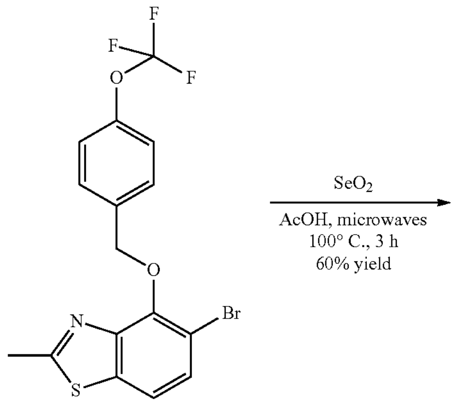

-continued

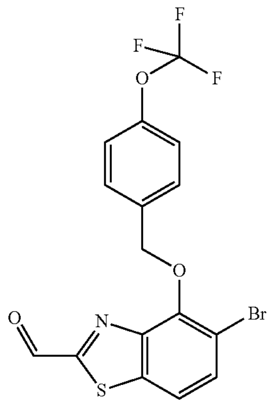

To a solution of 5-bromo-2-methyl-4-[[4-(trifluoromethoxy)phenyl]methoxy]-1,3-benzothiazole (1.12 g, 2.68 mmol) in 15 mL of acetic acid was added selenium dioxide (1.78 g, 16.07 mmol). The mixture was heated at 100° C. by using microwave irradiation for 3 hours.

Then, the crude was concentrated in vacuum. Water was added and the mixture was extracted with ethyl acetate. The organic layers were combined and washed once with water and once with saturated aqueous solution of NaCl. The organic phase was dried over $MgSO_4$ and concentrated in vacuo. The crude product obtained was purified by column chromatography on silica gel using a mixture of heptane and dichloromethane as eluent (gradient: 0% dichloromethane—25'→30% dichloromethane—35'→100% dichloromethane) to give yellow oil (696 mg, 609% yield). LCMS: $t_R$=1.05 min., MS: m/z (ES+)=432 (M+H$^+$).

Step 6

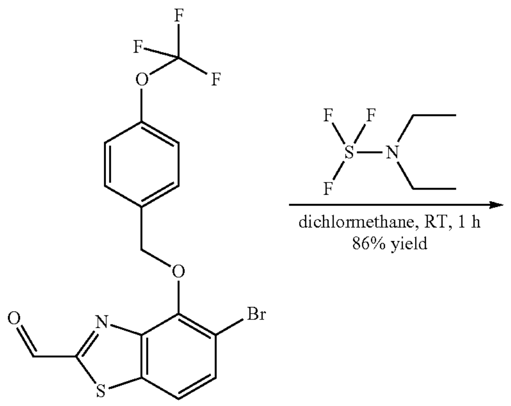

-continued

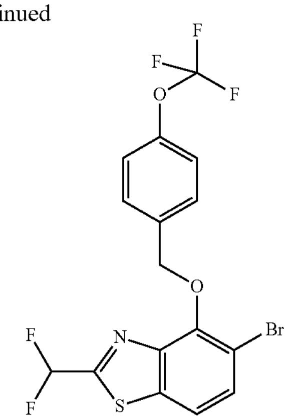

To a solution of 5-bromo-4-[[4-(trifluoromethoxy)phenyl] methoxy]-1,3-benzothiazole-2-carbaldehyde (330 mg, 763 µmol) in 5 mL of dichloromethane was added diethylaminosulfur trifluoride (246 µl, 1.92 mmol). The mixture was stirred at room temperature for 60 minutes. Water was added and the mixture was extracted with dichloromethane. The organic layers were combined and washed once with water and once with saturated aqueous solution of NaCl. The organic phase was dried over $MgSO_4$ and concentrated in vacuo. The crude product obtained was purified by column chromatography on silica gel using a mixture of heptane and dichloromethane as eluent (gradient: 0% dichloromethane—15'→40% dichloromethane—30'→100% dichloromethane) to give colorless oil (297 mg, 86% yield). LCMS: $t_R$=1.08 min., MS: m/z (ES+)=454 (M+H$^+$).

Step 7

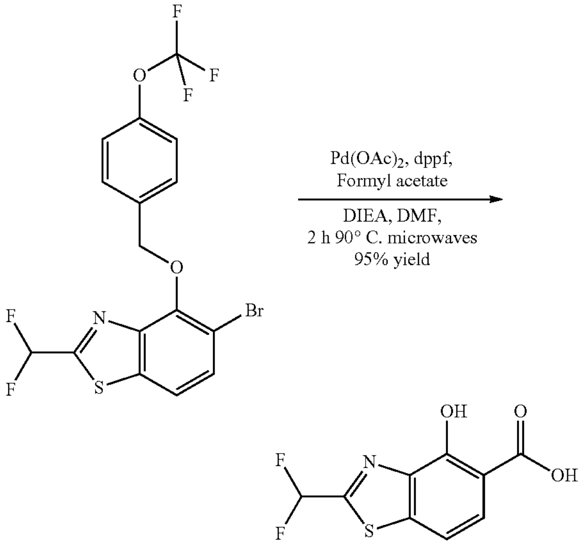

To a solution of 5-bromo-2-(difluoromethyl)-4-[[4-(trifluoromethoxy)phenyl]methoxy]-1,3-benzothiazole (148 mg, 325.84 µmol) in 5 mL of anhydrous DMF was added $Pd(OAc)_2$ (20 mg, 89.08 µmol) and 1,1'-bis(diphenylphosphino)ferrocene (dppf) (65 mg, 113.73 µmol). The reaction mixture was put under vacuum and DIEA (200 µl, 1.15 mmol) was added followed by addition of formyl acetate (128 µl, 1.63 mmol) dropwise. The mixture was heated at 90° C. by using microwave irradiation for 2 hours. Then, the crude was concentrated in vacuum. A solution of NaOH 1N was added and the mixture was extracted with diethyl ether. Then, the aqueous layer was acidified with HCl 1M solution and washed four times with ethyl acetate. The organic layers were collected and washed once with water and once with saturated aqueous solution of NaCl. The organic phases were dried over $Na_2SO_4$ and concentrated in vacuum. The crude product obtained was a beige powder (76 mg, 95% yield). LCMS: $t_R$=0.59 min., MS: m/z (ES+)=246 (M+H$^+$).

Step 8

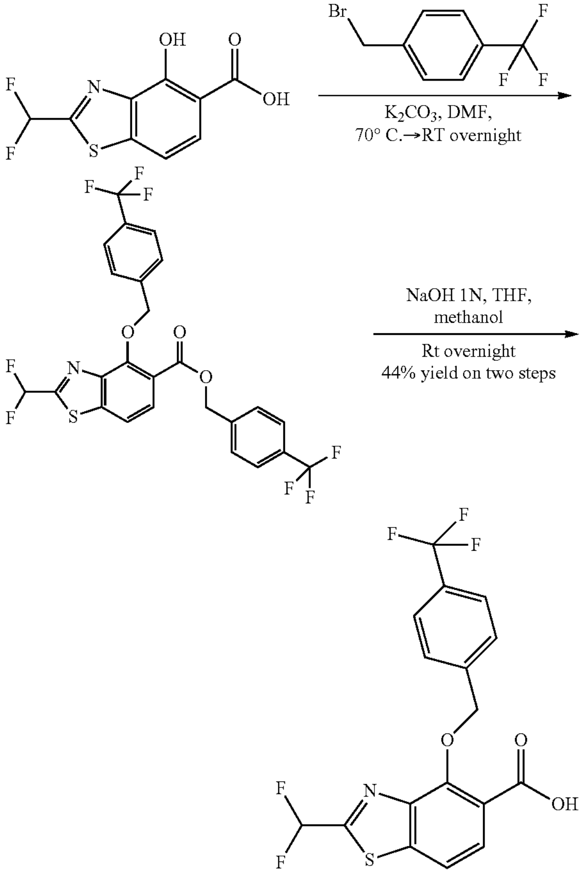

To a solution of 2-(difluoromethyl)-4-hydroxy-1,3-benzothiazole-5-carboxylic acid (152 mg, 620 µmol) in 20 mL of N,N-dimethylformamide were added potassium carbonate (257 mg, 1.86 mmol) and 4-(trifluoromethyl)benzyl bromide (741 mg, 3.10 mmol). The mixture was heated at 70° C. overnight. The crude was concentrated in vacuo and extracted with ethyl acetate. The organic layer was washed once with water and once with saturated aqueous solution of NaCl. The organic layers were collected, dried over $Na_2SO_4$ and concentrated in vacuum. The crude product obtained was purified by column chromatography on silica gel using a mixture of heptane and dichloromethane as eluent (gradient: 0% dichloromethane—60'→30% dichloromethane—15'→100% dichloromethane) to give a beige powder (182 mg). To a solution of [4-(trifluoromethyl)phenyl]methyl 2-(difluoromethyl)-4-[[4-(trifluoromethyl)phenyl]

methoxy]-1,3-benzothiazole-5-carboxylate (180 mg, 320.60 μmol) in 10 ml of tetrahydrofuran and 10 ml of methanol was added a solution of sodium hydroxide 1M (5 ml, 5 mmol). The mixture was stirred at room temperature overnight. The crude was concentrated in vacuum. Water and a solution of HCl 1N were added until pH was 7. Then, the mixture was extracted three times with ethyl acetate. The organic layers were combined and washed once with water and once with saturated aqueous solution of NaCl. The organic phases were dried over $MgSO_4$ and concentrated in vacuo. The crude product obtained was a white powder (110 mg, 44% yield on two steps). LCMS: $t_R$=0.86 min., MS: m/z (ES+)=404 (M+H$^+$).

Intermediate Example 31. Preparation of 2-(1-fluorocyclopropyl)-4-[[4-(trifluoromethyl)phenyl]methoxy]-1,3-benzothiazole-5-carboxylic acid

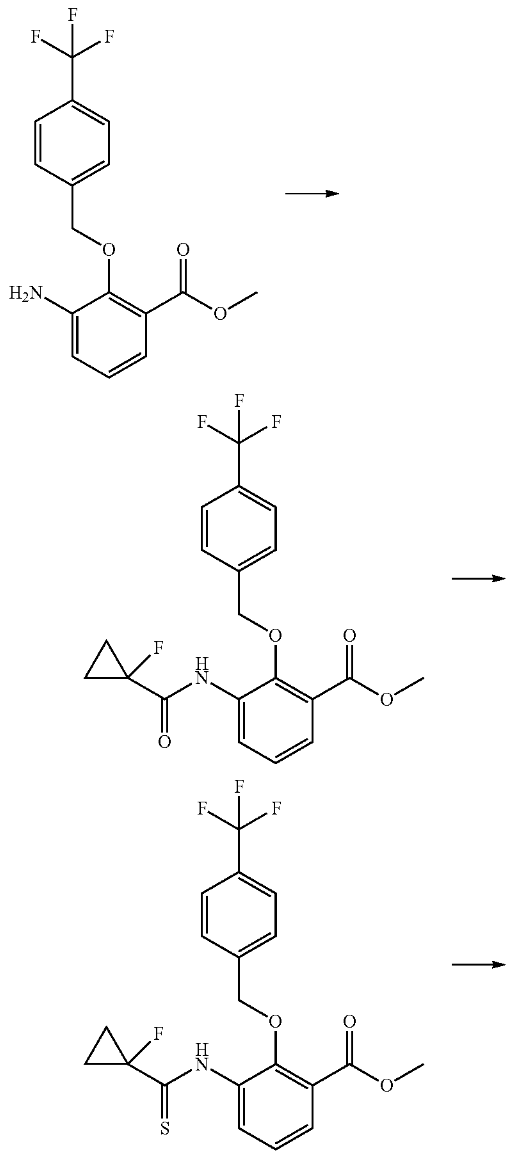

-continued

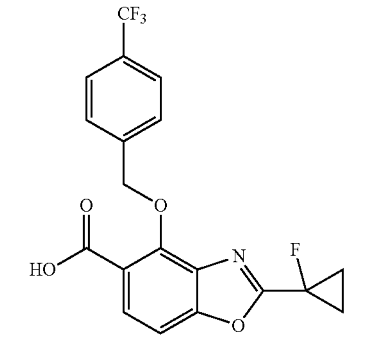

Step 1

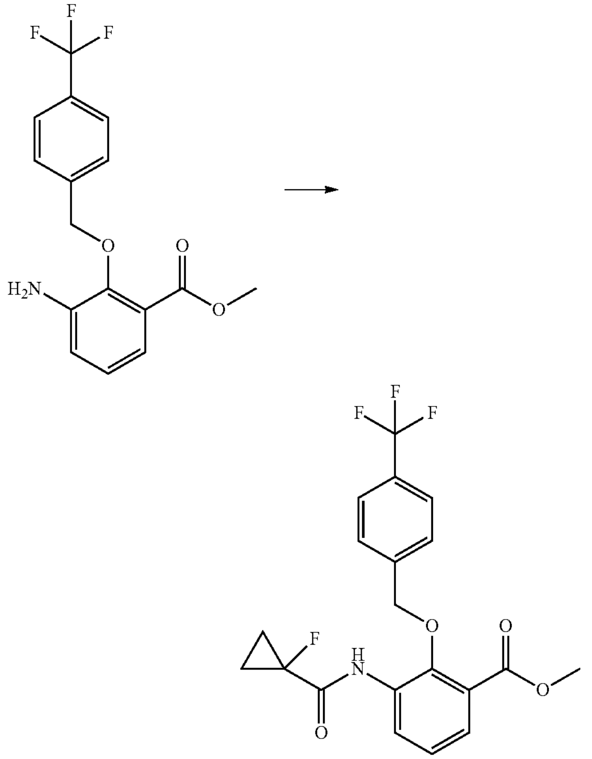

To a stirred solution of 1-fluorocyclopropanecarboxylic acid (0.384 g, 3.69 mmol) in DMF (8 mL) was added TEA (0.933 g, 9.22 mmol) and HATU (2.92 g, 7.69 mmol), then the mixture was stirred at 25° C. for 0.5 hours. 1-fluorocyclopropane carboxylic acid (0.384 g, 3.69 mmol) was added to the mixture and stirred at 25° C. for 16 hours. TLC (PE/EA=8/1) showed the starting material was consumed and a new spot on TLC was formed. The mixture was added water (8 mL) and extracted with EA (10 mL×3), the combined organic layers was dried over $Na_2SO_4$, purified by silica gel column chromatography (petroleum ether/EA from 100% to 90%) to give methyl 3-[(1-fluorocyclopropanecarbonyl)amino]-2-[[4-(trifluoromethyl) phenyl]methoxy]benzoate (1.12 g, 2.72 mmol, yield: 88.6%) as a white solid. LCMS purity: 99% at UV254, MS: m/z (ES$^+$)=412 (M+H$^+$).

Step 2

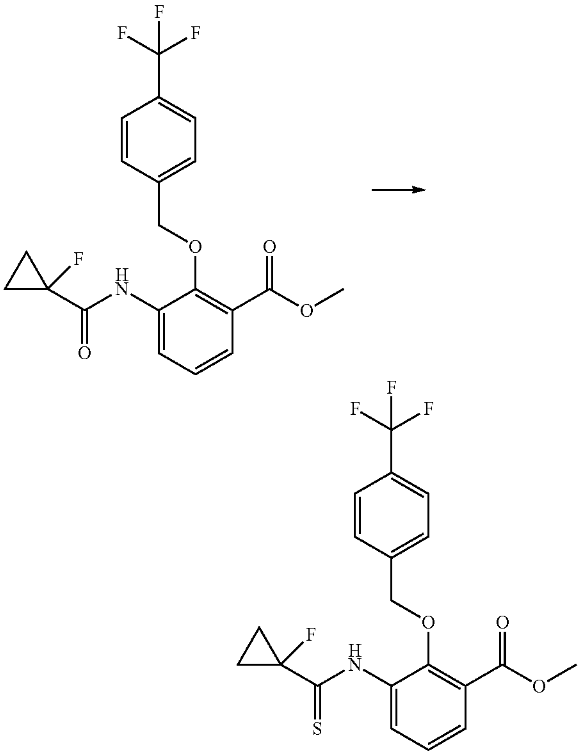

Lawesson's reagent (1.10 g, 2.72 mmol) was added to a suspension of methyl 3-[(1-fluorocyclopropanecarbonyl)amino]-2-[[4-(trifluoromethyl)phenyl]methoxy]benzoate (1.12 g, 2.72 mmol) in toluene (8.00 mL) at room temperature, and the mixture was stirred at 70° C. for 16 hours. LCMS showed the starting material was consumed and desired MS was detected, the mixture was evaporated to dryness and purified by silica gel column chromatography (PE/EA=5/1) to give methyl 3-[(1-fluorocyclopropanecarbothioyl)amino]-2-[[4-(trifluoromethyl) phenyl]methoxy] benzoate (1.00 g, 2.34 mmol, yield: 85.9%) as yellow solid. LCMS purity: 99% at UV254, MS: m/z ($ES^+$)=428 ($M+H^+$).

Step 3

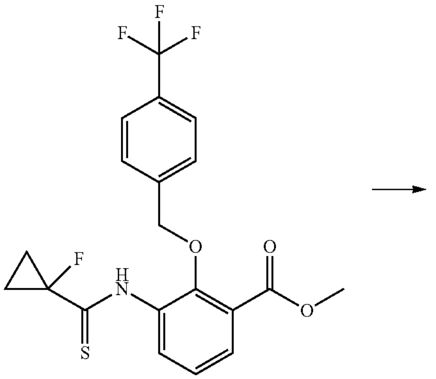

-continued

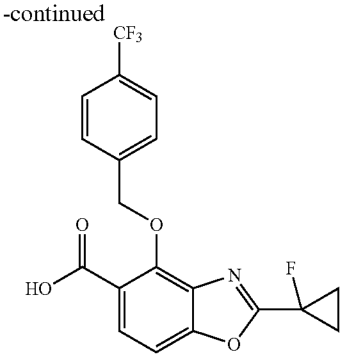

To a solution of methyl 3-[(1-fluorocyclopropanecarbothioyl)amino]-2-[[4-(trifluoromethyl)phenyl]methoxy]benzoate (0.500 g, 1.17 mmol) in $H_2O$ (6.00 mL) was added KOH (0.263 g, 0.00468 mol) and $K_3[Fe(CN)_6]$(1.35 g, 0.409 mmol), then the mixture was stirred at 60° C. for 17 hours. LCMS showed the starting material was consumed and desired product was detected, the mixture was adjusted the pH=4 with HCl (2 M), extracted with EA (15 mL×3), the combined organic layers were dried over $Na_2SO_4$, filtered and evaporated to dryness, which was purified by silica gel column chromatography (DCM) to give to give 2-(1-fluorocyclopropyl)-4-[[4-(trifluoromethyl)phenyl]methoxy]-1,3-benzothiazole-5-carboxylic acid (0.190 g, 0.462 mmol, yield: 39.5%) as white solid. LCMS purity: 99% at UV254, MS: m/z ($ES^+$)=412 ($M+H^+$).

Preparation of Compounds

Example 32-1: Preparation of (S)-3,3-dimethyl-2-(4-((4-(trifluoromethoxy)benzyl)oxy)benzo[b]thiophene-5-carboxamido)butanoic acid

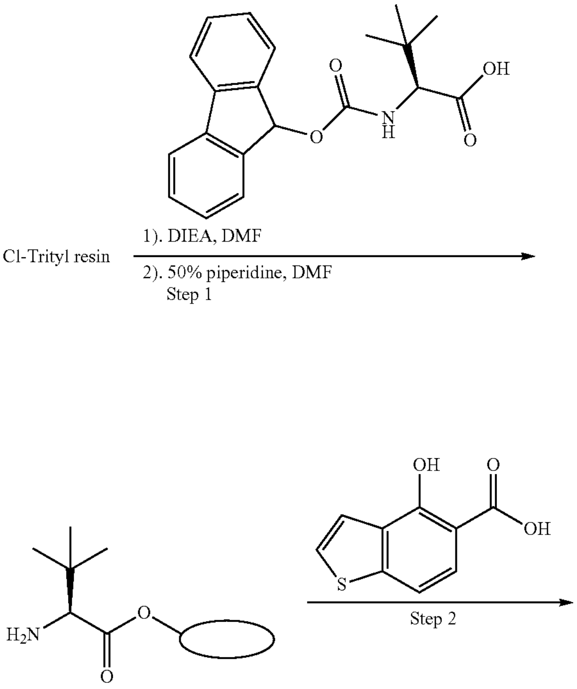

-continued

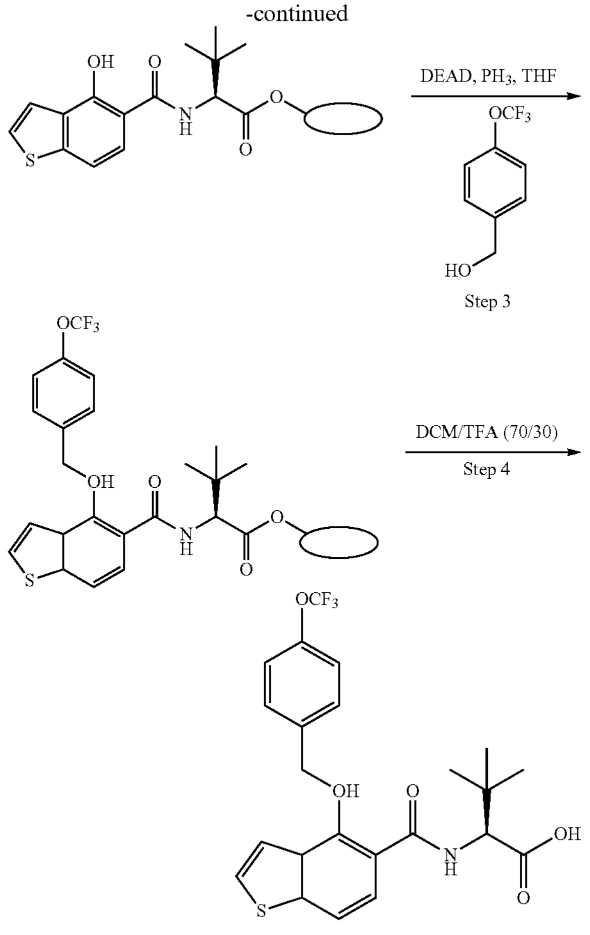

4

Step 1

1 g of 2-ChloroTrityl chloride resin (100-200 mesh, Advanced ChemTech) S=1.7 mmol/g was swollen 1 h, rt in dry DMF in 20 mL syringe, then drained. Solution of 6.8 mmol (4 eq.) of L-Fmoc-AA-OH was dissolved in 8 mL dry DMF and 3.5 mL (=21 mmol) of DIEA was added, and resulting slurry in syringe was shaken 12 h at rt. Drained resin was washed 5 times using 10 mL of dry DMF via 2 minute shaking followed by draining. Fmoc deprotection was achieved via 2 times 20 min rt treatment with 12 mL of (1:1) PIP/DMF (Small sample −40 mg of dry resin, was used in 'fmoc-reading procedure' to establish resin substitution. Usually S=0.6-0.8 mmol/g was achieved). After that, 5 times wash was applied, using 10 mL of dry DMF via 2 minute shaking followed by draining. The prepared AA-preloaded resin was used in next step as is.

Step 2

0.2 g of AA-preloaded resin in a syringe, swollen in DMF, was mixed with solution of 0.64 mmol (=4 eq.) of aromatic-hydroxy-acid pre-activated via treatment of 0.64 mmol=244 mg HATU in 4 mL DMF and 0.33 mL DIEA (2 mmol). Slurry was shaken for 12 h at rt, then washed 5 times with 8 mL of DMF and 4 times with 8 mL of THF. Drained resin was dried in vacuum 12 h, and used in next step as is.

Step 3

Solution of 0.8 mmol (5 eq.) of respective $R_3$-alcohol, 0.8 mmol=210 mg $PPh_3$ in 5 mL of dry THF was added to the syringe containing 0.2 g of dry resin from step 2. Capped syringe was cooled to −5° C. in fridge. Precooled solution of 0.8 mmol=162 mg DIAD in 0.4 mL of dry THF was added and shaken syringe was allowed to reach rt (1 h). Resin in syringe was washed 8 times with 6 mL of dry THF. Drained resin was dried in vacuum 12 h, and used in next step as is.

Step 4

Syringe containing 0.2 g of resin from step 3 was shaken as slurry with mixture 2% TFA, 5% TIPS in DCM for 1 h at rt. Drained liquid was collected and resin retreated 3 more times (20 minutes each) with the same mixture. Collected extracts were evaporated with stream of nitrogen, and oily residue was dried in vacuum 12 h rt. This residue was dissolved in 2 mL of DMF and injected to HPLC, pure product containing fractions were lyophilized. Yields varied from 30 to 75%.

LCMS: $t_R$=2.77 min., MS: m/z (ES+)=482 (M+$H^+$).

The following compounds (examples 32-1 through 32-14) exemplified below are prepared in a manner analogous to Example 32-1 described above.

Example 32-2: 2-(4-((4,4-difluorocyclohexyl) methoxy)-benzo[b]thiophene-5-carboxamido)-3-methyl-3-phenylbutanoic acid

1

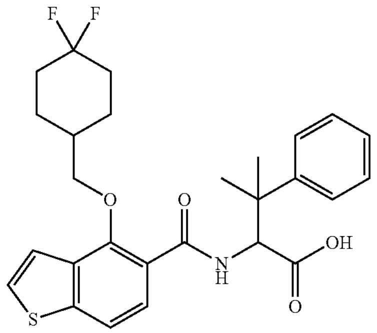

LCMS: $t_R$=4.03 min., MS: m/z (ES+)=502 (M+$H^+$).

Example 32-3: 2-(4-((4,4-difluorocyclohexyl) methoxy)-benzo[b]thiophene-5-carboxamido)-3-methyl-3-phenylbutanoic acid

2

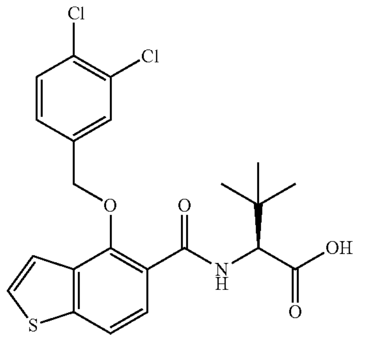

LCMS: $t_R$=2.53 min., MS: m/z (ES+)=467 (M+$H^+$).

Example 32-4: 2-(4-((4,4-difluorocyclohexyl)methoxy)-benzo[b]thiophene-5-carboxamido)-2-(1-methylcyclohexyl)acetic acid

3

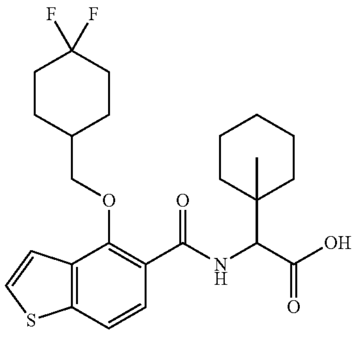

LCMS: $t_R$=4.11 min., MS: m/z (ES+)=480 (M+H$^+$).

Example 32-5: 3-methyl-3-phenyl-2-(4-((4-((trifluoromethyl)thio)benzyl)oxy)-benzo[b]thiophene-5-carboxamido)butanoic acid

5

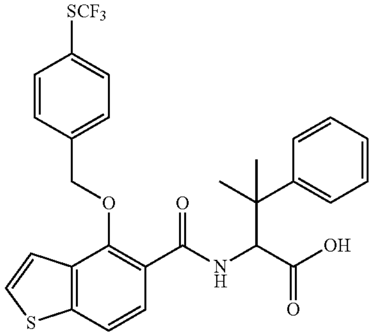

LCMS: $t_R$=4.23 min., MS: m/z (ES+)=560 (M+H$^+$).

Example 32-6:2-(1-methylcyclohexyl)-2-(4-((4-(trifluoromethoxy)benzyl)oxy)-benzo[b]thiophene-5-carboxamido)acetic acid

6

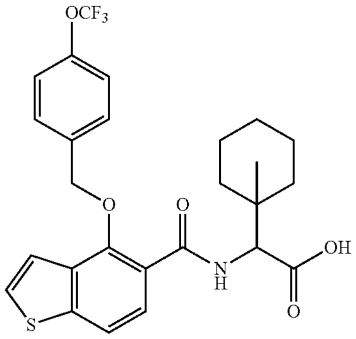

LCMS: $t_R$=4.28 min., MS: m/z (ES+)=522 (M+H$^+$).

Example 32-7: (2S)-2-(4-((4,4-difluorocyclohexyl)methoxy)-benzo[b]thiophene-5-carboxamido)-3,3-dimethylbutanoic acid

7

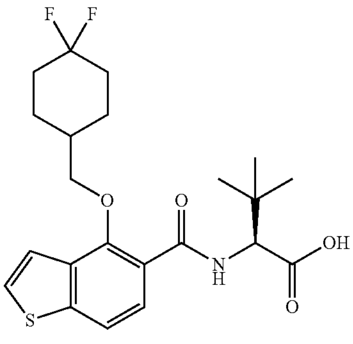

LCMS: $t_R$=3.85 min., MS: m/z (ES+)=440 (M+H$^+$).

Example 32-8: (2S)-2-(4-((4-(difluoromethoxy)benzyl)oxy)-benzo[b]thiophene-5-carboxamido)-3,3-dimethylbutanoic acid

8

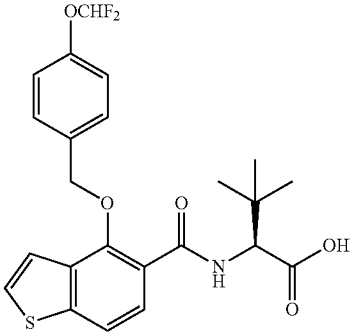

LCMS: $t_R$=2.55 min., MS: m/z (ES+)=464 (M+H$^+$).

Example 32-9: (2S)-3,3-dimethyl-2-(4-((4-(trifluoromethyl)benzyl)oxy)-benzo[b]thiophene-5-carboxamido)butanoic acid

9

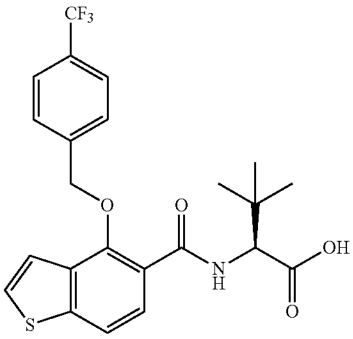

LCMS: $t_R$=3.98 min., MS: m/z (ES+)=466 (M+H$^+$).

Example 32-10: (2S)-2-(4-((4,4-difluorocyclohexyl)methoxy)-benzo[b]thiophene-5-carboxamido)-3,3-dimethylpentanoic acid

10

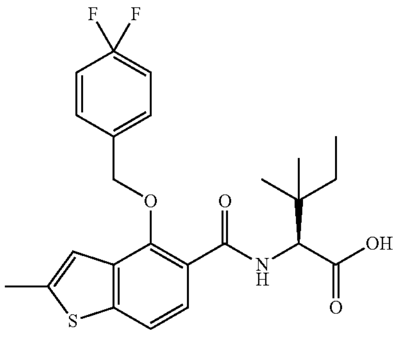

LCMS: $t_R$=3.97 min., MS: m/z (ES+)=454 (M+H$^+$).

Example 32-11: (2S)-3,3-dimethyl-2-(4-((4-((trifluoromethyl)thio)benzyl)oxy)-benzo[b]thiophene-5-carboxamido)butanoic acid

11

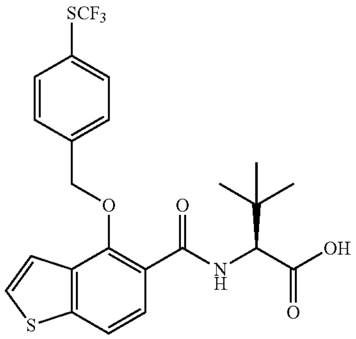

LCMS: $t_R$=4.05 min., MS: m/z (ES+)=498 (M+H$^+$).

Example 32-12: (2S)-3,3-dimethyl-2-(4-((4-((trifluoromethyl)thio)benzyl)oxy)-benzo[b]thiophene-5-carboxamido)butanoic acid

12

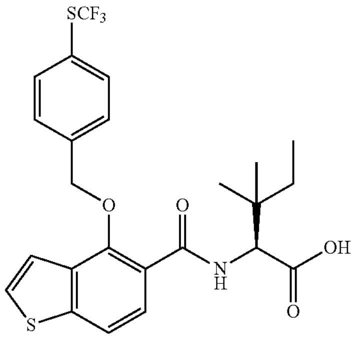

LCMS: $t_R$=4.20 min., MS: m/z (ES+)=512 (M+H$^+$).

Example 32-13: (2S)-2-(4-(benzo[d]thiazol-2-ylmethoxy)-benzo[b]thiophene-5-carboxamido)-3,3-dimethylbutanoic acid

13

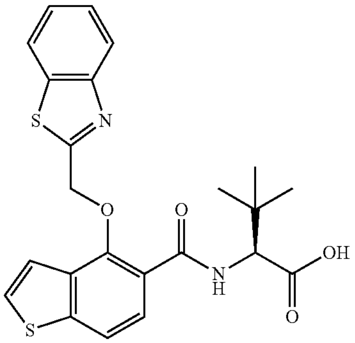

LCMS: $t_R$=2.27 min., MS: m/z (ES+)=455 (M+H$^+$).

Example 32-14: (2S)-2-(4-(cyclohexylmethoxy)-benzo[b]thiophene-5-carboxamido)-3,3-dimethylbutanoic acid

14

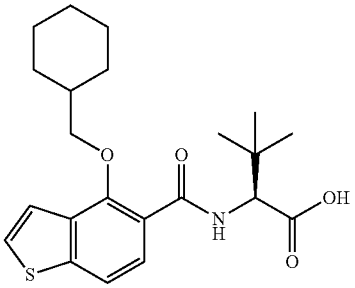

LCMS: $t_R$=2.61 min., MS: m/z (ES+)=404 (M+H$^+$).

Example 33-1. (2S)-2-[[3-chloro-2-methyl-4-[[4-(trifluoromethyl)phenyl]methoxy]benzothiophene-5-carbonyl]amino]-3,3-dimethyl-pentanoic acid

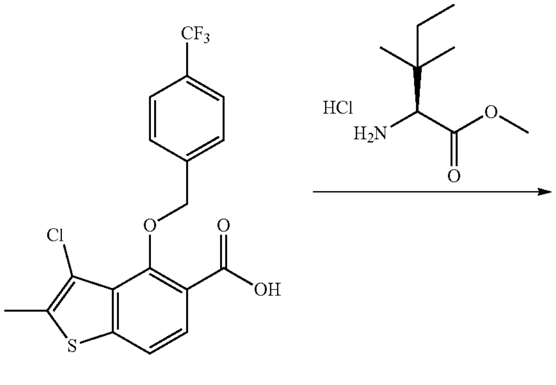

-continued

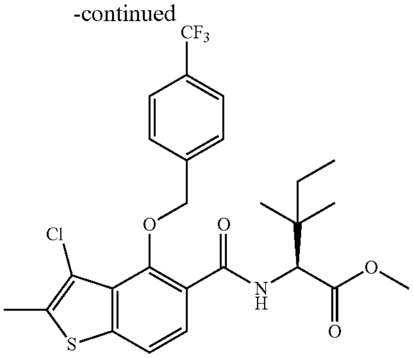

A mixture of 3-chloro-2-methyl-4-[[4-(trifluoromethyl) phenyl]methoxy]benzothiophene-5-carboxylic acid (65 mg, 0.162 mmol), and HATU (123 mg, 0.324 mmol) in DCM (10.0 mL) was stirred at room temperature for 0.5 h. Then methyl (2S)-2-amino-3,3-dimethyl-pentanoate hydrochloride (35 mg, 0.178 mmol), and TEA (53 mg, 0.486 mmol) were added. The resulting mixture was stirred at room temperature for 18 h. The mixture was diluted with DCM (15 mL), washed with water (25 mL), and aqueous $NH_4Cl$ solution (30 mL), dried over $Na_2SO_4$, filtered and concentrated under reduced pressure, the residue was purified by silica gel column (PE:EA=6:1) to afford the title compound (85 mg, 99%) as colorless oil.

LCMS Purity: 93%; MS: m/z ($ES^+$)=542 ($M+H^+$).

Step 2

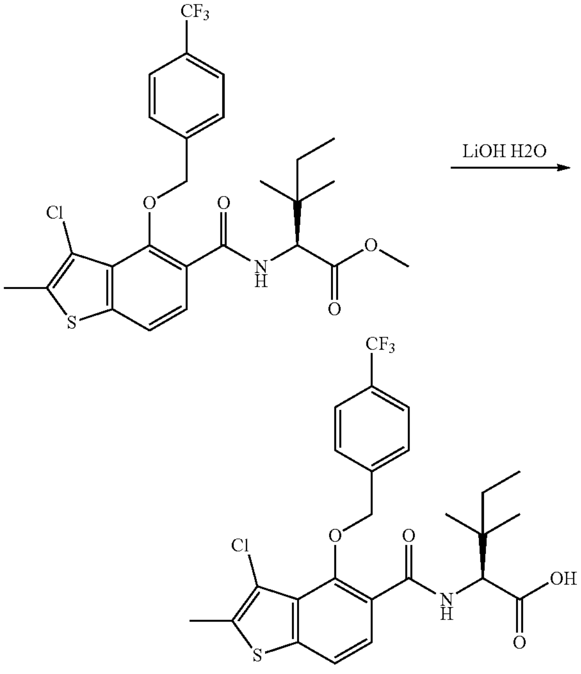

15

To a stirred solution of methyl (2S)-2-[[3-chloro-2-methyl-4-[[4-(trifluoromethyl)phenyl]methoxy]benzothiophene-5-carbonyl]amino]-3,3-dimethyl-pentanoate (85 mg, 0.154 mmol) in MeOH/THF/$H_2O$ (8 mL/12 mL/3 mL) was added $LiOH \cdot H_2O$ (453 mg, 10.8 mmol). The solution was stirred at 40° C. for overnight. The solution was concentrated and then acidified with aqueous hydrochloric acid (2 N) to pH=4-5, and extracted with EA (20 mL×3). The combined organic phase was washed with brine (40 mL), dried over anhydrous sodium sulfate, filtered and concentrated in vacuo to afford the title compound (82.4 mg, 100%) as white solid. LCMS: $t_R$=2.35 min; MS: m/z ($ES^+$)=528 ($M+H^+$).

$^1H$ NMR (400 MHz, $CDCl_3$) δ 8.21 (d, J=8.8 Hz, 1H), 8.08 (d, J=8.8 Hz, 1H), 7.69-7.62 (m, 5H), 5.29 (m, 2H), 4.61 (d, J=8.4 Hz, 1H), 2.54 (s, 3H), 1.21 (m, 2H), 0.82 (s, 3H), 0.77-0.73 (m, 6H).

The following compounds (examples 33-2 through 33-36) exemplified below are prepared in a manner analogous to Example 33-1 described above.

Example 33-2. (2S)-2-[[2-isopentyl-4-[[4-(trifluoromethyl)phenyl]methoxy]benzothiophene-5-carbonyl]amino]-3,3-dimethyl-butanoic acid

16

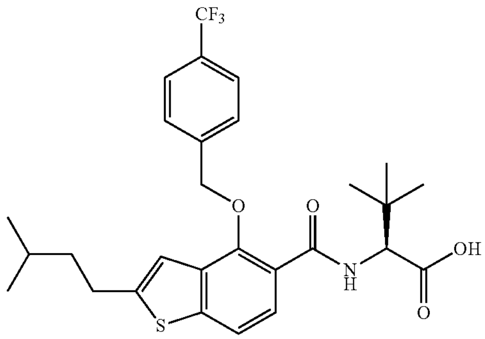

LCMS: $t_R$=2.39 min; MS: m/z ($ES^+$)=536 ($M+H^+$).

$^1H$ NMR (400 MHz, $CDCl_3$) δ 8.48-8.46 (d, J=7.6 Hz, 1H), 8.03-8.00 (m, 1H), 7.66-7.65 (m, 5H), 6.97 (s, 1H), 5.38-5.35 (d, J=12.4 Hz, 1H), 5.17-5.14 (d, J=11.6 Hz, 2H), 4.66-4.64 (d, J=8.4 Hz, 1H), 2.90-2.86 (m, 2H), 1.63-1.60 (m, 3H) ppm, 0.97-0.95 (m, 15H) ppm.

Example 33-3. (2S)-2-(2-(difluoromethyl)-4-((4-(trifluoromethyl)benzyl)oxy)-benzo[b]thiophene-5-carboxamido)-3,3-dimethylbutanoic acid

17

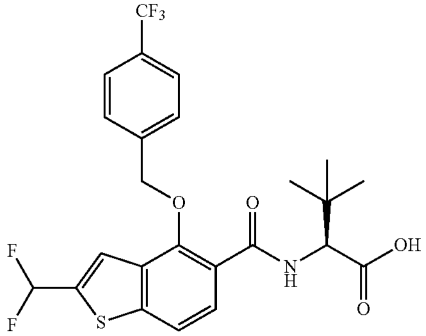

LCMS: $t_R$=2.06 min; MS: m/z ($ES^+$)=515 ($M+H^+$).

$^1$H NMR (400 MHz, MeOD) δ 7.91 (d, J=8.4 Hz, 1H), 7.86 (d, J=8.8 Hz, 1H), 7.75-7.69 (m, 5H), 7.00 (m, 1H), 5.48 (d, J=12.0 Hz, 1H), 5.33 (d, J=12.0 Hz, 1H), 4.51 (s, 1H), 1.02 (s, 9H) ppm.

Example 33-4. (2S)-2-(2-isopropyl-4-((4-(trifluoromethoxy)benzyl)oxy)-benzo[b]thiophene-5-carboxamido)-3,3-dimethylbutanoic acid

18

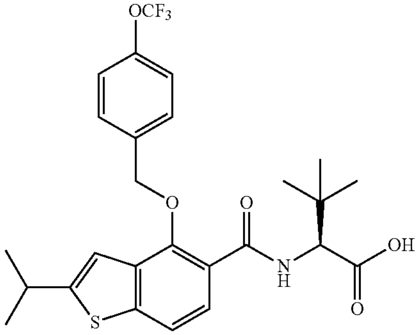

LCMS: $t_R$=2.35 min., MS: m/z (ES+)=524.1 (M+H$^+$).

$^1$H NMR (400 MHz, $CDCl_3$) δ 8.52 (d, J=8.4 Hz, 1H), 7.99 (d, J=8.4 Hz, 1H), 7.62 (d, J=8.8 Hz, 1H), 7.50 (d, J=8.4 Hz, 2H), 7.21 (d, J=8.0 Hz, 2H), 6.95 (s, 1H), 5.27 (d, J=12.0 Hz, 1H), 5.05 (d, J=12.0 Hz, 1H), 4.64 (d, J=8.8 Hz, 1H), 3.21-3.18 (m, 1H), 1.35 (d, J=7.2 Hz, 6H), 0.96 (s, 9H) ppm.

Example 33-5. (2S)-2-(2-chloro-4-((4-(trifluoromethyl)benzyl)oxy)-benzo[b]thiophene-5-carboxamido)-3,3-dimethylbutanoic acid

19

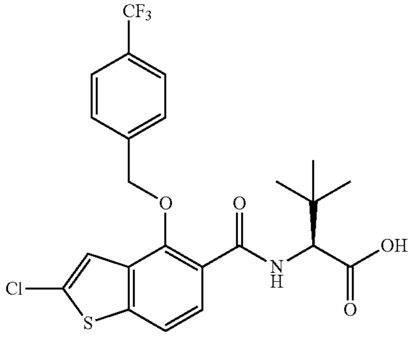

LCMS: $t_R$=2.25 min; 499 (M+H$^+$).

$^1$H NMR (400 MHz, $CDCl_3$) 8.36 (d, J=8.8 HZ, 1H), 8.09 (d, J=8.4 Hz, 1H), 7.69-7.61 (m, 5H), 7.18 (s, 1H), 5.38 (d, J=12.4 Hz, 1H), 5.16 (d, J=12.0 Hz, 1H), 4.66 (d, J=9.2 Hz, 1H), 0.98 (s, 9H) ppm.

Example 33-6. (2S)-2-(2-chloro-4-((4-(trifluoromethyl)benzyl)oxy)-benzo[b]thiophene-5-carboxamido)-3,3-dimethylpentanoic acid

20

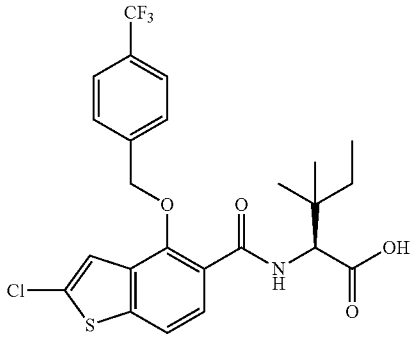

LCMS: $t_R$=2.30 min; MS: m/z (ES$^+$)=513 (M+H$^+$).

$^1$H NMR (400 MHz, $CDCl_3$) 8.35 (d, J=8.8 HZ, 1H), 8.10 (d, J=8.8 Hz, 1H), 7.70-7.61 (m, 5H), 7.19 (s, 1H), 5.37 (d, J=12.4 Hz, 1H), 5.15 (d, J=12.4 Hz, 1H), 4.71 (d, J=8.8 Hz, 1H), 1.31-1.26 (m, 2H), 0.92 (s, 3H), 0.86 (s, 3H), 0.84 (t, J=7.2 Hz, 3H) ppm.

Example 33-7. (2S)-2-(2-methoxy-4-((4-(trifluoromethyl)benzyl)oxy)-benzo[b]thiophene-5-carboxamido)-3,3-dimethylbutanoic acid

21

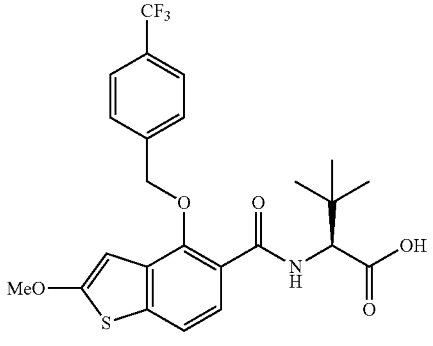

LCMS: $t_R$=2.16 min., MS: m/z (ES$^+$)=496 (M+H$^+$).

$^1$H NMR (400 MHz, $CDCl_3$) δ 8.45 (d, J=8.4 Hz, 1H), 7.94 (d, J=8.8 Hz, 1H), 7.68-7.62 (m, 4H), 7.52 (d, J=8.8 Hz, 1H), 6.25 (s, 1H), 5.34 (d, J=12.4 Hz, 1H), 5.10 (d, J=12.4 Hz, 1H), 4.66 (d, J=8.4 Hz, 1H), 3.93 (s, 3H), 0.99 (s, 9H) ppm.

Example 33-8. (2S)-3,3-dimethyl-2-(2-methyl-7-((4-(trifluoromethoxy)benzyl)oxy)-benzo[b]thiophene-6-carboxamido)butanoic acid

22

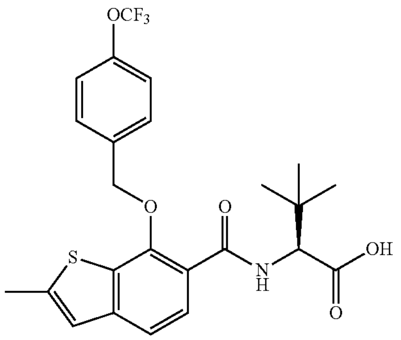

LCMS: $t_R$=2.33 min., MS: m/z ($ES^+$)=495 ($M+H^+$).

$^1H$ NMR (400 MHz, $CDCl_3$) δ 8.39 (d, J=8.4 Hz, 1H), 8.04 (d, J=8.4 Hz, 1H), 7.60 (d, J=8.4 Hz, 1H), 7.51 (d, J=8.4 Hz, 1H), 7.21 (d, J=8.4 Hz, 1H), 7.03 (s, 1H), 5.33-5.17 (m, 2H), 4.63 (d, J=8.0 Hz, 1H), 2.61 (s, 3H), 0.96 (s, 9H) ppm.

Example 33-9. (2S)-2-(3-chloro-2-methyl-4-((4-(trifluoromethoxy)benzyl)oxy)-benzo[b]thiophene-5-carboxamido)-3,3-dimethylpentanoic acid

23

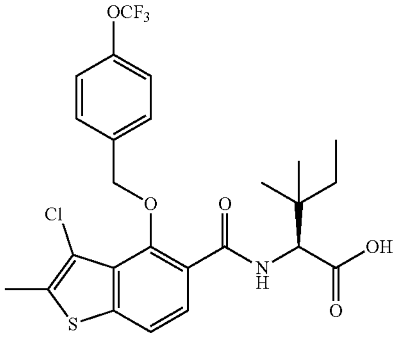

LCMS: $t_R$=2.38 min; MS: m/z ($ES^+$)=544 ($M+H^+$).

$^1H$ NMR (400 MHz, $CDCl_3$) 8.22 (d, J=8.4 Hz, 1H), 8.07 (d, J=8.4 Hz, 1H), 7.66 (d, J=8.4 Hz, 1H), 7.60 (d, J=8.4 Hz, 2H), 7.23 (d, J=8.0 Hz, 2H), 5.19 (s, 2H), 4.60 (d, J=8.4 Hz, 1H), 2.55 (s, 3H), 1.24 (q, 2H), 0.82 (s, 3H), 0.78 (q, 3H), 0.73 (s, 3H).

Example 33-10. (2S)-2-(2-ethyl-7-((4-(trifluoromethoxy)benzyl)oxy)-benzo[b]thiophene-6-carboxamido)-3,3-dimethylpentanoic acid

24

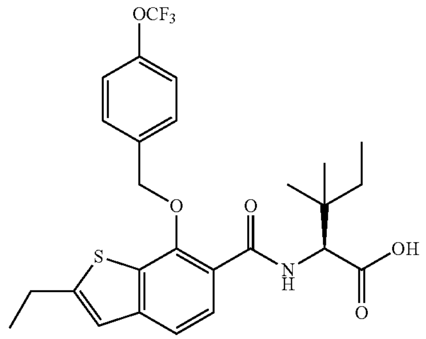

LCMS: $t_R$=2.33 min; MS: m/z ($ES^+$)=523 ($M+H^+$).

$^1H$ NMR (400 MHz, $CDCl_3$) δ 8.38 (d, J=8.4 Hz, 1H), 8.08 (d, J=8.4 Hz, 1H), 7.64 (d, J=8.4 Hz, 2H), 7.55 (d, J=7.6 Hz, 1H), 7.26 (d, J=8.8 Hz, 2H), 7.09 (s, 1H), 5.35 (d, J=11.2 Hz, 1H), 5.23 (d, J=10.4 Hz, 1H), 4.71 (d, J=8.4 Hz, 1H), 2.98 (dd, J=7.6 &14.4 Hz, 2H), 1.42 (t, J=7.2 Hz, 3H), 1.38-1.28 (m, 3H), 0.94 (s, 3H), 0.87 (s, 3H), 0.83 (t, J=7.2 Hz, 3H) ppm.

Example 33-11. (2S)-3,3-dimethyl-2-(2-methyl-7-((4-(trifluoromethyl)benzyl)oxy)-benzo[b]thiophene-6-carboxamido)butanoic acid

25

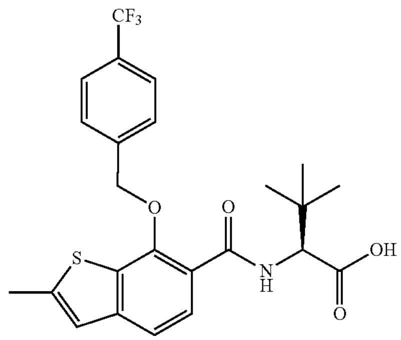

LCMS: $t_R$=2.23 min., MS: m/z ($ES^+$)=494 ($M+H^+$). 1H NMR (400 MHz, $CDCl_3$) δ 8.34 (d, J=8.4 Hz, 1H), 8.05 (d, J=8.0 Hz, 1H), 7.69 (m, J=8.4 Hz, 4H), 7.53 (d, J=8.0 Hz, 1H), 7.04 (S, 1H), 5.40 (d, 1H), 5.26 (d, 1H), 4.64 (d, 1H), 2.61 (s, 3H), 1.25 (s, 9H) ppm.

Example 33-12. (2S)-2-(2-isopropyl-7-((4-(trifluoromethoxy)benzyl)oxy)-benzo[b]thiophene-6-carboxamido)-3,3-dimethylbutanoic acid

26

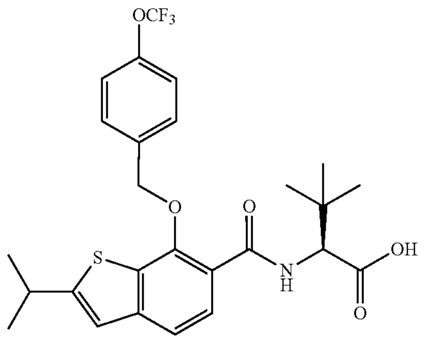

LCMS: $t_R$=2.31 min; MS: m/z ($ES^+$)=524 ($M+H^+$).

$^1$H NMR (400 MHz, MeOD) δ 7.86 (d, J=8.0 Hz, 1H), 7.70 (d, J=8.4 Hz, 1H), 7.59 (d, J=8.4 Hz, 1H), 7.33 (d, J=8.4 Hz, 1H), 7.19 (s, 1H), 5.45 (d, J=11.2 Hz, 1H), 5.21 (d, J=11.2 Hz, 1H), 4.52 (s, 1H), 3.33-3.30 (m, 1H), 1.43 (d, J=7.2 Hz, 6H), 1.00 (s, 9H) ppm.

Example 33-13. (2S)-3,3-dimethyl-2-(2-methyl-4-((4-(trifluoromethoxy)benzyl)oxy)-benzo[b]thiophene-5-carboxamido)butanoic acid

27

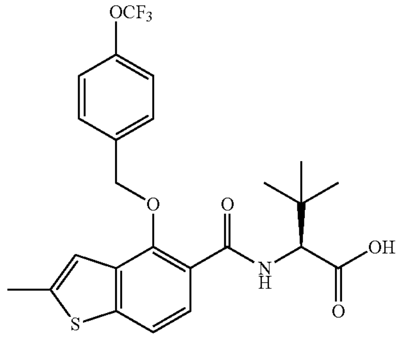

LCMS: $t_R$=2.25 min; MS: m/z ($ES^+$)=495 ($M+H^+$).

$^1$H NMR (400 MHz, $CDCl_3$) δ 8.52 (d, J=8.4 Hz, 1H), 8.02 (d, J=8.8 Hz, 1H), 7.63 (d, J=8.4 Hz, 1H), 7.55 (d, J=8.4 Hz, 2H), 7.25 (d, J=8.4 Hz, 2H), 6.99 (s, 1H), 5.30 (d, J=11.6 Hz, 1H), 5.11 (d, J=11.6 Hz, 1H), 4.67 (d, J=8.8 Hz, 1H), 2.59 (s, 3H), 0.97 (s, 9H).

Example 33-14. (2S)-2-(2-methoxy-4-((4-(trifluoromethyl)benzyl)oxy)-benzo[b]thiophene-5-carboxamido)-3,3-dimethylpentanoic acid

28

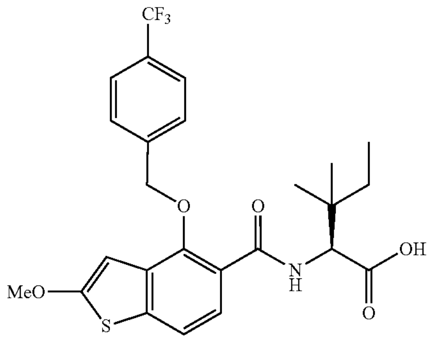

LCMS: $t_R$=2.21 min., MS: m/z ($ES^+$)=510 ($M+H^+$).

$^1$H NMR (400 MHz, $CDCl_3$) δ 8.41 (d, J=8.4 Hz, 1H), 7.94 (d, J=8.4 Hz, 1H), 7.69-7.63 (m, 4H), 7.52 (d, J=8.8 Hz, 1H), 6.27 (s, 1H), 5.34 (d, J=12.4 Hz, 1H), 5.11 (d, J=12.4 Hz, 1H), 4.71 (d, J=8.8 Hz, 1H), 3.94 (s, 3H), 1.35-1.27 (m, 2H), 0.94 (s, 3H), 0.89 (s, 3H), 0.82 (t, J=7.2 Hz, 3H) ppm.

Example 33-15. (2S)-2-(2-chloro-7-((4-(trifluoromethyl)benzyl)oxy)-benzo[b]thiophene-6-carboxamido)-3,3-dimethylpentanoic acid

29

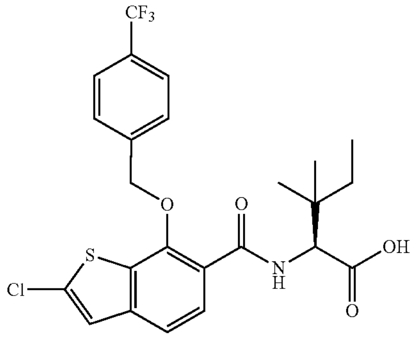

LCMS: $t_R$=2.33 min.; MS: m/z ($ES^+$)=514 (M+H)+.

$^1$H NMR (400 MHz, $CDCl_3$) δ 8.21 (d, J=6.4 Hz, 1H), 8.08 (d, J=6.4 Hz, 1H), 7.65-7.54 (m, 5H), 7.33-7.25 (m, 1H), 5.39 (d, J=11.2 Hz, 1H), 5.17 (d, J=10.4 Hz, 1H), 4.72 (d, J=6.4 Hz, 1H), 1.31 (s, J=5.6 Hz, 3H), 0.93-0.72 (m, 9H) ppm.

Example 33-16. (2S)-2-(2-isopentyl-4-((4-(trifluoromethyl)benzyl)oxy)-benzo[b]thiophene-5-carboxamido)-3,3-dimethylpentanoic acid

30

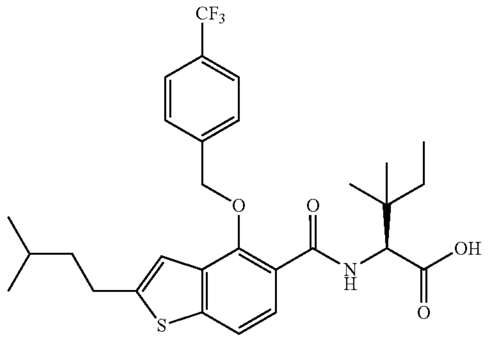

LCMS: $t_R$=2.46 min. MS: m/z ($ES^+$)=550 (M+H)+.

$^1$H NMR (400 MHz, MeOD) δ 7.79-7.69 (m, 6H), 7.12 (s, 1H), 5.45-5.42 (d, J=8.4 Hz, 1H), 5.28-5.25 (d, J=12.4 Hz, 1H), 4.60 (s, 1H), 2.95-2.92 (m, 2H), 1.66-1.59 (m, 3H), 1.39-1.28 (m, 3H), 0.98-0.96 (m, 9H) ppm, 0.95-0.84 (m, 6H) ppm.

Example 33-17. (2S)-3,3-dimethyl-2-(2-(thiazol-4-yl)-4-((4-(trifluoromethyl)benzyl)oxy)-benzo[b]thiophene-5-carboxamido)butanoic acid

31

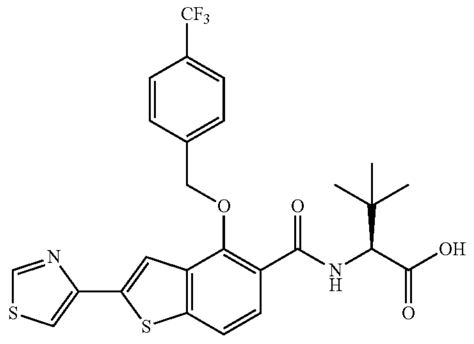

LCMS: $t_R$=2.17 min.; MS: m/z ($ES^+$)=548 (M+H)+.

$^1$H NMR (400 MHz, MeOD) δ 9.23 (s, 1H), 8.46 (d, J=8.8 Hz, 1H), 8.38 (d, J=1.6 Hz, 1H), 7.96 (s, 1H), 7.87-7.77 (m, 5H), 7.67 (d, J=8.0 Hz, 1H), 5.45 (d, J=12.0 Hz, 1H), 5.32 (d, J=12.0 Hz, 1H), 4.26 (d, J=8.4 Hz, 1H), 0.91 (s, 9H) ppm.

Example 33-18. (2S)-3,3-dimethyl-2-(2-methyl-7-((4-(trifluoromethoxy)benzyl)oxy)-benzo[b]thiophene-6-carboxamido)pentanoic acid

32

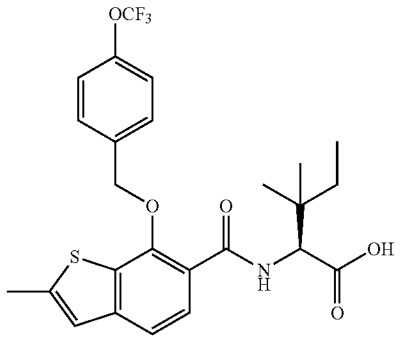

LCMS: $t_R$=2.29 min., MS: m/z ($ES^+$)=510.1 ($M+H^+$).

$^1$H NMR (400 MHz, $CDCl_3$) δ 8.36 (d, J=8.4 Hz, 1H), 8.05 (d, J=8.4 Hz, 1H), 7.60 (d, J=8.4 Hz, 2H), 7.51 (d, J=8.4 Hz, 1H), 7.22 (d, J=8.4 Hz, 2H), 7.04 (s, 1H), 5.32 (d, J=10.8 Hz, 1H), 5.18 (d, J=10.8 Hz, 1H), 4.69 (d, J=8.4 Hz, 1H), 2.61 (s, 3H), 1.35-1.25 (m, 2H), 0.92 (s, 3H), 0.85 (s, 3H), 0.81 (t, J=7.2 Hz, 3H) ppm.

Example 33-19. (2S)-3,3-dimethyl-2-(2-methyl-7-((4-(trifluoromethyl)benzyl)oxy)-benzo[b]thiophene-6-carboxamido)pentanoic acid

33

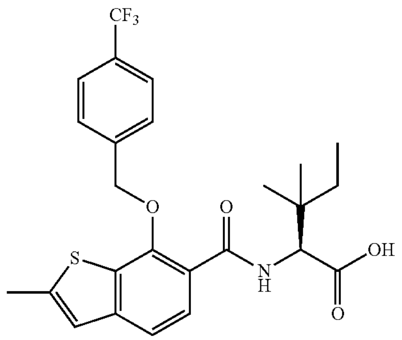

LCMS: $t_R$=2.27 min., MS: m/z ($ES^+$)=494 ($M+H^+$).

$^1$H NMR (400 MHz, $CDCl_3$) δ 8.05 (d, J=8.4 Hz, 1H), 7.71 (d, J=8.0 Hz, 1H), 7.66 (d, J=8.4 Hz, 4H), 7.53 (d, J=8.4 Hz, 1H), 7.04 (S, 1H), 5.37 (d, 1H), 5.25 (d, 1H), 4.70 (d, 1H), 2.61 (s, 3H), 1.30 (m, 2H), 0.918 (m, 6H) ppm.

Example 33-20. (2S)-3,3-dimethyl-2-(2-(thiazol-4-yl)-4-((4-(trifluoromethyl)benzyl)oxy)-benzo[b]thiophene-5-carboxamido)pentanoic acid

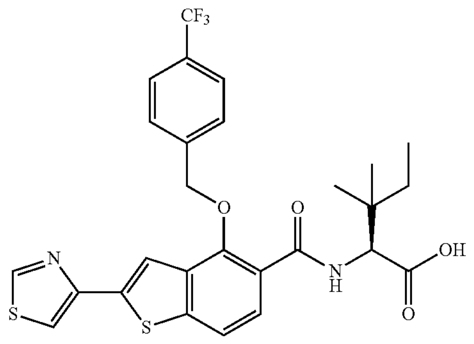

34

LCMS: $t_R$=2.20 min; MS: m/z ($ES^+$)=563 ($M+H^+$).

$^1$H NMR (400 MHz, CDCl3) δ δ 8.93 (s, 1H), 8.40 (d, J=8.8 Hz, 1H), 8.10 (d, J=8.4 Hz, 1H), 7.73 (d, J=11.2 Hz, 2H), 7.67 (s, 4H), 7.54 (s, 1H), 5.44 (d, J=12.4 Hz, 1H), 5.24 (d, J=12.4 Hz, 1H), 4.73 (d, J=8.4 Hz, 1H), 1.33-1.27 (m, 2H), 0.93 (s, 3H), 0.87 (s, 3H), 0.83 (t, J=7.6 Hz, 3H) ppm.

Example 33-21. (2S)-2-(2-ethyl-4-((4-(trifluoromethyl)benzyl)oxy)-benzo[b]thiophene-5-carboxamido)-3,3-dimethylbutanoic acid

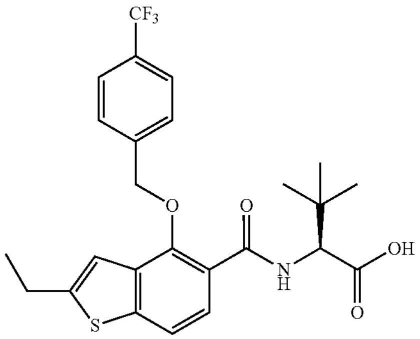

35

LCMS: $t_R$=2.20 min; MS: m/z ($ES^+$)=494 ($M+H^+$).

$^1$H NMR (400 MHz, $CDCl_3$) δ 8.49-8.47 (d, J=8.4 Hz, 1H), 8.03-8.00 (d, J=8.8 Hz, 1H), 7.68-7.63 (m, 5H), 6.97 (s, 1H), 5.38-5.35 (d, J=12.0 Hz, 1H), 5.17-5.14 (d, J=12.0 Hz, 1H), 4.66-4.64 (d, J=8.4 Hz, 1H), 2.93-2.91 (m, 2H), 1.37-1.33 (m, 3H), 0.97 (s, 9H) ppm.

Example 33-22. (2S)-2-(2-chloro-7-((4-(trifluoromethoxy)benzyl)oxy)-benzo[b]thiophene-6-carboxamido)-3,3-dimethylpentanoic acid

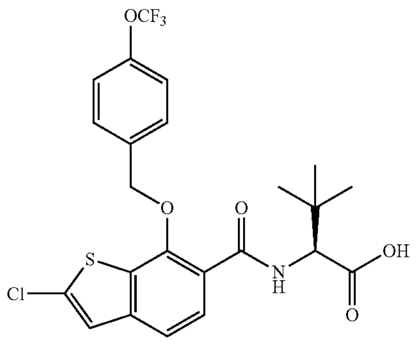

36

LCMS: $t_R$=1.59 min; MS: m/z ($ES^+$)=530 ($M+H^+$).

$^1$H NMR (400 MHz, MeOD) δ 7.84 (d, J=8.4 Hz, 1H), 7.67 (d, J=8.8 Hz, 1H), 7.62 (d, J=8.4 Hz, 1H), 7.41 (s, 1H), 7.32 (d, J=8.0 Hz, 1H), 5.43 (d, J=11.6 Hz, 1H), 5.25 (d, J=11.6 Hz, 1H), 4.60 (s, 1H), 1.42 (q, J=7.6 Hz, 2H), 0.99 (s, 3H), 0.95 (s, 3H), 0.91 (t, J=7.6 Hz, 3H) ppm.

Example 33-23. (2S)-2-(2-ethyl-4-((4-(trifluoromethoxy)benzyl)oxy)-3a,7a-benzo[b]thiophene-5-carboxamido)-3,3-dimethylbutanoic acid

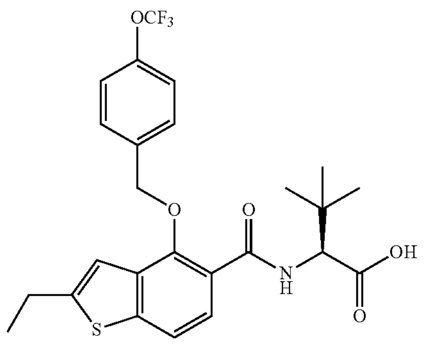

37

LCMS: $t_R$=2.13 min; MS: m/z ($ES^+$)=510 ($M+H^+$).

$^1$H NMR (400 MHz, $CDCl_3$) δ 8.53-8.50 (d, J=8.4 Hz, 1H), 8.03-8.00 (d, J=8.4 Hz, 1H), 7.66-7.63 (d, J=8.4 Hz, 1H), 7.55-7.53 (d, J=8.4 Hz, 2H), 7.25-7.23 (d, J=8.0 Hz, 2H), 6.99 (s, 1H), 5.31-5.28 (d, J=12 Hz, 1H), 5.11-5.09 (d, J=11.6 Hz, 1H), 4.66-4.64 (d, J=8.4 Hz, 1H), 2.96-2.90 (m, 2H), 1.38-1.36 (t, J=7.2 Hz, 3H), 0.98 (s, 9H) ppm.

Example 33-24. (2S)-3,3-dimethyl-2-(2-methyl-4-((4-(trifluoromethyl)benzyl)oxy)-benzo[b]thiophene-5-carboxamido)pentanoic acid

38

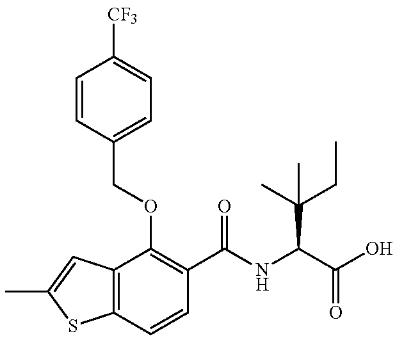

LCMS: $t_R$=2.24 min; MS: m/z ($ES^+$)=493 ($M+H^+$).

$^1$H NMR (400 MHz, CDCl3) δ 8.45 (d, J=8.4 Hz, 1H), 8.04 (d, J=8.4 Hz, 1H), 7.70-7.63 (m, 5H), 6.99 (s, 1H), 5.38-5.35 (m, 1H), 5.19-5.16 (m, 1H), 4.72 (d, J=8.8 Hz, 1H), 2.59 (s, 3H), 1.35-1.25 (m, 2H), 0.92 (s, 3H), 0.90 (s, 3H), 0.88 (t, J=7.6 Hz, 3H) ppm.

Example 33-25. (2S)-3,3-dimethyl-2-(2-(trifluoromethyl)-4-((4-(trifluoromethyl)benzyl)oxy)-benzo[b]thiophene-5-carboxamido)pentanoic acid

39

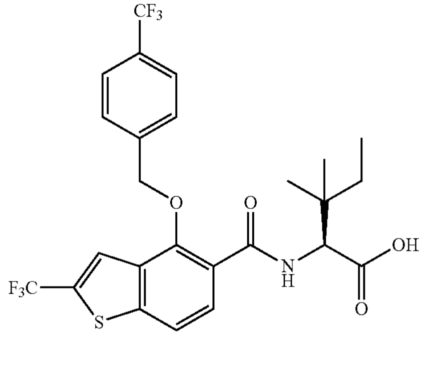

LCMS: $t_R$=2.30 min; MS: m/z ($ES^+$)=548 ($M+H^+$).

$^1$H NMR (400 MHz, $CDCl_3$) δ 8.28 (d, J=8.4 Hz, 1H), 8.23 (d, J=8.4 Hz, 1H), 7.79 (d, J=8.4 Hz, 1H), 7.68 (d, J=8. Hz, 2H), 7.61-7.59 (m, 3H), 5.42 (d, J=12.0 Hz, 1H), 5.18 (d, J=12.0 Hz, 1H), 4.74 (d, J=8.4 Hz, 1H), 1.35-1.30 (m, 2H), 0.95 (s, 3H), 0.90 (s, 3H), 0.87 (t, J=7.6 Hz, 3H) ppm.

Example 33-26. (2S)-2-(2-ethyl-7-((4-(trifluoromethoxy)benzyl)oxy)-benzo[b]thiophene-6-carboxamido)-3,3-dimethylbutanoic acid

40

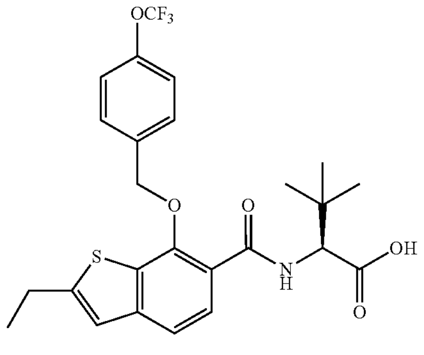

LCMS: $t_R$=2.28 min; MS: m/z ($ES^+$)=510 ($M+H^+$).

$^1$H NMR (400 MHz, $CDCl_3$) δ 8.40 (d, J=8.4 Hz, 1H), 8.08 (d, J=8.4 Hz, 1H), 7.64 (d, J=8.4 Hz, 2H), 7.55 (d, J=8.0 Hz, 1H), 7.28 (d, J=4.8 Hz, 2H), 7.09 (s, 1H), 5.34 (d, J=10.4 Hz, 1H), 5.23 (d, J=11.2 Hz, 1H), 4.65 (d, J=8.4 Hz, 1H), 2.98 (dd, J=8.4 &14.8 Hz, 2H), 1.42 (t, J=7.6 Hz, 3H), 0.98 (s, 9H) ppm.

Example 33-27. (2S)-2-(2-ethyl-4-((4-(trifluoromethyl)benzyl)oxy)-benzo[b]thiophene-5-carboxamido)-3,3-dimethylpentanoic acid

41

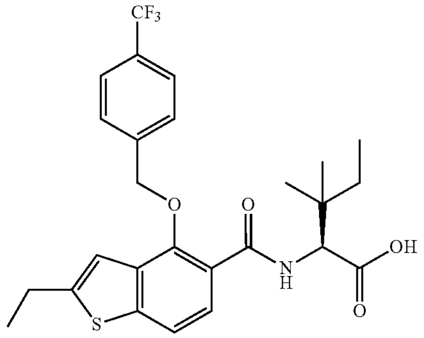

LCMS: $t_R$=LCMS: $t_R$=1.56 min; MS: m/z ($ES^+$)=508 ($M+H^+$).

$^1$H NMR (400 MHz, DMSO-$d_6$) δ 8.41-8.39 (d, J=8.8 Hz, 1H), 7.80-7.76 (m, 5H), 7.61-7.59 (d, J=8.0 Hz, 1H), 5.35-5.32 (d, J=12.4 Hz, 1H), 5.25-5.21 (d, J=12.8 Hz, 1H), 4.39-4.37 (d, J=12.4 Hz, 1H), 2.93-2.91 (m, 2H), 1.33-1.22 (m, 5H), 0.85-0.81 (m, 6H), 0.76-0.72 (m, 3H) ppm.

Example 33-28. (2S)-3,3-dimethyl-2-(2-(trifluoromethyl)-7-((4-(trifluoromethyl)benzyl)oxy)-[b]thiophene-6-carboxamido)pentanoic acid

42

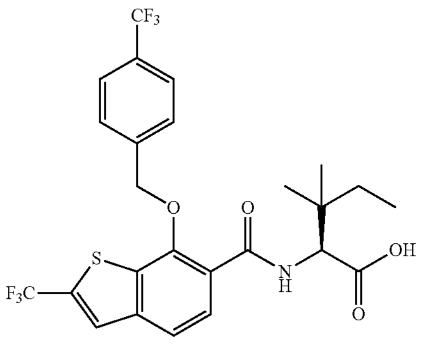

LCMS: $t_R$=2.32 min., MS: m/z (ES+)=548 (M+H$^+$).

$^1$H NMR (400 MHz, $CDCl_3$): δ 8.20-8.13 (m, 2H), 7.75-7.66 (m, 6H), 5.46-5.42 (m, 1H), 5.24-5.21 (m, 1H), 4.67-4.65 (m, 1H), 1.31-1.26 (m, 2H), 0.93-0.74 (m, 9H) ppm.

Example 33-29. (2S)-3,3-dimethyl-2-(7-((4-(trifluoromethoxy)benzyl)oxy)-2-(trifluoromethyl)-benzo[b]thiophene-6-carboxamido)pentanoic acid

43

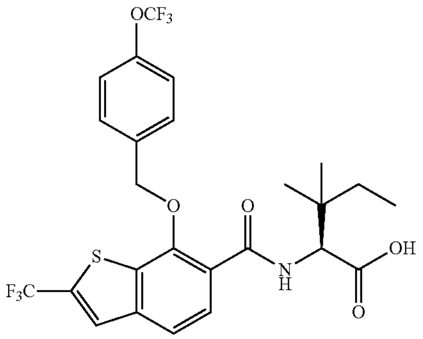

LCMS: $t_R$=2.33 min.; MS: m/z (ES+)=564 (M+H$^+$).

$^1$H NMR (400 MHz, CDCl3) δ 8.27 (d, J=8.4 Hz, 1H), 8.18 (d, J=8.0 Hz, 1H), 7.76-7.73 (m, 2H), 7.59 (d, J=7.2 Hz, 2H), 7.25 (d, J=8.4 Hz, 1H), 5.36 (d, J=11.2 Hz, 1H), 5.19 (d, J=11.2 Hz, 1H), 4.71 (d, J=9.2 Hz, 1H), 1.38-1.29 (m, 2H), 0.95 (s, 3H),), 0.89 (s, 3H), 0.84 (t, J=7.2 Hz, 3H) ppm.

Example 33-30. (2S)-3,3-dimethyl-2-(2-methyl-4-((4-(trifluoromethoxy)benzyl)oxy)-benzo[b]thiophene-5-carboxamido)pentanoic acid

44

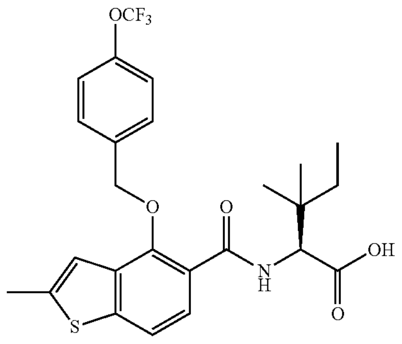

LCMS: $t_R$=2.17 min; MS: m/z (ES$^+$)=510 (M+H$^+$).

$^1$H NMR (400 MHz, $CDCl_3$) δ 8.49 (d, J=8.4 Hz, 1H), 8.03 (d, J=8.4 Hz, 1H), 7.63 (d, J=8.4 Hz, 1H), 7.55 (d, J=8.8 Hz, 2H), 7.25 (d, J=8.0 Hz, 2H), 6.99 (s, 1H), 5.30 (d, J=11.6 Hz, 1H), 5.11 (d, J=11.6 Hz, 1H), 4.72 (d, J=8.8 Hz, 1H), 2.59 (s, 3H), 1.34 (q, 2H), 0.92 (s, 3H), 0.87 (s, 3H), 0.84 (t, 3H).

Example 33-31. (2S)-2-(2-isopropyl-7-((4-(trifluoromethyl)benzyl)oxy)-benzo[b]thiophene-6-carboxamido)-3,3-dimethylbutanoic acid

45

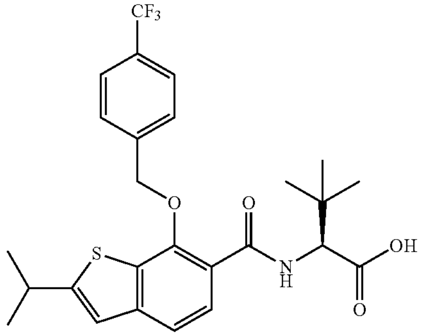

LCMS: $t_R$=2.32 min; MS: m/z (ES$^+$)=508 (M+H$^+$).

$^1$H NMR (400 MHz, $CDCl_3$) δ 8.40 (d, J=8.4 Hz, 1H), 8.08 (d, J=8.0 Hz, 1H), 7.72 (d, J=8.4 Hz, 2H), 7.66 (d, J=8.4 Hz, 2H), 7.56 (d, J=4.8 Hz, 1H), 7.10 (s, 1H), 5.40 (d, J=10.6 Hz, 1H), 5.25 (d, J=10.8 Hz, 1H), 4.65 (d, J=8.8 Hz, 1H), 3.30-3.23 (m, 1H), 1.43 (s, 3H), 1.41 (s, 3H), 0.96 (s, 9H) ppm.

Example 33-32. (2S)-2-(2-isopentyl-7-((4-(trifluoromethyl)benzyl)oxy)-benzo[b]thiophene-6-carboxamido)-3,3-dimethylpentanoic acid

46

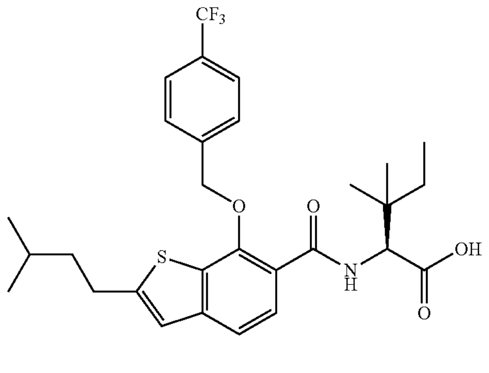

LCMS: $t_R$=2.51 min; MS: m/z ($ES^+$)=550 ($M+H^+$).

$^1H$ NMR (400 MHz, chloroform-d) δ 8.38 (d, J=8.4 Hz, 1H), 8.08 (d, J=8.4 Hz, 1H), 7.71-7.64 (m, 4H), 7.56 (d, J=8.0 Hz, 1H), 7.08 (s, 1H), 5.41 (d, J=11.6 Hz, 1H), 5.27 (d, J=11.6 Hz, 1H), 4.72 (d, J=8.4 Hz, 1H), 2.95-2.91 (m, 2H) ppm.

Example 33-33. (2S)-2-(2-chloro-7-((4-(trifluoromethyl)benzyl)oxy)-benzo[b]thiophene-6-carboxamido)-3,3-dimethylbutanoic acid

47

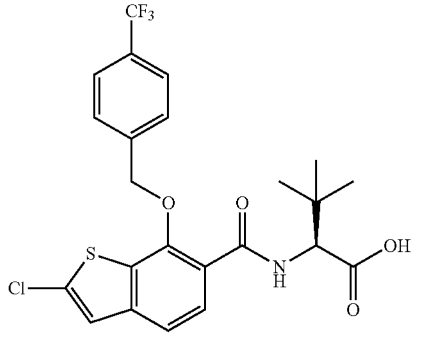

LCMS: $t_R$=2.14 min., MS: m/z ($ES^+$)=500 ($M+H^+$).

$^1H$ NMR (400 MHz, $CDCl_3$) δ 8.24 (d, J=8.0 Hz, 1H), 8.08 (d, J=8.4 Hz, 1H), 7.69-7.64 (m, 4H), 7.55 (d, J=8.4 Hz, 1H), 7.25 (s, 1H), 5.39 (d, J=11.6 Hz, 1H), 5.17 (d, J=11.6 Hz 1H), 4.64 (d, J=8.4 Hz 1H), 0.98 (s, 9H) ppm.

Example 33-34. (2S)-2-(2-isopropyl-4-((4-(trifluoromethyl)benzyl)oxy)-benzo[b]thiophene-5-carboxamido)-3,3-dimethylbutanoic acid

48

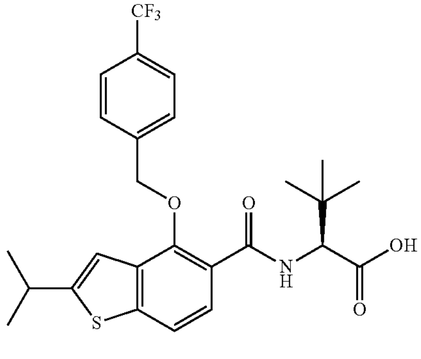

LCMS: $t_R$=2.17 min., MS: m/z ($ES^+$)=508 ($M+H^+$).

$^1H$ NMR (400 MHz, $CDCl_3$) δ 8.46 (d, J=8.4 Hz, 1H), 7.99 (d, J=8.4 Hz, 1H), 7.66-7.60 (m, 4H), 7.26 (s, 1H), 5.35 (d, J=11.6 Hz, 1H), 5.12 (d, J=11.6 Hz, 1H), 4.65 (d, J=8.4 Hz, 1H), 3.21-3.17 (m, 1H), 1.34 (d, J=6.8 Hz, 6H), 0.97 (s, 9H) ppm.

Example 33-35. (2S)-3,3-dimethyl-2-(4-((4-(trifluoromethoxy)benzyl)oxy)-2-(trifluoromethyl)-benzo[b]thiophene-5-carboxamido)pentanoic acid

49

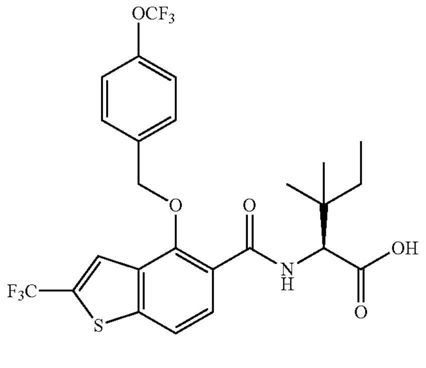

LCMS: $t_R$=2.34 min; MS: m/z ($ES^+$)=564 ($M+H^+$).

$^1H$ NMR (400 MHz, $CDCl_3$) δ 8.31 (d, J=8.8 Hz, 1H), 8.23 (d, J=8.4 Hz, 1H), 7.78 (d, J=8.4 Hz, 1H), 7.60 (s, 1H), 7.50 (d, J=8. Hz, 2H), 7.24 (d, J=8.0 Hz, 2H), 5.36 (d, J=12.0 Hz, 1H), 5.13 (d, J=12.0 Hz, 1H), 4.74 (d, J=8.4 Hz, 1H), 1.38-1.32 (m, 2H), 0.96 (s, 3H), 0.91 (s, 3H), 0.87 (t, J=7.6 Hz, 3H) ppm.

Example 33-36. (2S)-2-(2-(difluoromethyl)-4-((4-(trifluoromethyl)benzyl)oxy)-benzo[b]thiophene-5-carboxamido)-3,3-dimethylpentanoic acid

50

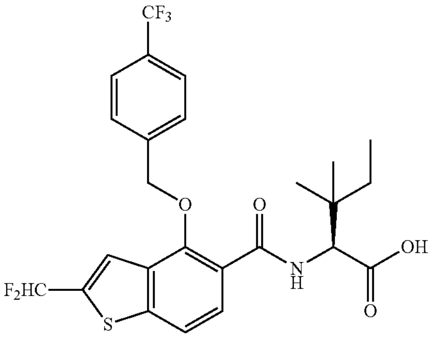

LCMS: $t_R$=2.06 min; MS: m/z ($ES^+$)=530 ($M+H^+$).

$^1$H NMR (400 MHz, MeOD) δ 7.90 (d, J=8.8 Hz, 1H), 7.84 (d, J=8.4 Hz, 1H), 7.69-7.40 (m, 5H), 7.26-6.99 (m, 1H), 5.48 (d, J=12.4 Hz, 1H), 5.30 (d, J=12.4 Hz, 1H), 1.41-1.31 (m, 4H), 0.96 (s, 3H), 0.93 (s, 3H), 0.87 (t, J=7.2 Hz, 2H) ppm.

Example 34-1. (S)-2-(2-chloro-3-methyl-4-((4-(trifluoromethoxy)benzyl)oxy)-benzo[b]thiophene-5-carboxamido)-3,3-dimethylpentanoic acid

51

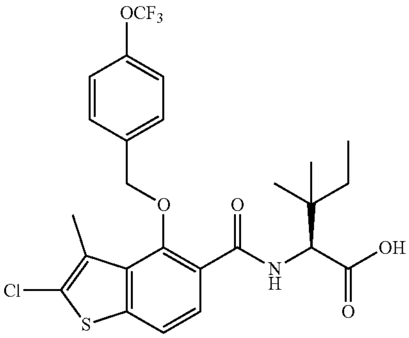

A 2 M solution of LiOH (2.91 ml, 5.83 mmol) in water was added to a stirring solution of methyl (S)-2-(7-chloro-1-((4-(trifluoromethyl)benzyl)oxy)-2-naphthamido)-3,3-dimethylbutanoate (296 mg, 582.75 μmol) in a mixture of 1,4-dioxane (6 ml, 70.14 mmol). The reaction mixture was stirred at 50° C. for overnight. Cooled to RT, then neutralized with 1N HCl until pH was about 4-5, then extracted with ethyl acetate. The combined organic extracts were washed with brine, dried over $MgSO_4$, filtered and concentrate. Purified on combiflash ($SiO_2$, 12 g) using a 0-10% MeOH (1% formic acid)/$CH_2Cl_2$ gradient to provide (S)-2-(2-chloro-3-methyl-4-((4-(trifluoromethoxy)benzyl)oxy)benzo[b]thiophene-5-carboxamido)-3,3-dimethylpentanoic acid (49 mg, 90.08 μmol, 91.4% yield) as a solid.

LCMS: $t_R$=1.64 min., MS: m/z (ES+)=544 ($M+H^+$).

1H NMR (400 MHz, $CDCl_3$) δ 7.97 (d, J=8.5 Hz, 1H), 7.91 (d, J=8.4 Hz, 1H), 7.58 (d, J=8.5 Hz, 1H), 7.47 (d, J=8.6 Hz, 2H), 7.23 (m, 2H), 5.10 (m, 2H), 4.63 (d, J=8.4 Hz, 1H), 2.49 (s, 3H), 1.26 (m, 2H), 0.82 (m, 9H).

$^{19}$F NMR (377 MHz, $CDCl_3$) δ −57.9.

The following compounds (examples 34-2 through 34-7) exemplified below are prepared in a manner analogous to Example 34-1 described above.

Example 34-2. (S)-2-(2-chloro-3-methyl-4-((4-(trifluoromethyl)benzyl)oxy)-benzo[b]thiophene-5-carboxamido)-2-(1-methylcyclobutyl)acetic acid

52

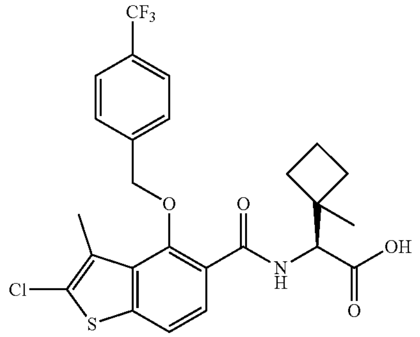

LCMS: $t_R$=1.61 min., MS: m/z (ES+)=524 ($M+H^+$). 1H NMR (400 MHz, $CDCl_3$) δ 7.98 (d, J=8.5 Hz, 1H), 7.78 (d, J=8.3 Hz, 1H), 7.60 (m, 5H), 5.19 (m, 2H), 4.87 (d, J=8.3 Hz, 1H), 2.46 (s, 3H), 2.27 (m, 1H), 2.08 (m, 4H), 1.78 (m, 3H), 1.47 (m, 1H).

$^{19}$F NMR (377 MHz, $CDCl_3$) δ −57.9.

Example 34-3. (S)-2-(2-chloro-3-methyl-4-((4-trifluoromethyl)benzyl)oxy)-benzo[b]thiophene-5-carboxamido)-3,3-dimethylpentanoic acid

53

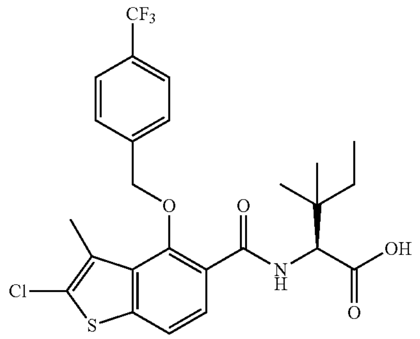

LCMS: Rt=1.63 min., MS: m/z (ES+)=528 ($M+H^+$)

$^1$H NMR (400 MHz, $CDCl_3$) δ 7.97 (d, J=8.5 Hz, 1H), 7.90 (d, J=8.5 Hz, 1H), 7.60 (m, 5H), 5.16 (m, 2H), 4.65 (dd, J=8.5, 0.7 Hz, 1H), 2.47 (s, 3H), 1.23 (m, 2H), 0.81 (m, 9H).

$^{19}$F NMR (377 MHz, $CDCl_3$) δ −62.6.

Example 34-4. (S)-2-(2-chloro-3-methyl-4-((4-trifluoromethoxy)benzyl)oxy)-benzo[b]thiophene-5-carboxamido)-3,3-dimethylbutanoic acid

54

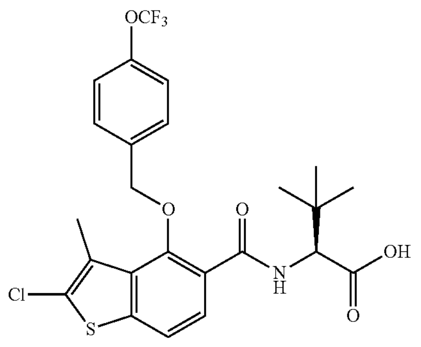

LCMS: $t_R$=1.60 min., MS: m/z (ES+)=530 (M+H$^+$).

$^1$H NMR (400 MHz, $CDCl_3$) δ 7.96 (d, J=8.5 Hz, 1H), 7.91 (d, J=8.3 Hz, 1H), 7.58 (d, J=8.4 Hz, 1H), 7.47 (d, J=8.6 Hz, 2H), 7.22 (m, 2H), 5.10 (m, 2H), 4.57 (d, J=8.3 Hz, 1H), 2.49 (s, 3H), 0.92 (s, 9H). $^{19}$F NMR (377 MHz, $CDCl_3$) δ −57.9.

Example 34-5. (S)-2-(2-chloro-3-methyl-4-((4-(trifluoromethoxy)benzyl)oxy)-benzo[b]thiophene-5-carboxamido)-2-(1-methylcyclopropyl)acetic acid

55

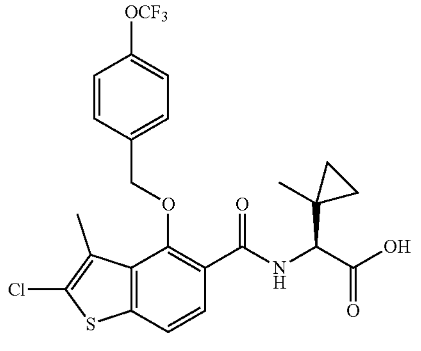

LCMS: $t_R$=1.57 min., MS: m/z (ES+)=528 (M+H$^+$).

$^1$H NMR (400 MHz, $CDCl_3$) δ 8.07 (d, J=7.1 Hz, 1H), 7.98 (d, J=8.4 Hz, 1H), 7.58 (d, J=8.4 Hz, 1H), 7.51 (m, 2H), 7.24 (m, 2H), 5.12 (m, 2H), 4.07 (d, J=7.1 Hz, 1H), 2.52 (s, 3H), 0.79 (s, 4H), 0.56 (dt, J=10.1, 5.3 Hz, 1H), 0.39 (dt, J=9.3, 5.5 Hz, 1H), 0.17 (m, 1H).

$^{19}$F NMR (377 MHz, $CDCl_3$) δ −57.9.

Example 34-6. (S)-2-(2-chloro-3-methyl-4-((4-(trifluoromethoxy)benzyl)oxy)-benzo[b]thiophene-5-carboxamido)-2-(1-methylcyclobutyl)acetic acid

56

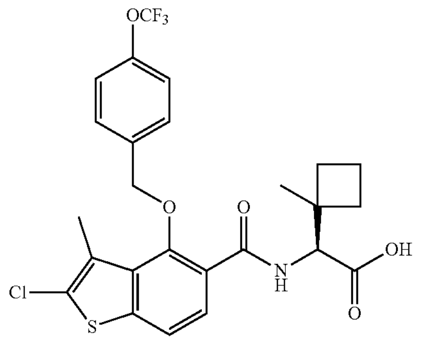

LCMS: $t_R$=1.62 min., MS: m/z (ES+)=542 (M+H$^+$).

$^1$H NMR (400 MHz, $CDCl_3$) δ 7.98 (d, J=8.5 Hz, 1H), 7.79 (d, J=8.1 Hz, 1H), 7.58 (dd, J=8.4, 0.7 Hz, 1H), 7.46 (d, J=8.4 Hz, 2H), 7.23 (m, 2H), 5.10 (m, 2H), 4.85 (d, J=8.0 Hz, 1H), 2.49 (s, 3H), 2.28 (dt, J=19.9, 10.6 Hz, 1H), 1.89 (m, 4H), 1.46 (m, 1H), 0.91 (s, 3H).

$^{19}$F NMR (377 MHz, $CDCl_3$) δ −57.9.

Example 34-7. (S)-2-(2-chloro-3-methyl-4-((4-(trifluoromethyl)benzyl)oxy)-benzo[b]thiophene-5-carboxamido)-2-(1-methylcyclopropyl)acetic acid

57

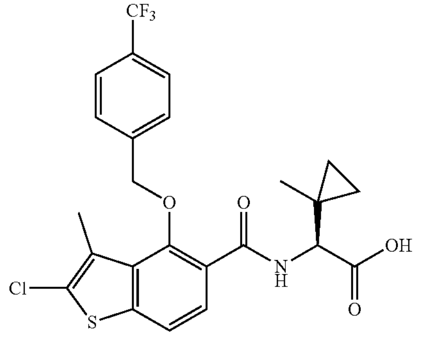

LCMS: $t_R$=1.55 min., MS: m/z (ES+)=512 (M+H$^+$).

$^1$H NMR (400 MHz, $CDCl_3$) δ 8.05 (d, J=7.3 Hz, 1H), 7.98 (d, J=8.4 Hz, 1H), 7.66 (d, J=8.2 Hz, 2H), 7.60 (m, 3H), 5.21 (m, 2H), 4.09 (d, J=7.2 Hz, 1H), 2.50 (s, 3H), 0.80 (m, 4H), 0.56 (dt, J=9.9, 5.3 Hz, 1H), 0.39 (m, 1H), 0.16 (dt, J=9.2, 5.4 Hz, 1H).

$^{19}$F NMR (377 MHz, $CDCl_3$) δ −62.59.

Example 35-1. Synthesis of (2S)-2-[[2-chloro-3-methyl-4-[[4-(trifluoromethyl)phenyl]methoxy]-benzothiophene-5-carbonyl]amino]-3,3-dimethyl-butanoic acid

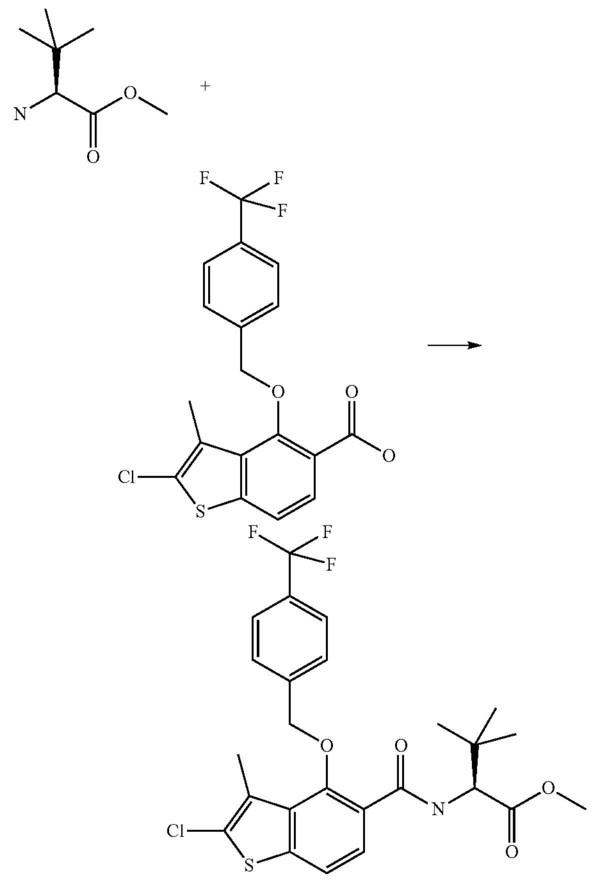

A flask equipped with stir bar, static nitrogen line was charged with 2-chloro-3-methyl-4-[[4-(trifluoromethyl)phenyl]methoxy]benzothiophene-5-carboxylic acid (182 mg, 0.5 mmol) and EtOAc (3 mL). To this solution was added DIPEA (185 mg, 0.3 mL, 1.435 mmol), followed by methyl (2S)-2-amino-3,3-dimethyl-butanoate (99 mg, 1.15 equiv.). The solution was cooled in an ice-water bath to 5° C. The reaction flask was charged with 2,4,6-tripropyl-1,3,5,2,4,6-trioxatriphosphorinane-2,4,6-trioxide (T3P, 0.6 mL of 50 wt % solution in EtOAc) drop-wise using a syringe with cooling in ice-water bath. The reaction flask was removed from the ice bath and the solution allowed to warm to rt after addition and then stirred at rt overnight until in-process LCMS indicated a complete reaction. The reaction was diluted with EtOAc (5 mL), and $NaHCO_3$ aq (3 mL). The two layers were separated and the organic solution was dried over $K_2CO_3$, filtered, and then concentrated. The residue was loaded onto a silica gel column, eluted with 10-20% EtOAc in Heptane, to obtain the product. 86.7 mg (88% yield) of the title compound as a thick liquid.

LCMS: $t_R$=1.70 min.; MS: m/z ($ES^+$)=528 ($M+H^+$).

Step 2

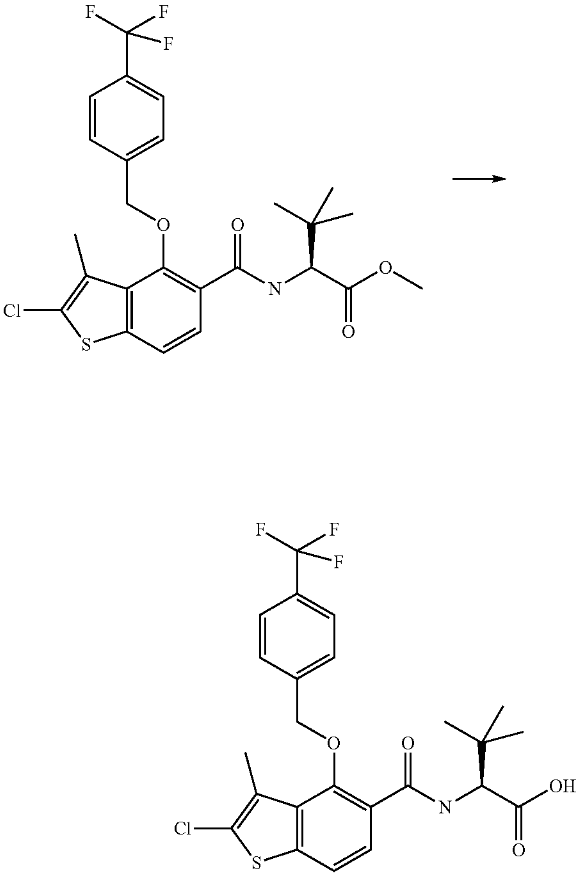

58

A round bottomed flask equipped with a stir bar, a temperature controller, a heating mantle and a static nitrogen line was charged with methyl (2S)-2-[[2-chloro-3-methyl-4-[[4-(trifluoromethyl)phenyl]methoxy]benzothiophene-5-carbonyl]amino]-3,3-dimethyl-butanoate (126 mg, 0.249 mmol), THF (2 mL), and MeOH (1.0 mL). A clear light yellow solution formed. 1 N NaOH (1.3 mL, 1.3 mmol, 5 equiv.)) was added. The resulting cloudy solution was heated to 50° C. (bath 55° C.) and held until in-process TLC indicated complete reaction (6 h). The solution was cooled to rt. EtOAc (5 mL) was added and the biphasic solution stirred vigorously in an ice bath. 1 N HCl (1.3 mL) was added over 5 min and stirred to obtain two clear liquid phases. The aq. phase was extracted with EtOAc. The combined organics were washed saturated aqueous NaCl (5 mL) and was then dried with $Na_2SO_4$. The solution was filtered and concentrated to obtain the title compound as a solid after dry under high vacuum.

LCMS: $t_R$=1.59 min, MS m/z MS: m/z ($ES^+$)=514 ($M+H^+$).

$^1$H NMR (400 MHz, $CDCl_3$) δ 7.94 (dd, J=11.8, 8.4 Hz, 2H), 7.71-7.49 (m, 4H), 5.15 (dd, J=69.3, 12.8 Hz, 2H), 4.58 (d, J=8.5 Hz, 1H), 2.46 (s, 3H), 0.91 (s, 9H).

The following compounds (examples 35-2 through 35-9) exemplified below are prepared in a manner analogous to Example 35-1 described above.

Example 35-2. (2S)-3,3-dimethyl-2-[[3-methyl-4-[[4-(trifluoromethyl)phenyl]methoxy]-benzothiophene-5-carbonyl]amino]butanoic acid

59

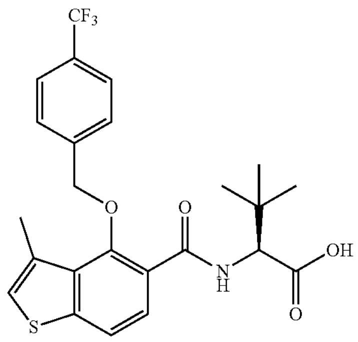

LCMS: $t_R$=1.47 min, MS: m/z (ES$^+$)=480 (M+H$^+$).

1H NMR (400 MHz, $CDCl_3$) δ 7.99 (dd, J=14.6, 8.5 Hz, 2H), 7.72 (d, J=8.5 Hz, 1H), 7.67-7.54 (m, 4H), 7.06 (t, J=1.3 Hz, 1H), 5.27 (d, J=13.0 Hz, 1H), 5.10 (d, J=12.9 Hz, 1H), 4.58 (d, J=8.5 Hz, 1H), 2.53 (d, J=1.2 Hz, 3H), 0.90 (s, 9H).

Example 35-3. (2S)-3,3-dimethyl-2-[[2-methyl-4-[[4-(trifluoromethyl)phenyl]methoxy]-1,3-benzothiazole-5-carbonyl]amino]butanoic acid

60

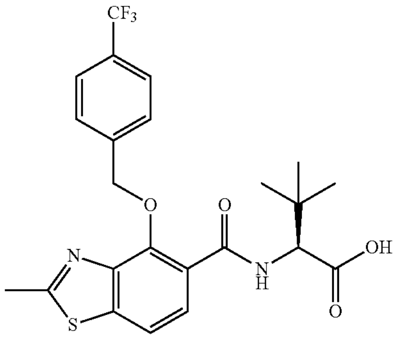

$^1$H NMR (400 MHz, DMSO-$d_6$) δ ppm 12.96-12.48 (m, 1H) 8.47 (d, J=8.44 Hz, 1H) 8.01-7.63 (m, 6H) 5.98-5.61 (m, 2H) 4.32 (d, J=8.44 Hz, 1H) 2.87 (s, 3H) 0.86 (s, 9H)

LCMS: $t_R$=0.91 min., MS: m/z (ES+)=481 (M+H$^+$).

Example 35-4. (2S)-2-[[2-(difluoromethyl)-4-[[4-(trifluoromethyl)phenyl]methoxy]-1,3-benzothiazole-5-carbonyl]amino]-3,3-dimethyl-butanoic acid

61

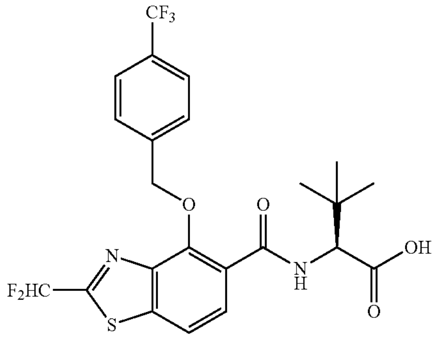

$^1$H NMR (400 MHz, DMSO-$d_6$) δ ppm 8.50 (d, J=8.44 Hz, 1H) 8.06 (d, J=7.56 Hz, 1H) 7.91 (d, J=7.56 Hz, 1H) 7.84-7.72 (m, 4H) 7.57 (t, J=53.63 Hz, 1H) 5.91-5.64 (m, 2H) 4.31 (d, J=8.44 Hz, 1H) 0.87 (s, 9H)

LCMS: $t_R$=0.91 min., MS: m/z (ES+)=517 (M+H$^+$).

Example 35-5. (2S)-2-[[2-cyclopropyl-4-[[4-(trifluoromethyl)phenyl]methoxy]-1,3-benzothiazole-5-carbonyl]amino]-3,3-dimethyl-butanoic acid

62

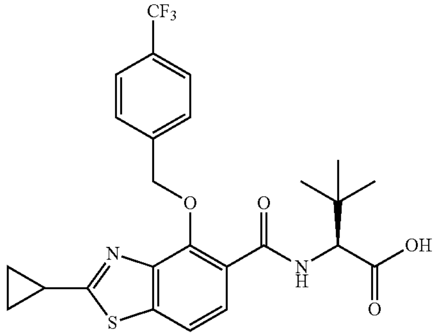

$^1$H NMR (400 MHz, DMSO-$d_6$) δ ppm 12.96-12.56 (m, 1H) 8.49 (d, J=8.44 Hz, 1H) 7.86-7.71 (m, 6H) 5.84-5.64 (m, 2H) 4.33 (d, J=8.44 Hz, 1H) 2.63-2.54 (m, 1H) 1.33-1.12 (m, 4H) 0.87 (s, 9H)

LCMS: $t_R$=0.97 min., MS: m/z (ES+)=507 (M+H$^+$).

Example 35-6. (2S)-2-[[2-cyclopropyl-4-[[4-(trifluoromethyl)phenyl]methoxy]-1,3-benzothiazole-5-carbonyl]amino]-3,3-dimethyl-pentanoic acid

63

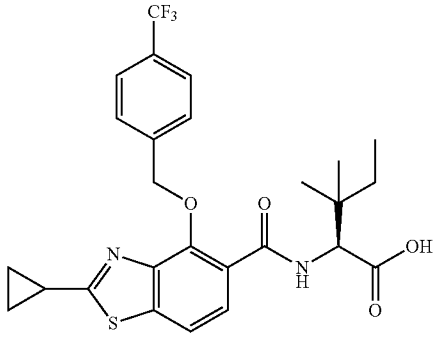

$^1$H NMR (400 MHz, DMSO-$d_6$) δ ppm 13.08-12.56 (m, 1H) 8.48 (d, J=8.80 Hz, 1H) 7.87-7.65 (m, 6H) 5.81-5.67 (m, 2H) 4.40 (d, J=8.80 Hz, 1H) 2.58 (m, 1H) 1.37-1.08 (m, 6H) 0.90-0.62 (m, 9H)

LCMS: $t_R$=1.00 min., MS: m/z (ES+)=521 (M+H$^+$).

Example 35-7. (2S)-2-[[2-cyclopentyl-4-[[4-(trifluoromethyl)phenyl]methoxy]-1,3-benzothiazole-5-carbonyl]amino]-3,3-dimethyl-butanoic acid

64

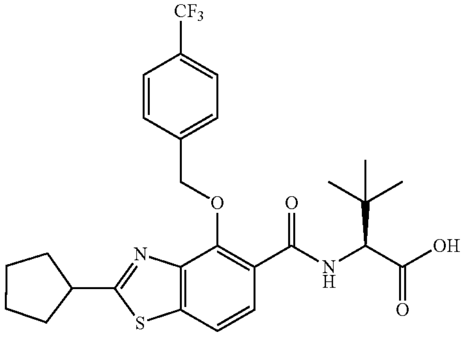

$^1$H NMR (400 MHz, $CDCl_3$) δ 8.66 (d, J=8.3 Hz, 1H), 8.09 (d, J=8.5 Hz, 1H), 7.75 (d, J=8.0 Hz, 2H), 7.63-7.52 (m, 3H), 5.79 (s, 2H), 4.52 (d, J=8.2 Hz, 1H), 3.59-3.49 (m, 2H), 2.27-2.17 (m, 2H), 2.01-1.71 (m, 6H), 0.90 (s, 9H).

LCMS: $t_R$=2.41 min.; MS: m/z (ES$^+$)=534 (M+H$^+$).

Example 35-8. (2S)-2-[[2-(1-fluorocyclopropyl)-4-[[4-(trifluoromethyl)phenyl]methoxy]-1,3-benzothiazole-5-carbonyl]amino]-3,3-dimethyl-butanoic acid

65

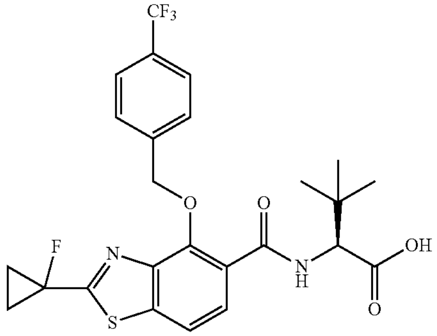

$^1$H NMR (400 MHz, DMSO-d) δ 12.76 (s, 1H), 8.49 (d, J=8.7 Hz, 1H), 7.94 (d, J=8.5 Hz, 1H), 7.82 (d, J=8.5 Hz, 1H), 7.74 (d, J=9.1 Hz, 4H), 5.72 (q, J=12.1 Hz, 2H), 4.34 (d, J=8.8 Hz, 1H), 1.89-1.75 (m, 2H), 1.62-1.50 (m, 2H), 0.88 (s, 9H).

LCMS: $t_R$=2.31 min. MS: m/z (ES$^+$)=525 (M+H$^+$).

Example 35-9. (2S)-2-[[2-cyclobutyl-4-[[4-(trifluoromethyl)phenyl]methoxy]-1,3-benzothiazole-5-carbonyl]amino]-3,3-dimethyl-butanoic acid

66

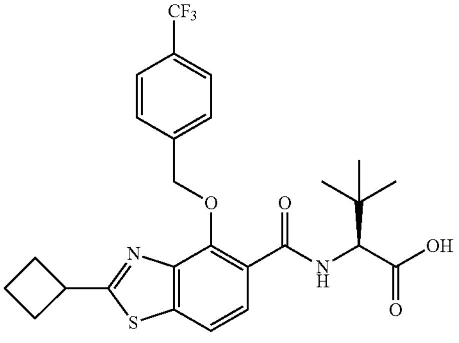

$^1$H NMR (400 MHz, DMSO-d) δ 12.81 (s, 1H), 8.52 (d, J=8.8 Hz, 1H), 8.06-7.42 (m, 6H), 5.83 (q, J=11.9 Hz, 2H), 4.35 (d, J=8.7 Hz, 1H), 4.12-3.79 (m, 1H), 2.50-2.31 (m, 4H), 2.12-1.93 (m, 2H), 0.88 (s, 9H).

LCMS: $t_R$=2.41 min.; MS: m/z (ES$^+$)=521 (M+H$^+$).

Biological Assays

Example 36: H441 Cell Emax and EC50

Cells

Two cell lines were used, the H441 carcinoma line and the CFHBE41o− (41o−) human bronchial epithelial line. Both cell lines expressed human Cystic Fibrosis Transmembrane Conductance Regulator (CFTR) harboring the ΔF508 mutation and with an in-frame fusion in CFTR extracellular loop 4 of Horse Radish Peroxidase (HRP) under control of the CMV promoter. In the presence of the HRP tag, ΔF508-CFTR transported to the cell surface was detectable upon addition of an HRP substrate (Luminata Forte). Both cell types were cultivated at 37° C. with $CO_2$.

The H441 cells were cultured in medium containing: 500 mls RPMI GIBCO 22400; 50 mls FBS GIBCO, 16000; 4.4 mls DPBS, no calcium, no magnesium GIBCO 14190 containing G418 AGScientific G1033 added to 50 mg/ml; and 5.5 mls Penicillin/Streptomycin 100× solution, Corning, 30-002-CL.

The 41o− cells were cultured in medium containing: 500 mls MEM (1X,) GIBCO, 11095; 50 mls FBS (Tet System) Clontech 631106; 5.5 mls Hepes (1M) GIBCO 15630; 5 mls GlutaMAX (100×) GIBCO 35050; 1.2 mls Puromycin (10 mg/ml) Invivogen ant-pr; and 2.2 mls of 50 mg/ml G418 solution.

The 41o− cells were grown on Becton/Dickinson Biocoat (collagen) T175 flasks or house-coated (see below) 2-stack or 5-stack tissue culture hotels. The house-coat contained 48 mls (240 mls) LHC Basal Medium GIBCO 12677019; 67 µls (335 µls) BSA Fraction V (7.5%) Sigma A8412-100; 1.5 mls (7.5 mls) 0.1% collagen SIGMA; and 0.5 mls (2.5 mls) human plasma fibronectine (1 mg/ml) GIBCO 3306-015 in sterile $H_2O$. The house-coat was poured on to the growing surface of the plastic ware to ensure coverage, poured off and incubated at 37° C. overnight (O/N) or longer.

For both cell types, the medium was changed every other day unless the culture was at low % confluence. Cells were used for the assays at ~75% confluence.

Assay

DMSO/Compound Dilutions Plate for 15-Point Dose-Response Testing

To a polypropylene (PP) 384-well plate, 15 µls DMSO was added to all wells in columns 1-22 and 24 (low Control). 15 µls of 260 µM VX809 (Lumacaftor), Selleckchem S1565, was added to column 23 wells (high Control). 15 µls of 10 mM test compound or VX809 (control) were added to wells of row A. Serial dilutions of Row A compound were performed 2×15 µls in rows A through 0 (15-point).

Medium Dilution Plate

A PP, 384-well plate containing the appropriate cell culture medium was prepared for each assay plate with 100 µls per well. For the doxycycline-induced 41o− cells, doxycycline for both the assay plate and the medium dilution plate was added at 0.0005 mg/ml to the medium.

Assay Plate

Both cell lines were plated for the assay at 30 µls per 384-well at $3.4\times10^{e5}$ cells per ml (~10K cells/well). H441 cells were plated on opaque, white, Corning plate 3704. 41o− cells were plated on collagen-coated opaque, white, Corning plate 356665. For 41o− cells, doxycycline was added to the medium.

Compound Addition/Assay Incubation

Using FX (Beckman) protocol, 10 µls diluted compound or medium was added per well to the Assay Plate as: 2 µls DMSO Dilution plate well is diluted in 100 µls of the Medium Dilution Plate well, mixed, and 10 µls is transferred to the Assay Plate.

The final assay dilution series is 24.5, 12.3, 6.1, 3.1, 1.5, 0.8, 0.4, 0.2, 0.1, 0.05, 0.02, 0.01, 0.006, 0.003, 0.001 and 0 µM. The 41o− assay plates were incubated at 37° C. w/$CO_2$, the H441 assay plates were incubated at 27° C. w/$CO_2$, each overnight for two nights.

Assay Result Determination

After being brought to room temperature, the assay plate liquid was removed. 30 uls of Luminata Forte (Millipore ELLUF0100) was added per well and incubated at room temperature for 10 min. The plates were then read on a Topcount, protocol LumiMatti (CPS, luminescence). The data was analyzed for % of maximum, maximum VX809 signal, and EC50 using Pearl and SPEED tools.

Example 37: TECC24 AUC Fold Over DMSO @10 uM

The effects of a test agent on CFTR-mediated transepithelial chloride transport was measured using TECC24 recording analysis. Test agents were solubilized in DMSO. Solubilized test agents were mixed with incubation medium containing DMEM/F12, Ultroser G (2%; Crescent Chemical, catalog #67042), Hyclone Fetal Clone 11(2%; GE Healthcare, catalog #SH30066.02), bovine brain extract (0.25%; Lonza, catalog #CC-4098), insulin (2.5 µg/mL), IL-13 (10 ng/mL), hydrocortisone (20 nM), transferrin (2.5 µg/mL), triiodothyronine (500 nM), ethanolamine (250 nM), epinephrine (1.5 µM), phosphoethanolamine (250 nM), and retinoic acid (10 nM). Primary human bronchial epithelial cells from a ΔF508 homozygous CF donor (CF-HBE cells; from University of North Carolina Cystic Fibrosis Tissue Procurement Center), grown on Transwell HTS 24-well cell culture inserts (Costar, catalog #3378), were exposed to test agents or controls dissolved in incubation medium. The CF-HBE cells were cultured at 36.5° C. for 48 hours before TECC24 recordings were performed in the presence or absence of test agent, a positive control or vehicle (DMSO).

Following incubation, the transwell cell culture inserts containing the test agent or control-treated CF-HBE cells were loaded onto a TECC24 apparatus (TECC v7 or MTECC v2; EP Design) to record the transepithelial voltage (VT) and resistance (TEER) using 4 AgCl electrodes per well configured in current-clamp mode. The apical and basolateral bath solutions both contained (in mM) 140 NaCl, 5 KCl, 2 $CaCl_2$, 1 $MgCl_2$, 10 Hepes, and 10 glucose (adjusted to pH 7.4 with NaOH). To inhibit basal Na+ absorption, the ENaC inhibitor benzamil (10 µM) was added to the bath. Then, the adenylate cyclase activator, forskolin (10 µM), was added to the bath to activate CFTR. The forskolin-stimulated Cl— transport was halted by addition of CFTR inhibitor-172 (20 µM) to the bath at the end of the experiment to confirm specificity. VT and TEER recordings were digitally acquired at routine intervals using TECC or MTECC software (EP Design). VT and TEER were transformed into equivalent transepithelial Cl-current (IEQ), and the Area Under the Curve (AUC) of the IEQ time course between forskolin and CFTR inhibitor-172 addition is generated using Excel (Microsoft). Efficacy is expressed as the ratio of the test agent AUC divided by vehicle AUC. EC50s based on AUC are generated using the non-linear regression log(agonist) vs. response function in Prism software (GraphPad) with Hill Slope fixed=1.

If a test agent increased the AUC of the forskolin-stimulated IEQ relative to vehicle in CF-HBE cells, and this increase was inhibited by CFTR inhibitor-172, then the test agent was considered a CFTR corrector.

Data for Compounds Example of 31-1 to 35-9 are provided in Table 2 below.

TABLE 2

| EXAMPLE No. | H441 cell Emax (%) | H441 cell EC50 (uM) | TECC24 AUC fold over DMSO |
|---|---|---|---|
| 31-1 | −10.7 | ND | ND |
| 32-2 | 111.9 | 3.203 | C |
| 32-3 | 206.9 | 1.348 | C |

TABLE 2-continued

| EXAMPLE No. | H441 cell Emax (%) | H441 cell EC50 (uM) | TECC24 AUC fold over DMSO |
|---|---|---|---|
| 32-4 | 78.7 | 4.371 | C |
| 32-5 | 93.5 | 0.496 | C |
| 32-6 | 142.3 | 3.300 | C |
| 32-7 | 126.8 | 6.891 | C |
| 32-8 | 4.1 | 4.560 | ND |
| 32-9 | 193.1 | 1.083 | C |
| 32-10 | 85.3 | 7.309 | C |
| 32-11 | 81.3 | 1.040 | B |
| 32-12 | 120.1 | 0.403 | B |
| 32-13 | 143.3 | 4.118 | C |
| 32-14 | 209.7 | 2.780 | C |
| 33-1 | 308.3 | 0.647 | A |
| 33-2 | 216.4 | 0.441 | B |
| 33-3 | 349.8 | 0.884 | A |
| 33-4 | 232.1 | 2.347 | A |
| 33-5 | 250.9 | 0.262 | A |
| 33-6 | 279.3 | 0.500 | A |
| 33-7 | 311.8 | 0.641 | A |
| 33-8 | 154.6 | 0.658 | A |
| 33-9 | 250.2 | 1.128 | A |
| 33-10 | 216.1 | 1.252 | B |
| 33-11 | 186.7 | 0.474 | B |
| 33-12 | 150.1 | 0.999 | C |
| 33-13 | 323.9 | 0.377 | A |
| 33-14 | 421.9 | 1.979 | A |
| 33-15 | 200.1 | 0.880 | A |
| 33-16 | 218.5 | 0.340 | B |
| 33-17 | 57.7 | 3.201 | C |
| 33-18 | 217.1 | 1.147 | A |
| 33-19 | 254.7 | 0.427 | A |
| 33-20 | 81.2 | 2.781 | C |
| 33-21 | 268.2 | 0.337 | A |
| 33-22 | 168.6 | 0.755 | A |
| 33-23 | 315.0 | 1.128 | A |
| 33-24 | 270.5 | 0.412 | A |
| 33-25 | 200.1 | 0.577 | A |
| 33-26 | 196.6 | 1.093 | B |
| 33-27 | 261.5 | 0.309 | A |
| 33-28 | 130.3 | 0.562 | A |
| 33-29 | 152.4 | 0.854 | B |
| 33-30 | 263.3 | 0.102 | A |
| 33-31 | 131.2 | 0.532 | C |
| 33-32 | 168.1 | 0.277 | B |
| 33-33 | 177.2 | 0.503 | B |
| 33-34 | 238.2 | 0.637 | A |
| 33-35 | 199.4 | 0.678 | A |
| 33-36 | 165.4 | 0.750 | A |
| 34-1 | 179.2 | 0.358 | A |
| 34-2 | 132.9 | 1.248 | A |
| 34-3 | 222.1 | 0.406 | A |
| 34-4 | 158.7 | 0.281 | A |
| 34-5 | 105.6 | 0.509 | A |
| 34-6 | 155.1 | 1.192 | A |
| 34-7 | 84.2 | 0.612 | A |
| 35-1 | 150.8 | 0.618 | A |
| 35-2 | 145.5 | 0.470 | C |
| 35-3 | 286.5 | 0.662 | A |
| 35-4 | ND | ND | A |
| 35-5 | ND | ND | A |
| 35-6 | ND | ND | A |
| 35-7 | ND | ND | A |
| 35-8 | ND | ND | A |
| 35-9 | ND | ND | A |

ND = Not determined;
"A" refers to AUC @10 μM > 6;
"B" refers to AUC @10 μM between 4-6;
"C" refers to AUC @10 μM < 4.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A compound of formula I:

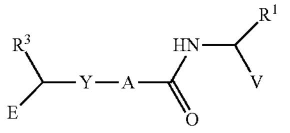

I or a pharmaceutically acceptable salt thereof, wherein:

A is selected from

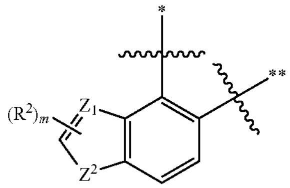

and

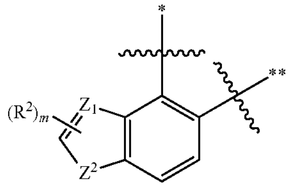

wherein * marks the point of attachment to Y and ** marks the point of attachment to —C(O)—;

$Z^1$ and $Z^2$ are each independently CH, S or N, wherein at least one of $Z^1$ and $Z^2$ is N or S;

Y is —O—;

E is $C_{3-9}$-cycloalkyl, $C_{6-10}$-aryl, 3-10 membered heteroaryl, or a 3-9 membered heterocycloalkyl, each of which is optionally substituted with one, two, three, four, or five occurrences of $R^5$;

V is —C(O)—O—$R^7$;

$R^1$ is

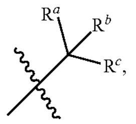

wherein $R^a$ is $C_{1-6}$ alkyl, $R^b$ is $C_{1-6}$ alkyl, $R^c$ is $C_{1-6}$ alkyl or $C_{6-10}$ aryl, or any two of $R^a$, $R^b$, and $R^c$, taken together with the atoms to which they are attached, form a $C_{3-9}$ cycloalkyl ring;

each $R^2$ is independently halo, $C_{1-6}$ alkyl, halo$C_{1-6}$ alkyl, —O—$C_{1-6}$ alkyl, —O-halo $C_{1-6}$ alkyl, $C_{3-9}$-cycloalkyl or 3-10 membered heteroaryl;

$R^3$ is H or alkyl;

each $R^5$ is independently halo, $C_{1-6}$ alkyl, $C_{1-6}$ haloalkyl, —O— $C_{1-6}$alkyl, —O—$C_{1-6}$haloalkyl, and —S—$C_{1-6}$haloalkyl;

$R^7$ is hydrogen, $C_{1-6}$-alkyl, $C_{6-10}$-aryl, or benzyl; and m is 0, 1, or 2.

2. The compound of claim 1, wherein A is

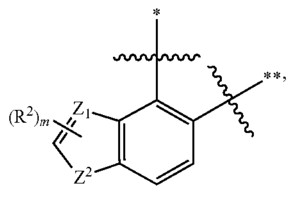

$Z^1$ is CH and $Z^2$ is S.

3. The compound of claim 1, wherein A is

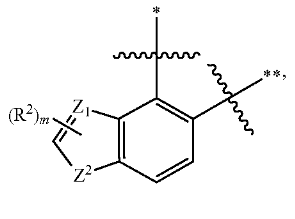

$Z^1$ is N and $Z^2$ is S.

4. The compound of claim 1, wherein A is

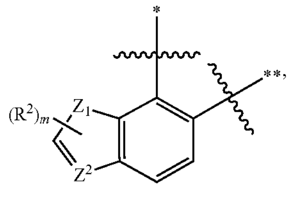

$Z^1$ is S and $Z^2$ is CH.

5. The compound of claim 1, wherein E is optionally substituted $C_{3-9}$-cycloalkyl, aryl, or 3-10 membered heteroaryl.

6. The compound of claim 1, wherein E is optionally substituted cyclohexyl, phenyl, or 2-benzthiazolyl.

7. The compound of claim 1, wherein $R^a$ is methyl.

8. The compound of claim 1, wherein $R^b$ is methyl.

9. The compound of claim 1, wherein $R^c$ is methyl, ethyl, or phenyl.

10. The compound of claim 1, wherein $R^a$ and $R^c$, taken together with the atoms to which they are attached, form a cyclopropyl, cyclobutyl or cyclohexyl ring.

11. The compound of claim 1, wherein $R^2$ is chloro, methyl, ethyl, isopropyl, isopentyl, —$CHF_2$, —$CF_3$, —OMe, cyclopropyl, cyclobutyl, cyclopentyl, or thiazolyl.

12. The compound of claim 1, wherein each $R^5$ is independently halo, $C_{1-4}$-alkyl, $C_{1-4}$-haloalkyl, —O—$C_{1-4}$-haloalkyl, or —S—$C_{1-4}$haloalkyl.

13. The compound of claim 1, wherein each $R^5$ is independently fluoro, chloro, —$CF_3$, —$OCHF_2$, —$OCF_3$, or —$SCF_3$.

14. The compound of claim 1, wherein the compound is selected from:

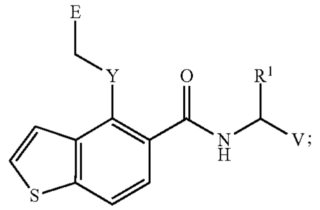

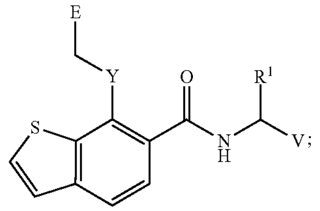

and

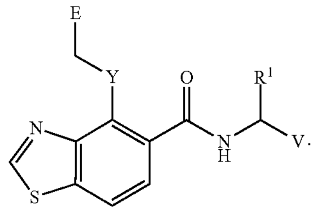

15. The compound of claim 1, wherein $R^1$ is in the α-configuration.

16. The compound of claim 15, where the compound of Formula (I) has the structure (IA):

(IA)

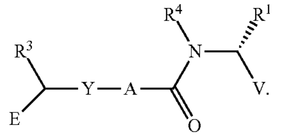

17. The compound of claim 1, wherein $R^1$ is in the (3-configuration.

18. The compound of claim 17, where the compound of Formula (I) has the structure (IB):

(IB)

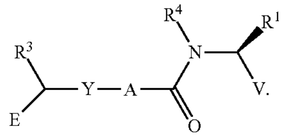

19. A compound selected from:
| Compound | Structure |
|---|---|
| 1 | 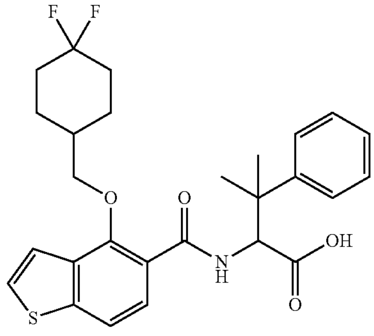 [SMILES: CC(C)(c1ccccc1)C(NC(=O)c1ccc2sccc2c1OCC1CCC(F)(F)CC1)C(=O)O] |
| 2 | 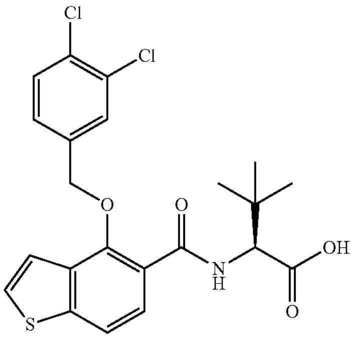 [SMILES: CC(C)(C)[C@H](NC(=O)c1ccc2sccc2c1OCc1ccc(Cl)c(Cl)c1)C(=O)O] |
| 3 | 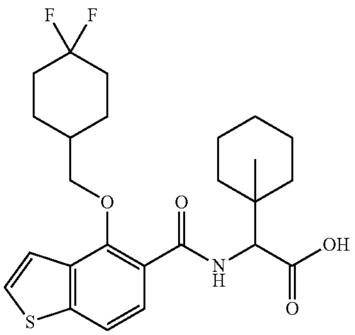 |
| 4 | 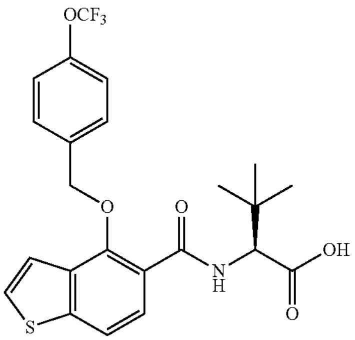 [SMILES: CC(C)(C)[C@H](NC(=O)c1ccc2sccc2c1OCc1ccc(OC(F)(F)F)cc1)C(=O)O] |
-continued
| Compound | Structure |
|---|---|
| 5 | 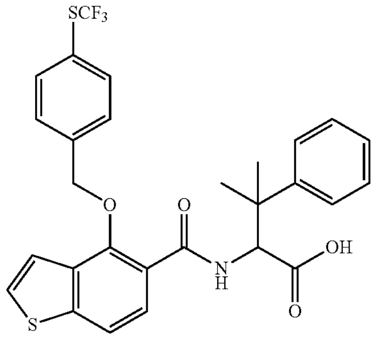 |
| 6 | 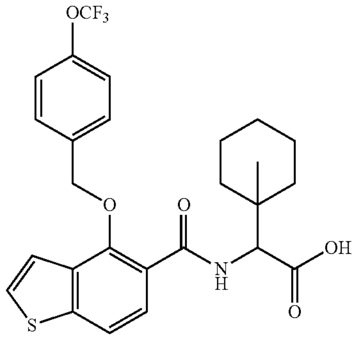 |
| 7 | 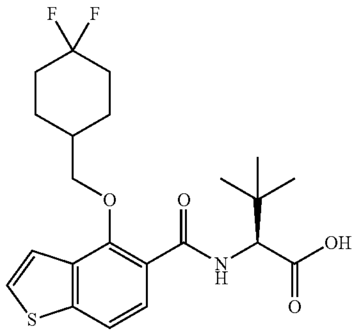 [SMILES: CC(C)(C)[C@H](NC(=O)c1ccc2sccc2c1OCC1CCC(F)(F)CC1)C(=O)O] |
| 8 | 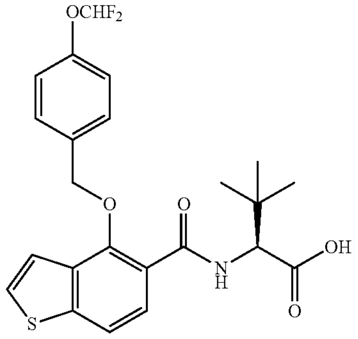 |

-continued
| Compound | Structure |
|---|---|
| 9 | 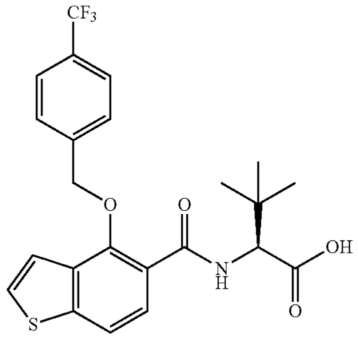 |
| 10 | 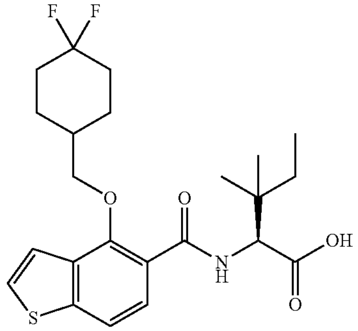 [SMILES: CCC(C)(C)[C@H](NC(=O)c1ccc2sccc2c1OCC1CCC(F)(F)CC1)C(=O)O] |
| 11 | 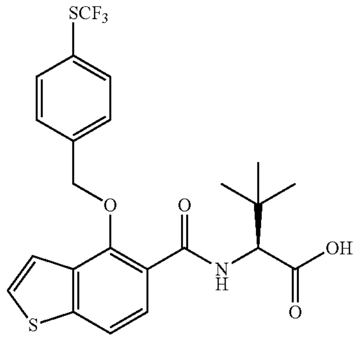 |
| 12 | 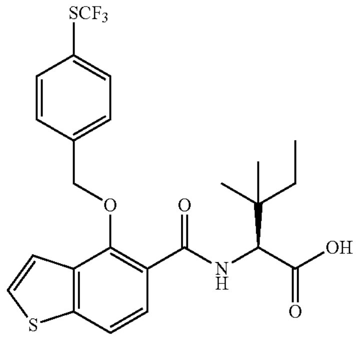 |
-continued
| Compound | Structure |
|---|---|
| 13 | 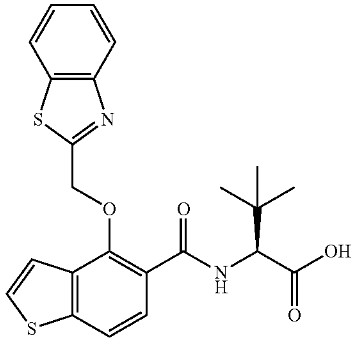 [SMILES: CC(C)(C)[C@H](NC(=O)c1ccc2sccc2c1OCc1nc2ccccc2s1)C(=O)O] |
| 14 | 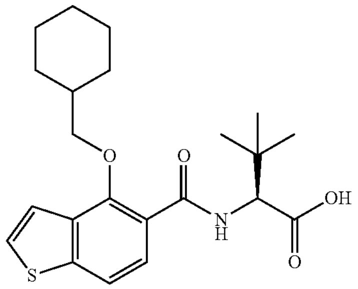 [SMILES: CC(C)(C)[C@H](NC(=O)c1ccc2sccc2c1OCC1CCCCC1)C(=O)O] |
| 15 | 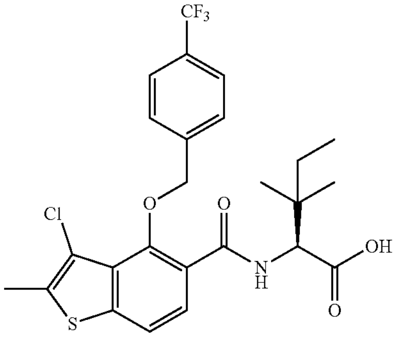 [SMILES: CCC(C)(C)[C@H](NC(=O)c1ccc2sc(C)c(Cl)c2c1OCc1ccc(C(F)(F)F)cc1)C(=O)O] |
| 16 | 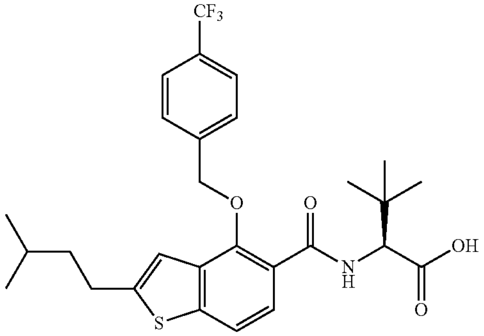 [SMILES: CC(C)CCc1cc2c(OCc3ccc(C(F)(F)F)cc3)c(C(=O)N[C@H](C(=O)O)C(C)(C)C)ccc2s1] |

-continued
| Compound | Structure |
| --- | --- |
| 17 | 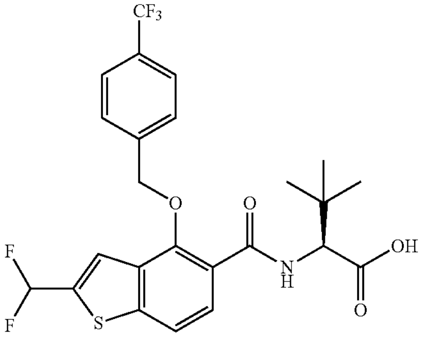 [SMILES: CC(C)(C)[C@H](NC(=O)c1ccc2sc(C(F)F)cc2c1OCc1ccc(C(F)(F)F)cc1)C(=O)O] |
| 18 | 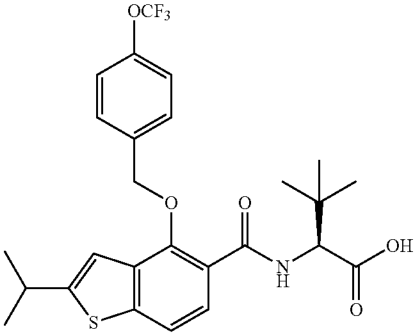 |
| 19 | 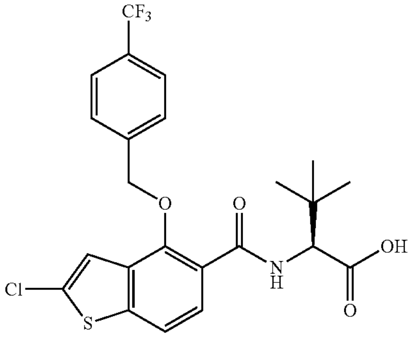 |
| 20 | 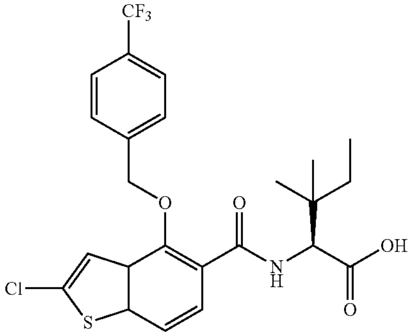 |
-continued
| Compound | Structure |
| --- | --- |
| 21 | 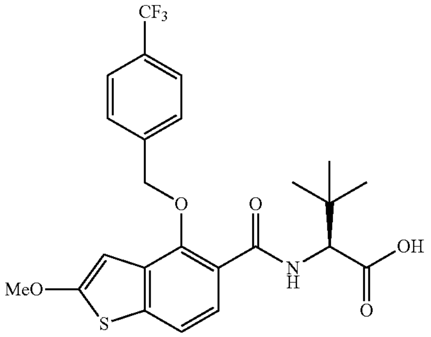 [SMILES: COc1cc2c(OCc3ccc(C(F)(F)F)cc3)c(C(=O)N[C@H](C(=O)O)C(C)(C)C)ccc2s1] |
| 22 | 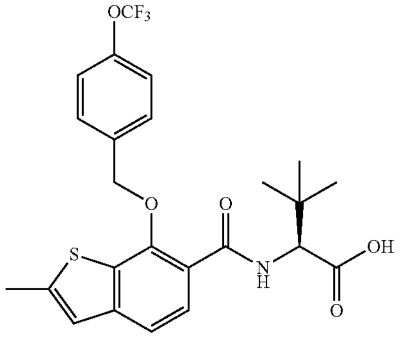 [SMILES: Cc1cc2ccc(C(=O)N[C@H](C(=O)O)C(C)(C)C)c(OCc3ccc(OC(F)(F)F)cc3)c2s1] |
| 23 | 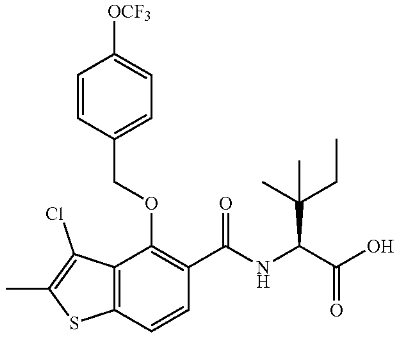 |
| 24 | 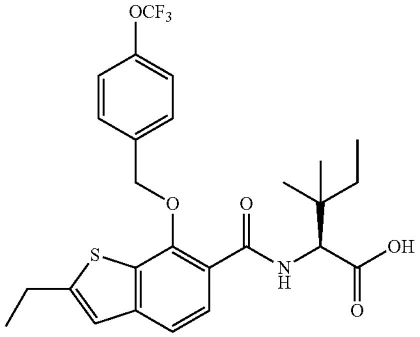 [SMILES: CCc1cc2ccc(C(=O)N[C@H](C(=O)O)C(C)(C)CC)c(OCc3ccc(OC(F)(F)F)cc3)c2s1] |

-continued
| Compound | Structure |
| --- | --- |
| 25 | 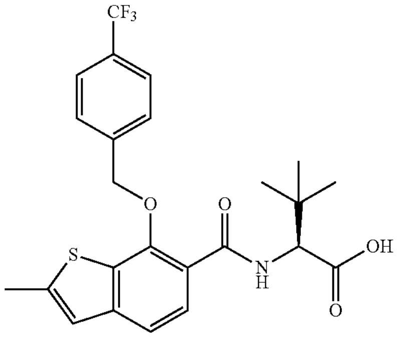 [SMILES: Cc1cc2ccc(C(=O)N[C@H](C(=O)O)C(C)(C)C)c(OCc3ccc(C(F)(F)F)cc3)c2s1] |
| 26 | 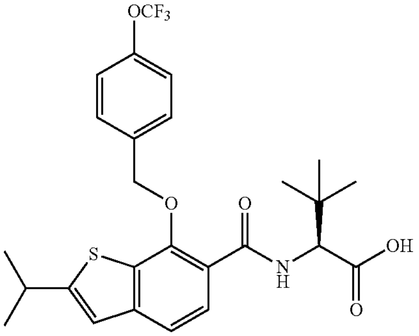 [SMILES: CC(C)c1cc2ccc(C(=O)N[C@H](C(=O)O)C(C)(C)C)c(OCc3ccc(OC(F)(F)F)cc3)c2s1] |
| 27 | 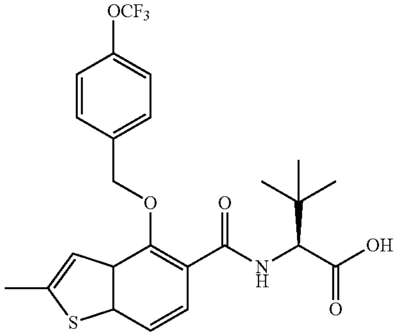 [SMILES: CC1=CC2C(OCc3ccc(OC(F)(F)F)cc3)=C(C(=O)N[C@H](C(=O)O)C(C)(C)C)C=CC2S1] |
| 28 | 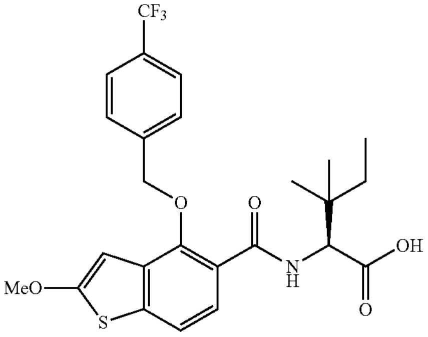 |
-continued
| Compound | Structure |
| --- | --- |
| 29 | 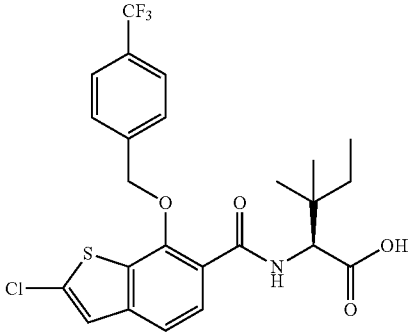 [SMILES: CCC(C)(C)[C@H](NC(=O)c1ccc2cc(Cl)sc2c1OCc1ccc(C(F)(F)F)cc1)C(=O)O] |
| 30 | 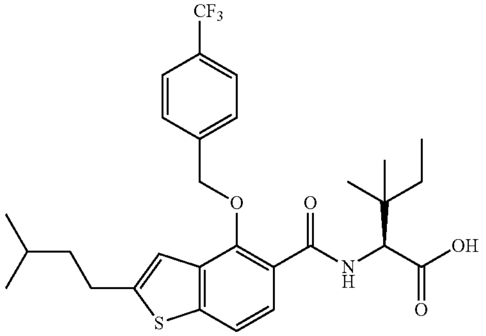 [SMILES: CCC(C)(C)[C@H](NC(=O)c1ccc2sc(CCC(C)C)cc2c1OCc1ccc(C(F)(F)F)cc1)C(=O)O] |
| 31 | 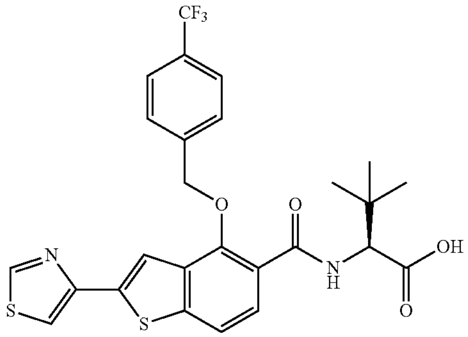 [SMILES: CC(C)(C)[C@H](NC(=O)c1ccc2sc(-c3cscn3)cc2c1OCc1ccc(C(F)(F)F)cc1)C(=O)O] |
| 32 | 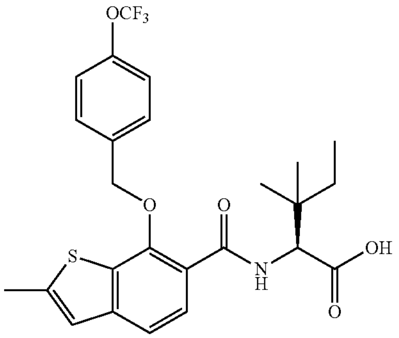 |

-continued
| Compound | Structure |
|---|---|
| 33 | 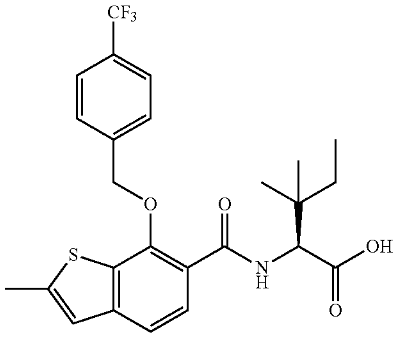 |
| 34 | 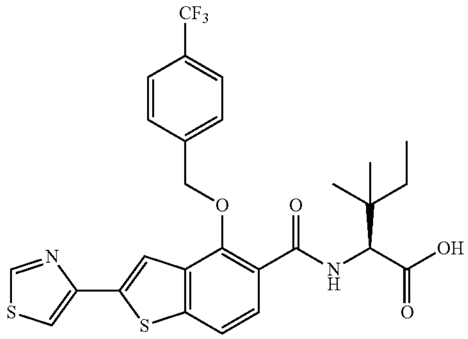 [SMILES: CCC(C)(C)[C@H](NC(=O)c1ccc2sc(-c3cscn3)cc2c1OCc1ccc(C(F)(F)F)cc1)C(=O)O] |
| 35 | 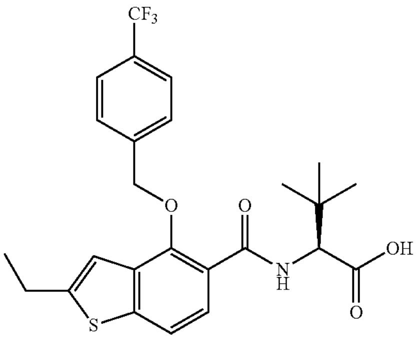 [SMILES: CCc1cc2c(OCc3ccc(C(F)(F)F)cc3)c(C(=O)N[C@H](C(=O)O)C(C)(C)C)ccc2s1] |
| 36 | 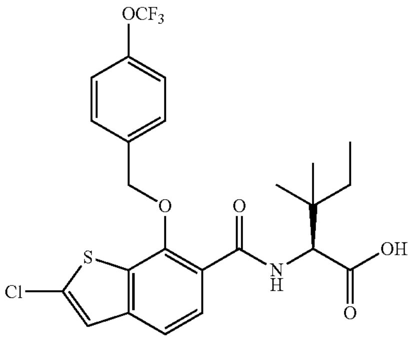 |
-continued
| Compound | Structure |
|---|---|
| 37 | 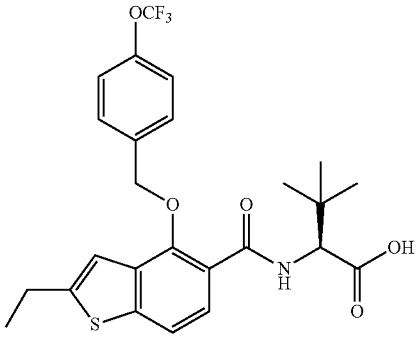 [SMILES: CCc1cc2c(OCc3ccc(OC(F)(F)F)cc3)c(C(=O)N[C@H](C(=O)O)C(C)(C)C)ccc2s1] |
| 38 | 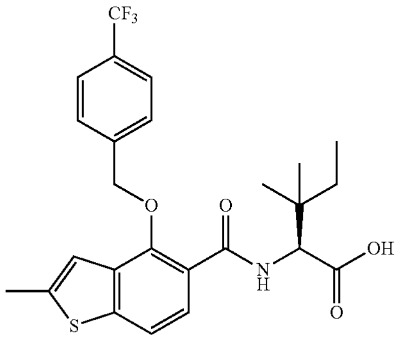 [SMILES: CCC(C)(C)[C@H](NC(=O)c1ccc2sc(C)cc2c1OCc1ccc(C(F)(F)F)cc1)C(=O)O] |
| 39 | 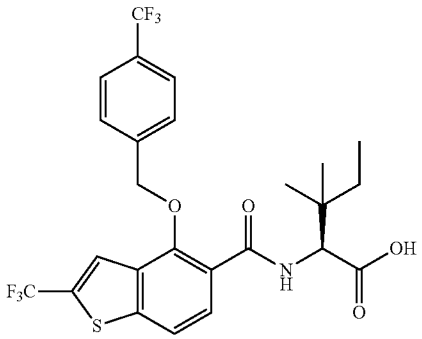 |
| 40 | 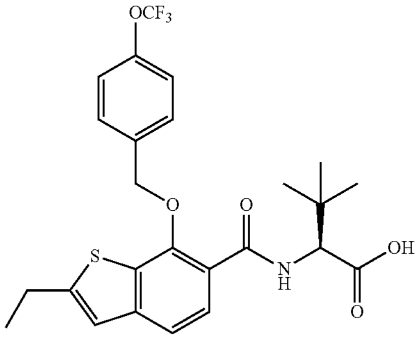 [SMILES: CCc1cc2ccc(C(=O)N[C@H](C(=O)O)C(C)(C)C)c(OCc3ccc(OC(F)(F)F)cc3)c2s1] |

-continued
| Compound | Structure |
|---|---|
| 41 | 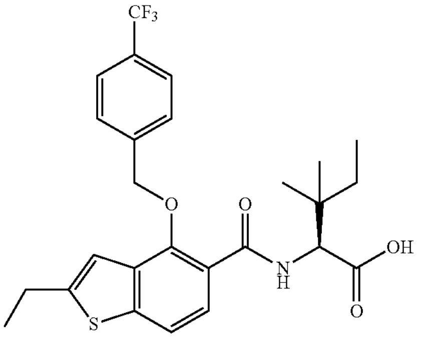 [SMILES: CCc1cc2c(OCc3ccc(C(F)(F)F)cc3)c(C(=O)N[C@H](C(=O)O)C(C)(C)CC)ccc2s1] |
| 42 | 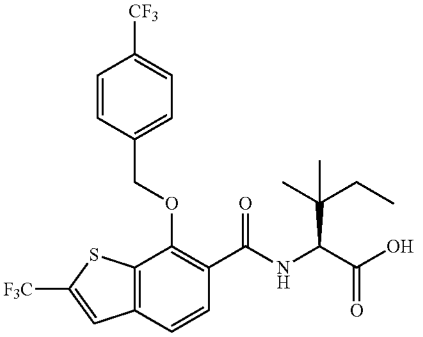 [SMILES: CCC(C)(C)[C@H](NC(=O)c1ccc2cc(C(F)(F)F)sc2c1OCc1ccc(C(F)(F)F)cc1)C(=O)O] |
| 43 | 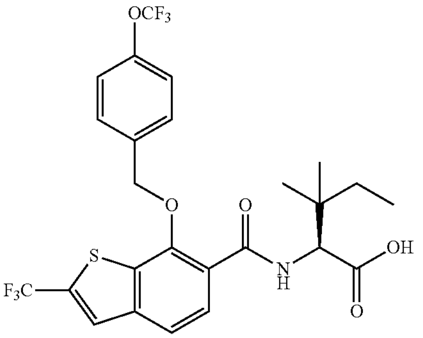 [SMILES: CCC(C)(C)[C@H](NC(=O)c1ccc2cc(C(F)(F)F)sc2c1OCc1ccc(OC(F)(F)F)cc1)C(=O)O] |
| 44 | 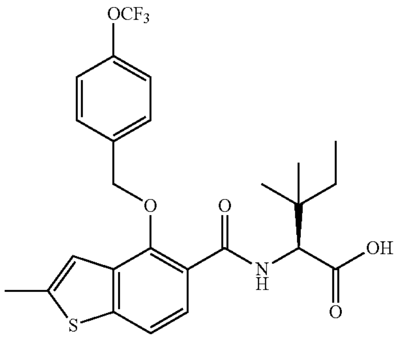 [SMILES: CCC(C)(C)[C@H](NC(=O)c1ccc2sc(C)cc2c1OCc1ccc(OC(F)(F)F)cc1)C(=O)O] |
-continued
| Compound | Structure |
|---|---|
| 45 | 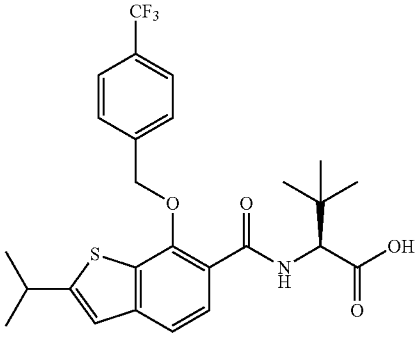 [SMILES: CC(C)c1cc2ccc(C(=O)N[C@H](C(=O)O)C(C)(C)C)c(OCc3ccc(C(F)(F)F)cc3)c2s1] |
| 46 | 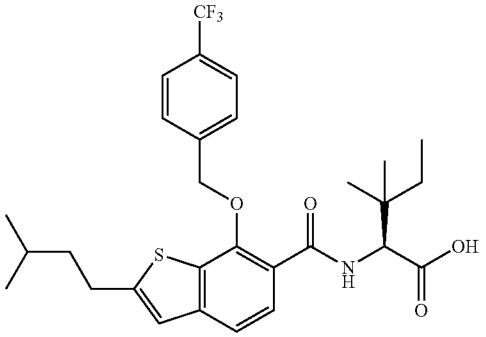 [SMILES: CCC(C)(C)[C@H](NC(=O)c1ccc2cc(CCC(C)C)sc2c1OCc1ccc(C(F)(F)F)cc1)C(=O)O] |
| 47 | 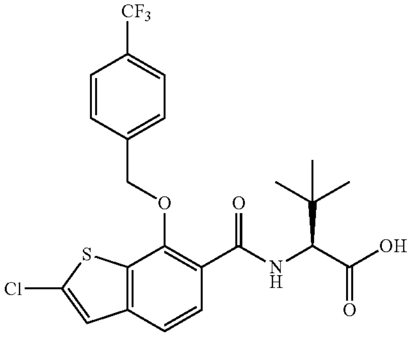 [SMILES: CC(C)(C)[C@H](NC(=O)c1ccc2cc(Cl)sc2c1OCc1ccc(C(F)(F)F)cc1)C(=O)O] |
| 48 | 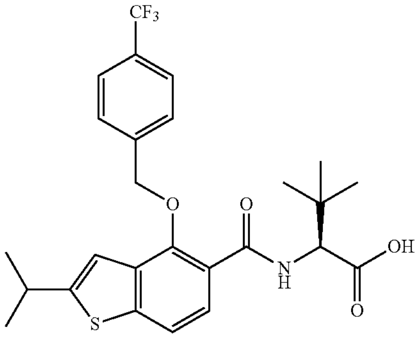 [SMILES: CC(C)c1cc2c(OCc3ccc(C(F)(F)F)cc3)c(C(=O)N[C@H](C(=O)O)C(C)(C)C)ccc2s1] |

-continued
| Compound | Structure |
|---|---|
| 49 | 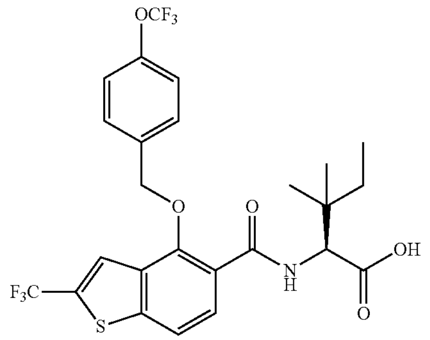 [SMILES: CCC(C)(C)[C@H](NC(=O)c1ccc2sc(C(F)(F)F)cc2c1OCc1ccc(OC(F)(F)F)cc1)C(=O)O] |
| 50 | 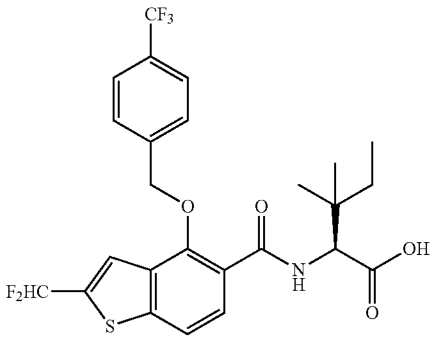 |
| 51 | 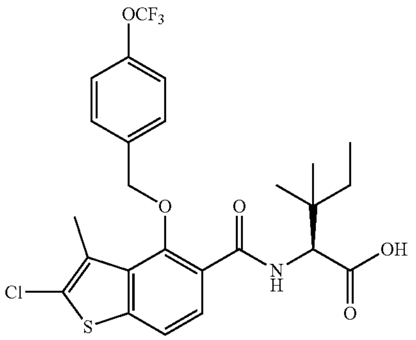 [SMILES: CCC(C)(C)[C@H](NC(=O)c1ccc2sc(Cl)c(C)c2c1OCc1ccc(OC(F)(F)F)cc1)C(=O)O] |
| 52 | 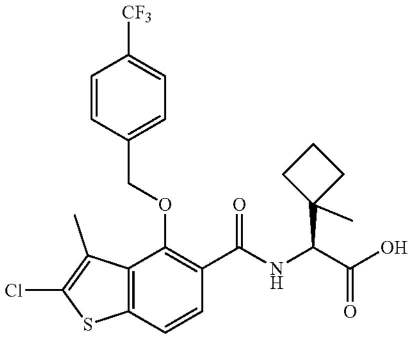 [SMILES: Cc1c(Cl)sc2ccc(C(=O)N[C@H](C(=O)O)C3(C)CCC3)c(OCc3ccc(C(F)(F)F)cc3)c12] |
| 53 | 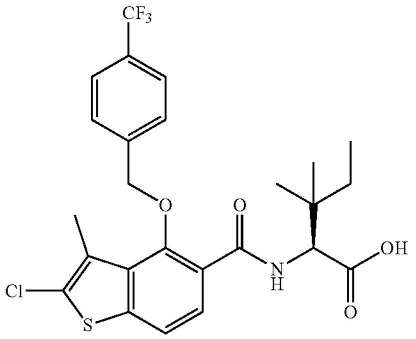 [SMILES: CCC(C)(C)[C@H](NC(=O)c1ccc2sc(Cl)c(C)c2c1OCc1ccc(C(F)(F)F)cc1)C(=O)O] |
| 54 | 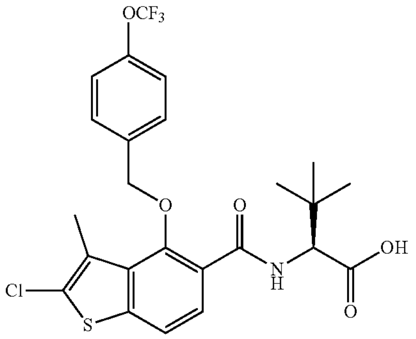 [SMILES: Cc1c(Cl)sc2ccc(C(=O)N[C@H](C(=O)O)C(C)(C)C)c(OCc3ccc(OC(F)(F)F)cc3)c12] |
| 55 | 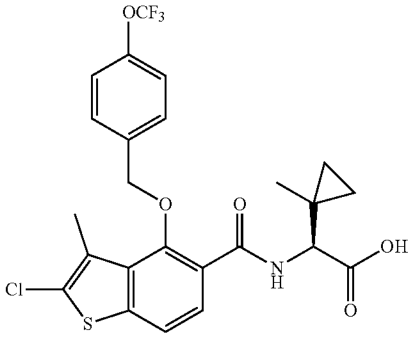 [SMILES: Cc1c(Cl)sc2ccc(C(=O)N[C@H](C(=O)O)C3(C)CC3)c(OCc3ccc(OC(F)(F)F)cc3)c12] |
| 56 | 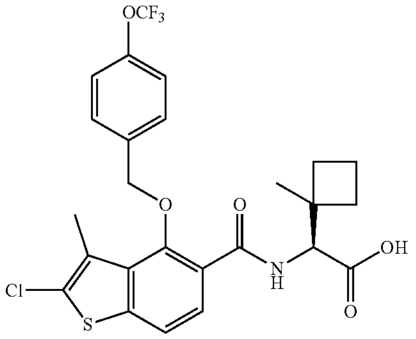 [SMILES: Cc1c(Cl)sc2ccc(C(=O)N[C@H](C(=O)O)C3(C)CCC3)c(OCc3ccc(OC(F)(F)F)cc3)c12] |

-continued
| Compound | Structure |
|---|---|
| 57 | 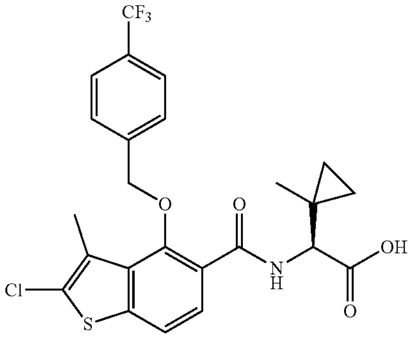 [SMILES: Cc1c(Cl)sc2ccc(C(=O)N[C@H](C(=O)O)C3(C)CC3)c(OCc3ccc(C(F)(F)F)cc3)c12] |
| 58 | 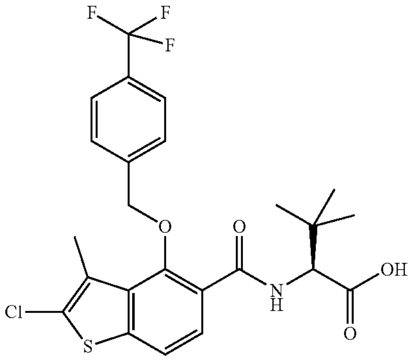 [SMILES: Cc1c(Cl)sc2ccc(C(=O)N[C@H](C(=O)O)C(C)(C)C)c(OCc3ccc(C(F)(F)F)cc3)c12] |
| 59 | 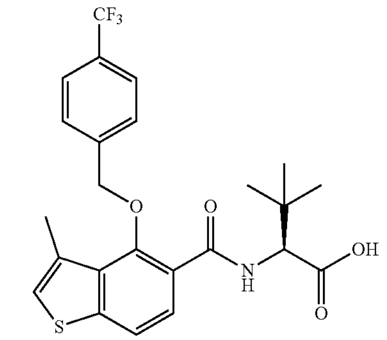 [SMILES: Cc1csc2ccc(C(=O)N[C@H](C(=O)O)C(C)(C)C)c(OCc3ccc(C(F)(F)F)cc3)c12] |
| 60 | 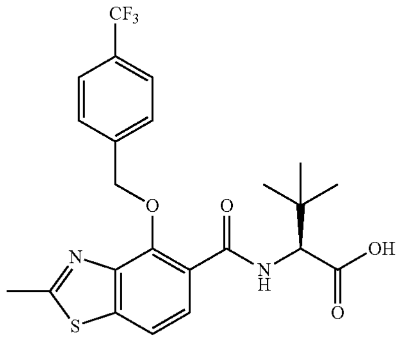 [SMILES: Cc1nc2c(OCc3ccc(C(F)(F)F)cc3)c(C(=O)N[C@H](C(=O)O)C(C)(C)C)ccc2s1] |
-continued
| Compound | Structure |
|---|---|
| 61 | 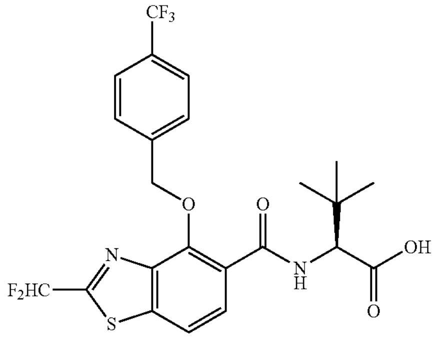 [SMILES: CC(C)(C)[C@H](NC(=O)c1ccc2sc(C(F)F)nc2c1OCc1ccc(C(F)(F)F)cc1)C(=O)O] |
| 62 | 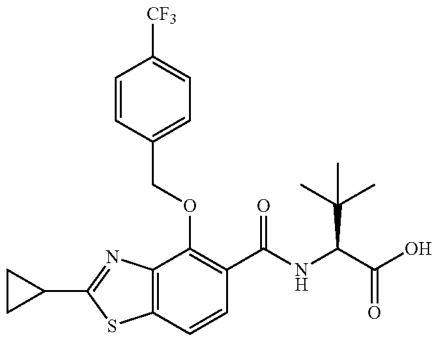 [SMILES: CC(C)(C)[C@H](NC(=O)c1ccc2sc(C3CC3)nc2c1OCc1ccc(C(F)(F)F)cc1)C(=O)O] |
| 63 | 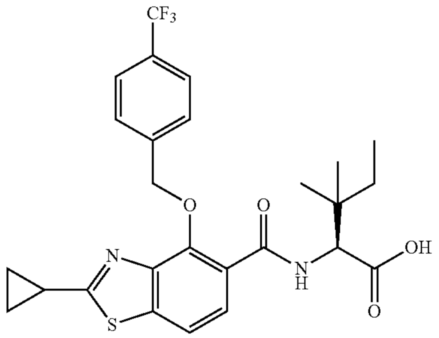 [SMILES: CCC(C)(C)[C@H](NC(=O)c1ccc2sc(C3CC3)nc2c1OCc1ccc(C(F)(F)F)cc1)C(=O)O] |
| 64 | 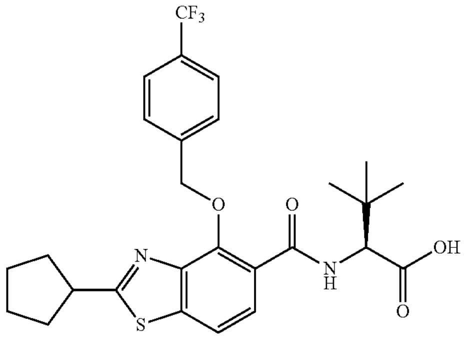 [SMILES: CC(C)(C)[C@H](NC(=O)c1ccc2sc(C3CCCC3)nc2c1OCc1ccc(C(F)(F)F)cc1)C(=O)O] |

-continued

| Compound | Structure |
|---|---|
| 65 | 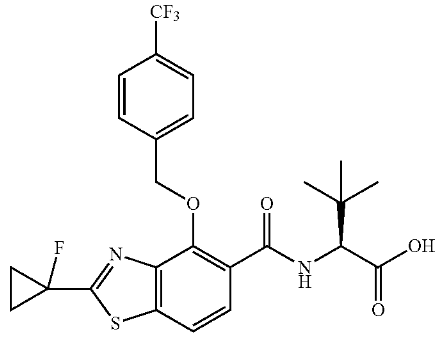 [SMILES: CC(C)(C)[C@H](NC(=O)c1ccc2sc(C3(F)CC3)nc2c1OCc1ccc(C(F)(F)F)cc1)C(=O)O] |

-continued

| Compound | Structure |
|---|---|
| 66 | 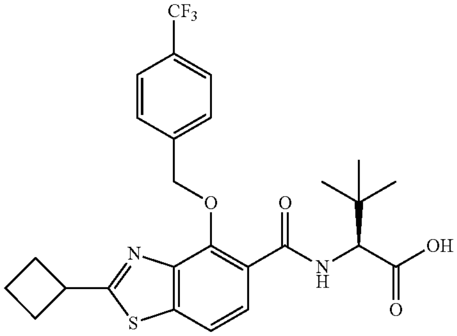 [SMILES: CC(C)(C)[C@H](NC(=O)c1ccc2sc(C3CCC3)nc2c1OCc1ccc(C(F)(F)F)cc1)C(=O)O] |

or a pharmaceutically acceptable salt thereof.

20. A pharmaceutical composition comprising a compound claim 1, and one or more pharmaceutically acceptable carriers or excipients.

21. The pharmaceutical composition of claim 20, further comprising one or more CFTR therapeutic agents.

22. A method of treating cystic fibrosis in a subject, comprising administering to the subject a therapeutically effective amount of a compound of claim 1.

23. The method of claim 22, wherein the subject is human.

* * * * *